(12) United States Patent
Casimiro-Garcia et al.

(10) Patent No.: US 10,906,888 B2
(45) Date of Patent: Feb. 2, 2021

(54) PYRIMIDINE CARBOXAMIDES AS INHIBITORS OF VANIN-1 ENZYME

(71) Applicant: Pfizer Inc., New York, NY (US)

(72) Inventors: Agustin Casimiro-Garcia, Concord, MA (US); Joseph Walter Strohbach, Wentzville, MO (US); David Hepworth, Concord, MA (US); Frank Eldridge Lovering, Acton, MA (US); Chulho Choi, Mystic, CT (US); Christophe Philippe Allais, Quaker Hill, CT (US); Stephen Wayne Wright, Old Lyme, CT (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 16/316,688

(22) PCT Filed: Jul. 7, 2017

(86) PCT No.: PCT/IB2017/054104
§ 371 (c)(1),
(2) Date: Jan. 10, 2019

(87) PCT Pub. No.: WO2018/011681
PCT Pub. Date: Jan. 18, 2018

(65) Prior Publication Data
US 2019/0315715 A1 Oct. 17, 2019

Related U.S. Application Data
(60) Provisional application No. 62/362,098, filed on Jul. 14, 2016.

(51) Int. Cl.
| | | |
|---|---|---|
| *C07D 401/14* | (2006.01) | |
| *C07D 403/14* | (2006.01) | |
| *C07D 413/14* | (2006.01) | |
| *C07D 471/08* | (2006.01) | |
| *C07D 487/04* | (2006.01) | |
| *C07D 487/10* | (2006.01) | |
| *C07D 491/107* | (2006.01) | |
| *C07D 498/10* | (2006.01) | |
| *C07D 498/18* | (2006.01) | |

(52) U.S. Cl.
CPC ......... *C07D 401/14* (2013.01); *C07D 403/14* (2013.01); *C07D 413/14* (2013.01); *C07D 471/08* (2013.01); *C07D 487/04* (2013.01); *C07D 487/10* (2013.01); *C07D 491/107* (2013.01); *C07D 498/10* (2013.01); *C07D 498/18* (2013.01)

(58) Field of Classification Search
CPC .. C07D 403/14; C07D 401/14; C07D 413/14; C07D 471/08; C07D 487/04; C07D 487/10; A61K 31/506
See application file for complete search history.

(56) References Cited

U.S. PATENT DOCUMENTS

| | | | |
|---|---|---|---|
| 5,811,428 A | 9/1998 | Suto et al. | |
| 2011/0053912 A1 | 3/2011 | Matsushima et al. | |

FOREIGN PATENT DOCUMENTS

| | | |
|---|---|---|
| JP | 2006151956 | 6/2006 |
| RU | 2413727 | 11/2004 |
| WO | 2000/62778 | 10/2000 |
| WO | 2000/64888 | 11/2000 |
| WO | 2000/71508 | 11/2000 |
| WO | 2000/71510 | 11/2000 |
| WO | 2000/71511 | 11/2000 |
| WO | 2001/19802 | 3/2001 |
| WO | 2001/83460 | 11/2001 |
| WO | 2002/40466 | 5/2002 |
| WO | 2003/016248 | 2/2003 |
| WO | 2003/086398 | 10/2003 |
| WO | 2003/091252 | 11/2003 |
| WO | 2004/096775 | 11/2004 |
| WO | 2005/049033 | 6/2005 |
| WO | 2005/075482 | 8/2005 |
| WO | 2005/084667 | 9/2005 |
| WO | 2005/097751 | 10/2005 |
| WO | 2005/121145 | 12/2005 |
| WO | 2006/044174 | 4/2006 |
| WO | 2007/027734 | 3/2007 |
| WO | 2007/088999 | 8/2007 |
| WO | 2007/093520 | 8/2007 |
| WO | 2008/153325 | 12/2008 |
| WO | 2008/157552 | 12/2008 |
| WO | 2009/016498 | 2/2009 |
| WO | 2010/020810 | 2/2010 |

(Continued)

OTHER PUBLICATIONS

Bartucci et al., Vanin-1: Its Physiological Function and Role in Diseases, International Journal of Molecular Sciences, 20, 3891, pp. 1-15 (2019).*

(Continued)

*Primary Examiner* — Deepak R Rao
(74) *Attorney, Agent, or Firm* — James T. Wasicak

(57) ABSTRACT

Compounds, pharmaceutically acceptable salts thereof, are disclosed wherein the compounds have the structure of (I) as defined in the specification. Corresponding pharmaceutical compositions, methods of treatment, methods of synthesis, and intermediates are also disclosed.

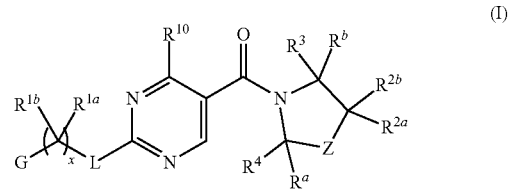

36 Claims, 2 Drawing Sheets

(56) References Cited

FOREIGN PATENT DOCUMENTS

| WO | 2010/113834 | 10/2010 |
|---|---|---|
| WO | 2010/132999 | 11/2010 |
| WO | 2011/133882 | 10/2011 |
| WO | 2011/133888 | 10/2011 |
| WO | 2011/133920 | 10/2011 |
| WO | 2011/136292 | 11/2011 |
| WO | 2011/150156 | 12/2011 |
| WO | 2012/016217 | 2/2012 |
| WO | 2012/031090 | 3/2012 |
| WO | 2012/068589 | 5/2012 |
| WO | 2012/080727 | 6/2012 |
| WO | 2012/080729 | 6/2012 |
| WO | 2013/041605 | 3/2013 |
| WO | 2013/151938 | 10/2013 |
| WO | 2013/155262 | 10/2013 |
| WO | 2014/048547 | 4/2014 |
| WO | 2014/085208 | 6/2014 |
| WO | 2014/181287 | 11/2014 |
| WO | 2015/048547 | 4/2015 |
| WO | 2016/193844 | 12/2016 |

OTHER PUBLICATIONS

Simone, Oncology: Introduction, Cecil Textbook of Medicine, 20th Edition, vol. 1, pp. 1004-101 O, 1996.*
Gura, Systems for identifying New Drugs Are Often Faulty, Cancer Models, Science, vol. 278, No. 5340, pp. 1041-1042, Nov. 1997.*
Johnson et al., Relationships between drug activity in NCI preclinical in vitro and in vivo models and early clinical trials, British Journal of Cancer (2001) 64(10): 1424-1431.*
Pearce et al., Failure modes in anticancer drug discovery and development, Cancer Drug Design and Discovery Edited by Stephen Neidle, Chapter 18, pp. 424-435 (2008).*
CAS registration No. 1910656-29-9, entered May 15, 2016.
CAS registration No. 1910613-84-1, entered STN: May 15, 2016.
CAS registration No. 1910495-41-8, entered STN: May 15, 2016.
CAS registration No. 1910494-11-9, entered STN: May 15, 2016.
CAS registration No. 1910494-04-0, entered STN: May 15, 2016.
CAS registration No. 1910034-14-8, entered STN: May 13, 2016.
CAS registration No. 1909643-11-3, entered STN: May 13, 2016.
CAS registration No. 1908764-08-8, entered STN: May 12, 2016.
CAS registration No. 1908309-34-1, entered STN: May 11, 2016.
CAS registration No. 1906380-56-0, entered STN: May 9, 2016.
CAS registration No. 1906349-00-5, entered STN: May 9, 2016.
CAS registration No. 1905750-85-7, entered STN: May 8, 2016.
CAS registration No. 1905731-35-2, entered STN: May 8, 2016.
CAS registration No. 1905564-01-3, entered STN: May 8, 2016.
CAS registration No. 1905229-95-9, entered STN: May 6, 2016.
CAS registration No. 1905173-67-2, entered STN: May 6, 2016.
CAS registration No. 1904845-31-3, entered STN: May 6, 2016.
CAS registration No. 1904542-80-8, entered STN: May 5, 2016.
CAS registration No. 1902700-37-1, entered STN: May 3, 2016.
CAS registration No. 1902640-19-0, entered STN: May 3, 2016.
CAS registration No. 1901623-89-9, entered STN: May 2, 2016.
CAS registration No. 1901213-45-3, entered STN: May 1, 2016.
CAS registration No. 1901196-85-7, entered STN: May 1, 2016.
CAS registration No. 1901064-31-0, entered STN: May 1, 2016.
CAS registration No. 1900908-24-8, entered STN: May 1, 2016.
CAS registration No. 1900815-35-1, entered STN: May 1, 2016.
CAS registration No. 1898778-91-0, entered STN: Apr. 27, 2016.
CAS registration No. 1898748-66-7, entered STN: Apr. 27, 2016.
CAS registration No. 1898717-33-3, entered STN: Apr. 27, 2016.
CAS registration No. 1910648-80-4, entered STN: May 15, 2016.
CAS registration No. 1905563-61-2, entered STN: May 8, 2016.
CAS registration No. 1901315-67-0, entered STN: May 1, 2016.
CAS registration No. 1906019-46-2, entered STN: May 8, 2016.
CAS registration No. 1905386-73-3, entered STN: May 6, 2016.
CAS registration No. 1900789-75-4, entered STN: May 1, 2016.

* cited by examiner

PYRIMIDINE CARBOXAMIDES AS INHIBITORS OF VANIN-1 ENZYME

This application is a 35 U.S.C. 371 National Stage of International Application No. PCT/IB2017/054104 filed Jul. 7, 2017, which claims the benefit of U.S. Provisional Application Ser. No. 62/362,098 filed Jul. 14, 2016, herein incorporated by reference in its entirety.

The present invention relates to novel heterocyclic compounds, or pharmaceutically acceptable salts thereof, and pharmaceutical compositions comprising the same. The present invention also relates to methods of treating a subject by administering a therapeutically effective amount of these compounds, or salts thereof, to a subject. In general, these compounds act as inhibitors of vanin-1 enzyme.

BACKGROUND

Vanin-1 is a cell surface associated, glycosylphosphatidyl inositol (GPI)—anchored protein which is expressed at high levels in kidney, liver and the small intestine. Vanin-1 expression can be up-regulated in multiple cell types under various inflammatory and oxidative stress conditions. Soluble Vanin-1 is found in serum of mice and humans indicating that Vanin-1 can be shed off the cell surface (Rommelaere S, et al. PPARalpha regulates the production of serum Vanin-1 by liver. FEBS Lett. 2013 Nov. 15; 587(22):3742-8). Three Vanin family members have been described in humans (Vanin-1, Vanin-2 and Vanin-3) and these are classified as members of the biotinidase branch of the nitrilase superfamily (Kaskow B J, et al. Diverse biological activities of the vascular non-inflammatory molecules—the Vanin pantetheinases. Biochem Biophys Res Commun. 2012 Jan. 13; 417(2):653-8).

To date the only known substrate for Vanin-1 is pantetheine and it is believed that Vanin-1 acts as the predominant pantetheinase in vivo catalyzing its hydrolysis to produce pantothenic acid (vitamin B5) and cysteamine (Pitari G, et al. Pantetheinase activity of membrane-bound vanin-1: lack of free cysteamine in tissues of vanin-1 deficient mice. FEBS Lett. 2000; 483:149-154). These products impact diverse biological processes. Panthothenic acid is a necessary factor in the synthesis of Coenzyme A (CoA), a cofactor involved in many metabolic processes such as fatty acid synthesis and oxidation of pyruvate. The amino-thiol cysteamine, the second product of Vanin-1 enzymatic reaction, impacts the cellular redox status (Kaskow B J, et al. Diverse biological activities of the vascular non-inflammatory molecules—the Vanin pantetheinases. Biochem Biophys Res Commun. 2012 Jan. 13; 417(2):653-8 and Nitto T, Onodera K. The Linkage between coenzyme A metabolism and inflammation: roles of Pantetheinase. Journal of pharmacological sciences 2013:123: 1-8).

Vanin-1-deficient mice show no developmental defects nor do they show obvious spontaneous phenotype. However, diverse Vanin-1-dependent phenotypes are revealed in situations of metabolic challenge and/or oxidative stress and tissue damage. Vanin-1-deficient mice exhibit resistance to oxidative tissue injury caused by γ-irradiation or by the administration of paraquat which is correlated with significantly increased glutathione levels (Berruyer C, et al. Vanin-1−/− mice exhibit a glutathione mediated tissue resistance to oxidative stress. Mol Cell Biol. 2004; 24:7214-7224). Vanin-1 deficient animals are also protected against multiple mouse models of IBD including DSS (dextran sulfate) and TNBS (trinitrobenzene sulfonate) colitis as evidenced by preserved mucosal barrier and reduced inflammatory infiltrate (Berruyer C, et al. Vanin-1 licenses inflammatory mediator production by gut epithelial cells and controls colitis by antagonizing peroxisome proliferator-activated receptor γ activity. J Exp Med. 2006:203:2817-2827 and et al. Vanin-1−/− mice show decreased NSAID- and Schistosoma-induced intestinal inflammation associated with higher glutathione stores. J Clin Invest. 2004; 113:591-597). In humans, Vanin-1 expression is significantly increased in the colonic mucosa from IBD patients and functional polymorphisms in the regulatory regions of the Vanin-1 gene are associated with susceptibility to inflammatory bowel diseases (Gensollen T, et. al. Functional polymorphisms in the regulatory regions of the VNN1 gene are associated with susceptibility to inflammatory bowel diseases. Inflamm Bowel Dis. 2013 October; 19(11):2315-25). In addition, patients with ulcerative colitis have an increased risk of developing colorectal cancer and Vanin-1 knock-out mice exhibit drastically reduced incidence of tumors in colitis associated cancer model (Pouyet L, et al. Epithelial vanin-1 controls inflammation-driven carcinogenesis in the colitis-associated colon cancer model. Inflamm Bowel Dis. 2010 January; 16(1):96-104).

Vanin-1 is a key activator for hepatic gluconeogenesis (Chen S, et al. Vanin-1 is a key activator for hepatic gluconeogenesis. Diabetes. 2014 June; 63(6):2073-85. doi: 10.2337/db13-0788. Epub 2014 Feb. 18). Vanin-1 regulates the activation of smooth muscle cells in vitro and development of neointimal hyperplasia in response to carotid artery ligation in vivo. Polymorphysims in VNN1 gene are associated with blood pressure and HDL levels further supporting Vanin-1's role in cardiovascular diseases. Vanin-1 deficiency prevents mice from the development of adrenocortical neoplasia in Sf-1 transgenic mice suggesting a role for Vanin-1 in certain cancers. In the context of infection, Vanin-1 deficiency reduces granuloma formation and tissue damage against *Coxiella burnetii*, a bacterium that causes Q fever. Vanin-1 is highly up-regulated in psoriatic skin lesions compared with normal individuals. Vnn-1 gene expression is also up-regulated in whole blood of patients with pediatric immune thrombocytopenia (ITP) where overexpression of VNN1, is associated with progression to chronic ITP. In addition, elevated Vanin-1 has been detected in the urine of patients with multiple renal disorders including systemic lupus erythematosus, nephrotoxicant-induced renal injury and type 2-diabetes (Rommelaere S, et al. PPARalpha regulates the production of serum Vanin-1 by liver. FEBS Lett. 2013 Nov. 15; 587(22):3742-8).

There is a need for novel and potent small molecule compounds which act as inhibitors of vanin-1 enzyme. Compounds reported as having vanin activity include, for example, those disclosed in WO 2014/048547. Co-pending U.S. Provisional Application 62/167,962, filed by Pfizer Inc on May 29, 2015, and co-pending U.S. Provisional Application 62/195,005, filed by Pfizer Inc on Jul. 21, 2015, both of which are incorporated herein by reference in its entirety.

SUMMARY

This invention relates to a compound of Formula I,

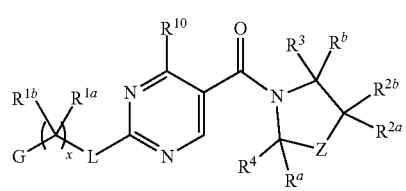

wherein

G is a 6-membered heteroaryl, with one, two or three N, wherein the heteroaryl is optionally substituted with one, two or three substituents selected from halogen, OH, cyano, $C_1$-$C_4$alkyl, —$NR^{8a}C(O)R^{8b}$, —$NR^{8a}SO_2R^{8b}$, $(CR^{6a}R^{6b})_qC(O)N(R^{8a})_2$, —$C(O)OH$, —$N(R^{8a})_2$, —$(CR^{6a}R^{6b})_rSO_2R^{8b}$, —$(CR^{6a}R^{6b})_rSO_2N(R^{8a})_2$, $C_1$-$C_4$alkoxy, —$S(C_1$-$C_3$alkyl$)$ or $C_3$-$C_5$cycloalkyl, wherein the alkyl, cycloalkyl and alkoxy are optionally substituted with one, two or three halogen, OH, $OCH_3$, or $C_3$-$C_5$cycloalkyl;

L is NH or O;

Z is a bond; —$(CR^{5a}R^{5b})_q$—; —$CH_2(CR^{5a}R^{5b})_m$—; or —$(CR^{5a}R^{5b})_m$—W—$(CR^{5a}R^{5b})_n$—, wherein W is S, O or $NR^7$;

or a pharmaceutically acceptable salt of said compound or a tautomer of said compound or said salt.

The invention also provides for pharmaceutical compositions comprising the compounds, methods of using the compounds, combination therapies utilizing the compounds and other therapeutic agents and methods of preparing the compounds. The invention also provides for intermediates useful in the preparation of the compounds of the invention.

In particular, the compounds of the invention, or pharmaceutically acceptable salts thereof, may inhibit the vanin-1 enzyme. Such compounds may therefore be useful for treating diseases or disorders that are mediated by, or otherwise associated with, inhibition of the vanin-1 enzyme, the method comprising administering to a subject in need thereof, an effective amount of a compound of the invention.

In another embodiment, the present invention further provides a method of inhibiting vanin-1 enzyme in a cell, comprising contacting the cell with a therapeutically effective amount of a compound of Formula I, or a pharmaceutically acceptable salt thereof, or a pharmaceutical composition comprising a therapeutically effective amount of a compound of Formula I, or a pharmaceutically acceptable salt thereof.

Inhibitors of vanin-1 enzyme may be used in the treatment of a variety of diseases or disorders related to systemic or tissue inflammation, inflammatory responses to infection or hypoxia, cellular activation and proliferation, lipid metabolism, fibrosis and in the treatment of viral infections. Therefore, inhibition of Vanin-1 would have the potential for multiple therapeutic indications over a wide range of unmet needs.

DETAILED DESCRIPTION

Figure 1:
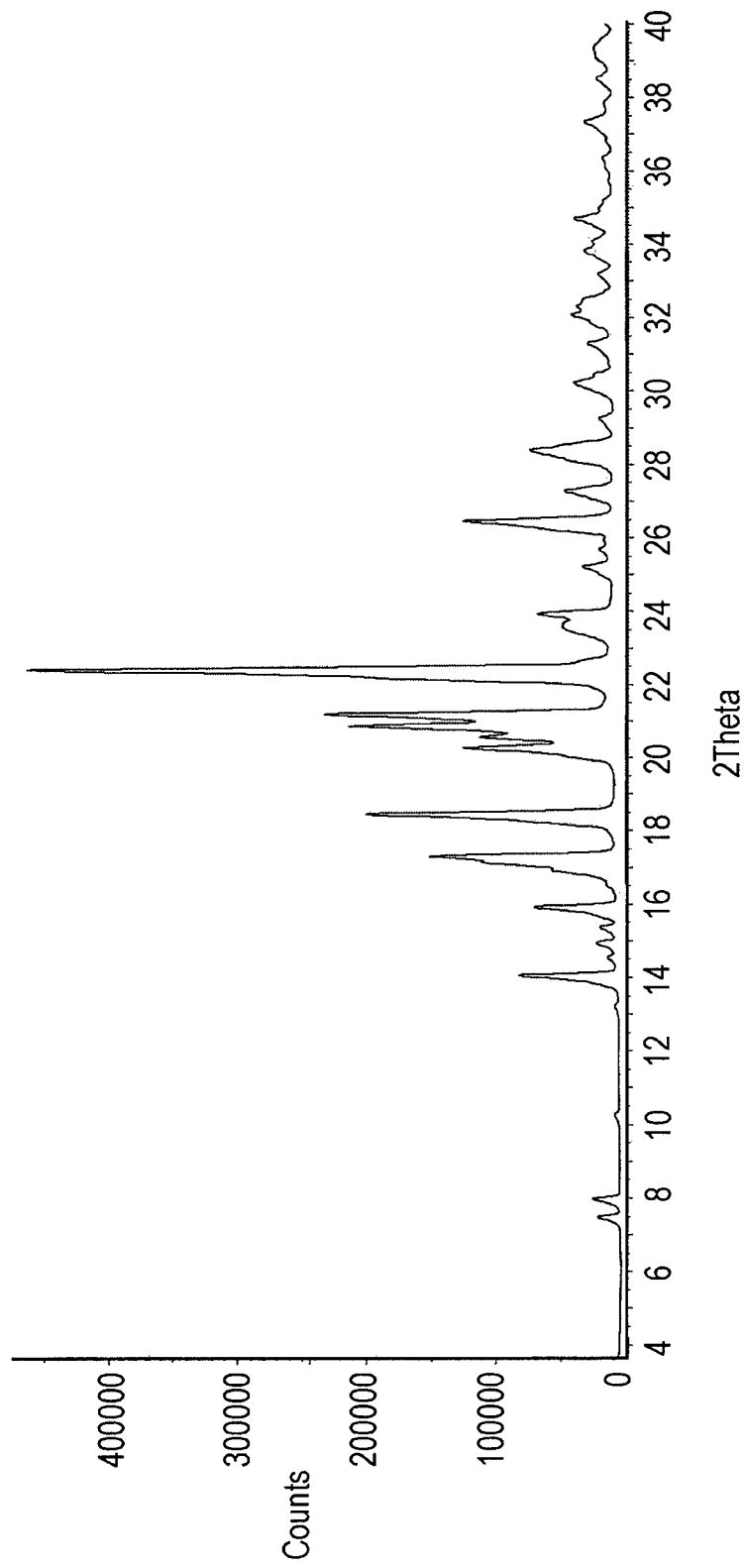
FIG. 1 is a PXRD pattern of Example 142.

The present invention relates to novel heterocyclic compounds of the invention which, in general, inhibit vanin-1 enzyme.

The present invention may be understood more readily by reference to the following detailed description of exemplary embodiments of the invention and the examples included therein. It is to be understood that this invention is not limited to specific methods of synthesis, which may of course vary. It is also to be understood that the terminology used herein is for the purpose of describing particular embodiments only and is not intended to be limiting.

All patents, patent applications and references referred to herein are hereby incorporated by reference in their entirety.

Other features and advantages of this invention will be apparent from this specification and the appendent claims which describe the invention. There are many features of this invention that are not necessarily fully captured by the claims. It is understood, however, that all such novel subject matter is part of the invention.

Definitions

Unless otherwise defined herein, scientific and technical terms used in connection with the present invention have the meaning commonly understood by those of ordinary skill in the art. As used in the specification and the appended claims, the singular forms "a", "an", and "the" include plural referents unless the context clearly dictates otherwise.

The term "about" refers to a relative term denoting an approximation of plus or minus 10% of the nominal value it refers, in one embodiment, to plus or minus 5%, in another embodiment, to plus or minus 2%. For the field of this disclosure, this level of approximation is appropriate unless the value is specifically stated require a tighter range.

The term "alkyl" refers to a linear or branched saturated hydrocarbon moiety, consisting solely of carbon and hydrogen atoms. In one embodiment from one to six carbon atoms; and in another embodiment from one to four carbon atoms; and in another embodiment one to three carbon atoms. Non-limiting examples of such substituents include methyl, ethyl, propyl (including n-propyl and isopropyl), butyl (including n-butyl, isobutyl, sec-butyl and tert-butyl), pentyl, isoamyl, hexyl and the like. As appropriate, an alkyl may be optionally substituted at each carbon as defined in the claims. Typical substitution includes, but is not limited to, fluoro, chloro, OH, cyano, alkyl (optionally substituted), alkoxy, cycloalkyl and the like.

In some instances, the number of carbon atoms in a hydrocarbon substituent (i.e., alkyl, cycloalkyl, etc.) is indicated by the prefix "$C_x$-$C_y$-" or "$C_{x-y}$", wherein x is the minimum and y is the maximum number of carbon atoms in the substituent. Thus, for example, "$C_1$-$C_6$-alkyl" or "$C_{1-6}$ alkyl" refers to an alkyl substituent containing from 1 to 6 carbon atoms. Illustrating further, $C_3$-$C_6$-cycloalkyl or $C_{3-6}$-cycloalkyl refers to saturated cycloalkyl containing from 3 to 6 carbon ring atoms.

The term "cycloalkyl" refers to a nonaromatic ring containing 3 to 12 carbons that is fully hydrogenated consisting of mono-, bi- or tricyclic rings. Accordingly, a cycloalkyl may be a single ring, which typically contains from 3 to 7 ring atoms. Examples include, but are not limited to, cyclopropyl, cyclobutyl, cyclopentyl, and cyclohexyl. Alternatively, 2 or 3 rings may be fused together, such as bicyclodecanyl and decalinyl. The term "cycloalkyl" also includes bridged bicycloalkyl systems such as, but not limited to, bicyclo[2.2.1]heptane and bicyclo[1.1.1]pentane. The cycloalkyl group may be optionally substituted as described herein, as appropriate, by 1 to 5 suitable substituents as defined herein, including but not limited to, for example, $C_1$-$C_4$alkyl, oxo, OH, $CH_2OH$, halogen, $C_1$-$C_4$alkoxy, cyano or $C(O)NH_2$, wherein said alkyl and alkoxy are optionally substituted with OH, halogen, $C(O)NH_2$, $C(O)NHCH_3$, $C(O)N(CH_3)_2$, —$S(C_1$-$C_4$alkyl$)$ or $C_3$-$C_5$cycloalkyl.

The term "heterocycloalkyl" means a monovalent saturated moiety, consisting of one to three rings, incorporating one, two, three or four heteroatoms (selected from N, O or S) and three to 12 carbon atoms. The heterocycloalkyl may be optionally substituted as defined herein. Examples of heterocycloalkyl moieties include, but are not limited to, optionally substituted piperidinyl, piperazinyl, homopiperazinyl, azepinyl, pyrrolidinyl, imidazolidinyl, morpholinyl, quinuclidinyl, thiadiazolylidinyl, benzothiazolidinyl, benzoazolylidinyl, dihydrofuryl, tetrahydrofuryl, dihydropyranyl, tetrahydropyranyl, thiamorpholinyl, thiamorpholinylsulfoxide, thiamorphilinylsulfone, dihydroquinolinyl, tetrahydroquinolinyl, tetrahydrisoquinolinyl, and the like. Heterocycloalkyls may be optionally substituted, as appropriate, by 1 to 5 suitable substituents as defined herein such as including but not limited to, for example, $C_1$-$C_4$alkyl, oxo, OH, $CH_2OH$, halogen, $C_1$-$C_4$alkoxy, cyano or $C(O)NH_2$, wherein said alkyl and alkoxy are optionally substituted with OH, halogen, $C(O)NH_2$, $C(O)NHCH_3$, $C(O)N(CH_3)_2$, —$S(C_1$-$C_4$alkyl) or $C_3$-$C_5$cycloalkyl. The term "heterocycloalkyl" also includes fused ring systems with, for example, a cycloalkyl, aryl or heteroaryl.

Unless otherwise indicated, the term "heteroalkyl," by itself or in combination with another term, means, unless otherwise stated, a saturated, straight or branched chain hydrocarbon radical consisting of the stated number of carbon atoms and from one to three heteroatoms selected from the group consisting of O, N and S, and wherein the nitrogen and sulfur atoms may optionally be oxidized and the nitrogen heteroatom may optionally be quaternized. The heteroatom(s) O, N and S may be placed at any interior position of the heteroalkyl group. The heteroatom S may be placed at any position of the heteroalkyl group, including the position at which the alkyl group is attached to the remainder of the molecule. Up to two heteroatoms may be consecutive.

The term "alkoxy" and "alkyloxy", which may be used interchangeably, refers to a moiety of the formula —OR, wherein R is a straight chain saturated alkyl or branched chain saturated alkyl moiety, as defined herein, bonded through an oxygen atom. The alkoxy group may be optionally substituted as defined herein. Non-limiting examples of such alkoxy groups are methoxy, ethoxy, propoxy, isopropoxy, butoxy, isobutoxy, tertiary butoxy, pentoxy and the like.

The term "aryl" means a carbocyclic aromatic system containing one or two rings wherein such rings may be fused. If the rings are fused, one of the rings must be fully unsaturated and the fused ring(s) may be fully saturated, partially unsaturated or fully unsaturated. The term "fused" means that a second ring is present (i.e., attached or formed) by having two adjacent atoms in common (i.e., shared) with the first ring. The term "fused" is equivalent to the term "condensed". The aryl group may be optionally substituted as defined herein. The term "aryl" embraces aromatic radicals such as phenyl, naphthyl, tetrahydronaphthyl, indanyl, biphenyl, benzo[b][1,4]oxazin-3(4H)-onyl, 2,3-dihydro-1H indenyl and 1,2,3,4-tetrahydronaphthalenyl. Aryls may be optionally substituted, as appropriate, by 1 to 5 suitable substituents as defined herein such as $C_1$-$C_4$alkyl, oxo, OH, $CH_2OH$, halogen, $C_1$-$C_4$alkoxy, cyano or $C(O)NH_2$, wherein said alkyl and alkoxy are optionally substituted with OH, halogen, $C(O)NH_2$, $C(O)NHCH_3$, $C(O)N(CH_3)_2$, —$S(C_1$-$C_4$alkyl) or $C_3$-$C_5$cycloalkyl and the like.

Unless otherwise indicated, the term "heteroalkyl," by itself or in combination with another term, means, unless otherwise stated, a saturated, straight or branched chain hydrocarbon radical consisting of the stated number of carbon atoms and from one to three heteroatoms selected from the group consisting of O, N and S, and wherein the nitrogen and sulfur atoms may optionally be oxidized and the nitrogen heteroatom may optionally be quaternized. The heteroatom(s) O, N and S may be placed at any interior position of the heteroalkyl group. The heteroatom S may be placed at any position of the heteroalkyl group, including the position at which the alkyl group is attached to the remainder of the molecule. Up to two heteroatoms may be consecutive.

The term "heteroaryl" refers to an aromatic ring structure containing from 5 to 6 ring atoms in which at least one of the ring atoms is a heteroatom (i.e., oxygen, nitrogen, or sulfur), with the remaining ring atoms being independently selected from the group consisting of carbon, oxygen, nitrogen, and sulfur. Examples of heteroaryl substituents include 6-membered ring substituents such as pyridyl, pyrazyl, pyrimidinyl, and pyridazinyl; and 5-membered ring substituents such as triazolyl, imidazolyl, furanyl, thiophenyl, pyrazolyl, oxazolyl, isoxazolyl, thiazolyl, 1,2,3-, 1,2,4-, 1,2,5-, or 1,3,4-oxadiazolyl and isothiazolyl. In a group that has a heteroaryl substituent, the ring atom of the heteroaryl substituent that is bound to the group may be one of the heteroatoms, or it may be a ring carbon atom. Similarly, if the heteroaryl substituent is in turn substituted with a group or substituent, the group or substituent may be bound to one of the heteroatoms, or it may be bound to a ring carbon atom. The term "heteroaryl" also includes pyridyl N-oxides and groups containing a pyridine N-oxide ring.

Further examples include furyl, thienyl, oxazolyl, thiazolyl, imidazolyl, pyrazolyl, triazolyl, tetrazolyl, isoxazolyl, isothiazolyl, oxadiazolyl, thiadiazolyl, pyridinyl, pyridazinyl, pyrimidinyl, pyrazinyl, pyridin-2(1H)-onyl, pyridazin-2(1H)-onyl, pyrimidin-2(1H)-onyl, pyrazin-2(1H)-onyl, imidazo[1,2-a]pyridinyl, pyrazolo[1,5-a]pyridinyl, 5,6,7,8-tetrahydroisoquinolinyl, 5,6,7,8-tetrahydroquinolinyl, 6,7-dihydro-5H-cyclopenta[b]pyridinyl, 6,7-dihydro-5H-cyclopenta[c]pyridinyl, 1,4,5,6-tetrahydrocyclopenta[c]pyrazolyl, 2,4,5,6-tetrahydrocyclopenta[c]pyrazolyl, 5,6-dihydro-4H-pyrrolo[1,2-b]pyrazolyl, 6,7-dihydro-5H-pyrrolo[1,2-b][1,2,4]triazolyl, 5,6,7,8-tetrahydro-[1,2,4]triazolo[1,5-a]pyridinyl, 4,5,6,7-tetrahydropyrazolo[1,5-a]pyridinyl, 4,5,6,7-tetrahydro-1H-indazolyl and 4,5,6,7-tetrahydro-2H-indazolyl. The heteroaryl can be optionally substituted, as appropriate, by 1 to 5 suitable substituents as defined herein such as $C_1$-$C_4$alkyl, oxo, OH, $CH_2OH$, halogen, $C_1$-$C_4$alkoxy, cyano or $C(O)NH_2$, wherein said alkyl and alkoxy are optionally substituted with OH, halogen, $C(O)NH_2$, $C(O)NHCH_3$, $C(O)N(CH_3)_2$, —$S(C_1$-$C_4$alkyl) or $C_3$-$C_5$cycloalkyl and the like.

Examples of single-ring heteroaryls and heterocycloalkyls include furanyl, dihydrofuranyl, tetrahydrofuranyl, thiophenyl, dihydrothiophenyl, tetrahydrothiophenyl, pyrrolyl, isopyrrolyl, pyrrolinyl, pyrrolidinyl, imidazolyl, isoimidazolyl, imidazolinyl, imidazolidinyl, pyrazolyl, pyrazolinyl, pyrazolidinyl, triazolyl, tetrazolyl, dithiolyl, oxathiolyl, oxazolyl, isoxazolyl, thiazolyl, isothiazolyl, thiazolinyl, isothiazolinyl, thiazolidinyl, isothiazolidinyl, thiaoxadiazolyl, oxathiazolyl, oxadiazolyl (including oxadiazolyl, 1,2,4-oxadiazolyl, 1,2,5-oxadiazolyl, or 1,3,4-oxadiazolyl), pyranyl (including 1,2-pyranyl or 1,4-pyranyl), dihydropyranyl, pyridinyl, piperidinyl, diazinyl (including pyridazinyl, pyrimidinyl, piperazinyl, triazinyl (including s-triazinyl, as-triazinyl and v-triazinyl), oxazinyl (including 2H-1,2-oxazinyl, 6H-1,3-oxazinyl, or 2H-1,4-oxazinyl), isoxazinyl (including o-isoxazinyl or p-isoxazinyl), oxazolidinyl, isoxazolidinyl, oxathiazinyl (including 1,2,5-oxathiazinyl or 1,2,6-oxathiazinyl), oxadiazinyl (including 2H-1,2,4-oxadiazinyl or 2H-1,2,5-oxadiazinyl), and morpholinyl.

The term "heteroaryl" also includes fused ring systems having one or two rings wherein such rings may be fused, wherein fused is as defined above. It is to be understood that if a carbocyclic or heterocyclic moiety may be bonded or otherwise attached to a designated substrate through differing ring atoms without denoting a specific point of attachment, then all possible points are intended, whether through a carbon atom or, for example, a trivalent nitrogen atom. For example, the term "pyridyl" means 2-, 3- or 4-pyridyl, the term "thienyl" means 2- or 3-thienyl, and so forth.

In some instances, the number of atoms in a cyclic substituent containing one or more heteroatoms (i.e., heteroaryl or heterocycloalkyl) is indicated by the prefix "x- to y-membered", wherein x is the minimum and y is the maximum number of atoms forming the cyclic moiety of the substituent. Thus, for example, "5- to 6-membered heteroaryl" refers to a heteroaryl containing from 5 to 6 atoms, including one or more heteroatoms, in the cyclic moiety of the heteroaryl. The heteroatoms for this invention are selected from nitrogen, oxygen and sulfur.

Specific embodiments of ring systems include, for example: 8-oxa-2-azaspiro[4.5]dec-2-yl,

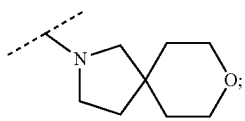

and 7-oxa-2-azaspiro[3.5]nonan-2-yl,

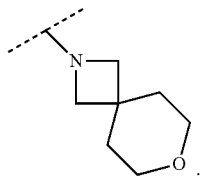

It would be apparent to one skilled in the art, based upon the examples described herein, that other ring systems are contemplated as part of this invention.

Further embodiments of ring systems include the following, that also incorporate exemplary ring substituents:

8-oxa-2-azaspiro[4.5]dec-2-yl, 7-oxa-2-azaspiro[3.5]non-2-yl, (3aR,4R,7aS)-rel-4-hydroxyoctahydro-2H-isoindol-2-yl, (3aR,4R,7aS)-rel-4-hydroxyoctahydro-2H-isoindol-2-yl, (8-anti)-8-methoxy-3-azabicyclo[3.2.1]oct-3-yl, (1R,5S,6R)-rel-6-(hydroxymethyl)-3-azabicyclo[3.1.0]hex-3-yl, 1,3-dihydro-2H-isoindol-2-yl, 3-azabicyclo[3.2.2]non-3-yl, [(3-endo)-3-hydroxy-8-azabicyclo[3.2.1]oct-8-yl, 2-oxa-6-azaspiro[3.5]non-6-yl, 8-oxa-3-azabicyclo[3.2.1]oct-3-yl, 1-oxa-7-azaspiro[3.5]non-7-yl, (7S,8aS)-7-fluorohexahydropyrrolo[1,2-a]pyrazin-2(1H)-yl, octahydropyrazino[1,2-a]azepin-2(1H)-yl, 8-azaspiro[4.5]dec-8-yl, 1-oxa-9-azaspiro[5.5]undec-9-yl, 6-oxa-9-azaspiro[4.5]dec-9-yl, 7,9-dimethyl-8-oxa-2-azaspiro[4.5]dec-2-yl, 1-oxa-8-azaspiro[4.5]dec-8-yl, 3-methyl-1-oxa-3,8-diazaspiro[4.5]decan-2-on-yl, 2-oxa-7-azaspiro[3.5]non-7-yl, (3aR,7aR)-rel-3a-(hydroxymethyl)octahydro-2H-isoindol-2-yl, 6-(trifluoromethyl)-3-azabicyclo[3.1.0]hex-3-yl, hexahydrocyclopenta[c]pyrrol-2(1H)-yl, 3-methyl-1,7-dioxa-3,10-diazaspiro[4.6]undecan-2-on-yl, (6S,7S)-rel-7-hydroxy-2-azaspiro[5.5]undec-2-yl, 4-methoxy-1-oxa-9-azaspiro[5.5]undec-9-yl, 3-oxa-8-azabicyclo[3.2.1]oct-8-yl, (6S,7R)-rel-7-hydroxy-2-azaspiro[5.5]undec-2-yl, 6-hydroxy-2-azaspiro[3.3]hept-2-yl, 2-oxa-5-azabicyclo[2.2.2]oct-5-yl, (7R,8aS)-7-hydroxyhexahydropyrrolo[1,2-a]pyrazin-2(1H)-yl, (1 S,4S)-5-methyl-2,5-diazabicyclo[2.2.1]hept-2-yl, (8aS)-7,7-difluorohexahydropyrrolo[1,2-a]pyrazin-2(1H)-yl, 7-ethyl-2,7-diazaspiro[4.4]non-2-yl, 2-methyl-2,6-diazaspiro[3.4]oct-6-yl, (3aR,6aS)-5-methylhexahydropyrrolo[3,4-c]pyrrol-2(1H)-yl, (8aS)-hexahydropyrrolo[1,2-a]pyrazin-2(1H)-yl, and (8aR)-hexahydropyrrolo[1,2-a]pyrazin-2(1H)-yl.

As used herein, unless otherwise noted, the terms "haloalkyl" and "haloalkoxy" are intended to include both branched and straight-chain saturated aliphatic "alkyl" or "alkoxy" groups respectively, wherein "alkyl" and "alkoxy" are as defined herein, having the specified number of carbon atoms and in which at least one hydrogen is replaced with a halogen atom. As used herein, the term "halogen atom" refers to F, Cl, Br and I. Haloalkyl groups include perhaloalkyl groups, wherein all hydrogens of an alkyl group have been replaced with halogens (e.g., —CF$_3$, —CF$_2$CF$_3$). In certain embodiments in which two or more hydrogen atoms are replaced by halogen atoms, the halogen atoms can be the same (e.g., CHF$_2$, —CF$_3$) or different (e.g., CF$_2$Cl). Where so indicated, haloalkyl or haloalkoxy groups can optionally be substituted with one or more substituents in addition to halogen. Examples of haloalkyl groups include, but are not limited to, fluoromethyl, dichloroethyl, trifluoromethyl, trichloromethyl, pentafluoroethyl, and pentachloroethyl groups.

As used herein, unless otherwise stated, the term "amido" refers to —C(=O)NH$_2$.

As used herein, unless otherwise stated, the term "halogen" or "halogen atom" refers to the group consisting of fluorine (which may be depicted as —F), chlorine (which may be depicted as —Cl), bromine (which may be depicted as —Br), or iodine (which may be depicted as —I).

As used herein, unless otherwise stated, the terms "hydroxy" and "hydroxyl" are used interchangeably and as used herein mean an —OH group. As used herein, unless otherwise noted, the terms "hydroxyalkyl" and "hydroxyalkoxy" are intended to include both branched and straight-chain saturated aliphatic "alkyl" or "alkoxy" groups respectively, wherein "alkyl" and "alkoxy" are as defined herein, having the specified number of carbon atoms and in which at least one hydrogen is replaced with a —OH group. Where so indicated, hydroxyalkyl and hydroxyalkoxy groups can optionally be substituted with one or more substituents in addition to —OH. Examples of hydroxyalkyl groups include, but are not limited to, CH$_2$OH, CH$_2$CH$_2$OH or CH$_2$(OH)CH$_2$OH.

As used herein, unless otherwise stated, the term "oxo" or "carbonyl" refers to =O.

As used herein, unless otherwise stated, the term "carboxy" refers to —CO$_2$H.

As used herein, unless otherwise stated, the term sulfonyl refers to —SO$_2$—.

As used herein, the term "substituted" is used throughout the specification. The term "substituted" is defined herein as a moiety, whether acyclic or cyclic, which has one or more (e.g. 1-10) hydrogen atoms replaced by a substituent as defined herein below. Substituents include those that are capable of replacing one or two hydrogen atoms of a single moiety at a time, and also those that can replace two hydrogen atoms on two adjacent carbons to form said substituent. For example, substituents that replace single hydrogen atoms include, but are not limited to, halogen, hydroxy, and the like. A two hydrogen atom replacement includes, but is not limited to, carbonyl, oximino, and the like. Substituents that replace two hydrogen atoms from adjacent carbon atoms include, but are not limited to, epoxy, and the like. When a moiety is described as "substituted" any number of its hydrogen atoms can be replaced, as described above. For example, difluoromethyl is a substituted $C_1$ alkyl; trifluoromethyl is a substituted $C_1$ alkyl; 4-hydroxyphenyl is a substituted aryl ring; (N,N-dimethyl-5-amino)octanyl is a substituted $C_8$ alkyl; 3-guanidinopropyl is a substituted $C_3$ alkyl; and 2-carboxy-3-fluoropyridinyl is a substituted heteroaryl.

A multi-moiety substituent is bound through the atom indicated by "—". To illustrate this the term "—$OC_1$-$C_3$hydroxyalkyl" is an $OC_1$-$C_3$alkyl group substituted by a hydroxy group. Further, any carbon number pre-fix attached to a multi-moiety substituent only applies to the moiety it immediately precedes. To illustrate, the term "cycloalkyl ($C_1$-$C_4$)alkyl" contains two moieties: alkyl and cycloalkyl. The ($C_1$-$C_4$) pre-fix on the cycloalkyl($C_1$-$C_4$)alkyl means that the alkyl moiety of the alkylcycloalkyl contains from 1 to 4 carbon atoms, the ($C_1$-$C_4$) pre-fix does not describe the cycloalkyl moiety.

If a group of substituents are collectively described as being optionally substituted by one or more of a list of substituents, the group may include (1) unsubstitutable substituents, (2) substitutable substituents that are not substituted by the optional substituents, and/or (3) substitutable substituents that are substituted by one or more of the optional substituents.

If a substituent is described such that it "may be substituted" or as being "optionally substituted" with up to a particular number of non-hydrogen substituents, that substituent may be either (1) not substituted; or (2) substituted by up to that particular number of non-hydrogen substituents or by up to the maximum number of substitutable positions on the substituents, whichever is less. Thus, for example, if a substituent is described as a heteroaryl optionally substituted with one, two or three substituents, then any heteroaryl with less than three substitutable positions would be optionally substituted by up to only as many non-hydrogen substituents as the heteroaryl has substitutable positions. To illustrate, tetrazolyl (which has only one substitutable position) would be optionally substituted with up to one non-hydrogen substituent.

At various places in the present specification, substituents of compounds are disclosed in groups or in ranges. It is specifically intended that the description include each and every individual sub-combination of the members of such groups and ranges.

For example, the term "$C_{1-6}$ alkyl" is specifically intended to individually disclose $C_1$, $C_2$, $C_3$, $C_4$, $C_5$, $C_6$, $C_1$-$C_6$, $C_1$-$C_5$, $C_1$-$C_4$, $C_1$-$C_3$, $C_1$-$C_2$, $C_2$-$C_6$, $C_2$-$C_5$, $C_2$-$C_4$, $C_2$-$C_3$, $C_3$-$C_6$, $C_3$-$C_5$, $C_3$-$C_4$, $C_4$-$C_6$, $C_4$-$C_5$, and $C_5$-$C_6$ alkyl. For example, the term "$C_{1-3}$ alkyl" is specifically intended to individually disclose $C_1$, $C_2$, $C_3$, $C_1$-$C_3$, $C_1$-$C_2$, and $C_2$-$C_3$ alkyl.

Compounds of the present invention may contain basic nitrogen atoms (e.g. alkyl amines or heterocycles such as pyridine etc.) which may be converted to N-oxides by treatment with an oxidizing agent (e.g. mCPBA and/or hydrogen peroxides) to afford other compounds of this invention. Thus, all nitrogen-containing compounds that may be converted to N-oxide (N→O or —$N^+$—$O^-$) derivatives are part of the invention.

If substituents are described as "independently" having more than one variable, each instance of a substituent is selected independent of the other from the list of variables available. Each substituent therefore may be identical to or different from the other substituent(s).

As used herein, the terms "Formula I", "Formula II", "Formula IIa-IIg: and/or "Formula Ia-Ig", may be hereinafter referred to as a "compound(s) of the invention," "the present invention," and collectively the "compound of Formula I." Accordingly, the term "compound of Formula I" or "compound of formula (I), and the like, includes the compounds of Formula I, Ia, Ib, Ic, Id, Ie, If and Ig, as well as the compounds of Formula II, IIa, IIb, IIc, IId, IIe, IIf and IIg, whether capitalized, bolded or not. Such terms are also defined to include all forms of the compound of Formula I, including hydrates, solvates, isomers, crystalline and non-crystalline forms, isomorphs, polymorphs, tautomers and metabolites thereof. For example, the compounds of the invention, or pharmaceutically acceptable salts thereof, may exist in unsolvated and solvated forms. When the solvent or water is tightly bound, the complex will have a well-defined stoichiometry independent of humidity. When, however, the solvent or water is weakly bound, as in channel solvates and hygroscopic compounds, the water/solvent content will be dependent on humidity and drying conditions. In such cases, non-stoichiometry will be the norm.

The compounds of the invention have asymmetric carbon atoms. The carbon-carbon bonds of the compounds of the invention may be depicted herein using a solid line (———), a solid wedge (▬▬◣), or a dotted wedge (·······ıııı). The use of a solid line to depict bonds to asymmetric carbon atoms is meant to indicate that all possible stereoisomers (e.g., specific enantiomers, racemic mixtures, etc.) at that carbon atom are included. The use of either a solid or dotted wedge to depict bonds to asymmetric carbon atoms is meant to indicate that only the stereoisomer shown is meant to be included or that the stereoisomer predominates the other stereoisomer. It is possible that compounds of Formula I may contain more than one asymmetric carbon atom. In those compounds, the use of a solid line to depict bonds to asymmetric carbon atoms is meant to indicate that all possible stereoisomers are meant to be included. For example, unless stated otherwise, it is intended that the compounds of Formula I can exist as enantiomers and diastereomers or as racemates and mixtures thereof. The use of a solid line to depict bonds to one or more asymmetric carbon atoms in a compound of Formula I and the use of a solid or dotted wedge to depict bonds to other asymmetric carbon atoms in the same compound is meant to indicate that a mixture of diastereomers is present.

Stereoisomers of Formula I include cis and trans isomers, optical isomers such as R and S enantiomers, diastereomers, geometric isomers, rotational isomers, conformational isomers, and tautomers of the compounds of the invention, including compounds exhibiting more than one type of isomerism; and mixtures thereof (such as racemates and diastereomeric pairs). Also included are acid addition or base addition salts wherein the counterion is optically active, for example, D-lactate or L-lysine, or racemic, for example, DL-tartrate or DL-arginine.

Figure 2:
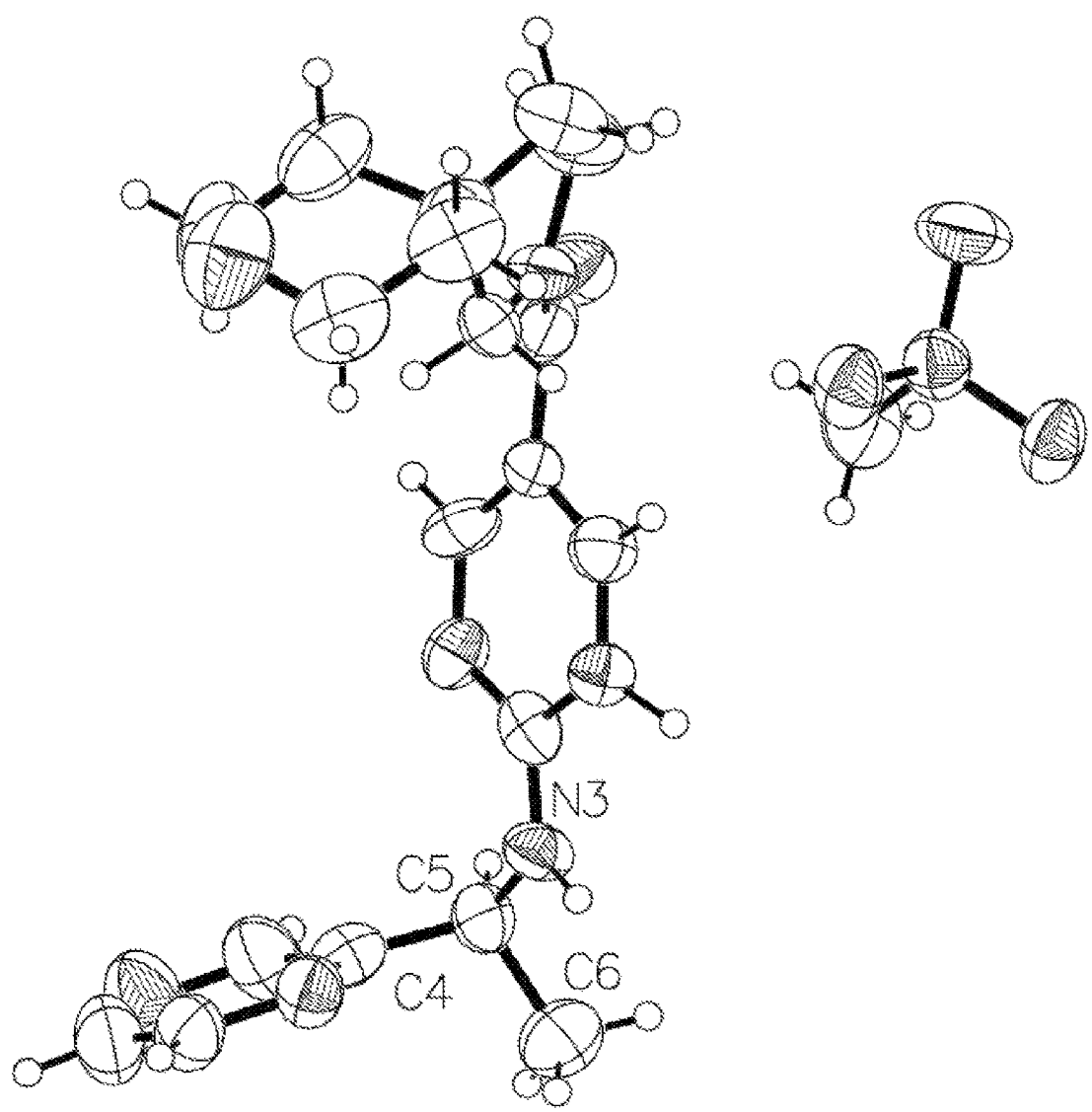
FIG. 2 is an X-ray crystal structure (ORTEP drawing) of Example 145a, 8-oxa-2-azaspiro[4.5]dec-2-yl(2-{[(1S)-1-(pyrazin-2-yl)ethyl]amino}pyrimidin-5-yl)methanone methanesulfonate.

For example, FIG. 2 depicts an X-ray crystal structure (ORTEP drawing) of Example 145a, 8-oxa-2-azaspiro[4.5] dec-2-yl(2-{[(1S)-1-(pyrazin-2-yl)ethyl]amino}pyrimidin-5-yl)methanone methanesulfonate. The single crystal X-Ray structure of example 145a is consistent with Example 145 having a "S" absolute configuration. By deduction, Example 146 was assigned the "R" enantiomer of this pair and displayed a ~100-fold loss of potency against vanin in the assay.

Example 145

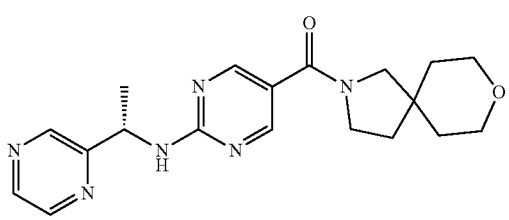

Example 146

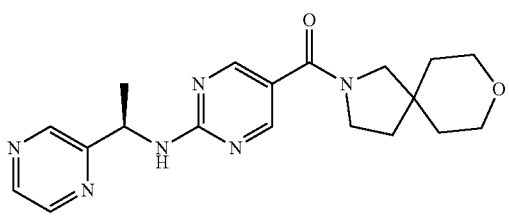

The above determinations were then used to extrapolate absolute configurations of other enantiomeric pairs of the compounds of the invention, possessing an asymmetric carbon at the same position as Example 145, as detailed in the Examples herein. In particular, the most potent enantiomer was assigned the "S" absolute configuration, based upon the configuration of Example 145, while the least potent enantiomer was assigned the "R" configuration. Accordingly, some of the Examples have a designation of "absolute stereochemistry inferred", based upon the above assumptions.

Optical isomers can be obtained in pure form by standard procedures known to those skilled in the art, which include, but are not limited to for example, chiral chromatography, diastereomeric salt formation, kinetic resolution, and asymmetric synthesis. It is also understood that the present teachings encompass all possible regioisomers, and mixtures thereof, which can be obtained in pure form by standard separation procedures known to those skilled in the art, and include, but are not limited to, column chromatography, thin-layer chromatography, and high-performance liquid chromatography.

When any racemate crystallizes, crystals of two different types are possible. The first type is the racemic compound (true racemate) referred to above wherein one homogeneous form of crystal is produced containing both enantiomers in equimolar amounts. The second type is the racemic mixture or conglomerate wherein two forms of crystal are produced in equimolar amounts each comprising a single enantiomer.

The compounds of the invention not only include compounds as hereinbefore defined, but also all forms of the compounds of the invention, including isomers (including optical, geometric and tautomeric isomers), hydrates, solvates, complexes, salts (including solvates and complexes thereof) crystalline and non-crystalline forms, isomorphs, polymorphs, isotopically-labeled derivatives, metabolites and prodrugs (including tautomeric forms of such prodrugs) thereof.

A "metabolite" of a compound disclosed herein is a derivative of that compound that is formed when the compound is metabolized. The term "active metabolite" refers to a biologically active derivative of a compound that is formed when the compound is metabolized. The term "metabolized," as used herein, refers to the sum of the processes (including, but not limited to, hydrolysis reactions and reactions catalyzed by enzymes, such as, oxidation reactions) by which a particular substance is changed by an organism. Thus, enzymes may produce specific structural alterations to a compound. For example, cytochrome P450 catalyzes a variety of oxidative and reductive reactions while uridine diphosphate glucuronyl transferases catalyze the transfer of an activated glucuronic-acid molecule to aromatic alcohols, aliphatic alcohols, carboxylic acids, amines and free sulfhydryl groups. Further information on metabolism may be obtained from The Pharmacological Basis of Therapeutics, 9th Edition, McGraw-Hill (1996), incorporated herein by reference. Metabolites of the compounds disclosed herein can be identified either by administration of compounds to a host and analysis of tissue samples from the host, or by incubation of compounds with hepatic cells in vitro and analysis of the resulting compounds. Both methods are well known in the art. In some embodiments, metabolites of a compound are formed by oxidative processes and correspond to the corresponding hydroxy-containing compound. In some embodiments, a compound is metabolized to pharmacologically active metabolites.

The compounds of the invention may exist in both unsolvated and solvated forms. The term "solvate" as used herein means a physical association of a compound with one or more solvent molecules, whether organic or inorganic, including water ('hydrate'). As noted above, the compounds of the invention, or pharmaceutically acceptable salts thereof, may exist in unsolvated and solvated forms. When the solvent or water is tightly bound, the complex will have a well-defined stoichiometry independent of humidity. When, however, the solvent or water is weakly bound, as in channel solvates and hygroscopic compounds, the water/solvent content will be dependent on humidity and drying conditions. In such cases, non-stoichiometry will be the norm.

The compounds of this invention may be used in the form of salts derived from inorganic or organic acids. Depending on the particular compound, a salt of the compound may be advantageous due to one or more of the salt's physical properties, such as enhanced pharmaceutical stability in differing temperatures and humidities, or a desirable solubility in water or oil. In some instances, a salt of a compound also may be used as an aid in the isolation, purification, and/or resolution of the compound.

Where a salt is intended to be administered to a patient (as opposed to, for example, being used in an in vitro context), the salt preferably is pharmaceutically acceptable. The term "pharmaceutically acceptable salt" refers to a salt prepared by combining a compound of the invention (e.g. a compound of Formula (I)) with an acid whose anion, or a base whose cation, is generally considered suitable for human consumption. Pharmaceutically acceptable salts are particularly useful as products of the methods of the present invention because of their greater aqueous solubility relative to the parent compound. For use in medicine, the salts of the compounds of this invention are non-toxic "pharmaceutically acceptable salts." Salts encompassed within the term "pharmaceutically acceptable salts" refer to non-toxic salts of the compounds of this invention which are generally prepared by reacting the free base with a suitable organic or inorganic acid.

Suitable pharmaceutically acceptable acid addition salts of the compounds of the present invention when possible include those derived from inorganic acids, such as hydrochloric, hydrobromic, hydrofluoric, boric, fluoroboric, phosphoric, metaphosphoric, nitric, carbonic, sulfonic, and sulfuric acids, and organic acids such as acetic, benzenesulfonic, benzoic, citric, ethanesulfonic, fumaric, gluconic, glycolic, isothionic, lactic, lactobionic, maleic, malic, methanesulfonic, trifluoromethanesulfonic, succinic, toluenesulfonic, tartaric, and trifluoroacetic acids. Suitable organic acids generally include but are not limited to aliphatic, cycloaliphatic, aromatic, araliphatic, heterocyclic, carboxylic, and sulfonic classes of organic acids.

Specific examples of suitable organic acids include but are not limited to acetate, trifluoroacetate, formate, propionate, succinate, glycolate, gluconate, digluconate, lactate, malate, tartaric acid, citrate, ascorbate, glucuronate, maleate, fumarate, pyruvate, aspartate, glutamate, benzoate, anthranilic acid, stearate, salicylate, p-hydroxybenzoate, phenylacetate, mandelate, embonate (pamoate), methanesulfonate, ethanesulfonate, benzenesulfonate, pantothenate, toluenesulfonate, 2-hydroxyethanesulfonate, sufanilate, cyclohexylaminosulfonate, algenic acid, .beta.-hydroxybutyric acid, galactarate, galacturonate, adipate, alginate, butyrate, camphorate, camphorsulfonate, cyclopentanepropionate, dodecylsulfate, glycoheptanoate, glycerophosphate, heptanoate, hexanoate, nicotinate, 2-naphthalesulfonate, oxalate, palmoate, pectinate, 3-phenylpropionate, picrate, pivalate, thiocyanate, and undecanoate.

Furthermore, where the compounds of the invention carry an acidic moiety, suitable pharmaceutically acceptable salts thereof may include alkali metal salts, i.e., sodium or potassium salts; alkaline earth metal salts, e.g., calcium or magnesium salts; and salts formed with suitable organic ligands, e.g., quaternary ammonium salts. In another embodiment, base salts are formed from bases which form non-toxic salts, including aluminum, arginine, benzathine, choline, diethylamine, diolamine, glycine, lysine, meglumine, olamine, tromethamine and zinc salts.

Organic salts may be made from secondary, tertiary or quaternary amine salts, such as tromethamine, diethylamine, N,N'-benzylethylenediamine, chloroprocaine, choline, diethanolamine, ethylenediamine, meglumine (N-methylglucamine), and procaine. Basic nitrogen-containing groups may be quaternized with agents such as lower alkyl (C.sub.1-C.sub.6) halides (e.g., methyl, ethyl, propyl, and butyl chlorides, bromides, and iodides), dialkyl sulfates (i.e., dimethyl, diethyl, dibutyl, and diamyl sulfates), long chain halides (i.e., decyl, lauryl, myristyl, and stearyl chlorides, bromides, and iodides), arylalkyl halides (i.e., benzyl and phenethyl bromides), and others.

In one embodiment, hemisalts of acids and bases may also be formed, for example, hemisulphate and hemicalcium salts.

Included within the scope of the invention are complexes such as clathrates, drug-host inclusion complexes wherein, in contrast to the aforementioned solvates, the drug and host are present in stoichiometric or non-stoichiometric amounts. Also included are complexes of the drug containing two or more organic and/or inorganic components which may be in stoichiometric or non-stoichiometric amounts. The resulting complexes may be ionised, partially ionised, or non-ionised. For a review of such complexes, see J Pharm Sci, 64 (8), 1269-1288 by Haleblian (August 1975).

The present invention includes all pharmaceutically acceptable isotopically-labelled compounds of the invention wherein one or more atoms are replaced by atoms having the same atomic number, but an atomic mass or mass number different from the atomic mass or mass number usually found in nature. Examples of isotopes suitable for inclusion in the compounds of the invention include isotopes of hydrogen, such as $^{2}H$ and $^{3}H$, carbon, such as $^{11}C$, $^{13}C$ and $^{14}C$, chlorine, such as $^{36}Cl$, fluorine, such as $^{18}F$, iodine, such as $^{123}I$ and $^{125}I$, nitrogen, such as $^{13}N$ and $^{15}N$, oxygen, such as $^{15}O$, $^{17}O$ and $^{18}O$, phosphorus, such as $^{32}P$, and sulphur, such as $^{35}S$. Certain isotopically-labelled compounds of formula (I), for example, those incorporating a radioactive isotope, are useful in drug and/or substrate tissue distribution studies. The radioactive isotopes tritium, i.e. $^{3}H$, and carbon-14, i.e. $^{14}C$, and $^{125}I$ are particularly useful for this purpose in view of their ease of incorporation and ready means of detection. Substitution with heavier isotopes such as deuterium, i.e. $^{2}H$, may afford certain therapeutic advantages resulting from greater metabolic stability, for example, increased in vivo half-life or reduced dosage requirements, and hence may be preferred in some circumstances. Substitution with positron emitting isotopes, such as $^{11}C$, $^{18}F$, $^{15}O$ and $^{13}N$, can be useful in Positron Emission Topography (PET) studies for examining substrate receptor occupancy. Isotopically-labeled compounds of formula (I) can generally be prepared by conventional techniques known to those skilled in the art or by processes analogous to those described in the accompanying Examples and Preparations using an appropriate isotopically-labeled reagents in place of the non-labeled reagent previously employed.

In some embodiments, compounds described herein could be prepared as prodrugs. A "prodrug" refers to an agent that is converted (e.g., either spontaneous or enzymatic) within the target physiological system into the parent drug in vivo. Prodrugs are designed to overcome problems associated with stability, toxicity, lack of specificity, or limited bioavailability. In some situations, they may be easier to administer than the parent drug. They may, for instance, be bioavailable by oral administration whereas the parent is not. The prodrug may also have improved solubility in pharmaceutical compositions over the parent drug. An example, without limitation, of a prodrug would be a compound described herein, which is administered as an ester (the "prodrug") to facilitate transmittal across a cell membrane where water solubility is detrimental to mobility but which then is metabolically hydrolyzed to the carboxylic acid, the active entity, once inside the cell where water-solubility is beneficial. A further example of a prodrug might be a short peptide (polyaminoacid) bonded to an acid group where the peptide is metabolized to reveal the active moiety. In certain embodiments, upon in vivo administration, a prodrug is chemically converted to the biologically, pharmaceutically or therapeutically active form of the compound. In certain embodiments, a prodrug is enzymatically metabolized by one or more steps or processes to the biologically, pharmaceutically or therapeutically active form of the compound. To produce a prodrug, a pharmaceutically active compound is modified such that the active compound will be regenerated upon in vivo administration. The prodrug can be designed to alter the metabolic stability or the transport characteristics of a drug, to mask side effects or toxicity, to improve the flavor of a drug or to alter other characteristics or properties of a drug. By virtue of knowledge of pharmacodynamic processes and drug metabolism in vivo, those of skill in this art, once a pharmaceutically active compound is known, can design prodrugs of the compound. (see, for example, Nogrady (1985) Medicinal Chemistry A Biochemical Approach, Oxford University Press, New York, pages 388-392; Silverman (1992), The Organic Chemistry of Drug Design and Drug Action, Academic Press, Inc., San Diego, pages 352-401, Saulnier et al., (1994), Bioorganic and Medicinal Chemistry Letters, Vol. 4, p. 1985). Prodrugs may be designed as reversible drug derivatives, for use as modifiers to enhance drug transport to site-specific tissues. See, e.g., Fedorak et al., Am. J. Physiol., 269:G210-218 (1995); McLoed et al., Gastroenterol, 106: 405-413 (1994); Hochhaus et al., Biomed. Chrom., 6:283-286 (1992); J. Larsen and H. Bundgaard, Int. J. Pharmaceutics, 37, 87 (1987); J. Larsen et al., Int. J. Pharmaceutics, 47, 103 (1988); Sinkula et al., J. Pharm. Sci., 64:181-210 (1975); T. Higuchi and V. Stella, Pro-drugs as Novel Delivery Systems, Vol. 14 of the A.C.S. Symposium Series; and Edward B. Roche, Bioreversible Carriers in Drug Design, American Pharmaceutical Association and Pergamon Press, 1987, all incorporated herein in their entirety.

Some preferred prodrugs are variations or derivatives of compounds that have groups cleavable under metabolic conditions. Common prodrugs include acid derivatives such as esters, such as carboxylic esters (e.g. ethyl esters) and phosphate esters prepared by reaction of parent acids with a suitable alcohol (e.g., a lower alkanol), or of parent alcohols with a suitable acid (e.g. phosphate esters of hydroxyl groups); amides prepared by reaction of the parent acid compound with an amine, or basic groups reacted to form an acylated base derivative (e.g., a lower alkylamide).

Compounds of the Invention

The invention is directed to the compound of Formula I, including the racemates, and/or diastereomer mixtures, as well as specific enantiomers and/or diastereomers thereof,

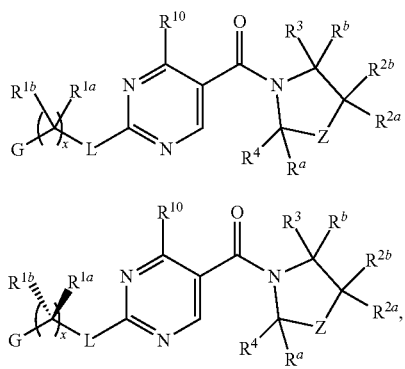

wherein

G is a 6-membered heteroaryl, with one, two or three N, wherein the heteroaryl is optionally substituted with one, two or three substituents selected from halogen, OH, cyano, $C_1$-$C_4$alkyl, —$NR^{8a}C(O)R^{8b}$, —$NR^{8a}SO_2R^{8b}$, —$(CR^{6a}R^{6b})_t$ $C(O)N(R^{8a})_2$, —$C(O)OH$, —$N(R^{8a})_2$, —$(CR^{6a}R^{6b})_t$ $SO_2R^{8b}$, —$(CR^{6a}R^{6b})_tSO_2N(R^{8a})_2$, $C_1$-$C_4$alkoxy, —$S(C_1$-$C_3$alkyl) or $C_3$-$C_5$cycloalkyl, wherein the alkyl, cycloalkyl and alkoxy are optionally substituted with one, two or three halogen, OH, $OCH_3$, or $C_3$-$C_5$cycloalkyl;

L is NH or O;

Z is a bond; —$(CR^{5a}R^{5b})_q$—; —$CH_2(CR^{5a}R^{5b})_m$—; or —$(CR^{5a}R^{5b})_m$—W—$(CR^{5a}R^{5b})_n$—, wherein W is S, O or $NR^7$;

$R^a$, $R^b$, $R^{1a}$ and $R^{1b}$ are each independently hydrogen, $C_1$-$C_4$alkyl, wherein the alkyl is optionally substituted with one, two or three halogen, OH, cyano, —$S(C_1$-$C_3$alkyl) or $C_1$-$C_4$alkoxy, optionally substituted with one, two or three fluoro;

or $R^{1a}$ and $R^{1b}$, together with the carbon to which they are bonded, form an oxo, $C_3$-$C_5$cycloalkyl, -(4- to 5-membered heterocycloalkyl) wherein said cycloalkyl or heterocycloalkyl are optionally substituted with one, two, three or four halogen, OH, $C_1$-$C_4$alkyl, —$S(C_1$-$C_3$alkyl) $C_1$-$C_4$alkoxy or cyano; and the heteroatom is selected from one or two N, S or O;

$R^{2a}$ and $R^{2b}$ are each independently hydrogen, OH, halogen, —$(CR^{6a}R^{6b})_tSO_2R^{8b}$, —$(CR^{6a}R^{6b})_tC(O)N(R^{8a})_2$, —$NR^{8a}C(O)R^{8b}$, —$NR^{8a}C(O)N(R^{8a})_2$, —$SO_2N(R^{8a})_2$, $C_1$-$C_4$alkyl, $C_1$-$C_4$alkoxy, $S(C_1$-$C_3$alkyl), cyano, —$(CR^{6a}R^{6b})_t$—$(C_3$-$C_6$cycloalkyl), —$(CR^{6a}R^{6b})_n$-(5- to 6-membered heterocycloalkyl) or —$(CR^{6a}R^{6b})_n$-(5- to 6-membered heteroaryl), wherein said heteroatoms of said heteroalkyl and heteroaryl are selected from one, two or three N, O or S; wherein said alkyl, cycloalkyl, heterocycloakyl and heteroaryl are optionally substituted with one, two, three or four $R^9$; or $R^{2a}$ and $R^{2b}$ together with the carbon to which they are bonded form a $C_3$-$C_9$cycloalkyl or a -(4- to 11-membered heterocycloalkyl), having one to three heteroatoms selected from N, O or S; wherein the cycloalkyl and heterocycloalkyl are optionally substituted with one, two or three $C_1$-$C_4$alkyl, $S(C_1$-$C_3$alkyl), OH, halogen, oxo, —$C(O)NH_2$, —$C(O)NHCH_3$, —$C(O)N(CH_3)_2$, $C_3$-$C_5$cycloalkyl or $C_1$-$C_4$alkoxy; or if substitution is at a N atom, then such N atom is substituted with $R^7$; or $R^{2a}$ or $R^{2b}$, and one of $R^{5a}$ or $R^{5b}$, together with the respective carbons to which they are bonded, form a $C_3$-$C_{12}$cycloalkyl, $C_6$-$C_{10}$aryl, -(5- to 6-membered heteroaryl) or a -(4- to 12-membered heterocycloalkyl), wherein said heteroaryl or heterocycloalkyl is optionally substituted with one, two, three or four $R^9$; or if substitution is at a N atom, then such N atom is substituted with $R^7$; or $R^{2a}$ or $R^{2b}$, and $R^7$, together with the respective atoms to which they are bonded form a -(4- to 12-membered heterocycloalkyl) or a -(5- to 6-membered heteroaryl), wherein said heterocycloalkyl or heteroaryl have one, two to three heteroatoms selected from N, O or S, wherein said heterocycloalkyl and heteroaryl are optionally substituted with one, two, three or four $R^9$; or if substitution is at a N atom, then such N atom is substituted with $R^7$;

$R^3$ is hydrogen, —$(CR^{6a}R^{6b})_tC(O)NH_2$, or $C_1$-$C_4$alkyl, wherein said alkyl is optionally substituted with one, two, three or four $R^9$; or $R^3$ and $R^b$, together with the carbon to which they are attached, form an oxo;

$R^4$ is hydrogen, —$(CR^{6a}R^{6b})_tC(O)NH_2$, or $C_1$-$C_4$alkyl, wherein said alkyl is optionally substituted with one, two, three or four $R^9$; or $R^3$ and $R^4$ taken together with the respective carbons to which they are bonded form a -(4- to 11-membered heterocycloalkyl), having one to two heteroatoms selected from N, O or S, wherein the heterocycloalkyl are optionally substituted with one, two, three or four $R^9$; or if substitution is at a N atom, then such N atom is substituted with $R^7$; or $R^4$ and $R^a$, together with the carbon to which they are attached, form an oxo;

$R^{5a}$ and $R^{5b}$ are each independently hydrogen, halogen, OH, —$(CR^{6a}R^{6b})_tC(O)R^{8b}$, —$(CR^{6a}R^{6b})_tC(O)NH_2$, $C_1$-$C_4$alkyl, $S(C_1$-$C_3$alkyl), $C_1$-$C_4$alkoxy, cyano, —$(CR^{6a}R^{6b})_t$—$(C_3$-$C_6$cycloalkyl) or —$(CR^{6a}R^{6b})_t$—$(C_3$-$C_6$heterocycloalkyl), wherein said alkyl, cycloalkyl and heterocycloalkyl are optionally substituted with one, two, three or four $R^9$; and the heteroatom is selected from one or two N, O, or S; or $R^{5a}$ and $R^{5b}$ taken together with the carbon to which they are bonded form a $C_3$-$C_9$cycloalkyl or a 4- to 11-membered heterocycloalkyl, wherein the heteroatom is selected from one or two N, S or O, wherein said cycloalkyl or heterocycloalkyl is optionally substituted with one, two, three or four $R^9$; or if substitution is at a N atom, then such N atom is substituted with $R^7$; or $R^3$ and either $R^{5a}$ or $R^{5b}$ taken together with the respective carbons to which they are bonded form a $C_3$-$C_{10}$cycloalkyl or -(4- to 12-membered heterocycloalkyl), wherein the heteroatom is selected from one or two N or O, wherein said cycloalkyl and heterocycloalkyl are optionally substituted with one, two, three or four $R^9$ or oxo; or if substitution is at a N atom, then such N atom is substituted with $R^7$;

$R^{6a}$ and $R^{6b}$ are each independently hydrogen, $C_1$-$C_4$alkyl, $S(C_1$-$C_3$alkyl), OH, $C_1$-$C_4$alkoxy, cyano or halogen;

$R^7$ is hydrogen; -(4- to 6-membered heterocycloalkyl), having 1 to 2 heteroatoms wherein said heteroatom is selected from O, N and S; $C_1$-$C_5$alkyl; $S(C_1$-$C_3$alkyl); C(O)$R^{8b}$; $SO_2R^{8b}$; $SO_2N(R^{8a})_2$; $C(O)N(R^{8a})_2$ or —($C_3$-$C_7$cycloalkyl), wherein said alkyl, heterocycloalkyl and cycloalkyl are optionally substituted with $R^a$;

$R^{8a}$ is hydrogen, $C_1$-$C_4$alkyl or —($C_3$-$C_7$cycloalkyl);

$R^{8b}$ is $C_1$-$C_4$alkyl, —($C_3$-$C_7$cycloalkyl), —$(CR^{6a}R^{6b})_t$$SO_2N(R^{8a})_2$, —$(CR^{6a}R^{6b})_tSO_2R^{8a}$ or —$(CR^{6a}R^{6b})_t$NHC(O)N($R^{8a}$)$_2$;

$R^9$ is hydrogen, $C_1$-$C_4$alkyl, $S(C_1$-$C_3$alkyl), OH, $CH_2OH$, halogen, $C_1$-$C_4$alkoxy, cyano or —C(O)$NH_2$, wherein said alkyl and alkoxy are optionally substituted with OH, halogen, —C(O)$NH_2$, —C(O)$NHCH_3$, —C(O)$N(CH_3)_2$, —$S(C_1$-$C_4$alkyl) or $C_3$-$C_5$cycloalkyl; or $R^9$ is oxo, provided that it is attached to a non-aromatic group;

$R^{10}$ is hydrogen or $C_1$-$C_3$alkyl;

m, n and t are each independently 0, 1 or 2; q is 1, 2 or 3; and x is 1 or 2; or pharmaceutically acceptable salts thereof.

In another embodiment, the invention is directed to compounds having the Formula Ia, Ib, Ic, Id, Ie, If and Ig.

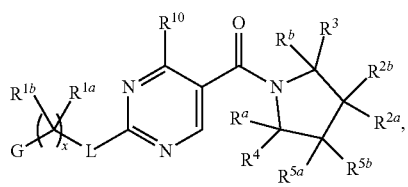

Ia

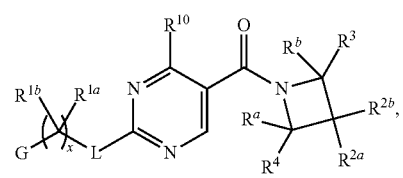

Ib

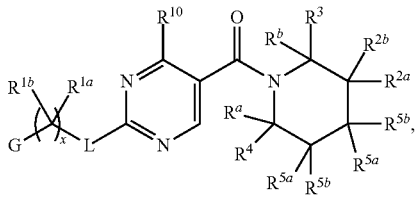

Ic

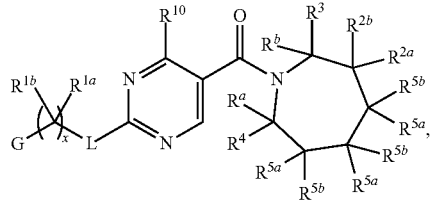

Id

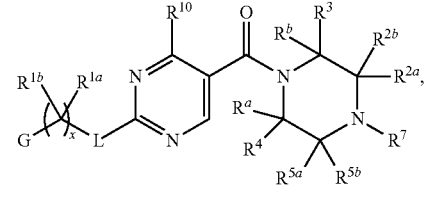

Ie

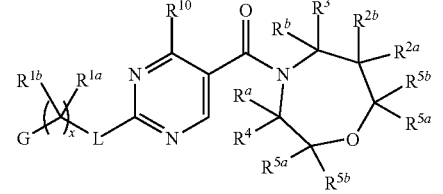

If or

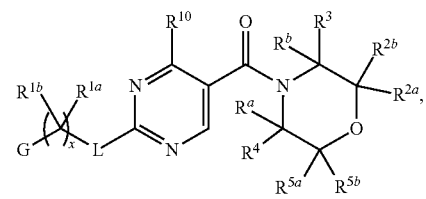

Ig

G is a 6-membered heteroaryl, with one, two or three N, wherein the heteroaryl is optionally substituted with one, two or three substituents selected from halogen, OH, cyano, $C_1$-$C_4$alkyl, —$NR^{8a}C(O)R^b$, —$NR^{1a}SO_2R^{8b}$, $(CR^{6a}R^{6b})_tC(O)N(R^{8a})_2$, —C(O)OH, —N($R^{8a}$)$_2$, —$(CR^{6a}R^{6b})_tSO_2R^{8b}$, —$(CR^{6a}R^{6b})_tSO_2N(R^{8a})_2$, $C_1$-$C_4$alkoxy, —$S(C_1$-$C_3$alkyl) or $C_3$-$C_5$cycloalkyl, wherein the alkyl, cycloalkyl and alkoxy are optionally substituted with one, two or three halogen, OH, $OCH_3$, or $C_3$-$C_5$cycloalkyl;

L is NH or O;

Z is a bond; —$(CR^{5a}R^{5b})_q$—; —$CH_2(CR^{5a}R^{5b})_m$—; or —$(CR^{5a}R^{5b})_m$—W—$(CR^{5a}R^{5b})_n$—, wherein W is S, O or $NR^7$; and $R^a$, $R^b$, $R^{1a}$, $R^{1b}$, $R^{2a}$, $R^{2b}$, $R^3$, $R^4$, $R^{5a}$, $R^{5b}$, $R^6$, $R^7$, $R^8$, $R^9$ and $R^{10}$, are as previously described herein; or a pharmaceutically acceptable salt thereof.

In another embodiment, G is a triazinyl, pyridazinyl, pyridonyl, pyridinyl, pyrazinyl or pyrimidinyl, optionally substituted with one, two or three substituents selected from halogen, OH, cyano, $C_1$-$C_4$alkyl, —$NR^aC(O)R^{8b}$, —$(CR^{6a}R^{6b})_tC(O)NH_2$, —C(O)OH, —N($R^{8a}$)$_2$, $C_1$-$C_4$alkoxy, wherein the alkyl and alkoxy are optionally substituted with one, two or three halogen, OH, $OCH_3$, $C_3$-$C_5$cycloalkyl or —$S(C_1$-$C_3$alkyl); or a pharmaceutically acceptable salt thereof.

In yet another embodiment, G is a pyrazinyl or a pyrimidinyl.

In another embodiment, L is NH.

Further embodiments of the invention include, but are not limited to compounds of Formula I, Formula Ia-Ig, and Formula IIa-IIg with new ring formations between, for example, the following substituents: $R^{1a}$ and $R^{1b}$, $R^{2a}$ and $R^{2b}$, $R^3$ and $R^4$, $R^{2a}$ or $R^{2b}$ and either $R^{5a}$ or $R^{5b}$, $R^3$ and either $R^{5a}$ or $R^{5b}$, and $R^{2a}$ or $R^{2b}$ and $R^7$.

In such embodiments, one skilled in the art would appreciate that upon such selected substituents, taken together with the atoms to which they are bonded, such substituents may take the form of a bond, if appropriate, or an "alkylene" or a "heteroalkylene" and would, respectively, therefore, ultimately form a cycloalkyl or a heterocycloalkyl.

The term "alkylene", as used herein, refers to a saturated, branched or straight chain or cyclic hydrocarbon diradical of the stated number of carbon atoms, typically 1-6 carbon atoms, and having two monovalent radical centers derived by the removal of two hydrogen atoms from the same or two different carbon atoms of a parent alkane. Typical alkylene radicals include, but are not limited to methylene (—CH$_2$—), 1,2-ethylene (—CH$_2$CH$_2$—), 2,2-dimethylene, 1,3-propylene (—CH$_2$CH$_2$CH$_2$—), 2-methylpropylene, 1,4-butylene (—CH$_2$CH$_2$CH$_2$CH$_2$—), and the like; optionally substituted as defined herein. Likewise, the term "heteroalkylene" means a divalent group derived from heteroalkyl (as defined above). For heteroalkylene groups, heteroatoms can also occupy either or both of the chain termini.

For example, in one embodiment, a new ring formation between $R^{2a}$ and $R^{2b}$ can create a cycloalkyl, optionally substituted, as exemplified in the following structure,

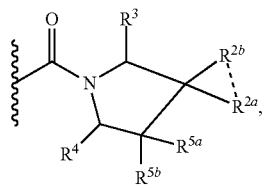

wherein the smallest cycloalkyl formed is cyclopropyl, and in that case, one of $R^{2a}$ or $R^{2b}$ comprises an ethylene (—CH$_2$CH$_2$—) and one a bond. Alternatively, both $R^{2a}$ or $R^{2b}$ comprise a methylene (—CH$_2$—). In a more specific embodiment, one skilled in the art would appreciate from the description herein and the examples that $R^{2a}$ and $R^{2b}$ could form the following new ring formation, optionally substituted as appropriate, ($R^{2a}$ and $R^{2b}$ labels left in for further clarification),

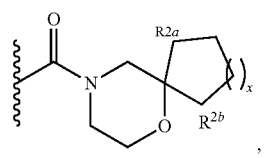

wherein one of $R^{2a}$ or $R^{2b}$ independently is a bond, methylene (—CH$_2$—), 1,2-ethylene (—CH$_2$CH$_2$—), 2,2-dimethylene, 1,3-propylene (—CH$_2$CH$_2$CH$_2$—), 2-methylpropylene, 1,4-butylene (—CH$_2$CH$_2$CH$_2$CH$_2$—), and the like; and x is 0-5.

Another embodiment of a new ring formation between $R^{2a}$ and $R^{2b}$ is wherein the two substituents form a -(4- to 11-membered heterocycloalkyl), optionally substituted as appropriate, such as described in the following exemplary formula. In this case,

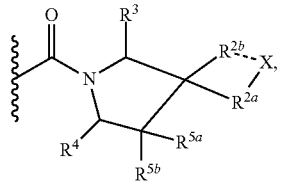

X is O, N or S and the smallest heterocycloalkyl is a 4-membered ring, optionally substituted as appropriate. In particular, a specific embodiment includes,

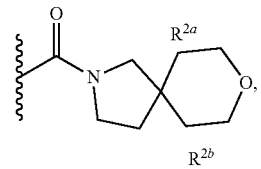 [SMILES: *C(=O)N1CCC2(CCOCC2)C1]

a heterocycloalkyl, wherein, for example, one of $R^{2a}$ or $R^{2b}$ independently is a bond, methylene (—CH$_2$—), 1,2-ethylene (—CH$_2$CH$_2$—), 2,2-dimethylene, 1,3-propylene (—CH$_2$CH$_2$CH$_2$—), 2-methylpropylene, 1,4-butylene (—CH$_2$CH$_2$CH$_2$CH$_2$—), and the like; and the other of $R^{2a}$ or $R^{2b}$ is a heteroalkylene.

In a further embodiment, a 9-carbon cycloalkyl new ring formation and an 11-membered heterocycloalkyl between $R^{2a}$ and $R^{2b}$ are depicted in the following structures:

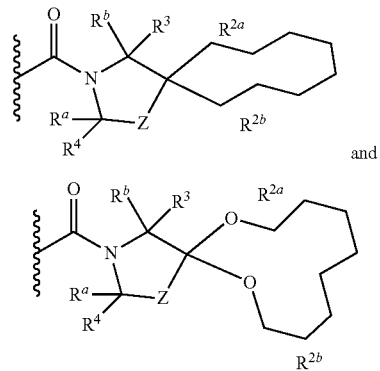

($R^{2a}$ and $R^{2b}$ labels left in for further clarification). Different variations of these cycloalkyl and heterocycloalkys are considered part of the present invention and are further described herein.

One skilled in the art would appreciate that the description of how $R^{2a}$ and $R^{2b}$ may form a new ring system as described above, may be extrapolated to the other substituents ($R^{1a}$ and $R^{1b}$, $R^3$ and $R^4$, $R^{2a}$ or $R^{2b}$ and either $R^{5a}$ or $R^{5b}$, $R^3$ and either $R^{5a}$ or $R^{5b}$, and $R^{2a}$ or $R^{2b}$ and $R^7$) that are described as forming new rings and such description is applicable, as appropriate.

For example, in another embodiment, a new ring formation can occur between substituents $R^{5a}$ and $R^{5b}$ to provide an optionally substituted cycloalkyl,

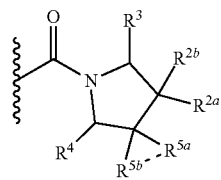

with the smallest being a cyclopropyl; wherein both $R^{5a}$ or $R^{5b}$ comprise a methylene (—CH$_2$—). Alternatively, one of $R^{5a}$ or $R^{5b}$ comprise an ethylene (—CH$_2$CH$_2$—). and the other a bond.

In another embodiment, such substituents could form a 4- to 7-membered heterocycloalkyl, optionally substituted,

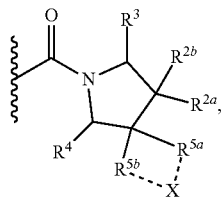

wherein the smallest heterocycloalkyl is a 4-membered ring (wherein X is N, O or S) and wherein $R^{5a}$ or $R^{5b}$ are independently a bond, an alkylene and, at least one of $R^{5a}$ or $R^{5b}$ comprises a heteroalkylene (e.g. —O—CH$_2$—).

In a more specific embodiment, one skilled in the art would appreciate from the description herein and the examples that $R^{5a}$ and $R^{5b}$ could form the following new ring formations ($R^{5a}$ and $R^{5b}$ labels left in for further clarification):

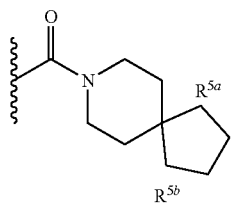

wherein $R^{5a}$ and $R^{5b}$ are independently a bond, a methylene (—CH$_2$—), 1,2-ethylene (—CH$_2$CH$_2$—), 2,2-dimethylene, 1,3-propylene (—CH$_2$CH$_2$CH$_2$—), 2-methylpropylene, or 1,4-butylene (—CH$_2$CH$_2$CH$_2$CH$_2$—), and the like; or

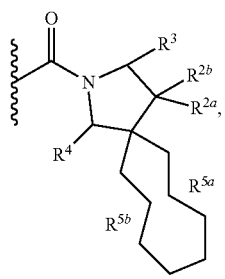

forming a cycloalkyl, wherein $R^{5a}$ and $R^{5b}$ are each 1,4-butylene (—CH$_2$CH$_2$CH$_2$CH$_2$—) in the later example.

In another embodiment, $R^{5a}$ and $R^{5b}$, being an alkylene or heteroalkylene group, form an optionally substituted heterocycloalkyl, such as

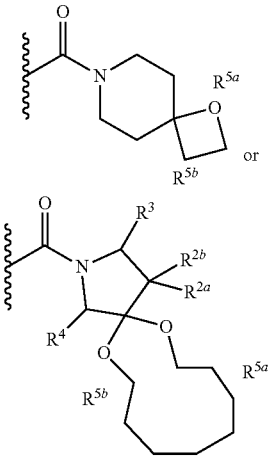

as described herein. Other specific embodiments of ring systems include, for example: 8-oxa-2-azaspiro[4.5]dec-2-yl,

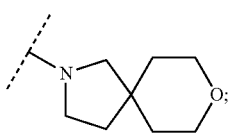

and 7-oxa-2-azaspiro[3.5]nonan-2-yl,

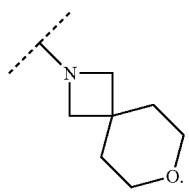

It would be apparent to one skilled in the art, based upon the examples described herein, that other possible ring systems are contemplated as part of this invention.

In another embodiment, a new ring formation can occur between substituents $R^{2a}$ or $R^{2b}$ and one of $R^{5a}$ or $R^{5b}$ to provide a $C_3$-$C_{12}$cycloalkyl, $C_6$-$C_{10}$aryl, -(5- to 12-membered heteroaryl) or a -(4- to 12-membered heterocycloalkyl) as exemplified in the following depictions,

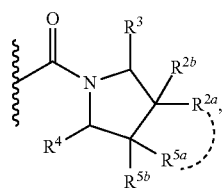

wherein the smallest cycloalkyl is a cyclopropyl and one of $R^{2a}$ or $R^{5a}$ comprises a methylene (—CH$_2$—) and one a bond, said cycloalkyl optionally substituted as appropriate. The following structures demonstrate the formation of the new cyclopropyl ring, wherein one of $R^{2a}$ or $R^{5a}$ is a bond:

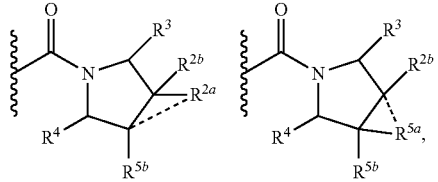

In another embodiment, or

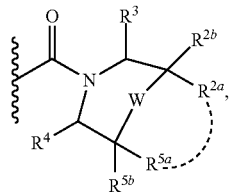

wherein W is defined herein as N, O, or S, and the smallest heterocycloalkyl formed is a 4-membered heterocycloalkyl, wherein one of $R^{2a}$ or $R^{5a}$ comprises a methylene (—CH$_2$—) and one a bond, said heterocycloalkyl optionally substituted as appropriate.

In particular, one skilled in the art would appreciate from the description herein and the examples that $R^{2a}$ and $R^{5b}$ could form the following specific exemplary new ring formations, optionally substituted as defined herein, ($R^{2a}$ and $R^{5a}$ labels remaining for clarification): a cycloalkyl,

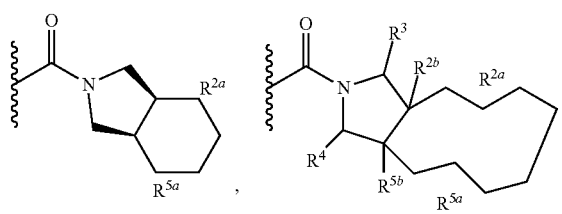

($R^{2a}$ and $R^{5a}$ are independently $C_1$-$C_4$alkylene; Z is —(CR$^{5a}$R$^{5b}$)$_q$—; and q is 1); or

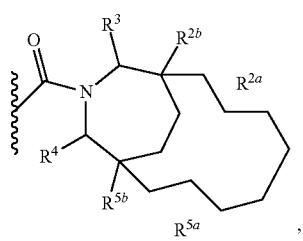

($R^{2a}$ and $R^{5a}$ are independently $C_1$-$C_4$alkylene; Z is —(CR$^{5a}$R$^{5b}$)$_q$—; and q is 3); an aryl,

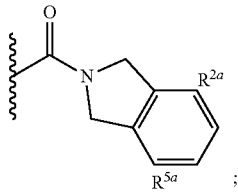

a heteroaryl,

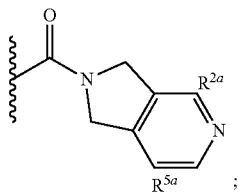

and a heterocycloalkyl,

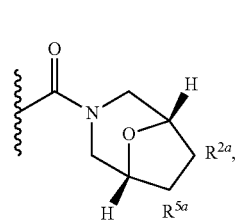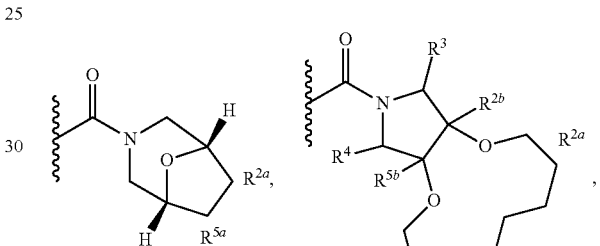

($R^{2a}$ and $R^{5a}$ are independently —O—$C_1$-$C_4$alkylene or $C_1$-$C_4$alkylene; Z is —(CR$^{5a}$R$^{5b}$)$_q$—; and q is 3); all of which are particular embodiments of this invention, as well as other possible ring formations.

In another embodiment, a new ring formation can occur between substituents $R^{2a}$ or $R^{2b}$ and $R^7$ to form a -(4- to 12-membered heterocycloalkyl) or a -(5- to 6-membered heteroaryl), having two to three heteroatoms selected from N, O or S, and wherein W is N as exemplified by the following structures:

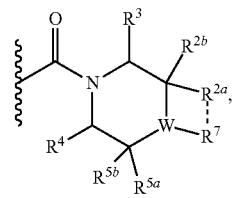

wherein the smallest heterocycloalky formed is a 4-membered ring, wherein $R^{2a}$ and $R^7$ is, for example, —CH$_2$—, optionally substituted as defined herein. One of ordinary skill in the art would appreciate that different combinations of substituent groups for $R^{2a}$ and $R^7$ could arrive at the 4-membered ring, as well as other ring sizes.

For example, in another embodiment of an heterocycloalkyl, optionally substituted as defined herein,

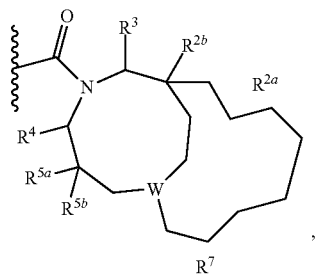

$R^{2a}$ is $C_1$-$C_4$alkylene (and in this example is 1,4-butylene (—$CH_2CH_2CH_2CH_2$—)); $R^7$ is $C_1$-$C_5$alkylene (and in this example, 1,5-pentylene (—$CH_2CH_2CH_2CH_2$—)); Z is —$(CR^{5a}R^{5b})_m$—W—$(CR^{5a}R^{5b})_n$—; and m and n are 2, to form a 12-membered heterocycloalkyl ring.

In a particular embodiment, one skilled in the art would appreciate from the description herein and the examples that $R^{2a}$ and $R^7$ could form the following specific new ring formations, optionally substituted as described herein, ($R^{2a}$ and $R^7$ labels remaining for clarification): a heterocycloalkyl,

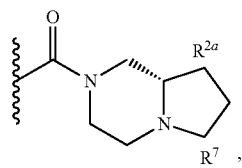

and a heteroaryl,

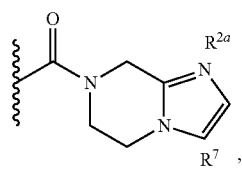

Both of these embodiments, and variations thereof, are contemplated as part of this invention, as well as other possible ring formations described herein.

In another embodiment, a new ring formation can occur between substituents $R^3$ and $R^4$ to provide a -(4- to 12-membered heterocycloalkyl), optionally substituted as defined herein, having one to two heteroatoms selected from N, O or S, as exemplified in the following structure,

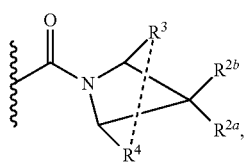

wherein the smallest heterocycloalkyl formed is a 4-membered ring, (assuming one of $R^3$ or $R^4$ comprises a methylene (—$CH_2$—) and the other a bond), such as depicted in the following:

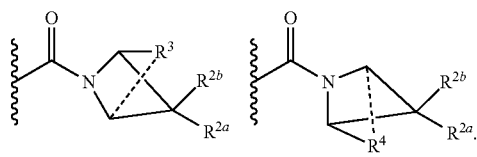

One of ordinary skill in the art would understand that, in this example, as well as others exemplified herein, the N of the amide is part of the new ring being formed and is, therefore, included in numbering the new ring system.

In a specific embodiment, one skilled in the art would appreciate from the description herein and the examples that $R^3$ and $R^4$ could form the following specific new ring formations ($R^3$ and $R^4$ labels remaining for clarification): the heterocycloalkyl,

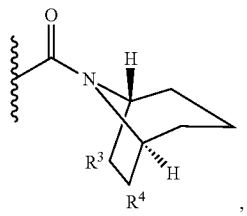

wherein different variations of $R^3$ or $R^4$ substituents could arrive at the 5-membered heterocycloalkyl described above. For example, $R^3$ and $R^4$ independently are a bond or $C_1$-$C_2$alkylene (e.g. methylene (—$CH_2$—), 1,2-ethylene (—$CH_2CH_2$—)). One of ordinary skill in the art would appreciate that many other new ring size formations are possible and are part of the contemplated invention described herein. For example, in another embodiment, a larger heterocycloalkyl may be formed,

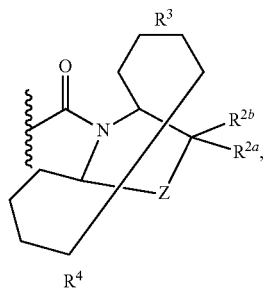

wherein $R^3$ and $R^4$, in this example, could each be 1,4-butylene (—$CH_2CH_2CH_2CH_2$—)) to form a 11-membered heterocycloalkyl ring.

In another embodiment, a new ring formation may occur between $R^3$ and $R^{5a}$ or $R^{5b}$ to provide for a $C_3$-$C_7$cycloalkyl or -(4- to 12-membered heterocycloalkyl), as exemplified in the following structure,

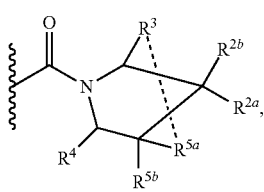

wherein the smallest heterocycloalkyl formed is a 4-membered ring (assuming $R^3$ or $R^{5a}$ is a bond).

In a particular embodiment, one skilled in the art would appreciate from the description herein and the examples that $R^3$ and $R^5$ could form the following specific new ring formations ($R^3$ and $R^5$ labels remaining for clarification): a heterocycloalkyl,

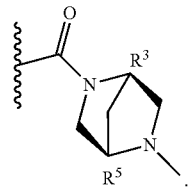

Other specific ring formations are contemplated as part of this invention and are described herein.

In another embodiment, a new ring formation may occur between $R^3$ and $R^{5a}$ or $R^{5b}$ to provide for a $C_3$-$C_7$cycloalkyl, wherein W is O or $NR^7$, as exemplified in the following structure,

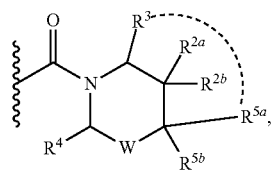

wherein the smallest cycloalkyl formed is cyclobutyl (assuming one of $R^3$ and $R^{5a}$ is a bond or $C_1$-$C_2$alkylene (e.g. methylene (—CH$_2$—),), as depicted in the following:

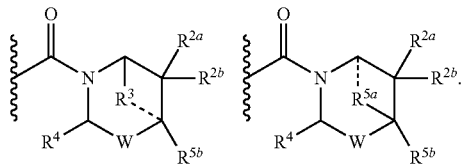

In a specific embodiment,

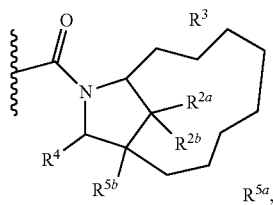

$R^3$ and $R^{5a}$ form an optionally substituted $C_{11}$cycloalkyl, wherein $R^3$ and $R^{5a}$, in this example, are each 1,4-butylene (—CH$_2$CH$_2$CH$_2$CH$_2$—)); Z is —(CR$^{5a}$R$^{5b}$)$_m$—W—(CR$^{5a}$R$^{5b}$)$_n$—; and m and n are 2. One skilled in the art would appreciate that different variations of $R^3$ and $R^{5a}$ are described herein, each of which would form different new ring sizes.

In an alternative embodiment, $R^3$ and $R^{5a}$ form an optionally substituted 12-membered heterocycloalkyl,

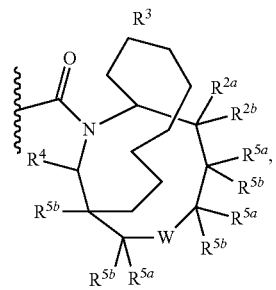

wherein W is N, O or S; and $R^3$ and $R^{5a}$, in this example, are each 1,4-butylene (—CH$_2$CH$_2$CH$_2$CH$_2$—)).

In another embodiment, $R^{1a}$ or $R^{1b}$ are each independently hydrogen, or $C_1$-$C_3$alkyl, wherein the alkyl is optionally substituted with one, two or three fluoro, OH, cyano or $C_1$-$C_4$alkoxy, optionally substituted with one, two or three fluoro; or $R^{1a}$ and $R^{1b}$, (as described above) together with the carbon to which they are bonded, form a $C_3$-$C_4$cycloalkyl or a 4-membered heterocycloalkyl, wherein said cycloalkyl or heterocycloalkyl are optionally substituted with one, two, three or four halogen, OH, $C_1$-$C_4$alkyl, S($C_1$-$C_3$alkyl), $C_1$-$C_4$alkoxy or cyano; or a pharmaceutically acceptable salt thereof.

In a specific embodiment, $R^{1a}$ and $R^{1b}$ are each independently hydrogen or methyl; or $R^{1a}$ and $R^{1b}$, together with the carbon to which they are bonded, form an optionally substituted cyclopropyl, cyclobutyl or an oxetane; or a pharmaceutically acceptable salt thereof.

In another embodiment, L is NH; $R^a$ and $R^b$ are H; and x is 1; or a pharmaceutically acceptable salt thereof. In another specific embodiment, $R^3$ and $R^4$ are each independently hydrogen or $C_1$-$C_4$alkyl, wherein said alkyl is optionally substituted with one, two, three or four $R^9$; or $R^3$ and $R^4$ taken together with the respective carbons to which they are bonded (as described above) form a -(4- to 12-membered heterocycloalkyl), having one to two heteroatoms selected from N, O or S, wherein the heterocycloalkyl is optionally substituted with one, two, three or four $R^9$; $R^9$ is OH, CH$_2$OH, halogen, $C_1$-$C_4$alkyl, $C_1$-$C_4$alkoxy or cyano; or a pharmaceutically acceptable salt thereof.

In another embodiment, G is selected from the following exemplary moieties: pyrazinyl, pyrimidinyl, pyridinyl or pyridazinyl, (each of which is optionally substituted with methyl, CH$_2$F, CHF$_2$ or CF$_3$); and wherein such moieties are either carbon-linked or nitrogen-linked; or a pharmaceutically acceptable salt thereof.

In a specific embodiment, $R^{2a}$ and $R^{2b}$ together with the carbon to which they are bonded form a oxetane, tetrahydrofuran, tetrahydropyran, cyclobutyl, cyclopentyl, or cyclohexyl, each of which is optionally substituted with one or two $C_1$-$C_4$alkyl or OH; or a pharmaceutically acceptable salt thereof.

In an another particular embodiment, $R^{2a}$ and $R^{2b}$ are each independently hydrogen; fluoro; OH; $C_1$-$C_4$alkyl; $C_1$-$C_4$alkoxy; $C_3$-$C_6$cycloalkyl; 5-membered heteroaryl, having one or two N; cyano; —SO$_2$CH$_3$; —C(O)NHR$^{8a}$; —NHC(O)NHR$^{8a}$; wherein said alkyl, alkoxy, cycloalkyl and heteroaryl are optionally substituted by one, two, three or four $R^9$; wherein $R^9$ is OH, fluoro, methyl, ethyl, methoxy or ethoxy; or a pharmaceutically acceptable salt thereof.

In another embodiment, one of $R^{2a}$ or $R^{2b}$, taken together with the carbon to which they are bonded, and one of $R^{5a}$ or $R^{5b}$, form a cyclopropyl, cyclobutyl, cyclopentyl, cyclohexyl, tetrahydrofuran or phenyl, wherein each is optionally substituted with one, two, three or four $R^9$, wherein $R^9$ is OH, $CH_2F$, $CHF_2$, $CF_3$, $CH_2OH$; or a pharmaceutically acceptable salt thereof.

In a particular, embodiment, the invention comprises a compound of Formula Ia

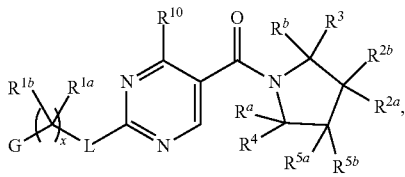

Ia wherein Z is —$(CR^{5a}R^{5b})_q$—; and q is 1;

$R^{2a}$ and $R^{2b}$ are each independently hydrogen, methyl, ethyl, propyl, isopropyl, methoxy or ethoxy, optionally substituted with $R^9$ wherein $R^9$ is OH; or $R^{2a}$ and $R^{2b}$, together with the carbon to which they are bonded, form a tetrahydrofuran, cyclobutane, cyclopentane, cyclohexane, oxetane, tetrahydropyran, pyrrolidine, azetidine, each of which is optionally substituted with one, two, three or four $R^9$; or $R^{2a}$ or $R^{2b}$, and one of $R^{5a}$ or $R^{5b}$, together with the respective carbons to which they are bonded, form a cyclopentane or cyclohexane, optionally substituted with one, two or three $R^9$; or a pharmaceutically acceptable salt of said compound or a tautomer of said compound or said salt.

In specific embodiments, the invention is directed to a compound of Formula IIa,

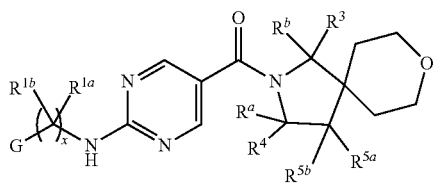

IIa wherein $R^{10}$ is hydrogen; and L is NH; G is pyrimidinyl or pyrazinyl; or a pharmaceutically acceptable salt thereof.

In a more specific embodiment, the invention is directed to a compound having the following absolute stereochemistry,

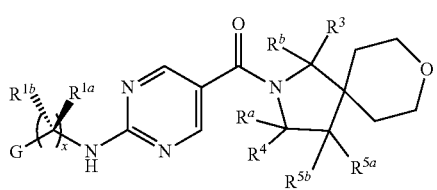

IIa wherein $R^{1a}$ is hydrogen; and $R^{1b}$ is methyl, ethyl, propyl, wherein each is optionally substituted with one, two or three fluoro; or a pharmaceutically acceptable salt thereof. And, in another embodiment, $R^a$, $R^b$, $R^3$, $R^4$, $R^{5a}$ and $R^{5b}$ are hydrogen; and x is 1; $R^{1b}$ is methyl or ethyl, optionally substituted with one, two or three fluoro, or a pharmaceutically acceptable salt thereof.

In another embodiment, the invention is directed to a compound of Formula Ib

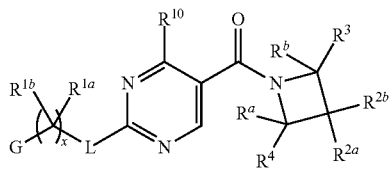

Ib wherein Z is a bond; or a pharmaceutically acceptable salt thereof. In particular, the invention is directed to compounds wherein $R^{2a}$ and $R^{2b}$ are each independently hydrogen, methyl, ethyl, propyl, isopropyl, methoxy or ethoxy, optionally substituted with $R^9$ wherein $R^9$ is OH; or $R^{2a}$ and $R^{2b}$ together with the carbon to which they are bonded form a tetrahydrofuran, cyclobutane, cyclopentane, cyclohexane, oxetane, tetrahydropyran, pyrrolidine, azetidine, each of which is optionally substituted with one, two, three or four $R^9$; or a pharmaceutically acceptable salt thereof.

In another aspect, the invention is directed to the compound of Formula IIb,

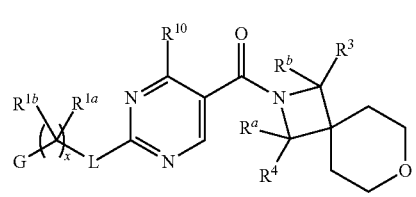

IIb wherein $R^{10}$ is hydrogen; and L is NH; or a pharmaceutically acceptable salt thereof. In a specific embodiment, the compound of Formula IIb has the absolute stereochemistry as depicted herein:

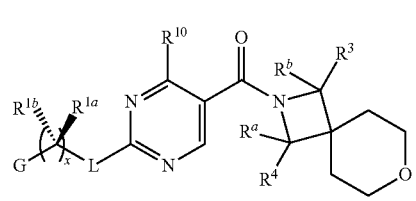

IIb wherein $R^{1a}$ is hydrogen; and $R^{1b}$ is methyl, ethyl or propyl, each of which is optionally substituted by one, two or three fluoro; or a pharmaceutically acceptable salt thereof. In another aspect, $R^a$, $R^b$, $R^3$ and $R^4$ are hydrogen; x is 1; $R^{1b}$ is methyl or ethyl, optionally substituted with one, two or three fluoro; and G is pyrimidinyl or pyrazinyl; or a pharmaceutically acceptable salt thereof.

In another embodiment, the invention is directed to a compound of Formula

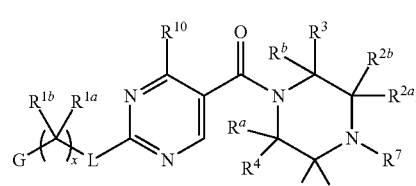

Ie wherein Z is —(CR$^{5a}$R$^{5b}$)$_m$—W—(CR$^{5a}$R$^{5b}$)$_n$—, W is NR$^7$, m is 1, and n is 0; or a pharmaceutically acceptable salt thereof. In another aspect, L is NH; and R$^{2a}$ or R$^{2b}$ and R$^7$, together with the respective atoms to which they are bonded form a -(4- to 12-membered heterocycloalkyl), having one or two heteroatoms selected from N or O, wherein said heterocycloalkyl is optionally substituted with one, two, three or four R$^9$; or a pharmaceutically acceptable salt thereof. In another aspect, R$^a$, R$^b$, R$^3$, R$^4$, R$^{5a}$ and R$^{5b}$ are hydrogen and the heterocycloalkyl formed is a pyrrole; or a pharmaceutically acceptable salt thereof. Yet another aspect of the invention is the compound of Formula IIe,

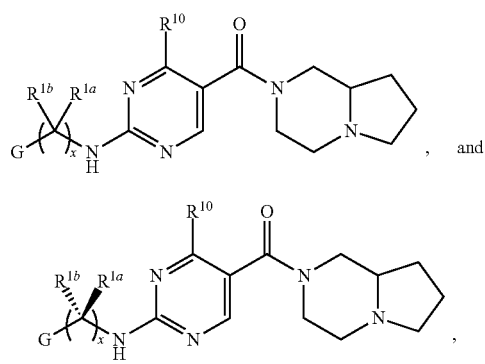

wherein R$^{1a}$ is hydrogen; and R$^{1b}$ is methyl, ethyl, propyl, each of which is optionally substituted by one, two or three fluoro; or a pharmaceutically acceptable salt thereof. In a particular aspect, G is pyrimidinyl or pyrazinyl, or a pharmaceutically acceptable salt thereof.

In another embodiment, the invention is directed to a compound of Formula Ic

Ic

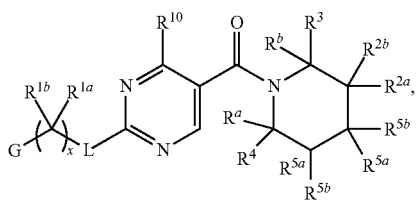

wherein Z is —(CR$^{5a}$R$^{5b}$)$_q$—; and q is 2;

R$^{5a}$ and R$^{5b}$ are each independently hydrogen, OH, fluoro, cyano, C$_1$-C$_4$alkyl, C$_1$-C$_4$alkoxy, cyclopropyl, cyclobutyl, cyclopentyl, oxazolidinone, —(CR$^{6a}$R$^{6b}$)$_t$C(O)NH$_2$, optionally substituted with one, two, three or four R$^9$; or R$^{5a}$ and R$^{5b}$ taken together with the carbon to which they are bonded form a oxetane, tetrahydrofuran, tetrahydropyran, oxazolidinone, cyclopentane, cyclohexane, cyclobutane, cyclopropane, wherein said cycloalkyl or heterocycloalkyl are optionally substituted with one, two, three or four R$^9$;

R$^9$ is fluoro, OH or C$_1$-C$_4$alkoxy, and t is 0 or 1;

or a pharmaceutically acceptable salt thereof.

In a particular aspect of the invention, R$^a$, R$^b$, R$^3$, R$^4$, R$^{5a}$ and R$^{5b}$ are hydrogen and the heterocycloalkyl formed is a pyrrole; and L is NH; or a pharmaceutically acceptable salt thereof. In a more specific aspect, the compound of Formula IIc is IIc

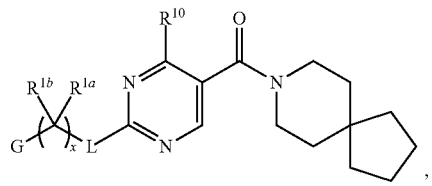

wherein G is pyrimidinyl or pyrazinyl; or a pharmaceutically acceptable salt thereof. In particular, the invention is directed to a compound having the absolute stereochemistry of, IIc

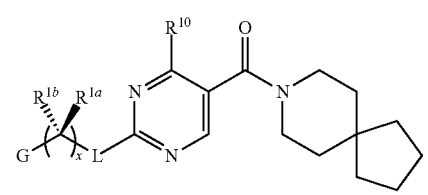

wherein R$^{1a}$ is hydrogen; and R$^{1b}$ is methyl, ethyl, propyl, each of which is optionally substituted with one, two or three fluoro; or a pharmaceutically acceptable salt thereof.

Specific embodiments of the invention include the examples 1-205, as described herein, the specific enantiomers thereof, as well as the racemate mixtures.

Vanin-1 Indications

On the basis of what is known the in the state of the art literature and the pattern of Vanin-1 expression in human health and disease systems, the compounds of the invention are also useful in treating and/or preventing a disease or condition mediated by or otherwise associated with a Vanin-1 enzyme. The use of compounds of the invention may be useful in diseases where there is evidence of oxidative stress and/or Vanin-1 enzyme upregulation; the method comprising administering to a subject in need thereof an effective amount of a compound of the invention.

The disease may be, but not limited to, one of the following classes: auto-immune diseases, inflammatory diseases, allergic diseases, metabolic diseases, infection-based diseases, trauma or tissue-injury based diseases, fibrotic diseases, cardiovascular diseases, respiratory diseases, renal diseases, dermatological diseases, liver diseases, gastrointestinal diseases, oral diseases, pain and sensory diseases, and hematopoietic diseases.

Specific autoimmune diseases include, but are not limited to: rheumatoid arthritis, osteoarthritis, psoriasis, allergic dermatitis, systemic lupus erythematosus (and resulting complications), Sjögren's syndrome, multiple sclerosis, asthma, glomerular nephritis, inflammatory bowel disease, Crohn's disease, ankylosing spondylitis, Behçet's disease, lupus nephritis, scleroderma, systemic scleroderma, alopecia universalis, acute disseminated encephalomyelitis, antiphospholipid antibody syndrome, atrophic gastritis of pernicious anemia, autoimmune alopecia, autoimmune hepatitis, autoimmune encephalomyelitis, autoimmune thrombocytopenia, chronic hepatitis, Cogan's syndrome, endometriosis, Goodpasture's syndrome, Graves' disease, Guillain-Barré syndrome, Hashimoto's disease (or Hashimoto's thyroiditis), hidradentitis suppurativa, idiopathic thrombocytopenia purpura, interstitial cystitis, membranous glomerulopathy, morphea, polyarteritis nodosa, polymyositis, primary biliary cirrhosis, systemic sclerosis, temporal arteritis, thyroiditis, vasculitis, vitiglio, Wegner's granulomatosis, palmoplantar keratoderma, systemic-onset Juvenile Idiopathic Arthritis (SJIA), or an indication listed in a separate category herein.

Specific inflammatory diseases include, but are not limited to: chronic obstructive pulmonary diseases, airway hyper-responsiveness, cystic fibrosis, acute respiratory distress syndrome, sinusitis, rhinitis, gingivitis, atherosclerosis, chronic prostatitis, glomerular nephritis, ulcerative colitis, uveitis, periodontal disease, or an indication listed in a separate category herein.

Specific pain conditions include, but are not limited to: inflammatory pain, pain due to burns, interstitial cystitis, post-traumatic injury, pain associated with irritable bowel syndrome, gout, pain associated with any of the other indications listed within this specification, or an indication listed in a separate category herein.

Specific respiratory, airway and pulmonary conditions include, but are not limited to: asthma (which may encompass chronic, late, bronchial, allergic, intrinsic, extrinsic or dust), chronic obstructive pulmonary disease, idiopathic pulmonary fibrosis, pulmonary arterial hypertension, cystic fibrosis, interstitial lung disease, acute lung injury, sarcoidosis, allergic rhinitis, chronic cough, bronchitis, recurrent airway obstruction, emphysema, or bronchospasm, or an indication listed in a separate disease category herein.

Specific gastrointestinal (GI) disorders include, but are not limited to: Irritable Bowel Syndrome (IBS), Inflammatory Bowel Disease (IBD), biliary colic and other biliary disorders, renal colic, diarrhea-dominant IBS, pain associated with GI distension, ulcerative colitis, Crohn's Disease, irritable bowel syndrome, Celiac disease, proctitis, eosinophilic gastroenteritis, mastocytosis, or an indication listed in a separate disease category herein.

Specific allergic diseases include, but are not limited to: anaphylaxis, allergic rhinitis, allergic dermatitis, allergic urticaria, angioedema, allergic asthma, allergic reactions to: food, drugs, insect bites, pollen; or an indication listed in a separate disease category herein.

Specific infection-based diseases include, but are not limited to: sepsis, septic shock, viral diseases, malaria, Lyme disease, ocular infections, conjunctivitis, Whipple Disease, or an indication listed in a separate disease category herein.

Specific trauma and tissue injury-based conditions include, but are not limited to: Renal glomerular damage, reperfusion injury (for example to heart, kidney, lung), spinal cord injury, tissue scarring, tissue adhesion, or an indication listed in a separate disease category herein.

Specific fibrotic diseases include, but are not limited to: Idiopathic pulmonary fibrosis, liver fibrosis, renal fibrosis, or an indication listed in a separate disease category herein.

Specific skin/dermatological diseases include, but are not limited to: psoriasis, atopic dermatitis, cutaneous lupus, acne, eczema, pruritus, scleroderma, Sweet Syndrome/neutrophilic dermatosis, neutrophilic panniculitis, acrodermatitis (form of pustular psoriasis), or an indication listed in a separate disease category herein.

Specific renal diseases include, but are not limited to: acute kidney injury (AKI) (sepsis-AKI, coronary artery bypass graft-AKI, cardiac surgery-AKI, non-cardiac surgery-AKI, transplant surgery-AKI cisplatin-AKI, contrast/imaging agent induced-AKI), glomerulonephritis, IgA nephropathy, crescentic GN, lupus nephritis, HIV associated nephropathy, membraneous nephropathy, C3 glomerulopathy, ANCA vasculitis, diabetic nephropathy, nephrotic syndrome, hypertensive nephrosclerosis, focal segmental glomerulosclerosis, Alport syndrome, Fanconi, syndrome, crystal nephropathy, nephrotic syndrome, amyloidosis, glomerulonephritis in SJIA, or an indication listed in a separate disease category herein.

Specific liver diseases include, but are not limited to: liver fibrosis, liver cirrhosis, nonalcoholic steatohepatitis (NASH), or an indication listed in a separate disease category herein.

Specific oral diseases include, but are not limited to: gingivitis, periodontal disease or an indication listed in a separate disease category herein.

Specific metabolic diseases include, but are not limited to: Type 2 diabetes (and resulting complications), hyperlipidemia, non-alcoholic fatty liver disease, metabolic syndrome, insulin resistance, obesity, or an indication listed in a separate disease category herein.

Compounds of the current invention are also useful in the treatment of a proliferative disease selected from a benign or malignant tumor, solid tumor, carcinoma of the brain, kidney, liver, adrenal gland, bladder, breast, stomach, gastric tumors, ovaries, colon, rectum, prostate, pancreas, lung, vagina, cervix, testis, genitourinary tract, esophagus, larynx, skin, bone or thyroid, sarcoma, glioblastomas, neuroblastomas, gastrointestinal cancer, especially colon carcinoma or colorectal adenoma, an epidermal hyperproliferation, psoriasis, prostate hyperplasia, a neoplasia, a neoplasia of epithelial character, adenoma, adenocarcinoma, keratoacanthoma, epidermoid carcinoma, large cell carcinoma, nonsmall-cell lung carcinoma, a mammary carcinoma, follicular carcinoma, undifferentiated carcinoma, or an indication listed in a separate disease category herein.

Cardiovascular conditions include, but are not limited to coronary heart disease, acute coronary syndrome, ischaemic heart disease, post-myocardial infarction cardiac remodeling atrial fibrillation, myocardial and vascular fibrosis, vascular wall hypertrophy, endothelial thickening, adverse remodeling, stroke, and the like, or an indication listed in a separate disease category herein.

Cardiovascular complications of type 2 diabetes are associated with inflammation, accordingly, the compounds of the present invention may be used to treat diabetes and diabetic complications such as macrovascular disease, hyperglycemia, metabolic syndrome, impaired glucose tolerance, fatty liver disease, cataracts, diabetic neuropathy, diabetic nephropathy, diabetic retinopathy, obesity, dyslipidemia, hypertension, hyperinsulinemia, and insulin resistance syndrome, or an indication listed in a separate disease category herein.

Linkage of oxidative stress and inflammation to disease has been demonstrated in neuroinflammatory and neurodegenerative conditions. Therefore, the compounds of the present invention are particularly indicated for use in the treatment of neuroinflammatory and neurodegenerative conditions (i.e., disorders or diseases) in mammals including humans such as multiple sclerosis, Alzheimer's disease; Parkinson's disease; brain injury; stroke; cerebrovascular diseases; dementia, acute stress disorder, generalized anxiety disorder, social anxiety disorder, panic disorder, post-traumatic stress disorder and obsessive-compulsive disorder; depression, or an indication listed in a separate disease category herein.

Typically, a compound of the invention is administered in an amount effective to treat a condition as described herein. The compounds of the invention are administered by any suitable route in the form of a pharmaceutical composition adapted to such a route, and in a dose effective for the treatment intended. Therapeutically effective doses of the compounds required to treat the progress of the medical condition are readily ascertained by one of ordinary skill in the art using preclinical and clinical approaches familiar to the medicinal arts.

The term "pharmaceutically acceptable" means the substance or composition must be compatible, chemically and/or toxicologically, with the other ingredients comprising a formulation, and/or the mammal being treated therewith.

The term "therapeutically effective amount" means an amount of a compound of the present invention that (i) treats or prevents the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein. In particular, effective amounts of the compounds of the invention generally include any amount sufficient to detectably modulate vanin-1 activity, and in one embodiment inhibit vanin-1 enzyme, or to alleviate symptoms of diseases associated with vanin-1 activity, and in one embodiment those associated with inhibition of vanin-1 enzyme, or susceptible to vanin-1 activity modulation, in one embodiment inhibition of vanin-1 enzyme.

For example, with respect to the treatment of asthma, a therapeutically effective amount preferably refers to the amount of a therapeutic agent that increases peak air flow by at least 5%, preferably at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100%.%. In reference to the treatment of cancer, a therapeutically effective amount refers to that amount which has the effect of (1) reducing the size of the tumor, (2) inhibiting (that is, slowing to some extent, preferably stopping) tumor metastasis, (3) inhibiting to some extent (that is, slowing to some extent, preferably stopping) tumor growth or tumor invasiveness, and/or (4) relieving to some extent (or, preferably, eliminating) one or more signs or symptoms associated with the cancer.

The term "abnormal cell growth" as used herein, unless otherwise indicated, refers to cell growth that is independent of normal regulatory mechanisms (e.g., loss of contact inhibition). Abnormal cell growth may be benign (not cancerous), or malignant (cancerous).

As used herein "cancer" refers to any malignant and/or invasive growth or tumor caused by abnormal cell growth. As used herein "cancer" refers to solid tumors named for the type of cells that form them, or cancers of blood, bone marrow, or the lymphatic system. Examples of solid tumors include but not limited to sarcomas and carcinomas. Examples of cancers of the blood include but not limited to leukemias, lymphomas and myeloma. The term "cancer" includes but is not limited to a primary cancer that originates at a specific site in the body, a metastatic cancer that has spread from the place in which it started to other parts of the body, a recurrence from the original primary cancer after remission, and a second primary cancer that is a new primary cancer in a person with a history of previous cancer of different type from latter one.

The term "treating", as used herein, unless otherwise indicated, means reversing, alleviating, inhibiting the progress of, delaying the progression of, delaying the onset of, or preventing the disorder or condition to which such term applies, or one or more symptoms of such disorder or condition. The term "treatment", as used herein, unless otherwise indicated, refers to the act of treating as "treating" is defined immediately above. The term "treating" also includes adjuvant and neo-adjuvant treatment of a subject. For the avoidance of doubt, reference herein to "treatment" includes reference to curative, palliative and prophylactic treatment, and to the administration of a medicament for use in such treatment.

The compounds of the invention may be administered orally. Oral administration may involve swallowing, so that the compound enters the gastrointestinal tract, or buccal or sublingual administration may be employed, by which the compound enters the blood stream directly from the mouth.

In another embodiment, the compounds of the invention may also be administered directly into the blood stream, into muscle, or into an internal organ.

Suitable means for parenteral administration include intravenous, intraarterial, intraperitoneal, intrathecal, intraventricular, intraurethral, intrasternal, intracranial, intramuscular and subcutaneous. Suitable devices for parenteral administration include needle (including microneedle) injectors, needle-free injectors and infusion techniques.

In another embodiment, the compounds of the invention may also be administered topically to the skin or mucosa, that is, dermally or transdermally. In another embodiment, the compounds of the invention can also be administered intranasally or by inhalation. In another embodiment, the compounds of the invention may be administered rectally or vaginally. In another embodiment, the compounds of the invention may also be administered directly to the eye or ear.

The dosage regimen for the compounds and/or compositions containing the compounds is based on a variety of factors, including the type, age, weight, sex and medical condition of the patient; the severity of the condition; the route of administration; and the activity of the particular compound employed. Thus the dosage regimen may vary widely. Dosage levels of the order from about 0.01 mg to about 100 mg per kilogram of body weight per day are useful in the treatment of the above-indicated conditions. In one embodiment, the total daily dose of a compound of the invention (administered in single or divided doses) is typically from about 0.01 to about 100 mg/kg. In another embodiment, the total daily dose of the compound of the invention is from about 0.1 to about 50 mg/kg, and in another embodiment, from about 0.5 to about 30 mg/kg (i.e., mg compound of the invention per kg body weight). In one embodiment, dosing is from 0.01 to 10 mg/kg/day. In another embodiment, dosing is from 0.1 to 1.0 mg/kg/day. Dosage unit compositions may contain such amounts or submultiples thereof to make up the daily dose. In many instances, the administration of the compound will be repeated a plurality of times in a day (typically no greater than 4 times). Multiple doses per day typically may be used to increase the total daily dose, if desired.

For oral administration, the compositions may be provided in the form of tablets containing from about 0.01 mg to about 500 mg of the active ingredient, or in another embodiment, from about 1 mg to about 100 mg of active ingredient. Intravenously, doses may range from about 0.1 to about 10 mg/kg/minute during a constant rate infusion.

"Patient" or "subject" refers to mammals and include, but are not limited to, canine, feline, bovine, caprine, equine, ovine, porcine, rodents, lagomorphs, primates, and the like, and encompass mammals in utero. In one embodiment, humans are suitable subjects. Human subjects may be of either gender and at any stage of development. The term "subject" or "patient" as used herein means any mammalian patient or subject to which the compounds of the invention can be administered. In an exemplary embodiment of the present invention, to identify subject patients for treatment according to the methods of the invention, accepted screening methods are employed to determine risk factors associated with a targeted or suspected disease or condition or to determine the status of an existing disease or condition in a subject. These screening methods include, but are not limited to for example, conventional work-ups to determine risk factors that may be associated with the targeted or suspected disease or condition. These and other routine methods allow the clinician to select patients in need of therapy using the methods and compounds of the present invention.

As used herein, the term "inhibitor(s) of vanin-1 enzyme" refers to a compound that binds to the vanin-1 enzyme and decreases the resulting enzymatic activity.

As used herein, the term "modulate" as used herein, refers to encompasses either a decrease or an increase in activity or expression depending on the target molecule.

As used herein, the term "other therapeutic agents" as used herein, refers to any therapeutic agent that has been used, is currently used or is known to be useful for treating a disease or a disorder encompassed by the present invention.

As used herein, the term "$IC_{50}$" refers to an amount, concentration or dosage of a particular test compound that achieves a 50% inhibition of a maximal response in an assay that measures such response. The value depends on the assay used.

In another embodiment, the invention comprises the use of one or more compounds of the invention for the preparation of a medicament for the treatment of the conditions recited herein.

For the treatment of the conditions referred to above, the compound of the invention can be administered as compound per se. Alternatively, pharmaceutically acceptable salts are suitable for medical applications because of their greater aqueous solubility relative to the parent compound.

In another embodiment, the present invention comprises pharmaceutical compositions. Such pharmaceutical compositions comprise a compound of the invention presented with a pharmaceutically acceptable carrier. The carrier can be a solid, a liquid, or both, and may be formulated with the compound as a unit-dose composition, for example, a tablet, which can contain from 0.05% to 95% by weight of the active compounds. A compound of the invention may be coupled with suitable polymers as targetable drug carriers. Other pharmacologically active substances can also be present.

The compounds of the present invention may be administered by any suitable route, preferably in the form of a pharmaceutical composition adapted to such a route, and in a dose effective for the treatment intended. The active compounds and compositions, for example, may be administered orally, rectally, parenterally, or topically.

Oral administration of a solid dose form may be, for example, presented in discrete units, such as hard or soft capsules, pills, cachets, lozenges, or tablets, each containing a predetermined amount of at least one compound of the present invention. In another embodiment, the oral administration may be in a powder or granule form. In another embodiment, the oral dose form is sub-lingual, such as, for example, a lozenge. In such solid dosage forms, the compounds of Formula I are ordinarily combined with one or more adjuvants. Such capsules or tablets may contain a controlled-release formulation. In the case of capsules, tablets, and pills, the dosage forms also may comprise buffering agents or may be prepared with enteric coatings.

In another embodiment, oral administration may be in a liquid dose form. Liquid dosage forms for oral administration include, for example, pharmaceutically acceptable emulsions, solutions, suspensions, syrups, and elixirs containing inert diluents commonly used in the art (e.g., water). Such compositions also may comprise adjuvants, such as wetting, emulsifying, suspending, flavoring (e.g., sweetening), and/or perfuming agents.

In another embodiment, the present invention comprises a parenteral dose form. "Parenteral administration" includes, for example, subcutaneous injections, intravenous injections, intraperitoneal injections, intramuscular injections, intrasternal injections, and infusion. Injectable preparations (e.g., sterile injectable aqueous or oleaginous suspensions) may be formulated according to the known art using suitable dispersing, wetting agents, and/or suspending agents.

In another embodiment, the present invention comprises a topical dose form. "Topical administration" includes, for example, transdermal administration, such as via transdermal patches or iontophoresis devices, intraocular administration, or intranasal or inhalation administration. Compositions for topical administration also include, for example, topical gels, sprays, ointments, and creams. A topical formulation may include a compound that enhances absorption or penetration of the active ingredient through the skin or other affected areas. When the compounds of this invention are administered by a transdermal device, administration will be accomplished using a patch either of the reservoir and porous membrane type or of a solid matrix variety. Typical formulations for this purpose include gels, hydrogels, lotions, solutions, creams, ointments, dusting powders, dressings, foams, films, skin patches, wafers, implants, sponges, fibers, bandages and microemulsions. Liposomes may also be used. Typical carriers include alcohol, water, mineral oil, liquid petrolatum, white petrolatum, glycerin, polyethylene glycol and propylene glycol. Penetration enhancers may be incorporated; see, for example, J. Pharm. Sci., 88(10), 955-958, by Finnin and Morgan (October 1999).

Formulations suitable for topical administration to the eye include, for example, eye drops wherein the compound of this invention is dissolved or suspended in a suitable carrier. A typical formulation suitable for ocular or aural administration may be in the form of drops of a micronized suspension or solution in isotonic, pH-adjusted, sterile saline. Other formulations suitable for ocular and aural administration include ointments, biodegradable (e.g., absorbable gel sponges, collagen) and non-biodegradable (e.g., silicone) implants, wafers, lenses and particulate or vesicular systems, such as niosomes or liposomes. A polymer such as cross-linked polyacrylic acid, polyvinyl alcohol, hyaluronic acid, a cellulosic polymer, for example, hydroxypropyl methyl cellulose, hydroxyethyl cellulose, or methyl cellulose, or a heteropolysaccharide polymer, for example, gelan gum, may be incorporated together with a preservative, such as benzalkonium chloride. Such formulations may also be delivered by iontophoresis.

For intranasal administration or administration by inhalation, the active compounds of the invention are conveniently delivered in the form of a solution or suspension from a pump spray container that is squeezed or pumped by the patient or as an aerosol spray presentation from a pressurized container or a nebulizer, with the use of a suitable propellant. Formulations suitable for intranasal administration are typically administered in the form of a dry powder (either alone, as a mixture, for example, in a dry blend with lactose, or as a mixed component particle, for example, mixed with phospholipids, such as phosphatidylcholine) from a dry powder inhaler or as an aerosol spray from a pressurized container, pump, spray, atomizer (preferably an atomizer using electrohydrodynamics to produce a fine mist), or nebulizer, with or without the use of a suitable propellant, such as 1,1,1,2-tetrafluoroethane or 1,1,1,2,3,3,3-heptafluoropropane. For intranasal use, the powder may comprise a bioadhesive agent, for example, chitosan or cyclodextrin.

In another embodiment, the present invention comprises a rectal dose form. Such rectal dose form may be in the form of, for example, a suppository. Cocoa butter is a traditional suppository base, but various alternatives may be used as appropriate.

Other carrier materials and modes of administration known in the pharmaceutical art may also be used. Pharmaceutical compositions of the invention may be prepared by any of the well-known techniques of pharmacy, such as effective formulation and administration procedures. The above considerations in regard to effective formulations and administration procedures are well known in the art and are described in standard textbooks. Formulation of drugs is discussed in, for example, Remington: *The Science and Practice of Pharmacy*, Mack Publishing Company, Easton, Pa., 21st Edition (2005); Liberman et al., Eds., Pharmaceutical Dosage Forms, Marcel Decker, New York, N.Y., 1980; and Kibbe et al., Eds., Handbook of Pharmaceutical Excipients ($3^{rd}$ Ed.), American Pharmaceutical Association, Washington, 1999. These articles are incorporated herein by reference.

The phrase "pharmaceutically acceptable carrier" as used herein means a pharmaceutically-acceptable material, composition or vehicle, such as a liquid or solid filler, diluent, excipient, solvent or encapsulating material, involved in carrying or transporting the subject agent from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations. A physiologically acceptable carrier should not cause significant irritation to an organism and does not abrogate the biological activity and properties of the administered compound.

An "excipient" refers to an inert substance added to a pharmacological composition to further facilitate administration of a compound. Examples of excipients include but are not limited to calcium carbonate, calcium phosphate, various sugars and types of starch, cellulose derivatives, gelatin, vegetable oils and polyethylene glycols.

The compounds of the present invention can be used, alone or in combination with other therapeutic agents, in the treatment of various conditions or disease states. The compound(s) of the present invention and other therapeutic agent(s) may be may be administered simultaneously (either in the same dosage form or in separate dosage forms) or sequentially. Simultaneous administration may be carried out by mixing the compounds prior to administration or by administering the compounds at the same point in time but at different anatomic sites or using different routes of administration.

The phrases "concurrent administration," "co-administration," "simultaneous administration," and "administered simultaneously" mean that the compounds are administered in combination.

The present invention includes the use of a combination of an Vanin-1 inhibitor compound as provided in the compound of Formula I and one or more additional pharmaceutically active agent(s). Accordingly, the present invention also includes pharmaceutical compositions comprising an amount of: (a) a first agent comprising a compound of Formula I or a pharmaceutically acceptable salt of the compound; (b) a second pharmaceutically active agent; and (c) a pharmaceutically acceptable carrier, vehicle or diluent.

The compounds of the present invention can be administered alone or in combination with one or more additional therapeutic agents. By "administered in combination" or "combination therapy" it is meant that a compound of the present invention and one or more additional therapeutic agents are administered concurrently to the mammal being treated. When administered in combination each component may be administered at the same time or sequentially in any order at different points in time. Thus, each component may be administered separately but sufficiently closely in time so as to provide the desired therapeutic effect. Thus, the methods of prevention and treatment described herein include use of combination agents.

The combination agents are administered to a mammal, including a human, in a therapeutically effective amount. By "therapeutically effective amount" it is meant an amount of a compound of the present invention that, when administered alone or in combination with an additional therapeutic agent to a mammal, is effective to treat the desired disease/condition e.g., inflammatory condition such as systemic lupus erythematosus. See also, T. Koutsokeras and T. Healy, Systemic lupus erythematosus and lupus nephritis, *Nat Rev Drug Discov*, 2014, 13(3), 173-174, for therapeutic agents useful treating lupus.

Combination Therapies

In particular, it is contemplated that the compounds of the invention may be administered with the following therapeutic agents:

Non-steroidal anti-inflammatory drugs (NSAIDs), including but not limited to, non-selective COX1/2 inhibitors such as piroxicam, naproxen, flubiprofen, fenoprofen, ketoprofen, ibuprofen, etodolac (Lodine), mefanamic acid, sulindac, apazone, pyrazolones (such as phenylbutazone), salicylates (such as aspirin); selective COX2 inhibitors such as: celecoxib, rofecoxib, etoricoxib, valdecoxib, meloxicam;

Immunomodulatory and/or anti-inflammatory agents, including but not limited to, methotrexate, leflunomide, ciclesonide chloroquine, hydroxychloroquine, d-penicillamine, auranofin, sulfasalazine, sodium aurothiomalate, cyclosporine, azathioprine, cromolyn, hydroxycarbamide, retinoids, fumarates (such as monomethyl and dimethyl fumarate), glatiramer acetate, mitoxantrone, teriflunomide, suplatast tosilate, mycophenolate mofetil and cyclophosphamide, laquinimod, voclosporin, PUR-118, AMG 357, AMG 811, BCT197;

Antimalarials, including but not limited to, hydroxychloroquine (Plaquenil) and chloroquine (Aralen), cyclophosphamide (Cytoxan), methotrexate (Rheumatrex), azathioprine (Imuran), mesalamine (Asacol) and sulfasalazine (Azulfidine):

Antibiotics, including but not limited to, Flagyl or ciprofloxacin;

Anti-TNFα agents, including but not limited to, infliximab, adalimumab, certolizumab pegol, golimumab and etanercept;

Anti-CD20 agents, including but not limited to, rituximab, ocrelizumab, ofatumumab and PF-05280586;

Antidiarrheals, such as diphenoxylate (Lomotil) and loperamide (Imodium);

Bile acid binding agents, such as cholestyramine, alosetron (Lotronex) and ubiprostone (Amitiza);

Laxatives, such as Milk of Magnesia, polyethylene glycol (MiraLax), Dulcolax, Correctol and Senokot, and anticholinergics or antispasmodics such as dicyclomine (Bentyl);

T lymphocyte activation inhibitors, including but not limited to, abatacept;

Glucocorticoid receptor modulators that may be dosed orally, by inhalation, by injection, topically, rectally, by ocular delivery, including but not limited to, betamethasone, prednisone, hydrocortisone, prednisolone, flunisolide, triamcinoline acetonide, beclomethasone, dipropionate, budesonide, fluticasone propionate, ciclesonide, mometasone furoate, fluocinonide, desoximetasone, methylprednisolone or PF-04171327;

Aminosalicyic acid derivatives, including but not limited to, sulfasalazine and mesalazine;

Anti integrin agents, including but not limited to, natalizumab, vedolizumab, PF-00547659, etrolizumab;

α1- or α2-adrenergic agonist agents including but not limited to: propylhexidrine, phenylephrine, phenylpropanolamine, pseudoephedrine or naphazoline hydrochloride, oxymethazoline hydrochloride, tetrahydrozoline hydrochloride, xylometazoline hydrochloride or ethylnorepinephrine hydrochloride;

β-adrenergic agonists, including but not limited to, metaproterenol, isoprotenerol, isoprenaline, albuterol, salbutamol, formoterol, salmeterol, terbutaline, orciprenaline, botolterol mesylate, pirbuterol;

Anticholinergic agents, including but not limited to, ipratropium bromide, tiotropium bromide, oxitropium bromide, aclindinium bromide, glycopyrrolate, pirenzipine or telenzepine; Inhaled long acting beta-agonists, long acting muscarinic antagonists and long acting corticosteroids, including but not limited, to those included in the following reference: Y. Mushtaq, The COPD pipeline, *Nat Rev Drug Discov,* 2014, 13(4), 253-254. http://dx.doi.orq/10.1038/nrd425;

Leukotriene pathway modulators, including but not limited to, 5-LO Inhibitors (such as zileuton), FLAP antagonists (such as veliflapon, fiboflapon), LTD4 antagonists (such as montelukast, zafirlukast or pranlukast;

H1 receptor antagonists, including but not limited to, cetirizine, loratidine, desloratidine, fexofenadine, astemizole, azelastine or chlorpheniramine;

PDE4 inhibitors, including but not limited to, apremilast, roflumilast or AN2728;

Vitamin D receptor modulators, including but not limited to, paricalcitol;

Nrf2 pathway activators, including but not limited to, fumarates, sulfurophane and bardoxolone methyl;

Modulators of the RAR-related orphan receptor (ROR) family, in particular RORg;

Modulator and/or antagonists of the chemokine receptors, including but not limited to, CCR2 antagonists (such as CCX140, BMS-741672, PF-4634817, CCX-872, NOX-E36), CCR2/5 antagonists (such as PF-4634817), CCR9 (such as vercirnon, CCX507), CCR1 modulators, CCR4 modulators, CCR5 modulators, CCR6 modulators, CXCR6 modulators, CXCR7 modulators) and CXCR2 modulators (such as danirixin, AZD5069);

Prostaglandins, including but not limited to, prostacyclin;

PDE5 inhibitors, including but not limited to, sildenafil, PF-489791, vardenafil and tadalafil;

Endothelin receptor antagonists, including but not limited to, bosentan, ambrisentan, sparsentan, atrasentan, zibotentan and macitentan;

Soluble guanylate cyclase activators, including but not limited to, riociguat;

Interferons, including but not limited to, interferon beta-1a interferon beta-1b;

Sphingosine 1-phosphate receptor modulators, including but not limited to, fingolimod, ponesimod;

Inhibitors of the complement pathway, including but not limited to, C5aR antagonists (such as CCX168, PMX-53, NN8210), $C_5$ inhibitors (such as eculizumab), inhibitors of complement factors B and D, inhibitors of MASP2 (such as OMS-721) and ARC-1905;

Inhibitors of Janus kinases (one of more of JAK1, JAK2, JAK3, TYK2), including but not limited to, decernotinib, cerdulatinib, JTE-052, ruxolitinib, tofacitnib, Baricitinib, Peficitinib, GLPG-0634, INCB-47986, INCB-039110, PF-04965842, XL-019, ABT-494, R-348, GSK-2586184, AC-410, BMS-911543, PF-06651600, and PF-06263276;

Inhibitors of other anti-inflammatory or immunomodulatory kinases, including but not limited to, spleen tyrosine kinase (SYK) inhibitors, p38 MAP kinase inhibitors (such as PF-3715455, PH-797804, AZD-7624, AKP-001, UR-13870, FX-005, semapimod, pexmetinib, ARRY-797, RV-568, dilmapimod, ralimetinib), PI3K inhibitors (such as GSK-2126458, pilaralisib, GSK-2269557), PI3 Kg and/or PI3Kd inhibitors (such as CAL-101/GS-1101, duvelisib), JNK inhibitors, ERK1 and/or 2 inhibitors, IKKb inhibitors, BTK inhibitors, ITK inhibitors, ASK1 inhibitors (such as GS-4997), PKC inhibitors (such as sotrastaurin), TrkA antagonists (such as CT-327), MEK1 inhibitors (such as E6201);

Antioxidants, including but not limited to, myeloperoxidase inhibitors (such as AZD-3241), NOX4 and other NOX enzymes (such as GKT-137831) and N-acetyl cysteine;

Inhibitors of IL5, including but not limited to, mepolizumab, reslizumab and benralizumab;

Inhibitors of IL4, including but not limited to, pascolizumab, altrakincept and pitrakinra;

Inhibitors of IL13, including but not limited to, tralokinumab, anrukinzumab and lebrikizumab;

Anti-IL6 agents, including but not limited to, tocilizumab, olokizumab, siltuximab, PF-4236921 and sirukumab;

Inhibitors/Antagonists of IL17/IL17R, including but not limited to, secukinumab, RG-7624, brodalumab and ixekizumab;

Antagonists of IL12 and/or IL23, including but not limited to, tildrakizumab, guselkumab, MEDI2070 and AMG 139;

Inhibitors of IL33, including but not limited to, AMG 282;

Inhibitors of IL9, including but not limited to, MEDI-528;

Inhibitors of GM-CSF, including but not limited to, MT203;

Anti CD4 agents, including but not limited to, tregalizumab and rigerimod;

CRTH2 antagonists, including but not limited to, AZD-1981;

Inhibitors of B lymphocyte stimulator (BLYS; also known as BAFF), a protein that is often increased in patients with SLE, including but not limited to, belimumab, tabalumab, blisibimod, and atacicept;

CD22-specific monoclonal antibodies, including but not limited to, epratuzumab;

Inhibitors of interferon-α, including but not limited to, sifalimumab and rontalizumab;

Inhibitor of type I interferon receptors, including but not limited to, MEDI-546;

FcγRIIB agonists, including but not limited to, SM-101;

Modified and/or recombinant versions of Heat Shock Protein 10 (Hsp10, also known as Chaperonin 10 or EPF), including but not limited to, INV-103;

Inhibitors of the TNF superfamily receptor 12A (TWEAK receptor), including but not limited to, BIIB-023, enavatuzumab, and RG-7212;

Inhibitors of xanthine oxidase, including but not limited to, allopurinol, benzbromarone, febuxostat, topiroxostat, tisopurine and inositols;

Inhibitors of URAT1 (also known as SLC22A12), including but not limited to, lesinurad, RDEA 3170, UR1102 and levotofispam;

Inhibitors of toll-like receptors (TLRs), including but not limited to, one or more of TLR7, TLR8, TLR9 (such as IMO-8400, IMO-3100, DV-1179), TLR2 and/or TLR 4 (such as VB-201, OPN-305);

Agonists of TLRs, including but not limited to, TLR7 (such as GSK2245035, AZD8848), TLR9 (such as AZD1419);

Activators SIRT1, including but not limited to, SRT2104;

A3 receptor agonists, including but not limited to, CF101;

Other agents of use of the treatment of psoriasis, including but not limited to, IDP-118, LAS41004, LEO 80185, LEO 90100, PH-10, WBI-1001, CNT01959, BT-061, cimzia, ustekinumab, MK-3222/SCH 900222, ACT-128800, AEB071, aiitretinoin, ASP015K, Apo805K1, BMS-582949, FP187, hectoral (doxercalciferol), LEO 22811, Ly3009104 (INCB28050), calcipotriene foam (STF 115469), tofacitinib (CP-690,550), M518101 and CycloPsorb™;

Antifibrotic agents, including but not limited to: pirfenidone, inhibitors of LOXL2 (such as Simtuzumab), FT-011, modulators of epiregulin and/or TGFβ (such as LY-3016859), modulators of TGFβ (such as LY-2382770, fresolimumab);

Prolyl hydroxylase inhibitors, including but not limited to, GSK1278863, FG-2216, ASP-1517/FG-4592, AKB-6548, JTZ-951, BAY-85-3934 and DS-1093;

Inhibitors of granulocyte macrophage colony-stimulating factor, including but not limited to, GSK3196165 (MOR103), PD-0360324 and mavrilimumab;

Inhibitors of MAdCAM and/or other cell adhesion molecules, including but not limited to, PF-00547659;

Inhibitors of connective tissue growth factor (CTGF), including but not limited to, PF-06473871; Inhibitors of cathepsin C, including but not limited to, GSK2793660;

Inhibitors of soluble epoxide hydrolase, including but not limited to, GSK2269557;

Inhibitors of the TNFR1 associated death domain protein, including but not limited to, GSK2862277;

Anti-CD19 agents, including but not limited to, MEDI-551 and AMG 729;

Anti-B7RP1 agents/inhibitors of ICOS ligand, including but not limited to, MED15872 and AMG-557;

Inhibitors of thymic stromal lymphoprotein, including but not limited to, AMG157;

Inhibitors of IL2, including but not limited to, daclizumab;

Checkpoint inhibitors, including but not limited to those which target CTLA4, PD-1, PD-L1, including but not limited to Ipilimumab, tremelimumab, nivolumab, pembrolizumab, avelumab, Inhibitors of Leucine rich repeat neuronal protein 6A, including but not limited to, Anti-Lingo (Biogen);

Inhibitors of integrins, including but not limited to, alpha-V/beta-6 (STX-100) and alpha-V/beta-3 (VPI-2690B);

Anti-CD40L agents, including but not limited to, CDP-7657;

Modulators of the dopamine D3 receptor, including but not limited to, ABT-614;

Inhibitors and/or modulators of galectin-3, including but not limited to, GCS-100 and GR-MD-02;

Agents for treating diabetic nephropathy, including but not limited to, DA-9801 and ASP-8232;

Agents for treating acute kidney injury, including but not limited to, THR-184, TRC-160334, NX-001, EA-230, ABT-719, CMX-2043, BB-3 and MTP-131;

Modulators of inflammasomes, including but not limited to, inhibitors of NLRP3;

Modulators of bromodomains, including but not limited to, BRD4;

Modulators of short-chain fatty acid receptors, including but not limited to, GPR43, GPR109; and Inhibitors of TRP channels, including but not limited to, TRPA1, TRPC3, TRPC5, TRPC6 and TRPC6.

Additional therapeutic agents include anti-coagulant or coagulation inhibitory agents, anti-platelet or platelet inhibitory agents, thrombin inhibitors, thrombolytic or fibrinolytic agents, anti-arrhythmic agents, anti-hypertensive agents, calcium channel blockers (L-type and T-type), cardiac glycosides, diuretics, mineralocorticoid receptor antagonists, NO donating agents such as organonitrates, NO promoting agents such as phosphodiesterase inhibitors, cholesterol/lipid lowering agents and lipid profile therapies, anti-diabetic agents, anti-depressants, anti-inflammatory agents (steroidal and non-steroidal), anti-osteoporosis agents, hormone replacement therapies, oral contraceptives, anti-obesity agents, anti-anxiety agents, anti-proliferative agents, anti-tumor agents, anti-ulcer and gastroesophageal reflux disease agents, growth hormone and/or growth hormone secretagogues, thyroid mimetics (including thyroid hormone receptor antagonist), anti-infective agents, anti-viral agents, anti-bacterial agents, and anti-fungal agents.

Agents used in an ICU setting are included, for example, dobutamine, dopamine, epinephrine, nitroglycerin, nitroprusside, etc.

Combination agents useful for treating vasculitis are included, for example, azathioprine, cyclophosphamide, mycophenolate, mofetil, rituximab, etc.

In another embodiment, the present invention provides a combination wherein the second agent is at least one agent selected from a factor Xa inhibitor, an anti-coagulant agent, an anti-platelet agent, a thrombin inhibiting agent, a thrombolytic agent, and a fibrinolytic agent. Exemplary factor Xa inhibitors include apixaban and rivaroxaban. Examples of suitable anti-coagulants for use in combination with the compounds of the present invention include heparins (e.g., unfractioned and low molecular weight heparins such as enoxaparin and dalteparin).

In another embodiment the second agent is at least one agent selected from warfarin, unfractionated heparin, low molecular weight heparin, synthetic pentasaccharide, hirudin, argatrobanas, aspirin, ibuprofen, naproxen, sulindac, indomethacin, mefenamate, droxicam, diclofenac, sulfinpyrazone, piroxicam, ticlopidine, clopidogrel, tirofiban, eptifibatide, abciximab, melagatran, disulfatohirudin, tissue plasminogen activator, modified tissue plasminogen activator, anistreplase, urokinase, and streptokinase.

In another embodiment, the agent is at least one anti-platelet agent. Especially preferred anti-platelet agents are aspirin and clopidogrel. The term anti-platelet agents (or platelet inhibitory agents), as used herein, denotes agents that inhibit platelet function, for example by inhibiting the aggregation, adhesion or granular secretion of platelets. Agents include, but are not limited to, the various known non-steroidal anti-inflammatory drugs (NSAIDS) such as aspirin, ibuprofen, naproxen, sulindac, indomethacin, mefenamate, droxicam, diclofenac, sulfinpyrazone, piroxicam, and pharmaceutically acceptable salts or prodrugs thereof. Of the NSAIDS, aspirin (acetylsalicyclic acid or ASA) and COX-2 inhibitors such as celecoxib or piroxicam are preferred. Other suitable platelet inhibitory agents include IIb/IIIa antagonists (e.g., tirofiban, eptifibatide, and abciximab), thromboxane-A2-receptor antagonists (e.g., ifetroban), thromboxane-A2-synthetase inhibitors, PDE3 inhibitors (e.g., Pletal, dipyridamole), and pharmaceutically acceptable salts or prodrugs thereof.

The term anti-platelet agents (or platelet inhibitory agents), as used herein, is also intended to include ADP (adenosine diphosphate) receptor antagonists, preferably antagonists of the purinergic receptors $P_2Y_1$ and $P_2Y_{12}$, with $P_2Y_{12}$ being even more preferred. Preferred $P_2Y_{12}$ receptor antagonists include ticagrelor, prasugrel, ticlopidine and clopidogrel, including pharmaceutically acceptable salts or prodrugs thereof. Clopidogrel is an even more preferred agent. Ticlopidine and clopidogrel are also preferred compounds since they are known to be gentle on the gastrointestinal tract in use.

The term thrombin inhibitors (or anti-thrombin agents), as used herein, denotes inhibitors of the serine protease thrombin. By inhibiting thrombin, various thrombin-mediated processes, such as thrombin-mediated platelet activation (that is, for example, the aggregation of platelets, and/or the granular secretion of plasminogen activator inhibitor-1 and/or serotonin) and/or fibrin formation are disrupted. A number of thrombin inhibitors are known to one of skill in the art and these inhibitors are contemplated to be used in combination with the present compounds. Such inhibitors include, but are not limited to, boroarginine derivatives, boropeptides, heparins, hirudin, argatroban, and melagatran, including pharmaceutically acceptable salts and prodrugs thereof. Boroarginine derivatives and boropeptides include N-acetyl and peptide derivatives of boronic acid, such as C-terminal alpha-aminoboronic acid derivatives of lysine, ornithine, arginine, homoarginine and corresponding isothiouronium analogs thereof. The term hirudin, as used herein, includes suitable derivatives or analogs of hirudin, referred to herein as hirulogs, such as disulfatohirudin. The term thrombolytics or fibrinolytic agents (or thrombolytics or fibrinolytics), as used herein, denote agents that lyse blood clots (thrombi). Such agents include tissue plasminogen activator (natural or recombinant) and modified forms thereof, anistreplase, urokinase, streptokinase, tenecteplase (TNK), lanoteplase (nPA), factor Vila inhibitors, PAl-1 inhibitors (i.e., inactivators of tissue plasminogen activator inhibitors), alpha2-antiplasmin inhibitors, and anisoylated plasminogen streptokinase activator complex, including pharmaceutically acceptable salts or prodrugs thereof. The term anistreplase, as used herein, refers to anisoylated plasminogen streptokinase activator complex, as described, for example, in EP 028,489, the disclosure of which is hereby incorporated herein by reference herein. The term urokinase, as used herein, is intended to denote both dual and single chain urokinase, the latter also being referred to herein as prourokinase. Examples of suitable anti-arrythmic agents include: Class I agents (such as propafenone); Class II agents (such as metoprolol, atenolol, carvadiol and propranolol); Class III agents (such as sotalol, dofetilide, amiodarone, azimilide and ibutilide); Class IV agents (such as ditiazem and verapamil); $K^+$ channel openers such as IAch inhibitors, and IKur inhibitors (e.g., compounds such as those disclosed in WO01/40231).

The compounds of the present invention may be used in combination with antihypertensive agents and such antihypertensive activity is readily determined by those skilled in the art according to standard assays (e.g., blood pressure measurements). Examples of suitable anti-hypertensive agents include: alpha adrenergic blockers; beta adrenergic blockers; calcium channel blockers (e.g., diltiazem, verapamil, nifedipine and amlodipine); vasodilators (e.g., hydralazine), diruetics (e.g., chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, torsemide, furosemide, musolimine, bumetanide, triamtrenene, amiloride, spironolactone); renin inhibitors; ACE inhibitors (e.g., captopril, zofenopril, fosinopril, enalapril, ceranopril, cilazopril, delapril, pentopril, quinapril, ramipril, lisinopril); AT-1 receptor antagonists (e.g., losartan, irbesartan, valsartan); ET receptor antagonists (e.g., sitaxsentan, atrasentan and compounds disclosed in U.S. Pat. Nos. 5,612,359 and 6,043,265); Dual ET/AII antagonist (e.g., compounds disclosed in WO 00/01389); neutral endopeptidase (NEP) inhibitors; vasopepsidase inhibitors (dual NEP-ACE inhibitors) (e.g., gemopatrilat and nitrates). An exemplary antianginal agent is ivabradine. Examples of suitable calcium channel blockers (L-type or T-type) include diltiazem, verapamil, nifedipine and amlodipine and mibefradil. Examples of suitable cardiac glycosides include digitalis and ouabain.

In one embodiment, a compound of the invention may be co-administered with one or more diuretics. Examples of suitable diuretics include (a) loop diuretics such as furosemide (such as LASIX™), torsemide (such as DEMADEX™), bemetanide (such as BUMEX™), and ethacrynic acid (such as EDECRIN™); (b) thiazide-type diuretics such as chlorothiazide (such as DIURIL™, ESIDRIX™ or HYDRODIURIL™), hydrochlorothiazide (such as MICROZIDE™ or ORETIC™), benzthiazide, hydroflumethiazide (such as SALURON™), bendroflumethiazide, methylchlorthiazide, polythiazide, trichlormethiazide, and indapamide (such as LOZOL™); (c) phthalimidine-type diuretics such as chlorthalidone (such as HYGROTON™), and metolazone (such as ZAROXOLYN™); (d) quinazoline-type diuretics such as quinethazone; and (e) potassium-sparing diuretics such as triamterene (such as DYRENIUM™), and amiloride (such as MIDAMOR™ or MODURETIC™). In another embodiment, a compound of the invention may be co-administered with a loop diuretic. In still another embodiment, the loop diuretic is selected from furosemide and torsemide. In still another embodiment, one or more compounds of the invention may be co-administered with furosemide. In still another embodiment, one or more compounds of the invention may be co-administered with torsemide which may optionally be a controlled or modified release form of torsemide.

In another embodiment, a compound of the invention may be co-administered with a thiazide-type diuretic. In still another embodiment, the thiazide-type diuretic is selected from the group consisting of chlorothiazide and hydrochlorothiazide. In still another embodiment, one or more compounds of the invention may be co-administered with chlorothiazide. In still another embodiment, one or more compounds of the invention may be co-administered with hydrochlorothiazide. In another embodiment, one or more compounds of the invention may be co-administered with a phthalimidine-type diuretic. In still another embodiment, the phthalimidine-type diuretic is chlorthalidone.

Examples of suitable combination mineralocorticoid receptor antagonists include spironolactone and eplerenone. Examples of suitable combination phosphodiesterase inhibitors include: PDE3 inhibitors (such as cilostazol); and PDE5 inhibitors (such as sildenafil).

The compounds of the present invention may be used in combination with cholesterol modulating agents (including cholesterol lowering agents) such as a lipase inhibitor, an HMG-CoA reductase inhibitor, an HMG-CoA synthase inhibitor, an HMG-CoA reductase gene expression inhibitor, an HMG-CoA synthase gene expression inhibitor, an MTP/Apo B secretion inhibitor, a CETP inhibitor, a bile acid absorption inhibitor, a cholesterol absorption inhibitor, a cholesterol synthesis inhibitor, a squalene synthetase inhibitor, a squalene epoxidase inhibitor, a squalene cyclase inhibitor, a combined squalene epoxidase/squalene cyclase inhibitor, a fibrate, niacin, an ion-exchange resin, an antioxidant, an ACAT inhibitor or a bile acid sequestrant or an agent such as mipomersen.

Examples of suitable cholesterol/lipid lowering agents and lipid profile therapies include: HMG-CoA reductase inhibitors (e.g., pravastatin, lovastatin, atorvastatin, simvastatin, fluvastatin, NK-104 (a.k.a. itavastatin, or nisvastatin or nisbastatin) and ZD-4522 (a.k.a. rosuvastatin, or atavastatin or visastatin)); squalene synthetase inhibitors; fibrates; bile acid sequestrants (such as questran); ACAT inhibitors; MTP inhibitors; lipooxygenase inhibitors; cholesterol absorption inhibitors; and cholesteryl ester transfer protein inhibitors.

Anti-inflammatory agents also include sPLA2 and IpPLA2 inhibitors (such as darapladib), 5 LO inhibitors (such as atrelueton) and IL-1 and IL-1 r antagonists (such as canakinumab).

Other atherosclerotic agents include agents that modulate the action of PCSK9, for example, called bococizumab.

Cardiovascular complications of type 2 diabetes are associated with deleterious levels of MPO, accordingly, the compounds of the present invention may be used in combination with anti-diabetic agents, particularly type 2 anti-diabetic agents. Examples of suitable anti-diabetic agents include (e.g. insulins, metfomin, DPPIV inhibitors, GLP-1 agonists, analogues and mimetics, SGLT1 and SGLT2 inhibitors) Suitable anti-diabetic agents include an acetyl-CoA carboxylase- (ACC) inhibitor such as those described in WO2009144554, WO2003072197, WO2009144555 and WO2008065508, a diacylglycerol O-acyltransferase 1 (DGAT-1) inhibitor, such as those described in WO09016462 or WO2010086820, AZD7687 or LCQ908, diacylglycerol O-acyltransferase 2 (DGAT-2) inhibitor, monoacylglycerol O-acyltransferase inhibitors, a PDE10 inhibitor, an AMPK activator, a sulfonylurea (e.g., acetohexamide, chlorpropamide, diabinese, glibenclamide, glipizide, glyburide, glimepiride, gliclazide, glipentide, gliquidone, glisolamide, tolazamide, and tolbutamide), a meglitinide, an α-amylase inhibitor (e.g., tendamistat, trestatin and AL-3688), an α-glucoside hydrolase inhibitor (e.g., acarbose), an α-glucosidase inhibitor (e.g., adiposine, camiglibose, emiglitate, miglitol, voglibose, pradimicin-Q, and salbostatin), a PPARγ agonist (e.g., balaglitazone, ciglitazone, darglitazone, englitazone, isaglitazone, pioglitazone and rosiglitazone), a PPAR a/γ agonist (e.g., CLX-0940, GW-1536, GW-1929, GW-2433, KRP-297, L-796449, LR-90, MK-0767 and SB-219994), a biguanide (e.g., metformin), a glucagon-like peptide 1 (GLP-1) modulator such as an agonist (e.g., exendin-3 and exendin-4), liraglutide, albiglutide, exenatide (Byetta®), albiglutide, lixisenatide, dulaglutide, semaglutide, NN-9924, TTP-054, a protein tyrosine phosphatase-1B (PTP-1B) inhibitor (e.g., trodusquemine, hyrtiosal extract, and compounds disclosed by Zhang, S., et al., Drug Discovery Today, 12(9/10), 373-381 (2007)), SIRT-1 inhibitor (e.g., resveratrol, GSK2245840 or GSK184072), a dipeptidyl peptidease IV (DPP-IV) inhibitor (e.g., those in WO2005116014, sitagliptin, vildagliptin, alogliptin, dutogliptin, linagliptin and saxagliptin), an insulin secreatagogue, a fatty acid oxidation inhibitor, an A2 antagonist, a c-jun amino-terminal kinase (JNK) inhibitor, glucokinase activators (GKa) such as those described in WO2010103437, WO2010103438, WO2010013161, WO2007122482, TTP-399, TTP-355, TTP-547, AZD1656, ARRY403, MK-0599, TAK-329, AZD5658 or GKM-001, insulin, an insulin mimetic, a glycogen phosphorylase inhibitor (e.g. GSK1362885), a VPAC2 receptor agonist, SGLT2 inhibitors, such as those described in E. C. Chao et al. Nature Reviews Drug Discovery 9, 551-559 (July 2010) including dapagliflozin, canagliflozin, empagliflozin, tofogliflozin (CSG452), ertugliflozin, ASP-1941, THR1474, TS-071, ISIS388626 and LX4211 as well as those in WO2010023594, a glucagon receptor modulator such as those described in Demong, D. E. et al. Annual Reports in Medicinal Chemistry 2008, 43, 119-137, GPR119 modulators, particularly agonists, such as those described in WO2010140092, WO2010128425, WO2010128414, WO2010106457, Jones, R. M. et al. in Medicinal Chemistry 2009, 44, 149-170 (e.g. MBX-2982, GSK1292263, APD597 and PSN821), FGF21 derivatives or analogs such as those described in Kharitonenkov, A. et al. et al., Current Opinion in Investigational Drugs 2009, 10(4)$_{359}$-364, TGR5 (also termed GPBAR1) receptor modulators, particularly agonists, such as those described in Zhong, M., Current Topics in Medicinal Chemistry, 2010, 10(4), 386-396 and INT777, GPR40 agonists, such as those described in Medina, J. C., Annual Reports in Medicinal Chemistry, 2008, 43, 75-85, including but not limited to TAK-875, GPR120 modulators, particularly agonists, high affinity nicotinic acid receptor (HM74A) activators, and SGLT1 inhibitors, such as GSK1614235. A further representative listing of anti-diabetic agents that can be combined with the compounds of the present invention can be found, for example, at page 28, line 35 through page 30, line 19 of WO2011005611. Preferred anti-diabetic agents are metformin and DPP-IV inhibitors (e.g., sitagliptin, vildagliptin, alogliptin, dutogliptin, linagliptin and saxagliptin). Other antidiabetic agents could include inhibitors or modulators of carnitine palmitoyl transferase enzymes, inhibitors of fructose 1,6-diphosphatase, inhibitors of aldose reductase, mineralocorticoid receptor inhibitors, inhibitors of TORC2, inhibitors of CCR2 and/or CCR5, inhibitors of PKC isoforms (e.g. PKCα, PKCβ, PKCγ), inhibitors of fatty acid synthetase, inhibitors of serine palmitoyl transferase, modulators of GPR81, GPR39, GPR43, GPR41, GPR105, Kv1.3, retinol binding protein 4, glucocorticoid receptor, somatostain receptors (e.g. SSTR1, SSTR2, SSTR3 and SSTR5), inhibitors or modulators of PDHK2 or PDHK4, inhibitors of MAP4K4, modulators of IL1 family including IL1beta, modulators of RXRalpha. In addition suitable anti-diabetic agents include mechanisms listed by Carpino, P. A., Goodwin, B. Expert Opin. Ther. Pat, 2010, 20(12), 1627-51.

Those skilled in the art will recognize that the compounds of this invention may also be used in conjunction with other cardiovascular or cerebrovascular treatments including PCI, stenting, drug eluting stents, stem cell therapy and medical devices such as implanted pacemakers, defibrillators, or cardiac resynchronization therapy.

The compounds of the present invention may be used in combination with neuroinflammatory and neurodegenerative agents in mammals. Examples of additional neuroinflammatory and neurodegenerative agents include antidepressants, antipsychotics, anti-pain agents, anti-Alzheimer's agents, and anti-anxiety agents.

Examples of particular classes of antidepressants that can be used in combination with the compounds of the invention include norepinephrine reuptake inhibitors, selective serotonin reuptake inhibitors (SSRIs), NK-1 receptor antagonists, monoamine oxidase inhibitors (MAOIs), reversible inhibitors of monoamine oxidase (RIMAs), serotonin and noradrenaline reuptake inhibitors (SNRIs), corticotropin releasing factor (CRF) antagonists, and atypical antidepressants. Suitable norepinephrine reuptake inhibitors include tertiary amine tricyclics and secondary amine tricyclics. Examples of suitable tertiary amine tricyclics and secondary amine tricyclics include amitriptyline, clomipramine, doxepin, imipramine, trimipramine, dothiepin, butriptyline, nortriptyline, protriptyline, amoxapine, desipramine and maprotiline. Examples of suitable SSRIs include fluoxetine, fluvoxamine, paroxetine, and sertraline. Examples of monoamine oxidase inhibitors include isocarboxazid, phenelzine, and tranylcyclopramine. Examples of suitable reversible inhibitors of monoamine oxidase include moclobemide. Examples of suitable SNRIs of use in the present invention include venlafaxine. Examples of suitable atypical antidepressants include bupropion, lithium, trazodone and viloxazine. Examples of anti-Alzheimer's agents include NMDA receptor antagonists such as memantine; and cholinesterase inhibitors such as donepezil and galantamine. Examples of suitable classes of anti-anxiety agents that can be used in combination with the compounds of the invention include benzodiazepines and serotonin 1A receptor (5-HT1A) agonists, and CRF antagonists. Suitable benzodiazepines include alprazolam, chlordiazepoxide, clonazepam, chlorazepate, diazepam, lorazepam, oxazepam, and prazepam. Suitable 5-HT1A receptor agonists include buspirone and ipsapirone. Suitable CRF antagonists include verucerfont. Suitable atypical antipsychotics include paliperidone, ziprasidone, risperidone, aripiprazole, olanzapine, and quetiapine. Suitable nicotine acetylcholine agonists include CP-601927 and varenicline. Anti-pain agents include pregabalin, gabapentin, clonidine, neostigmine, baclofen, midazolam, ketamine and ziconotide.

Accordingly, in one embodiment, the pharmaceutical combination comprises a therapeutically effective amount of a composition comprising:
a first compound, the first compound being a compound of Formula I or a pharmaceutically acceptable salt thereof;
a second compound being selected from an approved drug or a clinical candidate useful for the treatment of infectious or inflammatory diseases; and
an optional pharmaceutically acceptable carrier, vehicle or diluent.

In particular, the invention provides for a pharmaceutical combination comprising a therapeutically effective amount of a composition comprising:
a first compound, the first compound being a compound of Formula I or a pharmaceutically acceptable salt thereof; and
a second compound, the second compound being selected from the group consisting of antibodies or small molecules which include but are not limited to those that block the action of specific cytokines such as TNFa, IL12 and/or IL23, or inhibitors of leukocyte recruitment such as modulators of S1P receptors or integrin antagonists, or selective or non-selective inhibitors of the JAK kinases JAK1, JAK2, JAK3 and/or TYK2, inhibitors of leukocyte function such as PDE4 or SMAD7.

In a specific embodiment, the invention is directed to a pharmaceutical composition of a compound of Formula I wherein the second compound is selected from
(a) an anti-TNFa agent selected from infliximab, adalimumab, golimumab, and certolizumab pegol;
(b) an anti-IL-12 and/or IL-23 agent selected from ustekinumab;
(c) a modulator of S1P receptors selected from ozanimod;
(d) an integrin antagonist selected from vedolizumab, etrolizumab, and natalizumab;
(e) an inhibitor of JAK kinases selected from tofacitinib, filgotinib, PF-04965842, PF-06651600, and PF-06263276;
(f) a PDE4 inhibitor selected from apremilast; or
(g) a SMAD7 antisense oligonucleotides selected from mongersen.

Inasmuch as it may be desirable to administer a combination of active compounds, for example, for the purpose of treating a particular disease or condition, it is within the scope of the present invention that two or more pharmaceutical compositions, at least one of which comprises a compound of the invention, may conveniently be combined in the form of a kit suitable for co-administration of the compositions. Representative kits include at least one compound of the present invention and a package insert or other labeling including directions.

General Synthetic Schemes

Compounds of the present invention can be prepared in accordance with the procedures outlined herein, from commercially available starting materials, compounds known in the literature, or readily prepared intermediates, by employing standard synthetic methods and procedures known to those skilled in the art. Standard synthetic methods and procedures for the preparation of organic molecules and functional group transformations and manipulations can be readily obtained from the relevant scientific literature or from standard textbooks in the field. It will be appreciated that where typical or preferred process conditions (i.e., reaction temperatures, times, mole ratios of reactants, solvents, pressures, etc.) are given; other process conditions can also be used unless otherwise stated. Optimum reaction conditions can vary with the particular reactants or solvent used. Those skilled in the art will recognize that the nature and order of the synthetic steps presented can be varied for the purpose of optimizing the formation of the compounds described herein.

The processes described herein can be monitored according to any suitable method known in the art. For example, product formation can be monitored by spectroscopic means, such as nuclear magnetic resonance spectroscopy (e.g., $^1$H or $^{13}$C), infrared spectroscopy, spectrophotometry (e.g., UV-visible), mass spectrometry, or by chromatography such as high-performance liquid chromatograpy (HPLC), gas chromatography (GC), gel-permeation chromatography (GPC), or thin layer chromatography (TLC).

The reactions or the processes described herein can be carried out in suitable solvents, which can be readily selected by one skilled in the art. Suitable solvents typically are substantially nonreactive with the reactants, intermediates, and/or products at the temperatures at which the reactions are carried out, i.e., temperatures that can range from the solvent's freezing temperature to the solvent's boiling temperature. A given reaction can be carried out in one solvent or a mixture of more than one solvent. Depending on the particular reaction step, suitable solvents for a particular reaction step can be selected.

The routes below, including those mentioned in the Examples and Preparations, illustrate methods of synthesizing compounds of formula I. The skilled person will appreciate that the compounds of the invention, and intermediates thereof, may be made by methods other than those specifically described herein. One skilled in the art could, therefore, adapt the methods described herein, by synthetic methods known in the art. In particular, suitable guides to synthesis, functional group interconversions, use of protecting groups, and the like, include, for example: "Comprehensive Organic Transformations" by R C Larock, VCH Publishers Inc. (1989); Advanced Organic Chemistry" by J. March, Wiley Interscience (1985); "Designing Organic Synthesis" by S Warren, Wiley Interscience (1978); "Organic Synthesis—The Disconnection Approach" by S Warren, Wiley Interscience (1982); "Guidebook to Organic Synthesis" by RK Mackie and DM Smith, Longman (1982); "Protective Groups in Organic Synthesis" by TW Greene and PGM Wuts, John Wiley and Sons, Inc. (1999); and "Protecting Groups" by PJ, Kocienski, Georg Thieme Verlag (1994); and any updated versions of said standard works.

In addition, the skilled person will appreciate that it may be necessary or desirable at any stage in the synthesis of compounds of the invention to protect one or more sensitive groups, so as to prevent undesirable side reactions. In particular, it may be necessary or desirable to protect amino or carboxylic acid groups. The protecting groups used in the preparation of the compounds of the invention may be used in conventional manner. See, for example, those described in 'Greene's Protective Groups in Organic Synthesis' by Theodora W Greene and Peter G M Wuts, third edition, (John Wiley and Sons, 1999), in particular chapters 7 ("Protection for the Amino Group") and 5 ("Protection for the Carboxyl Group"), incorporated herein by reference, which also describes methods for the removal of such groups. In the general synthetic methods below, unless otherwise specified, the substituents are as defined above with reference to the compounds of formula I above.

Where ratios of solvents are given, the ratios are by volume.

The skilled person will appreciate that the experimental conditions set forth in the schemes that follow are illustrative of suitable conditions for effecting the transformations shown, and that it may be necessary or desirable to vary the precise conditions employed for the preparation of compounds of formula (I).

The derivatives of formula (I), exemplified herein, can be prepared by the procedures described in the general methods presented below or by routine modifications thereof. The present invention also encompasses any one or more of these processes for preparing the derivatives of formula (I), in addition to any novel intermediates used therein. The person skilled in the art will appreciate that the following reactions may be heated thermally or under microwave irradiation.

It will be further appreciated that it may be necessary or desirable to carry out the transformations in a different order from that described in the schemes, or to modify one or more of the transformations, to provide the desired compound of the invention.

According to a first process, compounds of formula (I), wherein L is N, may be prepared from compounds of formulae (IV) and (V), as illustrated by Scheme 1.

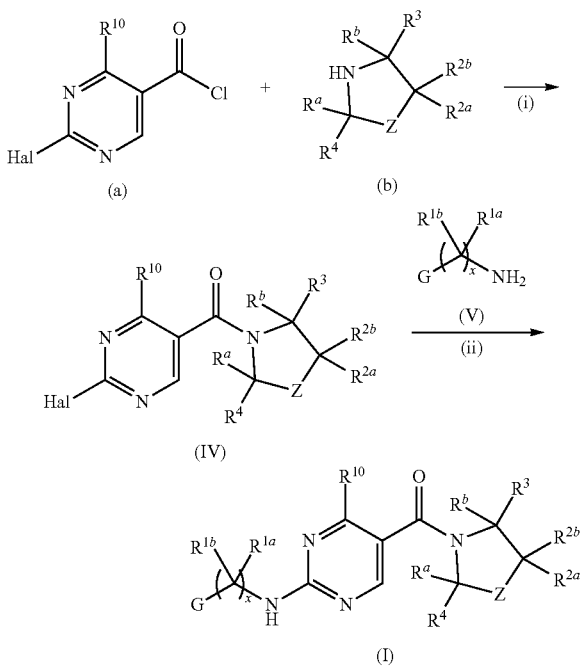

Hal = halogen, typically, Cl or F

Compounds of formulae (a), (b) and (V) are commercially available or may be synthesized by those skilled in the art according to the literature or preparations described herein.

Compounds of formula (IV) may be prepared from an acyl chloride of formula (a) and the amine of formula (b) according to process step (i), an amide bond formation step. Preferred conditions include the reaction in the presence of an organic base, such as triethylamine in THF or EtOAc, at elevated temperatures (60° C.).

Compounds of formula (I) may be prepared from compounds of formula (IV) and the amine of formula (V) according to process step (ii). Preferred conditions include the reaction of the amine of formula (V) with the halo compound of formula (IV) in the presence of a suitable organic base, such as DIPEA in a suitable aprotic solvent such DMF or NMP at elevated temperature e.g. 140° C.

Compounds of formula (IV) may alternatively be prepared from the acid of formula (VI) and the amine of formula (b) as illustrated in Scheme 2.

Scheme 2

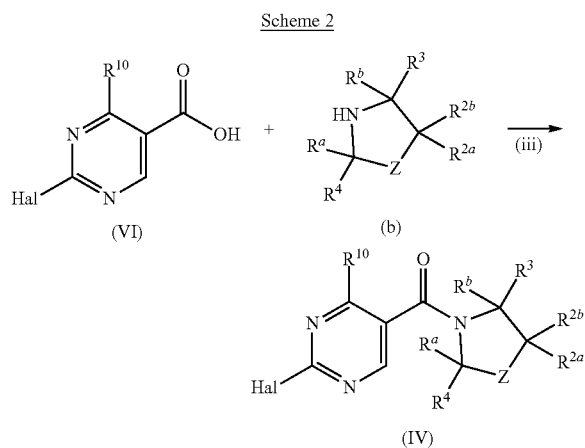

Hal = halogen, typically Cl or F

Compounds of formula (VI) are commercially available or may be synthesized by those skilled in the art according to the literature or preparations described herein.

Compounds of formula (IV) may be prepared from compounds of formula (VI) according to process step (iii), an amide bond formation step with amines of formula (b), wherein Z defined herein elsewhere, mediated by a suitable combination of amide bond coupling agent and organic base. Typical conditions comprise HATU or HBTU with triethylamine or DIPEA in DCM, DMF or DMA at room or elevated temperatures (e.g. about 80° C.), or using propylphosphonic anhydride (50% in EtOAc) in 2-MeTHF, THF or toluene with pyridine or DIPEA at elevated temperature e.g. about 60° C. Alternative conditions comprise treatment with phosphoryl trichloride in pyridine or with Ghosez's reagent in acetonitrile or dichloromethane at between −10° C. and reflux.

According to a second process, compounds of formula (I) may be prepared in an alternative sequence from compounds of formulae (b) and (VIII) as illustrated by Scheme 3.

Scheme 3

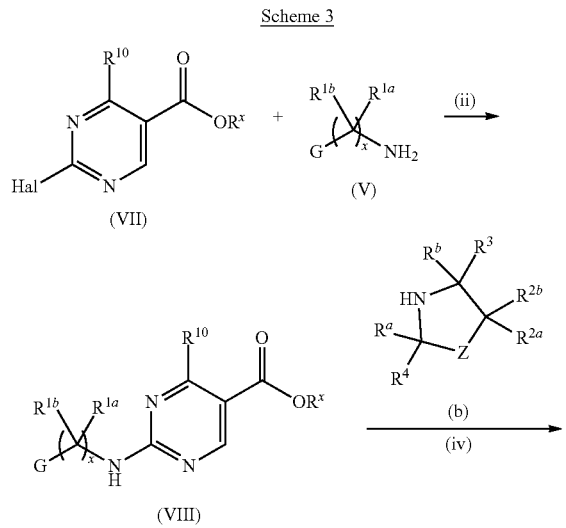

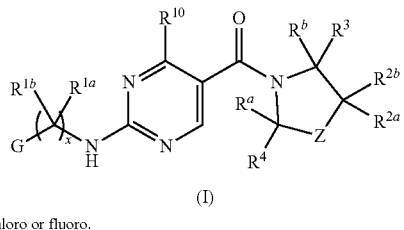

Hal = halogen, typically chloro or fluoro.

Compounds of formula (VIII) may be prepared from compounds of formula (VII), wherein $R^x$ is $C_1$-$C_4$, typically ethyl or methyl, and compounds of formula (V), wherein the amine of (V) is previously described as "L", according to process step (ii), as described in scheme 1. Preferred conditions include the reaction of the amine and halide in the presence of an organic base such as triethylamine or DIPEA in a solvent such as NMP under microwave irradiation at elevated temperatures eg 140° C. for up to 1 hr. Alternatively, the reaction of the amine and halide is conducted in the presence of an organic base, preferably DIPEA, in a suitable solvent, such as 2-propanol, dioxane, or THF, (optionally with DMSO as a co-solvent), at elevated temperatures, typically between 60 and 80° C.

Compounds of formula (I) may be prepared from compounds of formula (VIII) by treatment with an amine of formula (b) according to process step (iv). Preferred conditions are reaction in the presence of suitable coupling agent, typically TBD in a suitable aprotic solvent, such as DMF or NMP, at elevated temperature e.g. 50° C.

According to a third process, compounds of formula (I) may be prepared in an alternative sequence from compounds of formulae (IX) and (b) as illustrated by Scheme 4.

Scheme 4

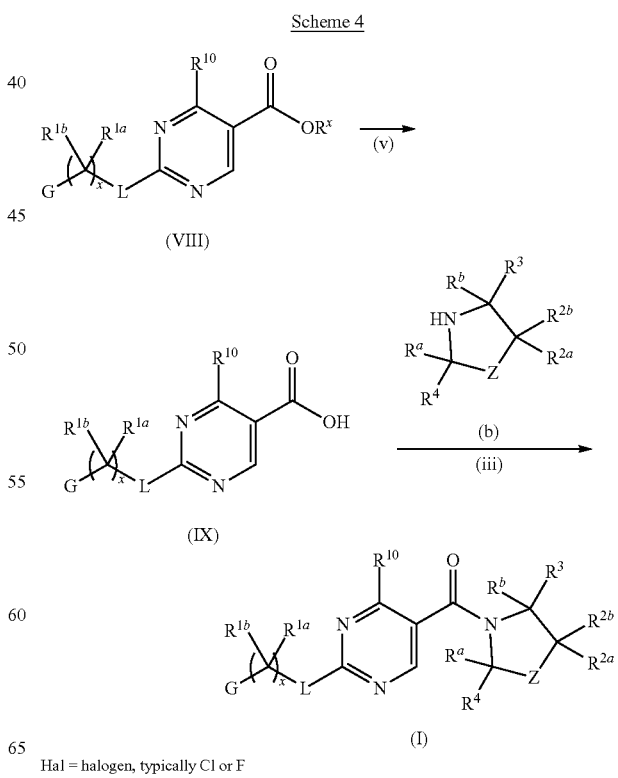

Hal = halogen, typically Cl or F

Compounds of formula (IX), wherein L is previously described herein, may be prepared from the ester of formula (VIII), wherein $R^x$ is $C_1$-$C_4$ alkyl, typically ethyl or methyl, according to process step (v), a hydrolysis step mediated by an inorganic base. Preferred conditions include aqueous lithium or sodium hydroxide in methanol or ethanol optionally with THF as a co-solvent between room temperature and 60° C.

Compounds of formula (I) may be prepared from compounds of formula (IX) according to process step (iii), an amide bond formation step with an amine of formula (b), wherein Z is previously described herein, mediated by a suitable combination of amide bond coupling agent and organic base, as described in Scheme 2.

Preferred conditions comprise HATU with triethylamine or DIPEA at elevated temperatures (e.g. about 60° C.), or using propylphosphonic anhydride in THF with DIPEA and triethylamine at an elevated temperature (e.g. about 60° C.).

According to a fourth process, compounds of formula (I) wherein L is O may be prepared from compounds of formula (IV), wherein Z is previously described herein, and an alcohol of formula (X) as illustrated by scheme 5.

Scheme 5

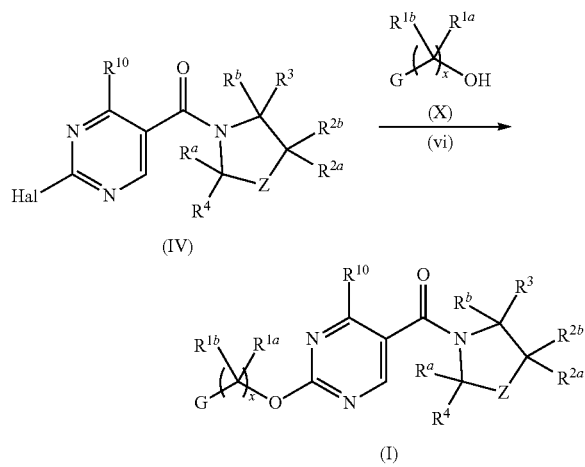

Hal = halogen, typically Cl or F

Compounds of formula (I) may be prepared from the compounds of formulae (IV) and (X) according to process step (vi). Typical conditions include treatment with a suitable non-nucleophilic base, such as LiHMDS in a suitable solvent such as DMF at temperatures below room temperature (e.g. 0° C.).

Scheme 6

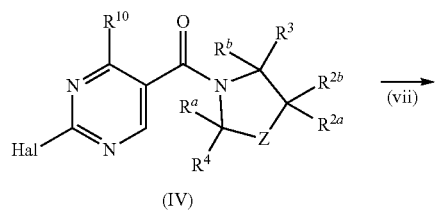

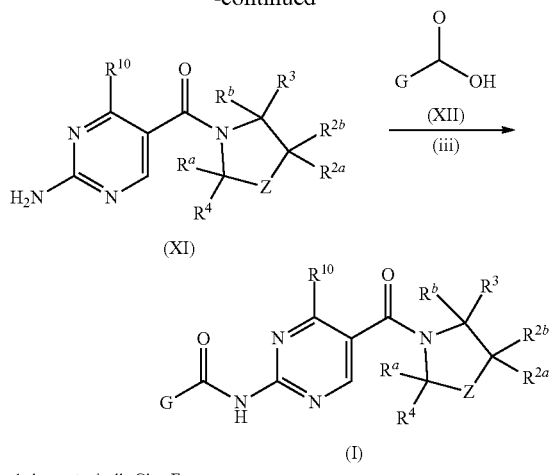

Hal = halogen, typically Cl or F

Compounds of formula (XI) may be prepared from compounds of formula (IV), wherein Z is previously described herein, according to process step (vii), a substitution nucleophilic aromatic with an ammonia source as described in Scheme 6. A preferred source of ammonia is an aqueous solution of an ammonium salt such as ammonium hydroxide. This step could also be performed in a different temperature range, typically a temperature above 80° C. and, preferentially, under microwave irradiations above 120° C.

Compounds of formula (I) may be prepared from compounds of formula (XI) according to process step (iii), an amide bond formation step with an acid of formula (XII), mediated by a suitable combination of amide bond coupling agent and organic base, as described in Scheme 2.

It will be apparent to those skilled in the art that many of the intermediates are commercially available and that where intermediates are not commercially available, numerous synthetic methods are available from the synthetic literature from which one skilled in the art would be able prepare such intermediates.

EXPERIMENTAL PROCEDURES AND WORKING EXAMPLES

The following illustrate the synthesis of various compounds of the present invention. Additional compounds within the scope of this invention may be prepared using the methods illustrated in these Examples, either alone or in combination with techniques generally known in the art.

It will be understood that the intermediate compounds of the invention depicted above are not limited to the particular enantiomer shown, but also include all stereoisomers and mixtures thereof. It will also be understood that compounds of Formula I can include intermediates of compounds of Formula I.

Abbreviations

In the Examples and Preparations that are set out below, and in the aforementioned Schemes, the following abbreviations, definitions and analytical procedures may be referred to. Other abbreviations common in the art are also used. Standard IUPAC nomenclature has been used.

AcOH is acetic acid;
AgF is silver fluoride;
AIBN is azobisisobutyronitrile;
Ar is argon;
aq is aqueous;
Bn is benzyl;
Boc is tert-butoxycarbonyl;
Boc$_2$O is di-tert-butyl dicarbonate;
br is broad;
tBu is tert-butyl;
tBuOH is tert-butanol;
n-BuLi is n-butyl lithium;
° C. is degrees celcius;
CBz-Cl is benzyl chloroformate;
CDCl$_3$ is deutero-chloroform;
Cs$_2$CO$_3$ is cesium carbonate;
CsF is cesium fluoride;
δ is chemical shift;
d is doublet;
DCM is dichloromethane; methylene chloride;
DBU is 1,8-Diazabicyclo[5.4.0]undec-7-ene
DIPEA is N-ethyldiisopropylamine, N,N-diisopropylethylamine;
DMA is N,N-dimethylacetamide;
DMF is N,N-dimethylformamide;
DMSO is dimethyl sulphoxide;
DPPA is diphenyl phosphoryl azide;
EDC=N-(3-Dimethylaminopropyl)-N'-ethylcarbodiimide hydrochloride and HOBt=1-Hydroxybenzotriazole hydrate are amide coupling reagents
Et$_2$O is diethyl ether;
EtOAc is ethyl acetate;
EtOH is ethanol;
Et$_3$N is triethylamine;
g is gram;
HATU is 1-[Bis(dimethylamino)methylene]-1H-1,2,3-triazolo[4,5-b]pyridinium 3-oxid hexafluorophosphate;
HBTU is N,N,N',N'-tetramethyl-O-(1H-benzotriazol-1-yl)uronium hexafluorophosphate;
HCl is hydrochloric acid;
HCO$_2$H is formic acid;
HPLC is high pressure liquid chromatography;
H$_2$O is water;
H$_2$O$_2$ is hydrogen peroxide;
Hr is hour, hrs are hours;
IMS is industrial methylated spirit;
K$_2$CO$_3$ is potassium carbonate;
KHSO$_4$ is potassium hydrogen sulphate;
KOAc is potassium acetate;
L is litre;
LCMS is liquid chromatography mass spectrometry;
LiALH$_4$ is lithium aluminium hydride;
LiHMDS is lithium bis(trimethylsilyl)amide;
LiOH.H$_2$O is lithium hydroxide monohydrate;
Li-Selectride® is lithium tri-sec-butylborohydride;
m is multiplet;
M is molar;
MeCN is acetonitrile;
MeMgBr is methyl magnesium bromide;
MeOH is methanol;
2-MeTHF is 2-methyl tetrahydrofuran
mg is milligram;
MgSO$_4$ is magnesium sulphate;
MHz is mega Hertz;
min is minutes;
mL is millilitre;
mmol is millimole;
mol is mole;
MS m/z is mass spectrum peak;
MsCl is mesyl chloride
NaCN is sodium cyanide;
NaBH$_4$ is sodium borohydride;
Na$_2$CO$_3$ is sodium carbonate;
NaH is sodium hydride;
NaHSO$_4$ is sodium hydrogen sulfate;
NaOH is sodium hydroxide;
Na$_2$SO$_4$ is sodium sulphate;
NBS is N-bromosuccinimide;
NH$_3$ is ammonia;
NH$_4$Cl is ammonium chloride;
NH$_4$HCO$_3$ is ammonium hydrogen carbonate;
NH$_2$NH$_2$.H$_2$O is hydrazine hydrate;
NH$_2$OH.HCl is hydroxylamine hydrochloride;
NH$_4$OH is ammonium hydroxide;
NH$_4$OAc is ammonium acetate;
NMP is 1-methyl-2-pyrrolidinone;
NMR is nuclear magnetic resonance;
Pd/C is palladium on carbon;
Pd(dppf)Cl$_2$ is [1,1'-bis(diphenylphosphino)ferrocene]dichloropalladium(II);
Pd(OH)$_2$ is palladium hydroxide;
Pd(OAc)$_2$ is palladium acetate;
Pet. Ether is petroleum ether;
pH is power of hydrogen;
ppm is parts per million;
PtO$_2$ is platinum (IV) oxide;
q is quartet;
rt is room temperature;
RT is retention time;
s is singlet;
sat. is saturated
SCX is strong cation exchange;
SFC is supercritical fluid chromatography
t is triplet;
T3P is propylphosphonic anhydride
TBAF is tert-butyl ammonium fluoride;
TBD is 1,5,7-triazabicyclo[4.4.0]dec-5-ene;
TBME is tert-butyl dimethyl ether;
TFA is trifluoroacetic acid;
THF is tetrahydrofuran;
Ti(OiPr)$_4$ is titanium (IV) propoxide;
TPTU is 2-(2-pyridon-1-yl)-1,1,3,3-tetramethyluronium tetrafluoroborate, an amide coupling agent.
μL is microlitre
μmol is micromole
$^1$H and $^{19}$F Nuclear magnetic resonance (NMR) spectra were in all cases consistent with the proposed structures. Characteristic chemical shifts (b) are given in parts-per-million downfield from tetramethylsilane (for $^1$H-NMR) and upfield from trichloro-fluoro-methane (for $^{19}$F NMR) using conventional abbreviations for designation of major peaks: e.g. s, singlet; d, doublet; t, triplet; q, quartet; m, multiplet; br, broad. The following abbreviations have been used for common solvents: CDCl$_3$, deuterochloroform; DMSO-d$_6$, deuterodimethylsulphoxide; and MeOH-d$_4$, deuteromethanol. Where appropriate, tautomers may be recorded within the NMR data; and some exchangeable protons may not be visible.

Mass spectra, MS (m/z), were recorded using either electrospray ionisation (ESI) or atmospheric pressure chemical ionisation (APCI).

Where relevant, and unless otherwise stated, the m/z data provided are for isotopes $^{19}$F, $^{35}$Cl, $^{79}$Br and 127I.

Wherein preparative TLC or silica gel chromatography have been used, one skilled in the art may choose any combination of solvents to purify the desired compound.

In general, reactions were followed by thin layer chromatography and/or liquid chromatography-mass spectrometry, and subjected to work-up when appropriate. It will be recognized by one skilled in the art that purifications may vary between experiments: in general, sorbents, solvents and the solvent ratios used for eluants/gradients were chosen to provide appropriate Rfs or retention times. It will also be recognized by one skilled in the art that HPLC purifications may be effected in a variety of ways, including the use of normal stationary phases, reverse stationary phases, chiral stationary phases, and supercritical eluants. The appropriate choices of conditions for chromatographic and HPLC purifications will be discerned by one skilled in the art.

Achiral Analytical HPLC Conditions

The following methods were used to characterize examples 1 to 129 from library protocols.

| Method CD05 | |
|---|---|
| Column | Xbridge C18 2.1 × 50 mm 5 μm |
| Temperature | 40° C. |
| Mobile Phase A | 0.05% NH$_4$OH in water |
| Mobile Phase B | 100% MeCN |
| Gradient - Initial | 5% B |
| Time 0.00 mins | 5% B |
| Time 0.50 mins | 5% B |
| Time 3.40 mins | 100% B |
| Time 4.20 mins | 100% B |
| Time 4.21 mins | 5% B |
| Time 4.70 mins | 5% B |
| Flow rate | 0.8 ml/min |
| Injection volume | 2 μl |
| Agilent | 1200 HPLC/1956 MSD/SEDEX 75 ELSD |
| Ionization Mode | API-ES |
| Polarity | Positive |
| Method AB00 | |
| Column | Xbridge C18 2.1 × 50 mm 5 μm |
| Temperature | 40° C. |
| Mobile Phase A | 0.0375% TFA in water |
| Mobile Phase B | 0.01875% TFA in MeCN |
| Gradient - Initial | 0% B |
| Time 0.00 mins | 0% B |
| Time 1.00 mins | 5% B |
| Time 4.00 mins | 70% B |
| Time 4.10 mins | 0% B |
| Time 4.70 mins | 0% B |
| Flow rate | 0.8 ml/min |
| Injection volume | 2 μl |
| Agilent | 1200 HPLC/1956 MSD/SEDEX 75 ELSD |
| Ionization Mode | API-ES |
| Polarity | Positive |
| Method AB01 | |
| Column | Xbridge C18 2.1 × 50 mm 5 μm |
| Temperature | 40° C. |
| Mobile Phase A | 0.0375% TFA in water |
| Mobile Phase B | 0.01875% TFA in MeCN |
| Gradient - Initial | 1% B |
| Time 0.00 mins | 1% B |
| Time 0.60 mins | 5% B |
| Time 4.00 mins | 100% B |
| Time 4.30 mins | 1% B |
| Time 4.70 mins | 1% B |
| Flow rate | 0.8 ml/min |
| Injection volume | 2 μl |
| Agilent | 1200 HPLC/1956 MSD/SEDEX 75 ELSD |
| Ionization Mode | API-ES |
| Polarity | Positive |

Achiral Preparative HPLC Conditions

The following methods were used to purify examples 1 to 129 from library protocols. Anyone skilled in the art will apply an appropriate gradient of solvent to afford the title compounds in adequate purity.

| | |
|---|---|
| AD01 | AD02 |
| Agela Durashell C18 250 × 21.2 mm*5 um column | Agela Durashell C18 250 × 21.2 mm*5 um column |
| MeCN-Water(0.225% TFA) | MeCN—NH$_4$OH (pH 10) |
| AD03 | AD04 |
| Agela Durashell C18 150 × 25 mm*5 um column | Agela Durashell C18 150 × 25 mm*5 um column |
| MeCN-Water(0.225% TFA) | MeCN—NH$_4$OH (pH 10) |
| PG01 | PG02 |
| Phenomenex Gemini C18 250 × 21.2 mm*10 um | Phenomenex Gemini C18 250 × 21.2 mm*10 um |
| MeCN-Water(0.225% TFA) | MeCN—NH$_4$OH (pH 10) |
| WX01 | |
| Waters Xbridge Prep OBD C18 150 × 30 mm*5 um | |
| MeCN—NH$_4$OH (pH 10) | |

Chiral analytical SFC Conditions

Method CA-A: column: Lux Cellulose-2 150×4.6 mm I.D., 3 μm; mobile phase: 40% EtOH (0.05% DEA) in COO$_2$; flow rate of 2.5 mL/min at 40° C.

Method CA-B: column: Chiralcel OD-3 150×4.6 mm I.D., 3 μm; mobile phase: EtOH (0.05% DEA) in CO$_2$ (from 5% to 40% in 5 min); flow rate: 2.5 mL/min at 35° C.

Method CA-C: column: Chiralpak AD-3 50×4.6 mm I.D., 3 μm; mobile phase: 40% of EtOH (0.05% DEA) in COO$_2$; flow rate: 4 mL/min at 40° C.

Method CA-D: column: Chiralpak AD-3 150×4.6 mm I.D., 3 μm; mobile phase: 40% of iso-propanol (0.05% DEA) in COO$_2$; flow rate of 2.5 mL/min Method CA-E: column: Chiralpak AS-3 100×4.6 mm I.D., 3 μm; mobile phase: EtOH (0.05% DEA) in CO$_2$ (from 5% to 40% in 4.5 min); flow rate: 2.8 mL/min Method CA-F: column: Chiralpak AD-3 150×4.6 mm I.D., 3 μm; mobile phase: iso-propanol (0.05% DEA) in CO$_2$ (from 5% to 40% in 5.5 min); flow rate: 2.5 mL/min at 35° C.

Method CA-G: column: Chiralpak AD-3 150×4.6 mm I.D., 3 μm; mobile phase: EtOH (0.05% DEA) in CO$_2$ (from 5% to 40% in 5.0 min); flow rate: 2.5 mL/min at 35° C.

Chiral Preparative SFC Conditions

Method CP-A: C2 250 mm*30 mm, 10 μm column, eluting with 55% EtOH (0.1% NH$_3$.H$_2$O) in CO$_2$ at a flow rate of 80 mL/min.

Method CP-B: OD 250 mm*30 mm, 10 μm column, eluting with 40% EtOH (0.1% NH$_3$.H$_2$O) in CO$_2$ at a flow rate of 80 mL/min.

Method CP-C: AD 250 mm*30 mm, 10 μm column, eluting with 50% of EtOH (0.05% NH$_3$.H$_2$O) in CO$_2$ at a flow rate of 80 mL/min.

Method CP-D: AD 250 mm*30 mm, 5 μm column, eluting with 40% of iso-propanol (0.05% DEA) in CO$_2$ at a flow rate of 50 mL/min.

Method CP-E: AS 250 mm*30 mm, 10 μm column, eluting with 20% EtOH (0.05% DEA) in CO$_2$ at a flow rate of 60 mL/min.

Method CP-F: OJ 250 mm*30 mm, 5 μm column, eluting with 25% MeOH (0.05% DEA) in CO$_2$ at a flow rate of 60 mL/min.

Method CP-G: AY 250 mm*30 mm, 10 μm column, eluting with 45% iso-propanol (0.1% NH$_3$.H$_2$O) in CO$_2$ at a flow rate of 80 mL/min.

Experimental Procedures

Experiments were generally carried out under inert atmosphere (nitrogen or argon), particularly in cases where oxygen- or moisture-sensitive reagents or intermediates were employed. Commercial solvents and reagents were generally used without further purification, including anhydrous solvents where appropriate (generally Sure-Seal™ products from the Aldrich Chemical Company, Milwaukee, Wis.). Products were generally dried under vacuum before being carried on to further reactions or submitted for biological testing. Mass spectrometry data is reported from either liquid chromatography-mass spectrometry (LCMS), atmospheric pressure chemical ionization (APCI) or gas chromatography-mass spectrometry (GCMS) instrumentation. Chemical shifts for nuclear magnetic resonance (NMR) data are expressed in parts per million (ppm, δ) referenced to residual peaks from the deuterated solvents employed.

For syntheses referencing procedures in other Examples or Methods, reaction conditions (length of reaction and temperature) may vary. In general, reactions were followed by thin layer chromatography and/or liquid chromatography-mass spectrometry, and subjected to work-up when appropriate. It will be recognized by one skilled in the art that purifications may vary between experiments: in general, sorbents, solvents and the solvent ratios used for eluants/gradients were chosen to provide appropriate $R_f$s or retention times. It will also be recognized by one skilled in the art that HPLC purifications may be effected in a variety of ways, including the use of normal stationary phases, reverse stationary phases, chiral stationary phases, and supercritical eluants. The appropriate choices of conditions for chromatographic and HPLC purifications will be discerned by one skilled in the art.

The following Preparations describe the preparation of certain intermediates used in the Methods and Examples that follow. The following Preparations, Methods and Examples are intended to illustrate particular embodiments of the invention and preparations thereto and are not intended to limit the specification, including the claims, in any manner. Unless noted otherwise, all reactants were obtained commercially.

Furthermore, some preparations, such as 59, 60 and 73, describe a synthetic route to a free base, while the salt form is the one actually characterized. One skilled in the art will appreciate that isolation of a salt could be performed by mixing the free base with corresponding acid in an appropriate solvent, according to standard procedure that can be found in the literature.

Vanin-1 Preparations

Preparation 1

2-[(Pyridin-3-ylmethyl)amino]pyrimidine-5-carboxylic Acid

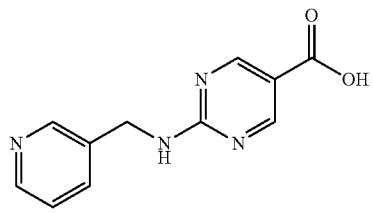 [SMILES: O=C(O)c1cnc(NCc2cccnc2)nc1]

LiOH.H$_2$O (1.22 g, 29.0 mmol) was added to a solution of ethyl 2-[(pyridin-3-ylmethyl)amino]pyrimidine-5-carboxylate (Preparation 7, 2.50 g, 9.68 mmol) in MeOH/H$_2$O (1:1, 20 mL) and the reaction stirred at 20° C. for 16 hrs. The mixture was concentrated in vacuo and the residue acidified to pH 4 by the dropwise addition of 1N HCl. The resulting solid was filtered off and dried under vacuum to afford the title compound as a brown solid, 2.00 g, 89%. $^1$H NMR (400 MHz, DMSO-d$_6$): b 4.59 (d, 2H), 7.34 (dd, 1H), 7.71 (d, 1H), 8.42-8.60 (m, 3H), 8.73 (s, 2H). LCMS m/z=231 [M+H]$^+$ Preparation 2

2-[(Pyrimidin-5-ylmethyl)amino]pyrimidine-5-carboxylic Acid

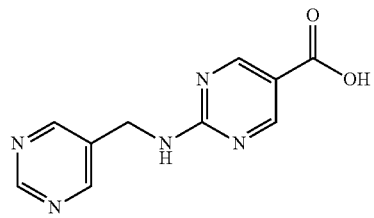 [SMILES: O=C(O)c1cnc(NCc2cncnc2)nc1]

LiOH.H$_2$O (971 mg, 23.1 mmol) was added to a suspension of ethyl 2-[(pyrimidin-5-ylmethyl)amino]pyrimidine-5-carboxylate (Preparation 8, 1.2 g, 4.63 mmol) in EtOH/THF/H$_2$O (70 mL, 4:2:1) and the reaction stirred at 60° C. for 2 hrs. The cooled reaction mixture was evaporated under reduced pressure. The residue was adjusted to pH 3 using 1N HCl solution and the resulting suspension stirred at 20° C. for 10 min. The solid was collected by filtration and washed with water (5 mL×2). The solid was co-evaporated with toluene three times to afford the title compound as a pale solid, 850 mg, 79%. $^1$H NMR (400 MHz, DMSO-d$_6$): δ 4.59 (d, 2H), 8.57 (dd, 1H), 8.71-8.78 (m, 3H), 9.07 (s, 1H), 12.85 (br s, 1H). LCMS m/z=232 [M+H]$^+$ Preparation 3

2-[(Pyrazin-5-ylmethyl)amino]pyrimidine-5-carboxylic acid

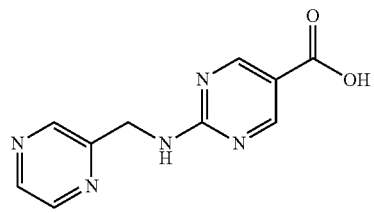

A solution of ethyl 2-[(pyrazin-5-ylmethyl)amino]pyrimidine-5-carboxylate (Preparation 9, 1710 mg, 6.60 mmol) in THF (13.2 mL) and MeOH (6.6 mL) was treated with a solution of LiOH.H$_2$O (830 mg, 19.8 mmol) in water (13.2 mL) and the resulting solution stirred at rt for 2 hrs. 1N HCl (35 mL) was added followed by sat. NH$_4$Cl solution and the mixture was concentrated under reduced pressure. The resulting aqueous layer was filtered and the resulting brown solid dried under reduced pressure to afford the title compound, 1.12 g, 73%. ¹H NMR (400 MHz, DMSO-d₆): b 4.72 (d, 2H), 8.50-8.61 (m, 4H), 8.72 (d, 1H), 12.79 (br s, 1H). LCMS m/z=232 [M+H]⁺

Preparation 4

2-{[(1S)-(1-(Pyrazin-2-yl)ethyl]amino}pyrimidine-5-carboxylic Acid

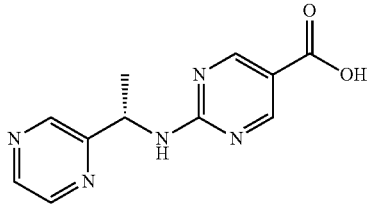 [SMILES: C[C@H](Nc1ncc(C(=O)O)cn1)c1cnccn1]

A solution of NaOH (838 mg, 21.0 mmol) in water (10 mL) was added drop wise over 30 mins. to a mixture of ethyl 2-{[(1S)-1-(pyrazin-2-yl)ethyl]amino}pyrimidine-5-carboxylate (Preparation 10, 2.29 g, 8.38 mmol) in THF (10 mL), MeOH (10 mL) and water (5 mL) and the reaction was then stirred for 20 mins. The mixture was concentrated in vacuo, and 6M HCl (3.5 mL) was added to lower the pH to ~2. The resulting solid was filtered off, washed with water and dried to afford the title compound as a pale yellow solid, 1.7 g, 82%. ¹H NMR (400 MHz, DMSO-d₆): b 1.55 (d, 3H), 5.24-5.32 (m, 1H), 8.50-8.59 (m, 3H), 8.63-8.76 (m, 3H), 12.75 (s, 1H). LCMS m/z=246 [M+H]⁺

Preparation 5

2-{[1-(Pyrimidin-5-yl)cyclopropyl]amino}pyrimidine-5-carboxylic Acid

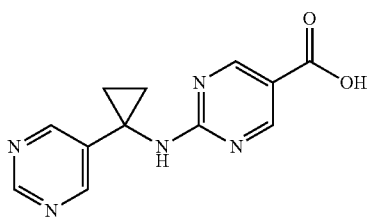 [SMILES: O=C(O)c1cnc(NC2(c3cncnc3)CC2)nc1]

NaOH (1.68 g, 42.1 mmol) was added to a yellow solution of ethyl 2-{[1-(pyrimidin-5-yl)cyclopropyl]amino}pyrimidine-5-carboxylate (Preparation 11, 2.00 g, 7.01 mmol) in MeOH/H₂O/THF (80.0 mL/15.0 mL/15.0 mL) and the resulting suspension stirred at 30° C. for 18 hrs. The reaction mixture was acidified to pH 2 using aq. HCl (2M). The solvent was removed under reduced pressure to give a yellow solid which was triturated with MeOH/THF (80 mL/40 mL), the solid was filtered off and the filtrate was concentrated in vacuo to provide the title compound as a grey solid, in quantitative yield. ¹H NMR (400 MHz, DMSO-d₆): δ 1.30-1.35 (m, 2H), 1.46-1.50 (m, 2H), 8.61 (s, 2H), 8.70-8.76 (m, 2H), 8.93 (s, 1H), 9.00 (s, 1H). LCMS m/z=258 [M+H]⁺

Preparation 6

2-{[1-(Pyrimidin-5-yl)ethyl]amino}pyrimidine-5-carboxylic Acid

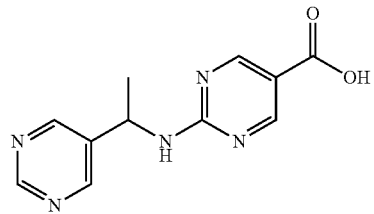 [SMILES: CC(Nc1ncc(C(=O)O)cn1)c1cncnc1]

LiOH.H₂O (691 mg, 16.5 mmol) was added to a yellow suspension of ethyl 2-{[1-(pyrimidin-5-yl)ethyl]amino}pyrimidine-5-carboxylate (Preparation 12, 900 mg, 3.29 mmol) in EtOH/THF/H₂O (70 mL, 4:2:1) and the reaction was stirred at 60° C. for 2 hrs. The cooled reaction was concentrated in vacuo, and the residue was adjusted to pH 3 with 1N HCl solution. The resulting suspension was stirred at 20° C. for 10 min, the solid collected by filtration and washed with water (5 mL×2). The solid was co-evaporated with toluene (3×) to give the title compound as a yellow solid, 170 mg, 21%. The filtrate was evaporated under reduced pressure and the resulting yellow oil purified by preparative HPLC using a Phenomenex Gemini C18 250*50 10μ column eluting with 0.225% aq. TFA in MeCN at a flow rate of 30 mL/min to afford additional product as a pale yellow solid, 195 mg, 24% yield. ¹HNMR (400 MHz, CDCl₃): δ 1.58 (d, 3H), 5.21-5.27 (m, 1H), 8.64-8.72 (m, 3H), 8.76 (s, 2H), 8.84 (s, 1H), 9.07 (s, 1H). LCMS m/z=246 [M+H]⁺

Preparation 7

Ethyl 2-[(pyridin-3-ylmethyl)amino]pyrimidine-5-carboxylate

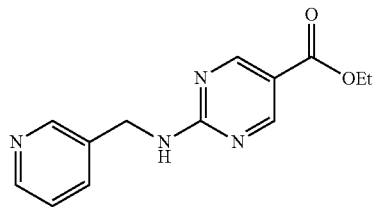 [SMILES: CCOC(=O)c1cnc(NCc2cccnc2)nc1]

DIPEA (7.27 g, 56.3 mmol) was added drop wise to a stirred solution of ethyl 2-chloropyrimidine-5-carboxylate (3.50 g, 218.8 mmol) and 3-pyridinemethanamine (2.03 g, 18.8 mmol) in dry THF (30 mL) and the reaction stirred at 60° C. for 16 hrs. The solvent was removed under reduced pressure and water (10 mL) was added. The mixture was extracted with EtOAc (40 mL×3) and the combined organic extracts dried (Na₂SO₄), filtered and concentrated in vacuo. The crude product was purified by column chromatography on silica gel eluting with Pet. Ether:EtOAc (100:0 to 7:93) to afford the title compound as a brown solid, 3.50 g, 72%. ¹H NMR (400 MHz, CDCl₃): δ 1.38 (t, 3H), 4.36 (q, 2H), 4.74 (d, 2H), 6.03 (br s, 1H), 7.29 (d, 1H), 7.68 (d, 1H), 8.55 (d, 1H), 8.63 (d, 1H), 8.85 (br s, 2H). LCMS m/z=259 [M+H]+

Preparation 8

Ethyl 2-[(Pyrimidin-5-ylmethyl)amino]pyrimidine-5-carboxylate

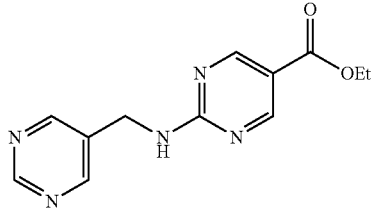 [SMILES: CCOC(=O)c1cnc(NCc2cncnc2)nc1]

A yellow solution of ethyl 2-chloropyrimidine-5-carboxylate (700 mg, 3.75 mmol), 5-pyrimidinemethanamine (450 mg, 4.13 mmol) and DIPEA (2420 mg, 18.8 mmol) in THF (20 mL) was stirred at 60° C. for 16 hrs. The cooled reaction was concentrated in vacuo to give a yellow oil. The crude product was purified by column chromatography on silica gel eluting with DCM: MeOH (100:0 to 88:12) to afford the title compound, as a yellow solid, 933 mg, 96%. $^1$H NMR (400 MHz, DMSO-$d_6$): δ 1.29 (t, 3H), 4.26 (q, 2H), 4.61 (d, 2H), 8.66 (br t, 1H), 8.77 (s, 4H), 9.08 (s, 1H). LCMS m/z=260 [M+H]+

Preparation 9

Ethyl 2-[(pyrazin-5-ylmethyl)amino]pyrimidine-5-carboxylate

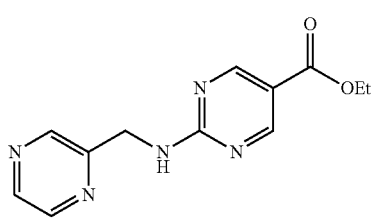 [SMILES: CCOC(=O)c1cnc(NCc2cnccn2)nc1]

2-Aminomethylpyrazine (3.51 g, 32.2 mmol) was added to a solution of ethyl 2-chloropyrimidine-5-carboxylate (6 g, 32.16 mmol) and DIPEA (5.4 g, 41.8 mmol) in 2-propanol (20 mL) and the reaction mixture was heated under reflux for 16 hrs. The cooled reaction mixture was concentrated in vacuo and the residue purified by column chromatography on silica gel eluting with EtOAc:petroleum ether (0:100 to 60:40) to afford the title compound as a yellow solid, 7.2 g, 86%. $^1$H NMR (400 MHz, CDCl$_3$): δ 1.37 (t, 3H), 4.35 (q, 2H), 4.86 (s, 2H), 6.71 (br s, 1H), 8.50 (s, 1H), 8.55 (s, 1H), 8.58 (s, 1H), 8.86 (br s, 2H). LCMS m/z=260 [M+H]+

Preparation 10

Ethyl 2-{[(1S)-1-(pyrazin-2-yl)ethyl]amino}pyrimidine-5-carboxylate

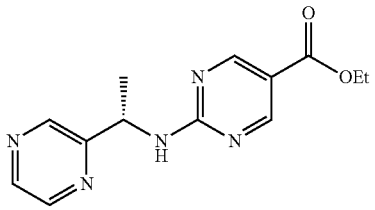 [SMILES: CCOC(=O)c1cnc(N[C@@H](C)c2cnccn2)nc1]

A solution of 1-(pyrazin-2-yl)ethanamine (469.0 g, 3810 mmol) in 2-propanol (1.9 L) was placed in a 5-L reactor equipped with a mechanical stirrer (glass rod, teflon paddle) and internal thermometer under N$_2$. Ethyl 2-chloropyrimidine-5-carboxylate (711 g, 3810 mmol) was added as a solid with stirring followed by DIPEA (640 g, 4950 mmol). The resulting solution was gradually warmed to 88° C., stirred for 7 hrs then allowed to cool. The content of the tank was transferred into a 6-L erlen meyer flask and the tank rinsed with 2-propanol. The solution was concentrated in vacuo to remove approximately half of the volume. The content of the erlenmeyer was transferred into a 10-L tank equipped with a jacket, a short-path distillation set-up connected to a 1 L flask and a mechanical stirrer. The erlenmeyer and the flask were rinsed with water until all the solids have been transferred. The resulting suspension was stirred at 50° C. under vacuum for 5 hrs and the mixture then allowed to cool to rt. Water (2 L) was added, the mixture stirred for 2 hrs then the solid was filtered off, washing through with water (500 mL). The solid was dried in vacuo. The filtrate was concentrated in vacuo and the resulting solid filtered off and dried to provide additional product. This was purified by chiral SFC separation, using a Chiralcel IC-H 50×250 column, eluting with 65:35 CO$_2$: MeCN at a flow rate of 250 mL/min, wavelength 215 nm to afford the title compound as a pale orange oil that crystallized on standing, 441 g. RT=1.38 min; $^1$H NMR (400 MHz, CDCl$_3$): δ 1.37 (t, 3H), 1.63 (d, 3H), 4.35 (q, 2H), 5.42 (quint., 1H), 6.58 (d, 1H), 8.49 (d, 1H), 8.54 (dd, 1H), 8.65 (d, 1H), 8.85 (br s, 2H). LCMS m/z=274 [M+H]+

Further elution provided the second enantiomer as an orange solid, 487 g.

Preparation 11

Ethyl 2-{[1-(pyrimidin-5-yl)cyclopropyl]amino}pyrimidine-5-carboxylate

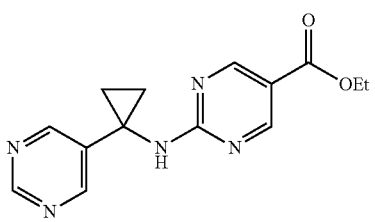 [SMILES: CCOC(=O)c1cnc(NC2(c3cncnc3)CC2)nc1]

DIPEA (17.3 mL, 99.5 mmol) was added in one portion to a yellow suspension of 1-(pyrimidin-5-yl)cyclopropanamine hydrochloride (Preparation 26, 4.87 g, 19.9 mmol) in THF (120 mL) and the solution was stirred at 45° C. for 15 min. Ethyl 2-chloropyrimidine-5-carboxylate (3.71 g, 19.9 mmol) was added in one portion and the resulting yellow suspension was heated at 60° C. for 18 hrs. The mixture was cooled to 18° C., the resulting solid filtered off and the filtrate concentrated in vacuo to give a yellow oil. The crude product was purified by column chromatography on silica gel eluting with EtOAc: Pet. Ether (50:50 to 90:10) to afford the title compound as a yellow solid, 3.31 g, 58%. $^1$H NMR (400 MHz, MeOD-d$_4$): δ 1.35 (t, 3H), 1.40-1.45 (m, 2H), 1.47-1.52 (m, 2H), 4.32 (q, 2H), 8.69 (s, 2H), 8.76-8.84 (m, 2H), 8.96 (s, 1H). LCMS m/z=286 [M+H]$^+$ Preparation 12

Ethyl 2-{[1-(pyrimidin-5-yl)ethyl]amino}pyrimidine-5-carboxylate

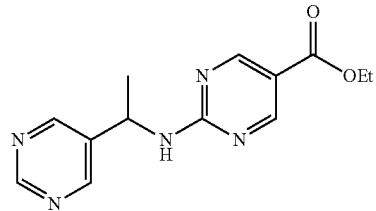 [SMILES: CCOC(=O)c1cnc(NC(C)c2cncnc2)nc1]

A yellow suspension of ethyl 2-chloropyrimidine-5-carboxylate (600 mg, 3.22 mmol), 1-(5-pyrimidin-yl)ethanamine (436 mg, 3.54 mmol) and DIPEA (2.08 g, 16.1 mmol) in THF (20 mL) and DMSO (3 mL) was stirred at 60° C. for 16 hrs. The cooled reaction was concentrated in vacuo to give a yellow oil. The residue was partitioned between DCM (20 mL) and water (10 mL), the layers were separated and the aqueous was extracted with DCM (35 mL×2). The combined organic layers were washed with water (10 mL×2), dried (Na$_2$SO$_4$), filtered and concentrated under reduced pressure to give a yellow oil. The crude product was purified by column chromatography on silica gel eluting with DCM: MeOH (100:0 to 88:12) to afford the title compound as a yellow oil, 88% yield. $^1$H NMR (400 MHz, CDCl$_3$): δ 1.36 (t, 3H), 1.67 (d, 3H), 4.34 (q, 2H), 5.21-5.29 (m, 1H), 6.06 (br d, 1H), 8.77 (s, 2H), 8.82 (s, 2H), 9.13 (s, 1H). LCMS m/z=274 [M+H]$^+$ Preparation 13

Ethyl 2-if{[(6-methylpyridin-3-yl)methyl]amino}pyrimidine-5-carboxylate

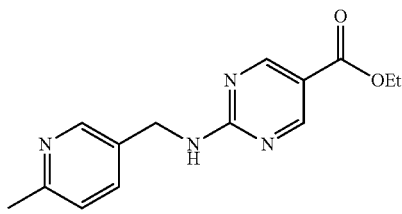 [SMILES: CCOC(=O)c1cnc(NCc2ccc(C)nc2)nc1]

6-Methyl-3-pyridinemethanamine (1.0 g, 8.19 mmol) was added to a solution of ethyl 2-chloropyrimidine-5-carboxylate (1.53 g, 8.19 mmol) and DIPEA (1.59 g, 12.3 mmol) in 2-propanol (8 mL) and the resulting mixture was heated under reflux for 8 hrs. The cooled mixture was concentrated under reduced pressure and the residue purified by column chromatography on silica gel eluting with EtOAc: Pet. Ether (0:100 to 30:70) to afford the title compound as a yellow solid, 1.5 g, 67%. $^1$H NMR (400 MHz, CDCl$_3$): δ 1.37 (t, 3H), 2.55 (s, 3H), 4.35 (q, 2H), 4.67 (d, 2H), 7.12 (d, 1H), 7.56 (dd, 1H), 8.45 (d, 1H). 8.85 (br s, 2H). LCMS m/z=273 [M+H]$^+$ Preparation 14

Ethyl 2-{[1-(pyrazin-2-yl)cyclobutyl]amino}pyrimidine-5-carboxylate

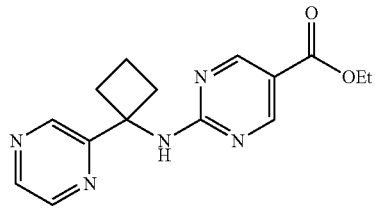 [SMILES: CCOC(=O)c1cnc(NC2(c3cnccn3)CCC2)nc1]

Ethyl 2-fluoropyrimidine-5-carboxylate (Preparation 21, 1.7 g, 9.99 mmol) was added to a solution of 1-(pyrazin-2-yl)cyclobutanamine (Preparation 42, 1.7 g, 11.39 mmol) and DIPEA (2.58 g, 20.0 mmol) in dioxane (60 mL) under N$_2$ and the reaction stirred at 80° C. for 16 hrs. The mixture was concentrated in vacuo and the residue purified by column chromatography on silica gel eluting with pet. ether:EtOAc (100:0 to 35:65) to provide the title compound as a yellow oil, 2.1 g, 70%. $^1$H NMR (400 MHz, CDCl$_3$): δ 1.33 (t, 3H), 2.06-2.18 (m, 1H), 2.19-2.25 (m, 1H), 2.48-2.52 (m, 2H), 2.86-2.91 (m, 2H), 4.31 (q, 2H), 6.53 (br s, 1H), 8.41 (s, 1H), 8.55 (s, 1H), 8.73-8.87 (m, 3H). LCMS m/z=300 [M+H]$^+$ Preparation 15

Ethyl 2-{[2-(pyrazin-2-yl)propan-2-yl]amino}pyrimidine-5-carboxylate

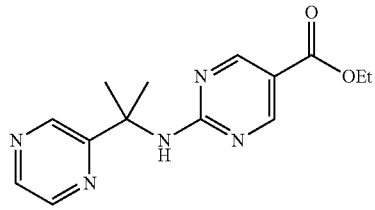 [SMILES: CCOC(=O)c1cnc(NC(C)(C)c2cnccn2)nc1]

Ethyl 2-fluoropyrimidine-5-carboxylate (Preparation 21, 1.4 g, 8.23 mmol) was added to a solution of 2-pyrazin-2-ylpropan-2-amine (Commercial, 1.69 g, 12.3 mmol) and DIPEA (2.13 g, 16.5 mmol) in dioxane (25 mL) under N$_2$ and the reaction stirred at 80° C. for 16 hrs. The mixture was concentrated in vacuo and the residue purified by column chromatography on silica gel eluting with pet. ether:EtOAc (100:0 to 60:40) to provide the title compound, 1.2 g, 51%.

¹HNMR (400 MHz, CDCl₃): δ 1.33 (t, 3H), 1.85 (s, 6H), 4.31 (q, 2H), 6.57 (s, 1H), 8.42 (s, 1H), 8.49 (s, 1H), 8.66-8.80 (m, 3H). LCMS m/z=288 [M+H]⁺

Preparation 16

Ethyl 2-{[1-(6-methylpyridin-3-yl)ethyl]amino}pyrimidine-5-carboxylate

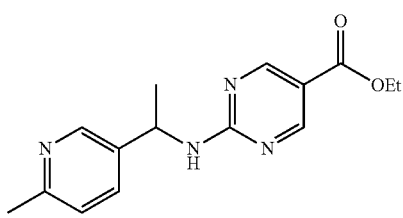 [SMILES: CCOC(=O)c1cnc(NC(C)c2ccc(C)nc2)nc1]

1-(6-Methylpyridin-3-yl)ethanamine (Preparation 30a, 10.9 g, 80.4 mmol) was added to a solution of ethyl 2-chloropyrimidine-5-carboxylate (15 g, 80.39 mmol) and DIPEA (13.5 g, 105 mmol) in 2-propanol (48 mL) and the resulting mixture heated under reflux for 16 hrs. The cooled mixture was concentrated in vacuo and the residue was purified by column chromatography on silica gel eluting with EtOAc: pet. Ether (0:100 to 30:70) to provide the title compound as a yellow solid, 16 g (69%). ¹H NMR (400 MHz, CDCl₃): δ 1.36 (t, 3H), 1.61 (d, 3H), 2.55 (s, 3H), 4.33 (q, 2H), 5.22-5.30 (m, 1H), 5.92 (br d, 1H), 7.13 (d, 1H), 7.58 (dd, 1H), 8.54 (d, 1H), 8.82 (s, 2H). LCMS m/z=287 [M+H]⁺

Preparation 17

Ethyl 2-{[(1S)-1-(6-methylpyridin-3-yl)ethyl]amino}pyrimidine-5-carboxylate and

Preparation 18

Ethyl 2-{[(1R)-1-(6-methylpyridin-3-yl)ethyl]amino}pyrimidine-5-carboxylate

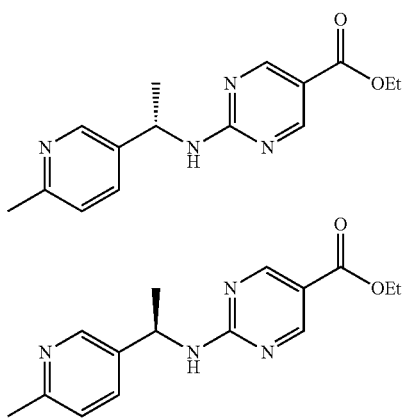

Ethyl 2-{[1-(6-methylpyridin-3-yl)ethyl]amino}pyrimidine-5-carboxylate (Preparation 16) was further purified by SFC separation using the following: AD 250 mm*50 mm, 10 μm column; 60% EtOH (0.1% NH₃.H₂O) in CO₂ at 200 ml/min, 38° C.; to provide ethyl 2-{[(1S)-1-(6-methylpyridin-3-yl)ethyl]amino}pyrimidine-5-carboxylate as a yellow oil (RT: 6.311 min, 5.73 g, 44%). ¹H NMR (400 MHz, CDCl₃): δ 1.36 (t, 3H), 1.60 (d, 3H), 2.54 (s, 3H), 4.33 (q, 2H), 5.22-5.29 (m, 1H), 5.94 (br d, 1H), 7.12 (d, 1H), 7.57 (dd, 1H), 8.53 (d, 1H), 8.81 (s, 2H). LCMS m/z=287 [M+H]⁺. α[D]²⁶=134.90 (c=1.012, CHCl₃).

Further elution provided ethyl 2-{[(1R)-1-(6-methylpyridin-3-yl)ethyl]amino}pyrimidine-5-carboxylate as a yellow oil (RT: 7.481 min, 5.77 g, 44%). ¹H NMR (400 MHz, CDCl₃): δ 1.36 (t, 3H), 1.60 (d, 3H), 2.53 (s, 3H), 4.33 (q, 2H), 5.22-5.29 (m, 1H), 5.98 (br d, 1H), 7.11 (d, 1H), 7.56 (dd, 1H), 8.53 (d, 1H), 8.81 (s, 2H). LCMS m/z=287 [M+H]⁺. $\alpha_{[D]}^{25.7}$=−129.4° (c=1.151, CHCl₃)

Preparation 19

Ethyl 4-methyl-2-{[1-(pyrimidin-5-yl)cyclopropyl]amino}pyrimidine-5-carboxylate

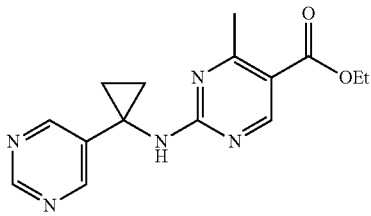 [SMILES: CCOC(=O)c1cnc(NC2(c3cncnc3)CC2)nc1C]

1-(Pyrimidin-5-yl)cyclopropanamine hydrochloride (Preparation 26, 573 mg, 2.39 mmol) was added to a solution of ethyl 2-chloro-4-methylpyrimidine-5-carboxylate (400 mg, 1.99 mmol) and DIPEA (515 mg, 3.99 mmol) in NMP (4 mL) and the resulting mixture stirred under microwave irradiation at 140° C. for 40 min. The cooled mixture was diluted with EtOAc (200 mL), washed with brine (100 mL), H₂O (100 mL), dried (Na₂SO₄) and concentrated in vacuo. The crude product was purified by column chromatography on silica gel eluting with Pet. Ether:EtOAc (80:20 to 40:60) to afford the title compound as a yellow gum, 200 mg, 33%. ¹H NMR (400 MHz, CDCl₃): δ 1.35 (t, 3H), 1.42 (br s, 4H), 2.64 (s, 3H), 4.31 (q, 2H), 6.22 (br s, 1H), 8.67 (br s, 2H), 8.82 (br s, 1H), 9.04 (s, 1H). LCMS m/z=300 [M+H]⁺

Preparation 20

Ethyl 4-methyl-2-[(pyrazine-2-ylmethyl)amino]pyrimidine-5-carboxylate

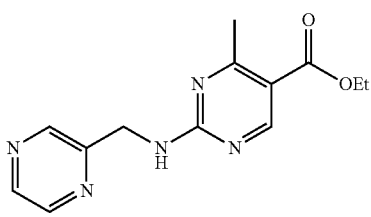 [SMILES: CCOC(=O)c1cnc(NCc2cnccn2)nc1C]

The title compound was obtained as an off white solid, in 59% yield from ethyl 2-chloro-4-methylpyrimidine-5-carboxylate and 2-(aminomethyl)pyrazine, following an analogous method to that described in Preparation 19, except DCM:MeOH was used as the column eluent. ¹H NMR (400 MHz, CDCl₃): δ 1.36 (t, 3H), 2.66 (s, 3H), 4.32 (q, 2H), 4.85 (d, 2H), 6.63 (br s, 1H), 8.48 (s, 1H), 8.53 (dd, 1H), 8.66 (s, 1H), 8.63 (br s, 1H). LCMS m/z=274 [M+H]⁺

Preparation 21

Ethyl 2-fluoropyrimidine-5-carboxylate

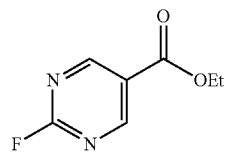

AgF (6.8 g, 53.6 mmol) was added in one portion to a colorless solution of ethyl 2-chloropyrimidine-5-carboxylate (5.0 g, 26.80 mmol) in MeCN (100 mL) and the resulting suspension stirred at 70° C. for 16 hrs. The cooled mixture was filtered and the filtrate was concentrated in vacuo to a volume of approx. 10 mL. The solution was purified by column chromatography on silica gel eluting with pet. ether:EtOAc (80:20) to provide the title compound as a yellow solid 2.9 g, 64%. ¹H NMR (400 MHz, CDCl₃): δ 1.43 (t, 3H), 4.45 (q, 2H), 9.21 (s, 2H). LCMS m/z=171 [M+H]⁺

Preparation 22

(2-Chloropyrimidin-5-yl)(8-oxa-2-azaspiro[4.5]dec-2-yl)methanone

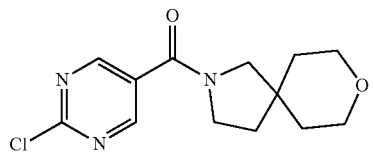 [SMILES: O=C(c1cnc(Cl)nc1)N1CCC2(CCOCC2)C1]

To a −10° C. slurry of 2-chloropyrimidine-5-carboxylic acid (30 g, 189.2 mmol) and 8-oxa-2-azaspiro[4.5]decane hydrochloride (36.6 g, 206.0 mmol) in acetonitrile (210 mL), was slowly added propylphosphonic anhydride solution (273 mL, 458.9 mmol, 50% in EtOAc). Then a solution of Et₃N (96 mL, 688.3 mmol) in acetonitrile (90 mL) was added over a period of 3 h, keeping the temperature below −5° C. The mixture was stirred at this temperature for 10 minutes, then water (300 mL) was added. The resulting slurry was evaporated under reduced pressure (35° C., 90 mmHg) until no more distillation was observed, then cooled down to 5° C. The slurry was filtered and the solid washed with water (90 mL). The resulting white solid was dried in a vacuum oven at 40° C., providing the title compound, 49.75 g, 96%. ¹H NMR (400 MHz, CDCl₃): δ 1.55-1.61 (m, 2H), 1.65-1.69 (m, 2H), 1.89-1.98 (m, 2H), 3.37 (s, 1H), 3.57-3.82 (m, 7H), 8.82 (s, 2H). LCMS m/z=282 [M+H]⁺

Preparation 23

(2-Chloropyrimidin-5-yl)(7-oxa-2-azaspiro[3.5]non-2-yl)methanone

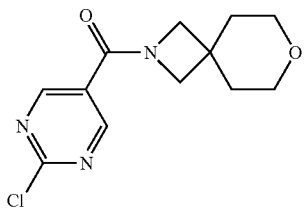 [SMILES: O=C(c1cnc(Cl)nc1)N1CC2(CCOCC2)C1]

A yellow suspension of 2-chloropyrimidine-5-carboxylic acid (3.0 g, 18.92 mmol), 7-oxa-2-azaspiro[3.5]nonane (2.89 g, 22.72 mmol), propylphosphonic anhydride solution (12.0 g, 37.8 mmol, 50% in EtOAc) and Et₃N (9.57 g, 94.6 mmol) in THF (50 mL) was stirred at 60° C. for 16 hrs. The cooled mixture was diluted with EtOAc (300 mL) washed with sat. aqueous NH₄Cl (150 mL), brine (150 mL), dried (Na₂SO₄) and concentrated in vacuo. The crude product was purified by column chromatography on silica gel eluting with Pet. Ether:EtOAc (100:0 to 50:50) to afford the title compound as a pale yellow solid, 3.07 g, 61%. ¹H NMR (400 MHz, DMSO-d₆): δ 1.64-1.79 (m, 4H), 3.43-3.48 (m, 2H), 3.52-3.56 (m, 2H), 3.81 (s, 2H), 4.16 (s, 2H), 9.00 (s, 2H). LCMS m/z=268 [M+H]⁺

Preparation 24

2-(Pyrimidin-5-yl)propan-2-amine hydrochloride

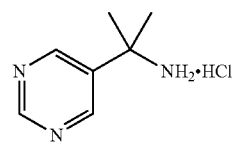

A solution of tert-butyl [2-(pyrimidin-5-yl)propan-2-yl]carbamate (Preparation 33, 5.7 g, 24.02 mmol) in 1M HCl in MeOH (20 mL) was stirred at 20° C. for 2 hrs. The reaction mixture was evaporated under reduced pressure, the residue washed with EtOAc, filtered and dried to afford the title compound as a white solid, 4.0 g, 96%. ¹H NMR (400 MHz, DMSO-d₆): δ 1.71 (s, 6H), 8.20 (br s, 1H), 9.09 (s, 2H), 9.15-9.18 (m, 3H). LCMS m/z=138 [M+H]⁺

Preparation 25

1-(Pyrimidin-5-yl)cyclobutanamine hydrochloride

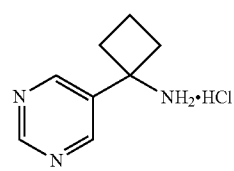

The title compound was obtained in quantitative yield from tert-butyl [1-(pyrimidin-5-yl)cyclobutyl]carbamate (Preparation 34), following the procedure described in Preparation 24. $^1$H NMR (400 MHz, DMSO-d$_6$): δ 1.81-1.86 (m, 1H), 2.17-2.24 (m, 1H), 2.63-2.72 (m, 4H), 9.03 (s, 2H), 9.17-9.28 (m, 4H). LCMS m/z=150 [M+H]$^+$ Preparation 26

1-(Pyrimidin-5-yl)cyclopropanamine hydrochloride

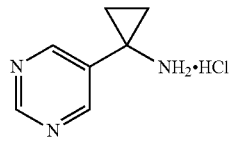

A solution of tert-butyl [1-(pyrimidin-5-yl)cyclopropyl] carbamate (Preparation 35) (19.0 g, 80.8 mmol) in 1M HCl in MeOH (200 mL) was stirred at 25° C. for 2 hrs. The solvent was removed under reduced pressure to afford the title compound as a yellow solid, 13.6 g (98%). $^1$H NMR (400 MHz, DMSO-d$_6$): δ 1.30-1.35 (m, 2H), 1.46-1.51 (m, 2H), 8.92 (s, 2H), 9.15 (s, 1H), 9.33 (br s, 3H). LCMS m/z=136 [M+H]$^+$ Preparation 27

(1S)-1-(Pyrazin-2-yl)ethanamine hydrochloride

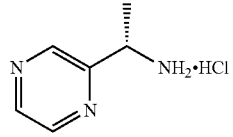

A mixture of 2-methyl-N-[(1S)-1-(pyrazin-2-yl)ethyl] propane-2-sulfinamide (Preparation 46, 320 mg, 1.41 mmol) in 1M HCl in MeOH (8 mL) was stirred at 0° C. for 1 hr. The resulting suspension was evaporated under reduced pressure to afford the title compound as an off-white solid in quantitative yield. $^1$H NMR (400 MHz, MeOD-d$_4$): δ 1.69 (d, 3H), 4.75-4.82 (m, 1H), 8.69 (d, 1H), 8.78 (dd, 1H), 8.82 (d, 1H). LCMS m/z=124 [M+H]

Preparations 28 to 30

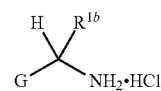

The compounds were prepared from the appropriate sulfinamide starting material in approximately quantitative yield, following the procedure described in Preparation 27.

| Preparation | 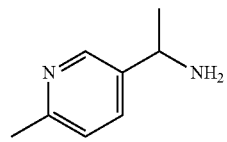 | Starting Material; Name; Data |
|---|---|---|
| 28 | (pyrazin-2-yl with NH$_2$·HCl, R configuration) | Preparation 47: 2-methyl-N-[(1R)-1-(pyrazin-2-yl)ethyl]propane-2-sulfinamide (1R)-1-(Pyrazin-2-yl)ethanamine hydrochloride $^1$H NMR (400 MHz, MeOD-d$_4$): δ 1.68 (d, 3H), 4.77-4.84 (m, 1H), 8.70 (d, 1H), 8.81 (dd, 1H), 8.84 (d, 1H). LCMS m/z = 124 [M + H]$^+$ |
| 29 | (pyrimidin-5-yl with NH$_2$·HCl) | Preparation 48, 2-methyl-N-[1-(pyrimidin-5-yl)ethyl]propane-2-sulfinamide 1-(Pyrimidin-5-yl)ethanamine hydrochloride $^1$H NMR (400 MHz, DMSO-d$_6$): δ 1.61 (d, 3H), 4.46-4.58 (m, 1H), 8.94 (br s, 2H), 9.04 (s, 2H), 9.20 (s, 1H), 10.33 (br s, 1H). LCMS m/z = 124 [M + H]$^+$ |
| 30 | (6-methylpyridin-3-yl with NH$_2$·HCl) | Preparation 49, 2-methyl-N-[1-(6-methylpyridin-3-yl)ethyl]propane-2-sulfinamide 1-(6-Methylpyridin-3-yl)ethanamine hydrochloride $^1$H NMR (400 MHz, MeOD-d$_4$): δ 1.76 (d, 3H), 2.87 (s, 3H), 4.77-4.85 (m, 1H), 8.07 (d, 1H), 8.67 (dd, 1H), 8.92 (d, 1H). LCMS m/z = 137 [M + H]$^+$ |

Preparation 30

1-(6-Methylpyridin-3-yl)ethanamine

Zn powder (20.9 g, 320 mmol) was added in portions to a refluxing solution of (1E)-N-hydroxy-1-(6-methylpyridin-3-yl)ethanamine (Preparation 55, 16.0 g, 106.54 mmol) and NH$_4$OAc (10.7 g, 139 mmol) in EtOH (137 mL) and NH$_4$OH (228 mL) and the resulting mixture was stirred at 95° C. for 16 hrs. The cooled mixture was evaporated under reduced pressure and the residue basified with aq. NaOH to pH>12. The resulting suspension was filtered, the solids washed with DCM, the organic filtrate was washed with brine, dried (Na₂SO₄), filtered off and the filtrate evaporated under reduced pressure to afford the title compound as a yellow oil, 14.3 g (98%). ¹H NMR (400 MHz, DMSO-d₆): δ 1.23 (d, 3H), 2.42 (s, 3H), 3.94-4.01 (m, 1H), 7.16 (d, 1H), 7.64 (dd, 1H), 8.40 (d, 1H). LCMS m/z=137 [M+H]⁺

Preparation 31

3-(Pyrazin-2-yl)oxetan-3-amine

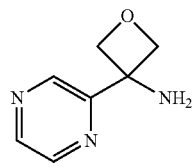 [SMILES: NC1(c2cnccn2)COC1]

A solution of 2-methyl-N-[3-(pyrazin-2-yl)oxetan-3-yl]propane-2-sulfinamide (Preparation 44, 2.2 g, 8.62 mmol) in EtOAc (10 mL) and HCl/EtOAc (1M, 5 mL) was stirred at 0° C. for 5 min. The resulting precipitate was filtered off. The filter cake was dissolved in MeOH (50 mL), NaHCO₃ added (4 g) and the mixture stirred at 25° C. for 15 min. The mixture was diluted with DCM (80 mL) filtered and the filtrate concentrated in vacuo. The crude material was purified by column chromatography on silica gel eluting with MeOH: EtOAc (0:100 to 5:95) to afford the compound as a yellow oil, 400 mg, 10%. ¹H NMR (400 MHz, CDCl₃): δ 4.77-4.82 (m, 2H), 4.89-4.93 (m, 2H), 9.03 (s, 2H), 9.18 (s, 1H). LCMS m/z=152 [M+H]⁺

Preparation 32

3-(Pyrimidin-5-yl)oxetan-3-amine

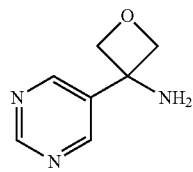 [SMILES: NC1(c2cncnc2)COC1]

The title compound was obtained as a yellow oil in 93% yield from 2-methyl-N-[3-(pyrazin-2-yl)oxetan-3-yl]propane-2-sulfinamide (Preparation 44), following an analogous method to that described in Preparation 31. ¹H NMR (400 MHz, CDCl₃): δ 4.78 (m, 2H), 4.90 (m, 2H), 9.03 (s, 2H), 9.18 (s, 1H). LCMS m/z=152.1 [M+H]⁺

Preparation 33

Tert-butyl [2-(pyrimidin-5-yl)propan-2-yl]carbamate

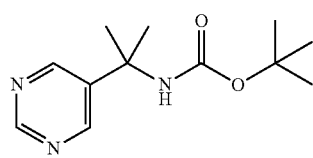 [SMILES: CC(C)(C)OC(=O)NC(C)(C)c1cncnc1]

DPPA (2330 mg, 8.45 mmol) was added to a solution of Et₃N (dried over KOH) (855 mg, 8.45 mmol) and 2-methyl-2-(pyrimidin-5-yl)propanoic acid (Preparation 36, 1170 mg, 7.04 mmol) in distilled t-BuOH (20 mL) and the mixture heated to 110° C. for 16 hrs. The cooled mixture was poured into aq. NH₄Cl solution and extracted with EtOAc (100 mL×3). The combined organic extracts were dried (MgSO₄), filtered and evaporated under reduced pressure. The residue was purified by column chromatography on silica gel eluting with 0-40% EtOAc in Pet. Ether to provide the title compound as a colorless oil, 1.03 g, 62%. ¹H NMR (400 MHz, CDCl₃): δ 1.38 (br s, 9H), 1.65 (s, 6H), 5.12 (br s, 1H), 8.76 (s, 2H), 9.08 (s, 1H). LCMS m/z=238 [M+H]⁺

Preparation 34

Tert-butyl [1-(pyrimidin-5-yl)cyclobutyl]carbamate

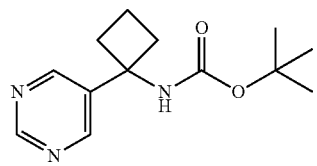 [SMILES: CC(C)(C)OC(=O)NC1(c2cncnc2)CCC1]

The title compound was obtained in 34% yield from 1-(pyrimidin-5-yl)cyclobutane-1-carboxylic acid (Preparation 37), following the method described in Preparation 33. ¹H NMR (400 MHz, CDCl₃): δ 1.36 (br s, 9H), 1.80-1.98 (m, 1H), 2.10-2.21 (m, 1H), 2.42-2.48 (m, 2H), 2.53-2.57 (m, 2H), 8.79 (s, 2H), 9.09 (s, 1H). LCMS m/z=250 [M+H]⁺

Preparation 35

Tert-butyl [1-(pyrimidin-5-yl)cyclopropyl]carbamate

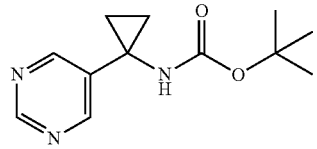 [SMILES: CC(C)(C)OC(=O)NC1(c2cncnc2)CC1]

DPPA (13.50 g, 49.0 mmol) and Et₃N (6.19 g, 61.20 mmol) were added to a suspension of 1-(pyrimidin-5-yl)cyclopropane-1-carboxylic acid (Preparation 38, 6.7 g, 40.81 mmol) in t-BuOH (120 mL) at 30° C. The resulting mixture was degassed with N₂ and stirred at 100° C. for 16 hrs. The cooled mixture was concentrated in vacuo and the residue partitioned between aq. NH₄Cl (50 mL) and pet. ether (50 mL). The mixture was stirred at 0° C. for 10 min and the resulting solid collected by filtration. The solid was washed consecutively with aq.NaHCO₃ (20 mL), water (20 mL) and pet. ether (20 mL) then dried in vacuo to afford the title product as a white solid, 8.1 g, 84% yield. ¹H NMR (400 MHz, CDCl₃): δ 1.24-1.32 (m, 2H), 1.38-1.48 (m, 11H), 5.27-5.40 (m, 1H), 8.61 (s, 2H), 9.06 (s, 1H). LCMS m/z=236 [M+H]⁺

Preparation 36

2-Methyl-2-(pyrimidin-5-yl)propanoic Acid

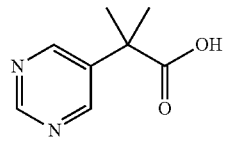

NaOH (635 mg, 15.9 mmol) was added to a solution of methyl 2-methyl-2-(pyrimidin-5-yl)propanoate (Preparation 39, 1.43 g, 7.94 mmol) in THF (5 mL) and H$_2$O (5 mL) and the reaction stirred at 15° C. for 2 hrs. The mixture was concentrated in vacuo, the aqueous solution extracted with EtOAc (5 mL) then acidified with HCl (1N) to pH=3. This aqueous solution was extracted with further EtOAc, and the organic extract evaporated under reduced pressure. The crude product was suspended in a solution of (DCM:MeOH=5:1)(20 mL). The mixture was filtered and the filtrate evaporated under reduced pressure to provide the title compound as a white solid, 1.3 g (99% yield). $^1$H NMR (400 MHz, DMSO-d$_6$): δ 1.47 (s, 6H), 8.76 (s, 2H), 8.99 (s, 1H). LCMS m/z=165 [M−H]$^-$

Preparation 37

1-(Pyrimidin-5-yl)cyclobutane-1-carboxylic Acid

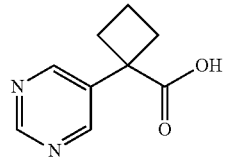 [SMILES: O=C(O)C1(c2cncnc2)CCC1]

NaOH (1.08 g, 27.1 mmol) was added to a solution of methyl 1-(pyrimidin-5-yl)cyclobutane-1-carboxylate (Preparation 40, 2.6 g, 13.53 mmol) in THF (5 mL) and H$_2$O (5 mL) and the resulting mixture stirred at 18° C. for 2 hrs. The reaction was concentrated in vacuo and the residue acidified with 2N HCl to pH=6 (white solid formed). The solid was collected by filtration and washed with water (5 mL×2). The solid was co-evaporated with toluene three times to afford the title compound as a white solid, 1.10 g, 43% yield. $^1$H NMR (400 MHz, DMSO-d$_6$): δ 1.81-1.92 (m, 1H), 1.98-2.10 (m, 1H), 2.49-2.58 (m, 2H), 2.70-2.79 (m, 2H), 8.74 (s, 2H), 9.09 (s, 1H). LCMS m/z=179 [M+H]$^+$

Preparation 38

1-(Pyrimidin-5-yl)cyclopropane-1-carboxylic Acid

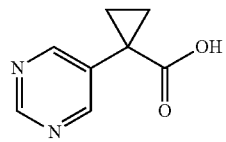 [SMILES: O=C(O)C1(c2cncnc2)CC1]

The title compound was obtained in 77% yield from methyl 1-(pyrimidin-5-yl)cyclopropane-1-carboxylate (Preparation 41), following a similar method to that described in Preparation 37, except the reaction was conducted using THF/MeOH/H$_2$O (1:1:1) as solvent. $^1$H NMR (400 MHz, DMSO-d$_6$): δ 1.28-1.33 (m, 2H), 1.49-1.54 (m, 2H), 8.78 (s, 2H), 9.07 (s, 1H), 12.69 (br s, 1H). LCMS m/z=163 [M−H]$^-$

Preparation 39

Methyl 2-methyl-2-(pyrimidin-5-yl)propanoate

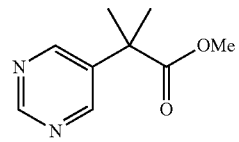

LiHMDS (39.4 mL, 39.4 mmol, 1M solution in THF) was added drop wise to a −78° C. solution of methyl 2-(pyrimidin-5-yl)acetate (1.5 g, 9.86 mmol) in THF (20 mL) under N$_2$. The resulting mixture was stirred at −78° C. for 1 hr. A solution of iodomethane (15.1 g, 106.38 mmol) in THF (10 mL) was added drop wise to the reaction mixture at −78° C. After complete addition, the resulting brown solution was allowed to warm to 18° C. and stirred for 16 hrs. The reaction was poured into saturated NH$_4$Cl solution (200 mL) and the mixture extracted with EtOAc (200 mL×3). The combined organic extracts were washed with brine, dried (Na$_2$SO$_4$), filtered and concentrated in vacuo to afford a brown liquid. The crude product was purified by column chromatography on silica gel eluting with Pet. Ether:EtOAc (100:0 to 70:30) to provide the title compound as a yellow oil, 1.3 g, 73%. $^1$H NMR (400 MHz, CDCl$_3$): δ 1.63 (s, 6H), 3.67 (s, 3H), 8.73 (s, 2H), 9.10 (s, 1H). LCMS m/z=181 [M+H]$^+$

Preparation 40

Methyl 1-(pyrimidin-5-yl)cyclobutan-1-carboxylate

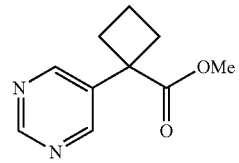 [SMILES: COC(=O)C1(c2cncnc2)CCC1]

LiHMDS (56.2 mL, 56 mmol, 1M solution in THF) was added drop wise to a stirred yellow solution of methyl 2-(pyrimidin-5-yl)acetate (8.00 g, 47 mmol) in THF (150 mL) at −70° C. under N$_2$ and the reaction was stirred at −70° C. for 1 hr. A solution of 1,3-diiodopropane (13.8 g, 46.8 mmol) in THF (20 mL) was added drop wise to the reaction at −70° C. and the mixture allowed to warm to 20° C. slowly and stirred for 1 hr. The reaction mixture was again cooled to −70° C. and an additional portion of LiHMDS (1M in THF, 56.2 mL, 56.2 mmol) was added drop wise. After addition, the reaction was allowed to warm to 20° C. slowly and stirred for an additional hour. The reaction was poured into saturated NH$_4$Cl solution (60 mL) the mixture extracted with EtOAc (300 mL×3). The combined organic extracts were washed with brine, dried (Na₂SO₄) filtered and concentrated in vacuo. The crude product was purified by column chromatography on silica gel eluting with pet. ether:EtOAc (100:0 to 65:35) to afford the title compound as a yellow oil, 1.95 g, 22% yield. $^1$H NMR (400 MHz, CDCl₃): 1.90-2.04 (m, 1H), 2.12-2.25 (m, 1H), 2.48-2.59 (m, 2H), 2.87-2.96 (m, 2H), 3.67 (s, 3H), 8.66 (s, 2H), 9.09 (s, 1H). LCMS m/z=193 [M+H]⁺

Preparation 41

Methyl 1-(pyrimidin-5-yl)cyclopropan-1-carboxylate

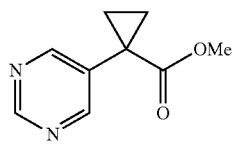 [SMILES: COC(=O)C1(c2cncnc2)CC1]

LiHMDS (1M solution in THF, 211 mL, 211 mmol) was added drop wise at −70° C. to a stirred solution of methyl 2-(pyrimidin-5-yl)acetate (26.73 g, 175.7 mmol) in THF (200 mL) and the resulting mixture was stirred at this temperature for 1 hr. A solution of 1,3,2-dioxathiolane 2,2-dioxide (26.2 g, 211 mmol) in THF (200 mL) was added drop wise so as to maintain the temperature at −70° C. and on complete addition, the reaction was brought slowly to −20° C. and stirred for 1.5 hr. The reaction mixture was again cooled to −72° C. and an additional portion of LiHMDS (1M in THF, 211 mL, 211 mmol) added. The reaction mixture was then allowed to warm to room temperature and stirred for 15 hrs. The reaction was quenched with saturated NH₄Cl solution (300 mL) and the mixture extracted with EtOAc (3×500 mL). The combined organic extracts were washed with brine, dried (Na₂SO₄) and concentrated in vacuo. The crude product was purified by column chromatography eluting with pet. Ether:EtOAc (100:0 to 65:35) to afford the title compound as a yellow oil, 25.0 g, 80%. $^1$H NMR (400 MHz, CDCl₃): δ 1.20-1.25 (m, 2H), 1.67-1.74 (m, 2H), 3.63 (s, 3H), 8.69 (s, 2H), 9.03 (s, 1H). LCMS m/z=179 [M+H]⁺

Preparation 42

1-(Pyrazin-2-yl)cyclobutanamine

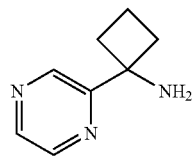 [SMILES: NC1(c2cnccn2)CCC1]

A solution of acetyl chloride (18.8 g, 240 mmol) in MeOH (60 mL) was added to a solution of 2-methyl-N-[1-(pyrazin-2-yl)cyclobutyl]propane-2-sulfinamide (Preparation 43, 3.4 g, 13.42 mmol) in MeOH (5 mL) maintaining the reaction temperature below 10° C. On complete addition, the reaction was stirred at 20° C. for 1 hr. The reaction mixture was concentrated in vacuo and the residue dissolved in MeOH (60 mL). NaHCO₃ solid was added until no gas was released. The suspension was filtered and washed with MeOH. The filtrate was concentrated in vacuo and the residue dissolved in DCM (60 mL). The suspension was filtered again, washing through with DCM. The filtrate was evaporated under reduced pressure to afford the title compound as a brown solid, 1.7 g, 85%. $^1$H NMR (400 MHz, DMSO-d₆): 1.90-2.02 (m, 1H), 2.11-2.25 (m, 1H), 2.53-2.70 (m, 4H), 8.68 (d, 1H), 8.71 (dd, 1H), 8.38-8.92 (br s, 2H), 9.09 (s, 1H). LCMS m/z=150 [M+H]⁺

Preparation 43

2-Methyl-N-[1-(pyrazin-2-yl)cyclobutyl]propane-2-sulfinamide

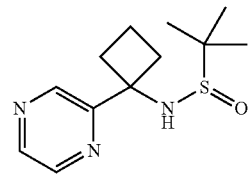 [SMILES: CC(C)(C)S(=O)NC1(c2cnccn2)CCC1]

n-BuLi (25.4 mL, 63.5 mmol, 2.5 M in hexane) was added drop wise to a −78° C. solution of 2-bromopyrazine (10.1 g, 63.5 mmol) in toluene (150 mL) under N₂. After 10 min at −78° C., a solution of N-cyclobutylidene-2-methylpropane-2-sulfinamide (Preparation 50, 10.0 g, 57.71 mmol) in toluene (50 mL) was added slowly. The resulting dark red solution was stirred for 1 hr at −78° C. The reaction was quenched by the addition of sat. NH₄Cl solution (10 mL) and the reaction mixture dried (MgSO₄), filtered and concentrated in vacuo to give a brown oil. The crude product was purified by column chromatography on silica gel eluting with pet. Ether:EtOAc (100:0 to 0:100) to MeOH:EtOAc (9:91) to afford the title compound as a yellow oil, 4.0 g, 27%. $^1$H NMR (400 MHz, CDCl₃): δ 1.21 (s, 9H), 1.86-1.96 (m, 1H), 2.08-2.19 (m, 1H), 2.58-2.78 (m, 4H), 3.62-3.75 (br s, 1H), 8.49 (d, 1H), 8.56 (dd, 1H), 8.80 (d, 1H). LCMS m/z=254 [M+H]⁺

Preparation 44

2-Methyl-N-[3-(pyrazin-2-yl)oxetan-3-yl]propane-2-sulfinamide

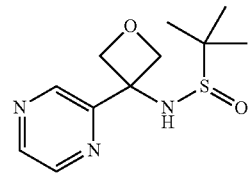 [SMILES: CC(C)(C)S(=O)NC1(c2cnccn2)COC1]

The title compound was prepared as a yellow oil in 25% yield from 2-methyl-N-(oxetan-3-ylidene)propane-2-sulfinamide (Preparation 51) and 2-bromopyrazine following the method described in Preparation 43. $^1$H NMR (400 MHz, CDCl₃): δ 1.29 (s, 9H), 4.94 (d, 1H), 5.07-5.15 (m, 2H), 5.35 (d, 1H), 8.56-8.58 (m, 1H), 8.59-8.60 (m, 1H), 9.08 (d, 1H). LCMS m/z=256 [M+H]⁺

Preparation 45

2-Methyl-N-[3-(pyrimidin-5-yl)oxetan-3-yl]propane-2-sulfinamide

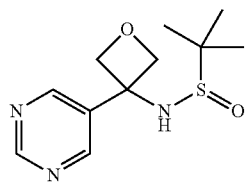 [SMILES: CC(C)(C)S(=O)NC1(c2cncnc2)COC1]

The title compound was prepared as a yellow oil in 14% yield from 2-methyl-N-(oxetan-3-ylidene)propane-2-sulfinamide (Preparation 51) and 5-bromopyrimidine following an analogous method to that described in Preparation 43, except THF was used as the reaction solvent. $^1$H NMR (400 MHz, CDCl$_3$): δ 1.22 (s, 9H), 4.86 (d, 1H), 5.06 (d, 1H), 5.14 (s, 2H), 8.86 (s, 2H), 9.20 (s, 1H). LCMS m/z=139 [M+H]$^+$

Preparation 46

(S)-2-methyl-N—((S)-1-(pyrazin-2-yl)ethyl)propane-2-sulfinamide and

Preparation 47

(S)-2-methyl-N—((R)-1-(pyrazin-2-yl)ethyl)propane-2-sulfinamide

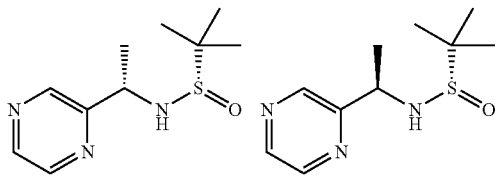

Dimethyl zinc (21.3 mL, 21.3 mmol, 1.0 M in toluene) was added in an oven-dried and N$_2$-purged flask, followed by MeMgBr (6.25 mL, 18.7 mmol, 3.0 M in ether) over 1 min with stirring at 15° C. and the solution allowed to stir for 20 mins. This solution was added drop wise over 30 min into a cooled (−68° C.) suspension of 2-methyl-N-[(E)-pyrazin-2-ylmethylidene]propane-2-sulfinamide (Preparation 53, 1.8 g, 8.52 mmol) in anhydrous THF (25.8 mL) and the reaction then allowed to stir at −68° C. for 1 hr. The reaction was quenched by the drop wise addition of saturated NH$_4$Cl soln. (10 mL) maintaining the temperature below −60° C. The mixture was then allowed to warm to rt, the resulting solid filtered off, washed with EtOAc (200 mL) and MeOH (20 mL) and the filtrate concentrated in vacuo. The crude product was purified by automated column chromatography on silica gel, eluting with EtOAc:DCM (20:80 to 95:5) to afford a yellow gum, 2.4 g. This was further purified by preparative HPLC using an Agela ASB 150*25 mm*5 um column, eluting with 16-46% (0.225% TFA in water):MeCN at a flow rate of 25 mL/min to afford 2-methyl-N-[(1S)-1-(pyrazin-2-yl)ethyl]propane-2-sulfinamide as a yellow oil, 740 mg. $^1$H NMR (400 MHz, CDCl$_3$): δ 1.20 (s, 9H), 1.64 (d, 3H), 3.95 (br d, 1H), 4.67-4.75 (m, 1H), 8.48 (d, 1H), 8.53 (dd, 1H), 8.61 (d, 1H). SFC RT [Method CA-G]=4.632 min Further elution provided 2-methyl-N-[(1R)-1-(pyrazin-2-yl)ethyl]propane-2-sulfinamide as a yellow oil, 700 mg. $^1$H NMR (400 MHz, CDCl$_3$): δ 1.25 (s, 9H), 1.55 (d, 3H), 4.26 (br s, 1H), 4.65-4.70 (m, 1H), 8.49 (d, 1H), 8.52 (dd, 1H), 8.62 (d, 1H). SFC RT [Method CA-G]=3.593 min

Preparation 48

2-Methyl-N-[1-(pyrimidin-5-yl)ethyl]propane-2-sulfinamide

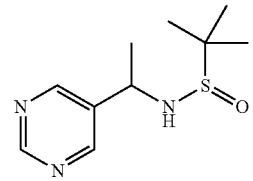

NaBH$_4$ (1610 mg, 42.6 mmol) was added portion wise to an ice-cooled solution of 2-methyl-N-[(1E)-1-(pyrimidin-5-yl)ethylidene]propane-2-sulfinamide (Preparation 52, 3.2 g, 14.20 mmol) in THF (25 mL) and MeOH (25 mL) and the resulting mixture stirred at 20° C. for 1 hr. The mixture was cooled to 0° C. and quenched with saturated NH$_4$Cl soln. (10 mL). The resulting solid was filtered off and the solid washed with DCM (100 mL) and MeOH (20 mL). The combined organic filtrates were dried over MgSO$_4$ and concentrated in vacuo. The residue was purified by column chromatography on silica gel eluting with pet. Ether: EtOAc (100:0 to 0:100), then MeOH:DCM, (0:100 to 30:70) to afford the title compound as a white solid, 1.6 g, 50% (title compound was isolated as a 1:1 mixture of diastereomers and used as is in the next step). $^1$H NMR (400 MHz, CDCl$_3$): δ 1.20 (s, 4.5H), 1.23 (s, 4.5H), 1.59 (d, 1.5H), 1.60 (d, 1.5H), 3.47 (br d, 0.5H), 3.59 (br d, 0.5H), 4.55-4.66 (m, 1H), 8.71 (s, 1H), 8.74 (s, 1H), 9.14 (s, 0.5H), 9.15 (s, 0.5H). LCMS m/z=228 [M+H]$^+$

Preparation 49

2-Methyl-N-[1-(6-methylpyridin-3-yl)ethyl]propane-2-sulfinamide

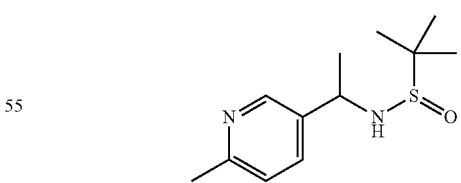

Me$_2$Zn (5.63 mmol, 1M in toluene, 5.63 mL) was added to an oven-dried and N$_2$-purged round-bottomed flask and MeMgBr (0.497 mmol, 3 M in ether) was added over 1 min. The solution was stirred at 15° C. for 30 min. This solution was added drop wise over 30 mins to a −78° C. solution of 2-methyl-N-[(E)-(6-methylpyridin-3-yl)methylidene]propane-2-sulfinamide (Preparation 54, 0.7 g, 3.31 mmol) in anhydrous THF (10 mL) so as to maintain the internal temperature below −70° C. Upon complete addition the reaction was stirred at −78° C. for 1 hr and then allowed to warm to 15° C. The reaction was quenched with sat. aqueous NH₄Cl solution, the mixture was filtered, and the residue concentrated under reduced pressure. The residue was purified by column chromatography on silica gel eluting with DCM:MeOH (100:0 to 60:40) to afford the title compound as a colorless oil, 650 mg, 76% (title compound was isolated in ~3:1 ratio with 1-(6-methylpyridin-3-yl)ethanol and was used as is in the next step). ¹H NMR (400 MHz, CDCl₃): δ 1.23 (s, 9H), 1.54 (d, 3H), 2.56 (s, 3H), 4.53-4.60 (m, 1H), 7.13-7.19 (m, 1H), 7.60 (dd, 1H), 8.50 (br s, 1H). LCMS m/z=241 [M+H]⁺

Preparation 50

N-Cyclobutylidene-2-methylpropane-2-sulfinamide

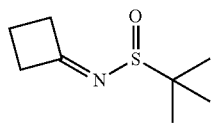

2-Methyl-2-propanesulfinamide (19 g, 153 mmol) and Ti(OiPr)₄ (81.1 g, 285 mmol) were added to a solution of cyclobutanone (10.0 g, 142 mmol) in anhydrous THF (180 mL) and the resulting yellow solution was heated at 50° C. for 6 hrs. The reaction was cooled with an ice-water bath, diluted with anhydrous MeOH (100 mL) and EtOAc (100 mL) then sat. aq. NaHCO₃ (20 mL) was added. The resulting suspension was stirred for 1 hr. The mixture was filtered, washed through with EtOAc and the filtrate was dried (Na₂SO₄) and concentrated in vacuo. The crude product was purified by column chromatography on silica gel eluting with pet. Ether: EtOAc (100:0 to 80:20) to provide the title compound as a pale yellow oil, 17.0 g, 69%. ¹H NMR (400 MHz, CDCl₃): δ 1.23 (s, 9H), 2.02-2.17 (m, 2H), 3.03-3.19 (m, 2H), 3.22-3.32 (m, 1H), 3.44-3.56 (m, 1H). LCMS m/z=174 [M+H]⁺

Preparation 51

2-Methyl-N-(oxetan-3-ylidene)propane-2-sulfinamide

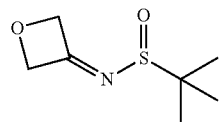

2-Methyl-2-propanesulfinamide (25.9 g, 214 mmol) followed by Ti(OiPr)₄ (110 g, 389 mmol) were added to a solution of oxetan-3-one (14.0 g, 194 mmol) in anhydrous THF (250 mL) and the reaction mixture was heated at 50° C. for 16 hrs. The reaction mixture was cooled in an ice bath, anhydrous MeOH (140 mL) was added followed by sat. aq. NaHCO₃ (20 mL) and the resulting suspension stirred for 1 hr. The solids were filtered off washing through with EtOAc. The filtrate was dried (Na₂SO₄) and concentrated in vacuo. The crude product was purified by column chromatography on silica gel column eluting with pet. Ether:EtOAc (100:0 to 80:20) to give the title product as a pale yellow oil, 15.0 g, 44%. ¹H NMR (400 MHz, CDCl₃): δ 1.25 (s, 9H), 5.38-5.50 (m, 2H), 5.61-5.67 (m, 1H), 5.74-5.81 (m, 1H). LCMS m/z=176 [M+H]⁺

Preparation 52

2-Methyl-N-[(1E)-1-(pyrimidin-5-yl)ethylidene]propane-2-sulfinamide

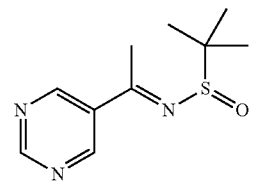

2-Methyl-2-propanesulfinamide (2.73 g, 22.5 mmol) and Ti(OiPr)₄ (11.6 g, 40.9 mmol) were added to a solution of 1-(5-pyrimidinyl)ethanone (2.5 g, 20.47 mmol) in DCM (100 mL) and the mixture was heated under reflux for 16 hrs. The mixture was cooled in an ice bath and diluted with anhydrous MeOH (20 mL) and aq. NaHCO₃ (5 mL). The resulting suspension was stirred for 1 hr then filtered, washed through with EtOAC. The filtrate was dried (Na₂SO₄) and concentrated in vacuo. The crude product was purified by column chromatography on silica gel column eluting with pet. Ether:EtOAc (100:0 to 50:50) to afford the title compound as a yellow oil, 3.2 g, 69%. (title compound was isolated in a ~85:15 mixture with 1-(5-pyrimidinyl)ethanone, and the mixture was used as is in the next step). ¹H NMR (400 MHz, CDCl₃): δ 1.32 (s, 9H), 2.80 (s, 3H), 9.15 (s, 2H), 9.28 (s, 1H). LCMS m/z=226 [M+H]⁺

Preparation 53

(S)-2-Methyl-N-[(E)-pyrazin-2-ylmethylidene]propane-2-sulfinamide

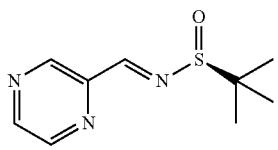

The title compound was obtained as a yellow gum in 37% yield from (S)-(−)-2-methyl-2-propanesulfinamide and pyrazine 2-carbaldehyde, following an analogous procedure to that described in Preparation 52. ¹H NMR (400 MHz, CDCl₃): δ 1.31 (s, 9H), 8.67 (d, 1H), 8.72 (dd, 1H), 8.75 (s, 1H), 9.25 (d, 1H). LCMS m/z=212 [M+H]⁺

Preparation 54

2-Methyl-N-[(E)-(6-methylpyridin-3-yl)methyl-idene]propane-2-sulfinamide

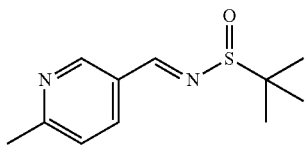

2-Methyl-2-propanesulfinamide (1.5 g, 12.4 mmol) and copper(II) sulfate (2.64 g, 16.5 mmol) were added to a solution of 6-methylpyridine-3-carboxaldehyde (1 g, 9.25 mmol) in DCM (30 mL) and the reaction heated to 50° C. for 18 hrs. The cooled mixture was filtered and washed with DCM. The filtrate was concentrated in vacuo. The residue was purified by column chromatography on silica gel eluting with EtOAc: Pet. Ether (0:100 to 80:20) to afford the title compound as a colourless oil, 1.55 g, 84% (title compound was isolated in a -3:1 mixture with 6-methylpyridine-3-carboxaldehyde, and the mixture was used as is in the next step). $^1$H NMR (400 MHz, CDCl$_3$): δ 1.26 (s, 9H), 2.63 (s, 3H), 7.28 (d, 1H), 8.08 (dd, 1H), 8.62 (s, 1H), 8.89 (d, 1H). LCMS m/z=225 [M+H]$^+$

Preparation 55

(1E)-N-Hydroxy-1-(6-methylpyridin-3-yl)ethanamine

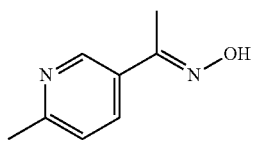

NH$_2$OH.HCl (26.2 g, 377 mmol) was added to a solution of 1-(6-methylpyridin-3-yl)ethan-1-one (17.0 g, 125.77 mmol) and sodium acetate (41.3 g, 503 mmol) in EtOH (125 mL) and H$_2$O (25 mL) and the resulting mixture was stirred at 25° C. for 7 hrs. The reaction mixture was diluted with EtOAc (1 L), washed with brine (400 mL×2), dried (Na$_2$SO$_4$), filtered and the filtrate evaporated under reduced pressure. The residue was washed with EtOH (10 mL) to provide the title compound as a white solid, 16.0 g, 85%. $^1$H NMR (400 MHz, DMSO-d$_6$): 2.16 (s, 3H), 2.48 (s, 3H), 7.26 (d, 1H), 7.90 (dd, 1H), 8.70 (d, 1H), 11.36 (s, 1H). LCMS m/z=151 [M+H]$^+$

Preparation 56

(3aR,4R,7aS)-rel-Octahydro-1H-isoindol-4-ol hydrochloride

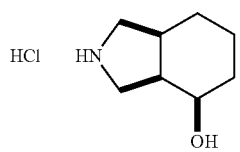

8.4% aq. HCl (300 mL) was added to a solution of tert-butyl (3aR,4R,7aS)-rel-4-hydroxyoctahydro-2H-isoindole-2-carboxylate (Preparation 57, 32.66 g, 0.136 mol) in 2-propanol (200 mL) and the mixture was heated under reflux for 1 hr. The cooled mixture was evaporated under reduced pressure and the residue triturated with ether, the resulting solid filtered off, washed with ether and dried to afford the title compound, 23.92 g, 99%. $^1$H NMR (400 MHz, MeOD-d$_4$): δ 1.28-1.80 (m, 8H), 2.41-2.45 (m, 1H), 2.54-2.59 (m, 1H), 3.19-3.39 (m, 4H), 3.96-3.99 (m, 1H). LCMS m/z=142 [M+H]$^+$

Preparation 57 tert-butyl (3aR,4R,7aS)-rel-4-hydroxyoctahydro-2H-isoindole-2-carboxylate

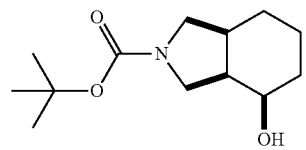

A mixture of (3aR,4R,7aS)-rel-2-benzyloctahydro-1H-isoindol-4-ol (Preparation 58, 56 g, 0.242 mol), ammonium formate (45.8 g, 0.726 mol) and 10% Pd/C (5 g) in MeOH (500 mL) was stirred at rt until no starting material remained by tlc analysis. The mixture was filtered and the filtrate evaporated under reduced pressure. The residue was dissolved in 2-propanol (500 mL) and Boc$_2$O (52.8 g, 0.242 mol) added. The mixture was heated under reflux for 30 min, then concentrated under reduced pressure. DCM (500 mL) was added, the mixture was washed with water (100 mL), 5% NaHSO$_4$ (100 mL) and again with water (100 mL). The organic layer was dried (MgSO$_4$) and co-evaporated with silica gel (100 g). The residue was purified on a silica gel column eluting with hexane:EtOAc (50:50) to afford the title compound, 32.66 g, 56%.

Preparation 58

(3aR,4R,7aS)-rel-2-Benzyloctahydro-1H-isoindol-4-ol

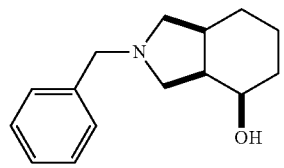

1N Solution of Li-Selectride® in THF (268 mL, 0.268 mol) was added at −78 C to a solution of 2-(phenylmethyl)-3aα,7aα-octahydro-1H-isoindol-4-one (Procedure R, WO 9422823) (56.0 g, 0.244 mol) in THF (600 mL) and the solution stirred for 2 hrs at −78° C., then allowed to warm to rt and stirred for a further 18 hrs. The mixture was concentrated in vacuo, the residue diluted with DCM, washed with water, sat. aq Na$_2$CO$_3$ and water then evaporated under reduced pressure to afford the title compound, 56.0 g, 99%.

Preparation 59

3-(Pyrrolidin-3-yl)-1H-pyrazole hydrochloride bis HCl Salt

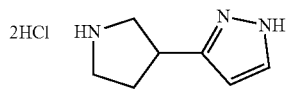

A mixture of tert-butyl (E)-3-(3-(dimethylamino)acryloyl)pyrrolidine-1-carboxylate (3.0 g, 11.18 mmol) and hydrazine (1.11 mL, 12.3 mmol) in EtOH (20 mL) was heated under reflux for 2 hr and the cooled reaction was evaporated under reduced pressure. The residue was dissolved in EtOH and treated with HCl (4M in dioxane) and the mixture was stirred at rt for 1 hr. 2-MeTHF was added and the resulting solid filtered off and dried to afford the title compound as a solid. $^1$H NMR (400 MHz, DMSO-$d_6$): δ 1.95-2.05 (m, 1H), 2.30-2.38 (m, 1H), 3.14-3.35 (m, 3H), 3.53-3.66 (m, 2H), 6.59 (d, 1H), 8.01 (d, 1H), 9.86 (br s, 2H), 13.29 (br s, 2H). LCMS m/z=138 [M+H]$^+$

Preparation 60

3-Methyl-5-(Pyrrolidin-3-yl)-1H-pyrazole hydrochloride bis HCl Salt

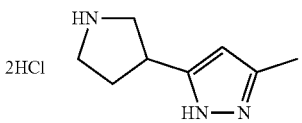

HCl in dioxane (4M solution, 50 mL) was added to a stirred solution of tert-butyl 3-(3-methyl-1H-pyrazol-5-yl)pyrrolidine-1-carboxylate (Preparation 61, 10.0 g, 39.84 mmol) in MeOH (30 mL) at 0° C. and the reaction stirred at rt for 16 hrs. The mixture was concentrated in vacuo and the residue triturated with dry Et$_2$O and dried under vacuum to afford the title compound as light yellow solid, 7.0 g, 94%. $^1$H NMR (400 MHz, DMSO-$d_6$): δ 1.93-2.05 (m, 1H), 2.28 (s, 3H), 2.30-2.40 (m, 1H), 3.11-3.34 (m, 3H), 3.57-3.67 (m, 2H), 6.55 (s, 1H), 9.88 (br s, 2H), 14.48 (br s, 2H). LCMS m/z=152 [M+H]$^+$

Preparation 61 tert-Butyl 3-(3-methyl-1H-pyrazol-5-yl)pyrrolidine-1-carboxylate

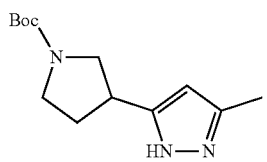 [SMILES: Cc1cc(C2CCN(C(=O)OC(C)(C)C)C2)[nH]n1]

NH$_2$NH$_2$.H$_2$O (5.32 g, 106.38 mmol) was added to a stirred solution of tert-butyl 3-[(2E)-3-(dimethylamino)but-2-enoyl]pyrrolidine-1-carboxylate (Preparation 62, 20.0 g, 70.92 mmol) in MeOH (250 mL) and the resulting mixture was heated under reflux for 2 hrs. The cooled mixture was concentrated in vacuo and the crude product purified by column chromatography on silica gel, eluting with MeOH:DCM (2:98 to 3:97) to afford the title compound as colorless oil, 12.0 g, 67%. LCMS m/z=251 [M+H]$^+$

Preparation 62 tert-Butyl 3-[(2E)-3-(dimethylamino)but-2-enoyl]pyrrolidine-1-carboxylate

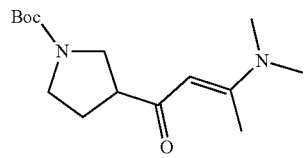 [SMILES: C/C(=C\C(=O)C1CCN(C(=O)OC(C)(C)C)C1)N(C)C]

A stirred solution of tert-butyl 3-acetyl-1-pyrrolidinecarboxylate (Commercial, 30 g, 140.66 mmol) and N,N-dimethylacetamide dimethyl acetal (180 mL) in a sealed tube was heated to 105° C. for 15 hrs. The cooled reaction mixture was concentrated under reduced pressure to afford the title compound, 20 g, which was used without further purification. LCMS m/z=283 [M+H]$^+$

Preparation 63

3-Ethyl-3-methoxypyrrolidine

10% Pd/C (300 mg) was added to a solution of benzyl 3-ethyl-3-methoxypyrrolidine-1-carboxylate (Preparation 64, 1.4 g, 5.32 mmol) in MeOH (10 mL) and the reaction stirred at 25° C. under an atmosphere of 15 psi H$_2$ for 2 hrs. The mixture was filtered through Celite® and the filtrate concentrated under reduced pressure to afford the title product as a colorless oil, 400 mg, 81%. $^1$H NMR (400 MHz, CDCl$_3$): δ 0.90 (t, 3H), 1.52-1.68 (m, 3H), 1.93 (ddd, 1H), 2.57 (d, 1H), 2.90-2.97 (m, 1H), 3.04-3.12 (m, 2H), 3.14 (s, 3H), 3.47 (br s, 1H). LCMS m/z=130 [M+H]$^+$

Preparation 64

Benzyl 3-ethyl-3-methoxypyrrolidine-1-carboxylate

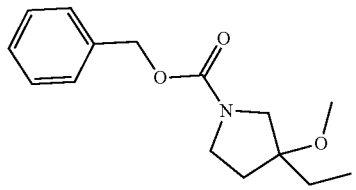 [SMILES: CCC1(OC)CCN(C(=O)OCc2ccccc2)C1]

NaH (375 mg, 15.6 mmol, 60% in mineral oil) was added to a solution of benzyl 3-ethyl-3-hydroxypyrrolidine-1-carboxylate (Preparation 65, 2.6 g, 10.43 mmol) in THF (25 mL) and the mixture stirred at 20° C. for 30 mins. Iodomethane (4.44 g, 31.3 mmol) was added and the reaction stirred at 60° C. for 16 hrs. The reaction was quenched by the addition of ice water, then extracted with EtOAc (200 mL×2). The combined organic extracts were washed with H₂O (200 mL), brine (200 mL), dried (Na₂SO₄) and concentrated. The crude product was purified by column chromatography on silica gel eluting with pet. Ether:EtOAc (100:0-40:60) to afford the title compound as a colourless oil, 1.5 g, 55%. ¹H NMR (400 MHz, CDCl₃): δ 0.90-0.95 (m, 3H), 1.59-1.75 (m, 3H), 2.04-2.10 (m, 1H), 3.14-3.18 (m. 4H), 3.45-3.68 (m, 3H), 5.10-5.18 (m, 2H), 7.31-7.39 (m, 5H). LCMS m/z=264 [M+H]⁺

Preparation 65

Benzyl 3-ethyl-3-hydroxypyrrolidine-1-carboxylate C

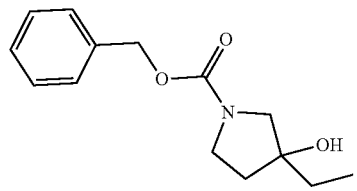 [SMILES: CCC1(O)CCN(C(=O)OCc2ccccc2)C1]

1-Carbobenzyloxy-3-pyrrolidinone (5.0 g, 22.81 mmol) in THF (10 mL) was added to a solution of EtMgBr (15.2 mL, 45.6 mmol, 3.0 M in Et₂O) in THF (40 mL) at 0° C. and the reaction was stirred for 2 hrs. Saturated aqueous NH₄Cl solution (100 mL) was added and the mixture was extracted with EtOAc (200 mL×3). The combined organic extracts were washed with H₂O (200 mL), dried (Na₂SO₄) and concentrated in vacuo. The crude product was purified by column chromatography on silica gel eluting with pet. Ether:EtOAc (100:0 to 50:50) to afford the title compound as a colourless oil, 2.6 g, 46%. ¹H NMR (400 MHz, CDCl₃): δ 0.96-1.04 (m, 3H), 1.63-1.71 (m, 2H), 1.76-1.98 (m, 2H), 3.29 (dd, 1H), 3.45 (dd, 1H), 3.55-3.64 (m, 2H), 5.08-5.18 (m, 2H), 7.29-7.39 (m, 5H). LCMS m/z=250 [M+H]⁺

Preparation 66

(3-Ethylpyrrolidin-3-yl)methanol

A mixture of (1-benzyl-3-ethylpyrrolidin-3-yl)methanol (104 g, 0.474 mol), ammonium formate (89.7 g, 1.42 mol) and 10% Pd/C (10 g) in MeOH (1 L) was heated under reflux for 1 hr. The cooled mixture was filtered and Et₃N (20 mL) was added. The mixture was evaporated under reduced pressure, and the residue was distilled twice, collecting at first the wide fraction and then the fraction in a boiling point (75-84° C. at 0.3-0.4 mmHg) to afford the title compound, 25.5 g, 42%. ¹H NMR (400 MHz, CDCl₃): δ 0.80 (t, 3H), 1.23-1.51 (m, 4H), 2.32 (d, 1H), 2.60-2.81 (m, 3H), 3.21 (s, 2H), 3.58 (br s, 2H). LCMS m/z=130 [M+H]⁺

Preparation 67

(1-Benzyl-3-ethylpyrrolidin-3-yl)methanol

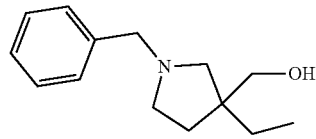 [SMILES: CCC1(CO)CCN(Cc2ccccc2)C1]

Methyl 1-benzyl-3-ethylpyrrolidine-3-carboxylate (110 g, 0.51 mol) was dissolved in THF (600 mL), and water (240 mL) added. NaBH₄ (9.5 g, 0.25 mol) was added in portions under stirring and cooling, maintaining the temperature of the mixture below 30° C. THF was evaporated, and 20% HCl was added to obtain an acid solution. The mixture was extracted with ether (3×150 mL), the pH of the aqueous phase was adjusted to 9 with concentrated alkali. This aqueous solution was extracted with DCM (2×300 mL), and the combined organic extracts were dried (Na₂SO₄) and evaporated to afford the title compound, 104 g, 94%.

Preparation 68

Methyl 1-benzyl-3-ethylpyrrolidine-3-carboxylate

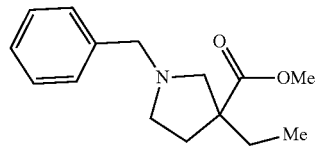 [SMILES: CCC1(C(=O)OC)CCN(Cc2ccccc2)C1]

A solution of methyl 2-ethylacrylate (99.5 g, 1.18 mol) and N-benzyl-1-methoxy-N-[(trimethylsilyl)methyl]methanamine (337 g, 1.42 mol) in toluene (1 L) was cooled to −3 C, and a 1N solution of TFA in DCM (118 mL, 118 mmol) was added drop wise under stirring. The reaction mixture was stirred under cooling for 40 min and then at room temperature for a further 18 hrs. The mixture was washed with saturated NaHCO₃ solution and brine, dried (MgSO₄) and evaporated under reduced pressure. The residue was distilled (bp 145° C. at 3 mmHg) to afford the title compound, 110 g, 43%.

Preparation 69

((3S,4S)-4-(Trifluoromethyl)pyrrolidin-3-yl)methanol

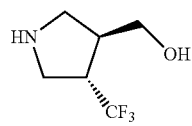

A solution of benzyl (3S,4S)-3-(hydroxymethyl)-4-(trifluoromethyl)pyrrolidine-1-carboxylate (Preparation 70, 5.6 g, 18.47 mmol) in EtOH (75 mL) was degassed using Ar$_{(g)}$ and 20% Pd(OH)$_2$ (1.81 g, 12.93 mmol) was added. The reaction mixture was hydrogenated at rt for 16 hrs and then filtered through Celite® washing through with 0.1% aq. NH$_3$ in EtOH (300 mL). The filtrate was evaporated under reduced pressure to afford the title compound as a brown gel, 3.0 g, 96%. $^1$H NMR (400 MHz, CDCl$_3$): δ 2.37-2.46 (m, 1H), 2.64-2.71 (m, 2H), 2.90 (dd, 1H), 3.04 (dd, 1H), 3.12 (dd, 1H), 3.17-3.22 (m, 1H), 3.61 (dd, 1H), 3.72 (dd, 1H). α$_{[D]}$$^{25.0}$=-44.4° (c=1.00, MeOH)

Preparation 70

Benzyl (3S,4S)-3-(Hydroxymethyl)-4-(trifluoromethyl)pyrrolidine-1-carboxylate

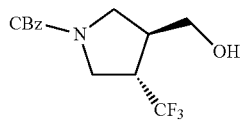

NaHCO$_3$ (29.79 g, 354.72 mmol) was added portion wise to a stirred solution of ((3S,4S)-rel-4-(trifluoromethyl)pyrrolidin-3-yl)methanol (*Bioorg. Med. Chem. Lett.* 1998, 8, 2833) (12.0 g, 70.94 mmol) in DCM:H$_2$O (396 mL, 3:2) at rt. The mixture was cooled to 0-5° C. and CBz-Cl (11.91 mL, 70.94 mmol) was added drop wise and the resulting reaction was stirred at rt for 16 hrs. The reaction was quenched with water and extracted with DCM (300 mL). The combined organic extracts were washed with water, dried (Na$_2$SO$_4$) and concentrated under reduced pressure. The crude product was purified by column chromatography on silica gel eluting with EtOAC:hexane, (30:70) to afford a racemic mixture, 17.4 g. This was separated by chiral prep. SFC using a CHIRALPAK AD-H (250×21 mm) column, mobile phase: COO$_2$: [MeCN:MeOH (1:1)]=80:20, and a total flow of 45 g/min to afford the title compound, 7.6 g. RT=3.56 min; $^1$H NMR (400 MHz, DMSO-d$_6$): δ 2.40-2.53 (m, 1H), 3.02-3.08 (m, 1H), 3.28-3.72 (m, 6H), 4.89-5.07 (m, 3H), 7.32-7.40 (m, 5H). LCMS m/z=321 [M+H]$^+$ Preparation 71

(3R,5S)-rel-5-Methylpiperidin-3-ol hydrochloride

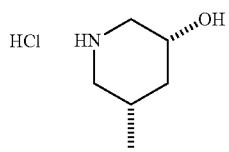

HCl in dioxane (4M, 40 mL) was added to a stirred solution of tert-butyl (3S,5R)-rel-hydroxy-5-methylpiperidine-1-carboxylate (Preparation 72, 3.5 g, 16.26 mmol) in DCM (40 mL) at 0° C. and the reaction was stirred at room temperature for 16 hrs. The mixture was concentrated in vacuo and the resulting solid triturated with diethyl ether and MeOH to afford the title compound as a white solid, 2.2 g, 89%. $^1$H NMR (400 MHz, DMSO-d$_6$): δ 0.85 (d, 3H), 1.01 (q, 1H), 1.77-1.95 (m, 2H), 2.28-2.40 (m, 2H), 3.00-3.12 (m, 1H), 3.13-3.25 (m, 1H), 3.70-3.80 (m, 1H), 5.32 (d, 1H), 9.09 (br s, 2H).
LCMS m/z=116 [M+H]$^+$ Preparation 72 tert-Butyl (3S,5R)-rel-hydroxy-5-methylpiperidine-1-carboxylate

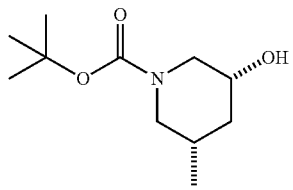

A saturated solution of HCl in EtOAc (80 mL) was added to a solution of 5-methyl-3-pyridinol (10.0 g, 91.6 mmol) in EtOAc (15 mL) and MeOH (5 mL) and the mixture stirred for 4 hr at 23° C. The resulting solid was filtered off and washed with EtOAc and dried under vacuum. The solid was dissolved in acetic acid (50 mL),10% PtO$_2$ (1.0 g) was added and the resulting reaction mixture was hydrogenated in a Parr autoclave (pressure 200 psi) for 16 hrs at 50° C. The cooled mixture was filtered through Celite® and the filtrate was concentrated to afford a brown gum, 5.0 g.

Boc-anhydride (10.79 mL, 49.45 mmol) was added drop wise to an ice-cooled stirred solution of the gum in 50% EtOAc/water (100 ml) and Na$_2$CO$_3$ (10.48 g, 98.89 mmol) and the resulting reaction was stirred at rt for 15 hrs. The mixture was extracted with EtOAc, the combined organic extracts washed with brine, dried (Na$_2$SO$_4$) and concentrated in vacuo. The crude product was purified by column chromatography on silica gel eluting with EtOAc:Hexane (20:80) to afford the title compound as a yellow liquid, 3.5 g, 49%. $^1$H NMR (400 MHz, DMSO-d$_6$): δ 0.80-0.91 (m, 4H), 1.38 (s, 9H), 1.44-1.47 (m, 1H), 1.86-1.90 (m, 1H), 2.05-2.32 (m, 2H), 3.28-3.34 (m, 1H), 3.75-3.86 (m, 1H), 3.94-4.03 (m, 1H), 4.91 (d, 1H).

Preparation 73

(3R,5R)-rel-5-Cyclopropylpiperidin-3-ol

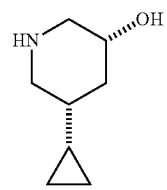

Pd(OH)$_2$/C (1.0 g) was added to a solution of (3R,5R)-rel-1-benzyl-3-(benzyloxy)-5-cyclopropylpiperidine (Preparation 74, 4.0 g, 15.85 mmol) in MeOH (150 mL), and the mixture stirred under 50 Psi H$_2$ at 60° C. for 18 hrs. The mixture was filtered and the filtrate concentrated in vacuo to afford the title compound, 1.2 g, 67%. $^1$H NMR (400 MHz, MeOH-d$_4$): δ 0.12-0.14 (m, 2H), 0.40-0.46 (m, 2H), 0.47-0.58 (m, 1H), 0.70-0.83 (m, 1H), 1.15 (q, 1H), 2.11-2.18 (m, 1H), 2.22-2.35 (m, 2H), 3.02 (dd, 1H), 3.09 (dd, 1H), 3.48-3.58 (m, 1H). LCMS m/z=142 [M+H]$^+$

Preparation 74

(3R,5R)-rel-1-Benzyl-3-(benzyloxy)-5-cyclopropylpiperidine

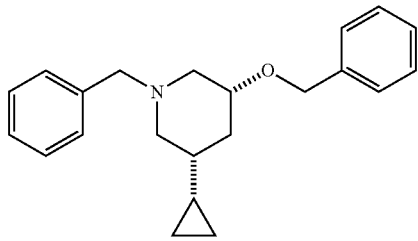 [SMILES: c1ccc(CO[C@@H]2C[C@H](C3CC3)CN(Cc3ccccc3)C2)cc1]

PtO$_2$ (0.90 g, 3.93 mmol) was added to a solution of 1-benzyl-3-(benzyloxy)-5-cyclopropylpyridinium bromide (Preparation 77, 15.6 g, 39.37 mmol) and Et$_3$N (7.1 mL, 51.17 mmol) in MeOH (360 mL) and the mixture was stirred under H$_2$ at 50 Psi for 6 hrs. The mixture was filtered and the filtrate was concentrated in vacuo. The crude was purified by column chromatography on silica gel eluting with pet. Ether:EtOAc (96:4 to 66:34) to afford the title compound as an oil, 4.5 g, 35% and the trans isomer as an oil, 0.9 g, 7%. $^1$H NMR (400 MHz, MeOH-d$_4$): δ 0.03-0.11 (m, 2H), 0.37-0.52 (m, 3H), 0.74-0.86 (m, 1H), 1.07 (q, 1H), 1.72-1.83 (m, 2H), 2.19-2.28 (m, 1H), 2.93 (dd, 1H), 3.13 (dd, 1H), 3.42-3.62 (m, 3H), 4.54 (q, 2H), 7.20-7.40 (m, 10H).

Preparation 75

(3R,5R)-rel-5-Isopropylpiperidin-3-ol

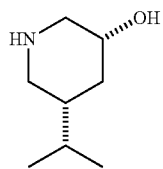

Pd/C (1.0 g) was added to (3R,5R)-rel-1-benzyl-5-isopropylpiperidin-3-ol (Preparation 76, 4.0 g, 15.85 mmol) in MeOH (150 mL), and the mixture stirred under 50 Psi H$_2$ at rt for 18 hrs. The mixture was filtered and the filtrate concentrated in vacuo to give the title compound as an oil, 2.3 g, 95%. $^1$H NMR (400 MHz, MeOH-d$_4$): 0.94 (d, 6H), 0.97 (q, 1H), 1.28-1.39 (m, 1H), 1.42-1.53 (m, 1H), 2.00-2.32 (m, 3H), 2.97 (d, 1H), 3.09 (dd, 1H), 3.50-3.61 (m, 1H). LCMS m/z=144 [M+H]$^+$

Preparation 76

(3R,5R)-rel-1-Benzyl-5-isopropylpiperidin-3-ol

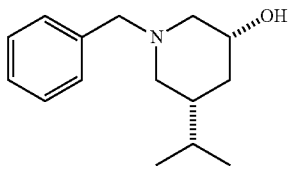 [SMILES: CC(C)[C@H]1C[C@@H](O)CN(Cc2ccccc2)C1]

PtO$_2$ (2.1 g, 9.40 mmol) was added to a solution of 1-benzyl-3-hydroxy-5-(propan-2-yl)pyridinium bromide (Preparation 78, 29 g, 94.09 mmol) and Et$_3$N (11.76 mL, 122.31 mmol) in MeOH (600 mL) and the mixture stirred under H$_2$ at 50 Psi for 6 hrs. PtO$_2$ was removed by filtration, and the filtrate was concentrated in vacuo. The crude product was purified by column chromatography on silica gel eluting with Pet. ether:EtOAc, (96:4 to 66:34) to afford the title compound as an oil, 7.4 g, 34%. Further elution provided the trans isomer as an oil, 3.7 g, 17%. $^1$H NMR (400 MHz, CDCl$_3$): δ 0.80-0.93 (m, 7H), 1.37-1.50 (m, 1H), 1.60-1.72 (m, 2H), 1.97-2.09 (m, 1H), 2.21 (s, 1H), 2.84 (d, 1H), 2.98 (dd, 1H), 3.40-3.63 (m, 2H), 3.65-3.76 (m, 1H), 7.20-7.40 (m, 5H). LCMS m/z=234 [M+H]$^+$

Preparation 77

1-benzyl-3-(benzyloxy)-5-cyclopropylpyridinium bromide

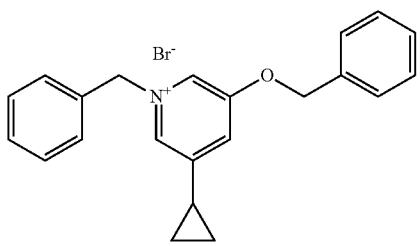 [SMILES: c1ccc(COc2cc(C3CC3)c[n+](Cc3ccccc3)c2)cc1 ; [Br-]]

To a solution of 3-(benzyloxy)-5-cyclopropylpyridine (Preparation 79, 7.80 g, 34.62 mmol) in MeCN (250 mL) was added benzyl bromide (5.92 g, 34.62 mmol) and the mixture stirred at 70-80° C. for 12 hrs. The reaction solution was concentrated in vacuo to afford the title compound, 13.70 g, 99%. LCMS m/z=316 [M+H]$^+$

Preparation 78

1-benzyl-3-hydroxy-5-(propan-2-yl)pyridinium bromide

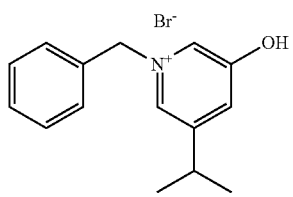 [SMILES: [Br-] ; CC(C)c1cc(O)c[n+](Cc2ccccc2)c1]

Benzyl bromide (13.7 g, 80.19 mmol) was added to a solution of 5-isopropylpyridin-3-ol (11.0 g, 80.19 mmol) in MeCN (300 mL) and the mixture heated at 70-80° C. for 6 hrs. The mixture was evaporated under reduced pressure to afford the title compound, 24.7 g, 99%. LCMS m/z=228 [M+H]$^+$

Preparation 79

3-(Benzyloxy)-5-cyclopropylpyridine

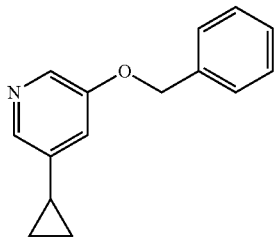 [SMILES: c1ccc(COc2cncc(C3CC3)c2)cc1]

To a solution of 3-(benzyloxy)-5-bromopyridine (12.7 g, 48.08 mmol) in dioxane:H$_2$O (4:1, v/v, 300 mL) were added cyclopropylboronic acid (8.26 g, 96.17 mmol), Na$_2$CO$_3$ (10.2 g, 96.17 mmol) and Pd(dppf)Cl$_2$ (1.5 g, 2.05 mmol) under N$_2$. The mixture was stirred at 80-100° C. for 3 days. The cooled reaction was extracted with DCM (400 mL×3), and the combined organic extracts washed with aq.NaHCO$_3$ (150 mL×2) and brine (100 mL), dried (Na$_2$SO$_4$), and concentrated in vacuo. The crude product was purified by column chromatography on silica gel eluting with Pet. ether:EtOAc, from (100:1 to 90:10) to afford the title compound as a solid, 9.2 g, 84%. LCMS m/z=226 [M+H]$^+$

Preparation 80

(3aR,7aR)-rel-Octahydro-3aH-isoindol-3a-ylmethanol

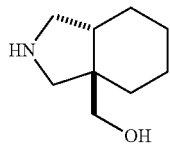 [SMILES: OC[C@]12CCCC[C@H]1CNC2]

((3aR,7aR)-rel-Benzyloctahydro-3aH-isoindol-3a-yl)methanol (Preparation 81, 69 g, 0.282 mol) was dissolved in MeOH (500 mL), Pd(OH)$_2$ (14 g) was added and the reaction stirred at 45° C. under an atmosphere of H$_2$ for 18 hrs. The mixture was filtered and the filtrate concentrated in vacuo to afford the title compound as a yellow oil, 41 g, 94%. $^1$H NMR (300 MHz, CDCl$_3$): δ 1.20-1.65 (m, 8H), 1.87-2.00 (m, 1H), 2.84-2.96 (m, 2H), 3.13-3.25 (m, 1H), 3.40-3.60 (m, 2H), 3.70-3.82 (m, 3H).

Preparation 81

((3aR,7aR)-rel-Benzyloctahydro-3aH-isoindol-3a-yl)methanol

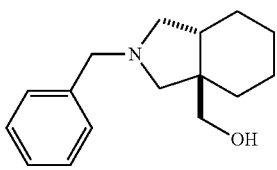 [SMILES: OC[C@]12CCCC[C@H]1CN(Cc1ccccc1)C2]

Ethyl (3aR,7aR)-rel-benzyloctahydro-3aH-isoindole-3a-carboxylate (Preparation 82, 128.7 g, 0.471 mol) was dissolved in THF (500 mL), the solution cooled in ice and LiAlH$_4$ (18 g, 0.471 mol) added portion wise and the reaction stirred for 2 hrs. NaOH solution was added slowly until no further bubbles formed, then the mixture was filtered and concentrated in vacuo. The crude was purified by column chromatography on silica gel to afford the title compound as a yellow oil, 69 g 60%.

Preparation 82

Ethyl (3aR,7aR)-rel-benzyloctahydro-3aH-isoindole-3a-carboxylate

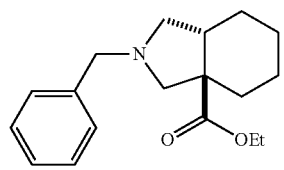 [SMILES: CCOC(=O)[C@]12CCCC[C@H]1CN(Cc1ccccc1)C2]

Ethyl cyclohex-1-ene-1-carboxylate (110 g, 0.786 mol) and N-(methoxymethyl)-N-(trimethylsilylmethyl)benzylamine (175.2 g, 0.786 mol) were dissolved in DCM (300 mL) and a solution of acetic acid (8.960 g, 0.079 mol) in DCM (50 mL) was added drop wise over a period for 30 mins with stirring. The reaction was stirred for 3 hrs then quenched with water, the layers separated and the organic layer dried and concentrated in vacuo. The crude was purified by column chromatography on silica gel to afford the title compound as a yellow oil, 128.7 g, 60%.

Preparation 83

[(3R,4R)-rel-3,4-Dimethylpyrrolidin-3-yl]methanol

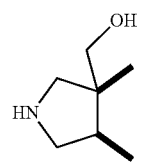

A mixture of ((3R,4R)-rel-1-benzyl-3,4-dimethylpyrrolidin-3-yl)methanol (Preparation 84, 68 g, 0.31 mol), ammonium formate (63 g, 0.93 mol) and 10% Pd/C (9 g) in MeOH (1 L) was stirred at rt for 18 hrs. The mixture was filtered, the filtrate evaporated, and the residue was distilled (bp 90-95° C. at 2-5 mmHg) to afford the title compound as an oil, 26 g, 65%. $^1$H NMR (400 MHz, DMSO-d$_6$): δ 0.77 (s, 3H), 0.79 (d, 3H), 1.69-1.77 (m, 1H), 2.28-2.36 (m, 2H), 2.78 (d, 1H), 2.97 (dd, 1H), 3.17 (s, 2H), 3.67 (br s, 2H). GCMS: 129 [M]

Preparation 84

((3R,4R)-rel-1-Benzyl-3,4-dimethylpyrrolidin-3-yl)methanol

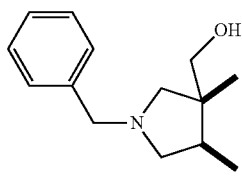 [SMILES: C[C@H]1CN(Cc2ccccc2)C[C@]1(C)CO]

A solution of methyl (3R,4R)-rel-1-benzyl-3,4-dimethylpyrrolidine-3-carboxylate (Preparation 85, 81 g, 0.327 mol) in THF (100 mL) was added at −3° C. to a suspension of LiAlH$_4$ (24.8 g, 0.655 mol) in THF (1.2 L). The reaction mixture was heated to room temperature over a period of 30 min and then refluxed for 1 hr. Then the mixture was cooled, quenched by the addition of water (45 mL), 15% NaOH (45 mL) and water (135 mL), filtered, washed with ether (3×200 mL) and evaporated to give the title product, 68 g, 95%.

Preparation 85

Methyl (3R,4R)-rel-1-benzyl-3,4-dimethylpyrrolidine-3-carboxylate

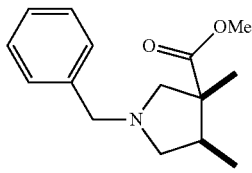 [SMILES: COC(=O)[C@@]1(C)CN(Cc2ccccc2)C[C@@H]1C]

A solution of methyl 2-methylbut-2-enoate (70 g, 0.61 mol) and N-benzyl-1-methoxy-N-[(trimethylsilyl)methyl]methanamine (175 g, 0.74 mol) in toluene (1 L) was cooled to 0° C., and 1N solution of trifluoroacetic acid in DCM (61 mL) was added drop wise under stirring. The reaction mixture was stirred under cooling for 40 min and then at rt for a further 18 hrs. The mixture was washed with saturated NaHCO$_3$ solution, then brine, dried (MgSO$_4$) and evaporated under reduced pressure. The residue was distilled (bp 123-125° C. at 0.3-0.4 mmHg) to afford the title compound, 81 g, 53%.

Preparation 86

Ethyl 2-{[3-(pyrazin-2-yl)oxetan-3-yl]amino}pyrimidine-5-carboxylate

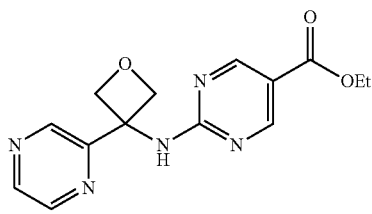 [SMILES: CCOC(=O)c1cnc(NC2(c3cnccn3)COC2)nc1]

To a solution of 3-(pyrazin-2-yl)oxetan-3-amine (Preparation 31, 213 mg, 1.41 mmol) and DIPEA (304 mg, 2.35 mmol) in dioxane (10 mL) was added ethyl 2-fluoropyrimidine-5-carboxylate (Preparation 21, 200 mg, 1.18 mmol) and the reaction was stirred at 100° C. for 4 hrs. The cooled reaction was diluted with EtOAc (50 mL) washed with brine (30 mL×3), dried (Na$_2$SO$_4$), filtered and the filtrate evaporated under reduced pressure. The residue was purified by column chromatography on silica gel eluting with pet.ether:EtOAc (50:50 to 100:0) to afford the title compound as a yellow solid, 158 mg, 44%. $^1$H NMR (400 MHz, MeOD-d$_4$): δ 1.33 (t, 3H), 4.31 (q, 2H), 4.99 (d, 2H), 5.15 (d, 2H), 8.50 (d, 1H), 8.61 (br s, 1H), 8.63 (d, 1H), 8.70 (dd, 1H), 8.87 (br s, 1H). LCMS m/z=302 [M+H]$^+$

Preparation 87

Ethyl 2-{[3-(pyrimidin-5-yl)oxetan-3-yl]amino}pyrimidine-5-carboxylate

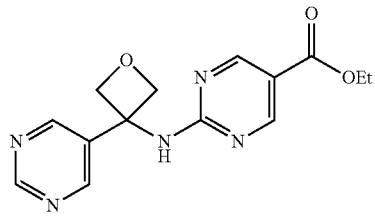 [SMILES: CCOC(=O)c1cnc(NC2(c3cncnc3)COC2)nc1]

To a solution of 3-(pyrimidin-5-yl)oxetan-3-amine (Preparation 32, 437 mg, 2.89 mmol) and DIPEA (622 mg, 4.81 mmol) in dioxane (20 mL) was added ethyl 2-chloropyrimidine-5-carboxylate (400 mg, 2.41 mmol) and the reaction stirred at 100° C. for 4 hrs. The cooled mixture was diluted with EtOAc (100 mL), washed with brine (30 mL×3), dried (Na$_2$SO$_4$), filtered and the filtrate evaporated under reduced pressure. The residue was purified by column chromatography eluting with pet. Ether: EtOAc (50:50 to 0:100) to afford the title compound as a yellow oil, 100 mg, 14%. $^1$H NMR (400 MHz, CDCl$_3$): δ 1.36 (t, 3H), 4.35 (q, 2H), 4.97-5.03 (m, 2H), 5.06 (d, 2H), 6.52 (s, 1H), 8.85 (br s, 2H), 8.95 (s, 2H), 9.18 (s, 1H). LCMS m/z=302 [M+H]$^+$

Preparation 88

2-{[2-(pyrazin-2-yl)propan-2-yl]amino}pyrimidine-5-carboxylic Acid

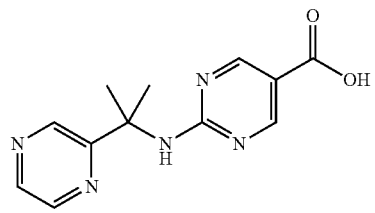 [SMILES: CC(C)(Nc1ncc(C(=O)O)cn1)c1cnccn1]

Water (2 mL) and LiOH—H$_2$O (161 mg, 6.66 mmol) was added to a mixture of ethyl 2-{[2-(pyrazin-2-yl)propan-2-yl]amino}pyrimidine-5-carboxylate (Preparation 15, 736 mg, 2.56 mmol) in THF (10 mL) and the reaction was stirred at ambient temperature for 2 hrs. The mixture was concentrated to ⅓ of the original volume and 1N HCl (6.66 mL, 6.66 mmol) slowly added. The resulting solids were filtered and washed with water. The solids were transferred to a round bottom flask and MeCN (5 mL) added and removed under reduced pressure twice. The resulting solids were dried to give afford the title compound as a tan solid, 571 mg, 86%. $^1$H NMR (400 MHz, DMSO-$d_6$): δ 1.72 (s, 6H), 8.36-8.83 (m, 6H), 12.82 (br s, 1H). LCMS m/z=260 [M+H]$^+$ Preparation 89

2-aminopyrimidin-5-yl)(8-oxa-2-azaspiro[4.5]dec-2-yl)methanone

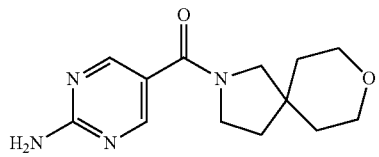

A suspension of (2-chloropyrimidin-5-yl)(8-oxa-2-azaspiro[4.5]dec-2-yl)methanone (Preparation 22, 200 mg, 0.710 mmol) in ammonium hydroxide solution (1.42 mL, c=0.5 M) was subjected to microwave irradiation at 120° C. for 30 minutes. The mixture was poured into brine and the pH was adjusted to 7 by the addition of 6N HCl. The mixture was extracted with CHCl$_3$/IPA (3:1, 10×). The organic extracts were dried over anhydrous sodium sulfate and concentrated under reduced pressure to give the desired material which was used without further purification, 171 mg, 92%. $^1$H NMR (400 MHz, CDCl$_3$): δ 1.52-1.72 (m, 4H), 1.85-1.94 (m, 2H), 3.40-3.83 (m, 8H), 5.28-5.40 (br s, 2H), 8.57 (s, 2H). LCMS m/z=263 [M+H]$^+$

EXAMPLES

Examples 1 to 32 were prepared in a library through an amide coupling of 2-[(pyridin-3-ylmethyl)amino]pyrimidine-5-carboxylic acid (Preparation 1) and 32 different amines or common amine salts, using the reaction protocol described below.

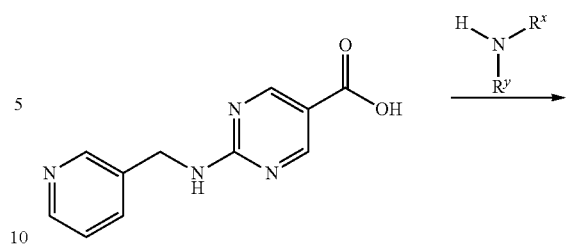

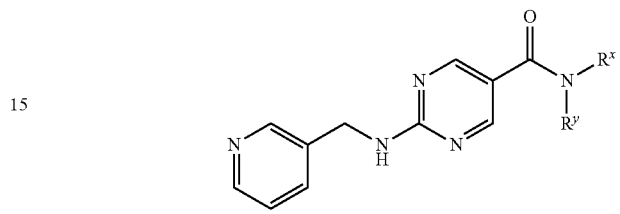

1. 2-[(Pyridin-3-ylmethyl)amino]pyrimidine-5-carboxylic acid (Preparation 1, 23.0 mg, 100 μmol, 1.0 eq.) was dispensed into 8 mL vials.
2. HATU (45.6 mg, 120 μmol, 1.2 eq.) was dispensed into the above vials.
3. DMF (1 mL) was dispensed into the above vials.
4. The vials were capped and shaken at 50° C. for 2 hrs.
5. The selected amine (120 μmol, 1.2 eq.) was dispensed into the above vials.
6. Et$_3$N (50 μl, 345 μmol, 3.45 eq.) was added into the above vial.
7. The vials were capped and shaken at 50° C. for 18 hrs.
8. Solvent was evaporated using a Speedvac.
9. The residues were purified by preparative HPLC using a Phenomenex Gemini C18 250×21.2 mm*10 μm column, eluting with MeCN: aq NH$_4$OH at an appropriate gradient of between 0 and 60% over up to 10 minutes to afford the title compounds.

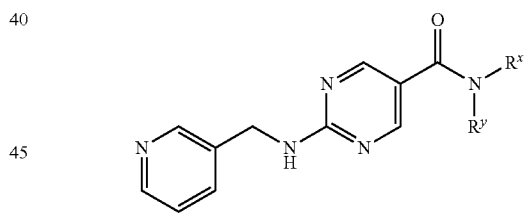

| Example | Structure/Name | Data; Analytical HPLC conditions |
|---|---|---|
| 1 | 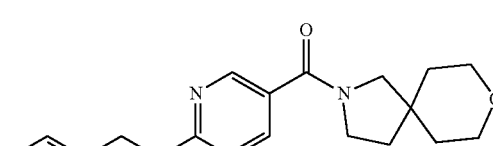  8-oxa-2-azaspiro[4.5]dec-2-yl{2-[(pyridin-3-ylmethyl)amino]pyrimidin-5-yl}methanone | LCMS RT = 1.967 mins LCMS m/z = 354 [M + H]$^+$ CD05 |

-continued

| Example | Structure/Name | Data; Analytical HPLC conditions |
|---|---|---|
| 2 | 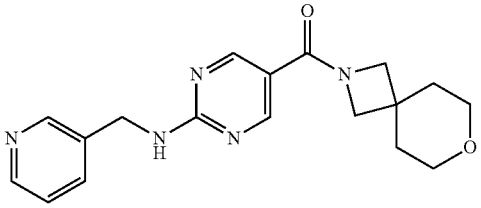<br>7-oxa-2-azaspiro[3.5]non-2-yl{2-[(pyridin-3-ylmethyl)amino]pyrimidin-5-yl}methanone | LCMS RT = 1.923 mins<br>LCMS m/z = 340<br>[M + H]⁺ CD05 |
| 3[a] | 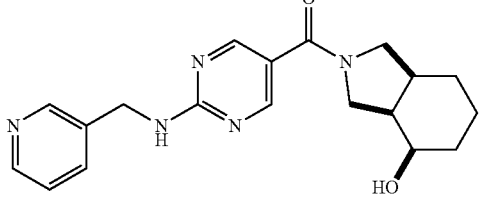<br>[(3aR,4R,7aS)-rel-4-hydroxyoctahydro-2H-isoindol-2-yl]{2-[(pyridin-3-ylmethyl)amino]pyrimidin-5-yl}methanone | LCMS RT = 1.974 mins<br>LCMS m/z = 354<br>[M + H]⁺ CD05 |
| 4[b] | 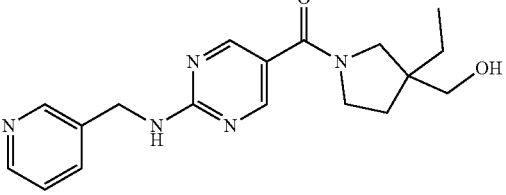<br>[3-ethyl-3-(hydroxymethyl)pyrrolidin-1-yl]{2-[(pyridin-3-ylmethyl)amino]pyrimidin-5-yl}methanone | LCMS RT = 1.979 mins<br>LCMS m/z = 342<br>[M + H]⁺ CD05 |
| 5 | 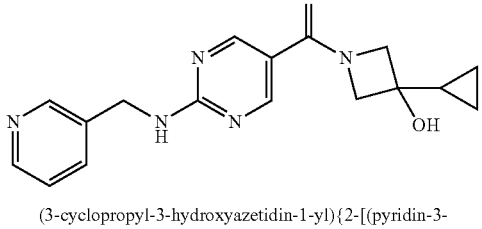<br>(3-cyclopropyl-3-hydroxyazetidin-1-yl){2-[(pyridin-3-ylmethyl)amino]pyrimidin-5-yl}methanone | LCMS RT = 1.909 mins<br>LCMS m/z = 326<br>[M + H]⁺ CD05 |
| 6 | 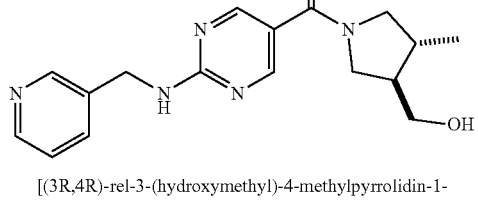<br>[(3R,4R)-rel-3-(hydroxymethyl)-4-methylpyrrolidin-1-yl]{2-[(pyridin-3-ylmethyl)amino]pyrimidin-5-yl}methanone | LCMS RT = 1.876 mins<br>LCMS m/z = 328<br>[M + H]⁺ CD05 |

| Example | Structure/Name | Data; Analytical HPLC conditions |
|---|---|---|
| 7 | 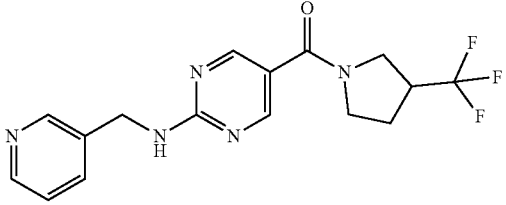<br>{2-[(pyridin-3-ylmethyl)amino]pyrimidin-5-yl}[3-(trifluoromethyl)pyrrolidin-1-yl]methanone | LCMS RT = 2.21 mins<br>LCMS m/z = 352<br>[M + H]⁺ CD05 |
| 8 | 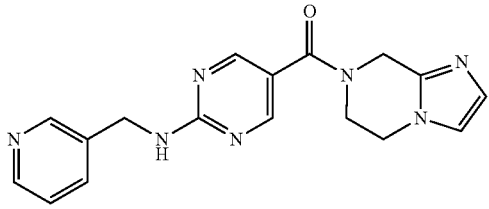<br>5,6-dihydroimidazo[1,2-a]pyrazin-7(8H)-yl{2-[(pyridin-3-ylmethyl)amino]pyrimidin-5-yl}methanone | LCMS RT = 1.793 mins<br>LCMS m/z = 336<br>[M + H]⁺ CD05 |
| 9 | 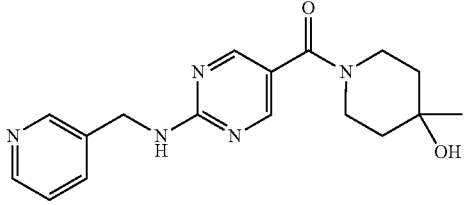<br>(4-hydroxy-4-methylpiperidin-1-yl){2-[(pyridin-3-ylmethyl)amino]pyrimidin-5-yl}methanone | LCMS RT = 1.827 mins<br>LCMS m/z = 328<br>[M + H]⁺ CD05 |
| 10 | 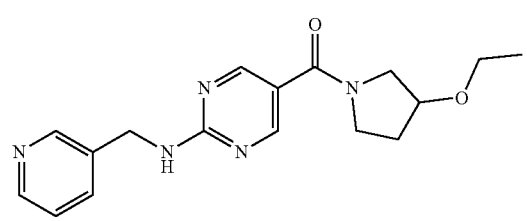<br>(3-ethoxypyrrolidin-1-yl){2-[(pyridin-3-ylmethyl)amino]pyrimidin-5-yl}methanone | LCMS RT = 2.013 mins<br>LCMS m/z = 328<br>[M + H]⁺ CD05 |
| 11 | 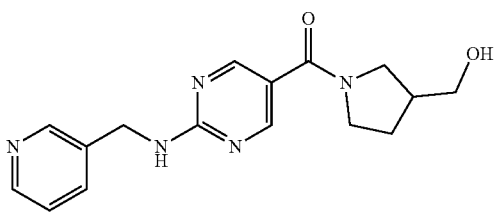<br>[3-(hydroxymethyl)pyrrolidin-1-yl]{2-[(pyridin-3-ylmethyl)amino]pyrimidin-5-yl}methanone | LCMS RT = 1.73 mins<br>LCMS m/z = 314<br>[M + H]⁺ CD05 |

-continued

| Example | Structure/Name | Data; Analytical HPLC conditions |
|---|---|---|
| 12 | 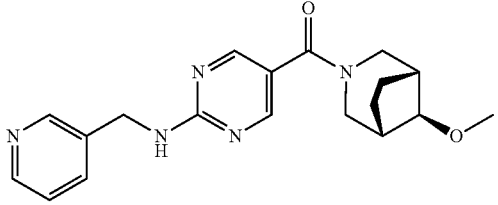<br>[(8-anti)-8-methoxy-3-azabicyclo[3.2.1]oct-3-yl]{2-[(pyridin-3-ylmethyl)amino]pyrimidin-5-yl}methanone | LCMS RT = 2.167 mins<br>LCMS m/z = 354<br>[M + H]$^+$ CD05 |
| 13 | 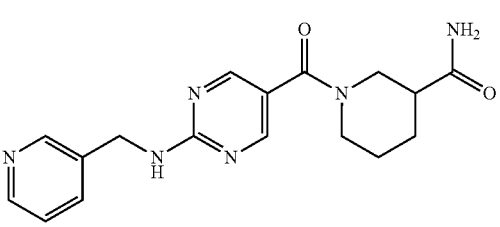<br>1-({2-[(pyridin-3-ylmethyl)amino]pyrimidin-5-yl}carbonyl)piperidin-3-carExampleamide | LCMS RT = 1.737 mins<br>LCMS m/z = 341<br>[M + H]$^+$ CD05 |
| 14 | 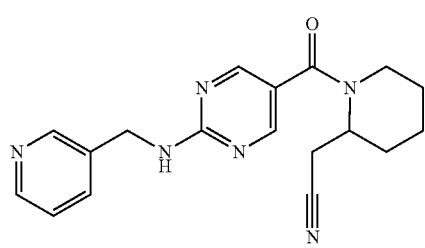<br>[1-({2-[(pyridin-3-ylmethyl)amino]pyrimidin-5-yl}carbonyl)piperidin-2-yl]acetonitrile | LCMS RT = 2.052 mins<br>LCMS m/z = 337<br>[M + H]$^+$ CD05 |
| 15 | 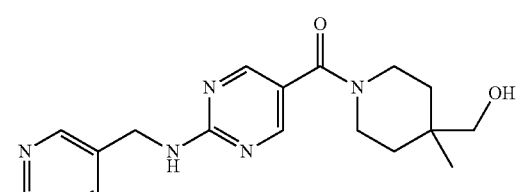<br>[4-(hydroxymethyl)-4-methylpiperidin-1-yl]{2-[(pyridin-3-ylmethyl)amino]pyrimidin-5-yl}methanone | LCMS RT = 1.761 mins<br>LCMS m/z = 342<br>[M + H]$^+$ AB01 |
| 16 | 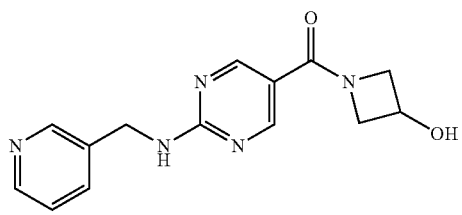<br>(3-hydroxyazetidin-1-yl){2-[(pyridin-3-ylmethyl)amino]pyrimidin-4-yl}methanone | LCMS RT = 1.578 mins<br>LCMS m/z = 286<br>[M + H]$^+$ CD05 |

-continued

| Example | Structure/Name | Data; Analytical HPLC conditions |
|---|---|---|
| 17 | 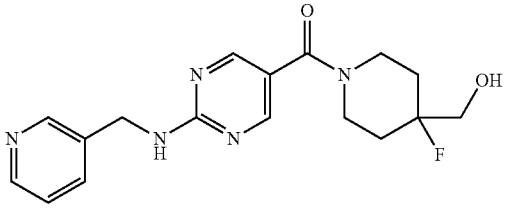<br>[4-fluoro-4-(hydroxymethyl)piperidin-1-yl]{2-[(pyridin-3-ylmethyl)amino]pyrimidin-5-yl}methanone | LCMS RT = 1.817 mins<br>LCMS m/z = 346<br>[M + H]+ CD05 |
| 18 | 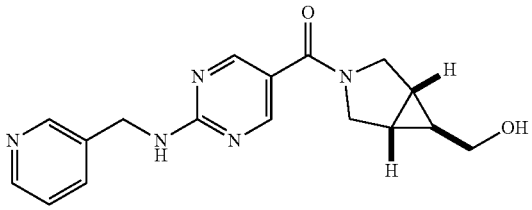<br>[(1R,5S,6r)-rel-6-(hydroxymethyl)-3-azabicyclo[3.1.0]hex-3-yl]{2-[(pyridin-3-ylmethyl)amino]pyrimidin-5-yl}methanone | LCMS RT = 1.763 mins<br>LCMS m/z = 326<br>[M + H]+ CD05 |
| 19 | 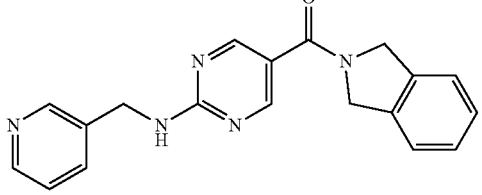<br>1,3-dihydro-2H-isoindol-2-yl{2-[(pyridin-3-ylmethyl)amino]pyrimidin-5-yl}methanone | LCMS RT = 2.292 mins<br>LCMS m/z = 332<br>[M + H]+ CD05 |
| 20 | 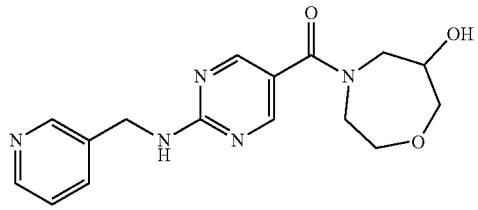<br>(6-hydroxy-1,4-oxazepan-4-yl){2-[(pyridin-3-ylmethyl)amino]pyrimidin-5-yl}methanone | LCMS RT = 1.638 mins<br>LCMS m/z = 330<br>[M + H]+ CD05 |
| 21 | 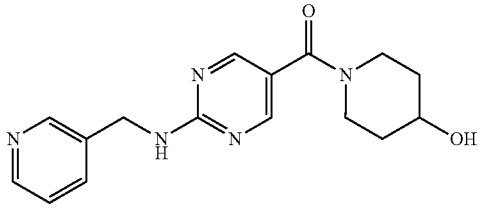<br>(4-hydroxypiperidin-1-yl){2-[(pyridin-3-ylmethyl)amino]pyrimidin-5-yl}methanone | LCMS RT = 1.7 mins<br>LCMS m/z = 314<br>[M + H]+ CD05 |

| Example | Structure/Name | Data; Analytical HPLC conditions |
|---|---|---|
| 22 | (3-hydroxypiperidin-1-yl){2-[(pyridin-3-ylmethyl)amino]pyrimidin-5-yl}methanone | LCMS RT = 1.778 mins<br>LCMS m/z = 314<br>[M + H]+ CD05 |
| 23 | N-[1-({2-[(pyridin-3-ylmethyl)amino]pyrimidin-5-yl}carbonyl)piperidin-3-yl]acetamide | LCMS RT = 1.793 mins<br>LCMS m/z = 355<br>[M + H]+ CD05 |
| 24 | 1-[4-({2-[(pyridin-3-ylmethyl)amino]pyrimidin-5-yl}carbonyl)piperazin-1-yl]ethanone | LCMS RT = 1.737 mins<br>LCMS m/z = 341<br>[M + H]+ CD05 |
| 25 | (3-hydroxypyrrolidin-1-yl){2-[(pyridin-3-ylmethyl)amino]pyrimidin-5-yl}methanone | LCMS RT = 1.64 mins<br>LCMS m/z = 300<br>[M + H]+ CD05 |
| 26 | (3-hydroxy-3-methylpiperidin-1-yl){2-[(pyridin-3-ylmethyl)amino]pyrimidin-5-yl}methanone | LCMS RT = 1.886 mins<br>LCMS m/z = 328<br>[M + H]+ CD05 |

-continued

| Example | Structure/Name | Data; Analytical HPLC conditions |
|---|---|---|
| 27 | 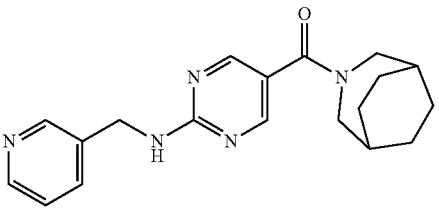<br>3-azabicyclo[3.2.2]non-3-yl{2-[(pyridin-3-ylmethyl)amino]pyrimidin-5-yl}methanone | LCMS RT = 2.256 mins<br>LCMS m/z = 338<br>[M + H]+ AB01 |
| 28 | 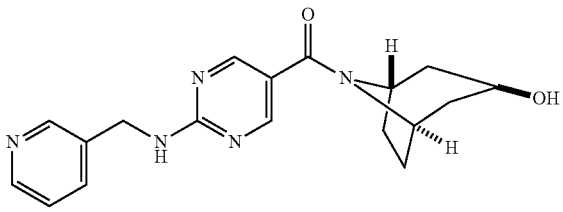<br>[(3-endo)-3-hydroxy-8-azabicyclo[3.2.1]oct-8-yl]{2-[(pyridin-3-ylmethyl)amino]pyrimidin-5-yl}methanone | LCMS RT = 1.681 mins<br>LCMS m/z = 340<br>[M + H]+ AB01 |
| 29 | 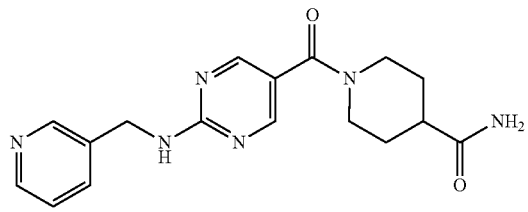<br>1-({2-[(pyridin-3-ylmethyl)amino]pyrimidin-5-yl}carbonyl)piperidine-4-carExampleamide | LCMS RT = 1.644 mins<br>LCMS m/z = 341<br>[M + H]+ CD05 |
| 30 | 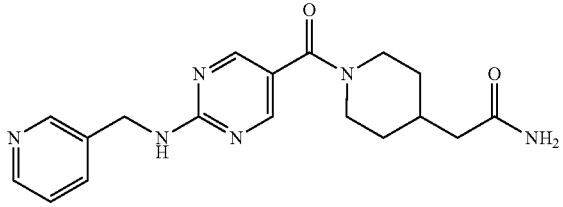<br>2-[1-({2-[(pyridin-3-ylmethyl)amino]pyrimidin-5-yl}carbonyl)piperidin-4-yl]acetamide | LCMS RT = 1.715 mins<br>LCMS m/z = 355<br>[M + H]+ CD05 |
| 31 | 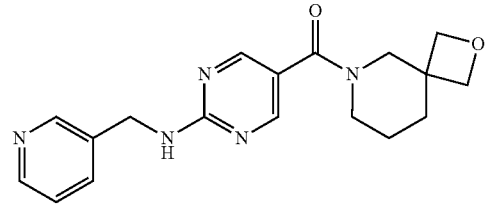<br>2-oxa-6-azaspiro[3.5]non-6-yl{2-[(pyridin-3-ylmethyl)amino]pyrimidin-5-yl}methanone | LCMS RT = 1.93 mins<br>LCMS m/z = 340<br>[M + H]+ CD05 |

| Example | Structure/Name | Data; Analytical HPLC conditions |
|---|---|---|
| 32 | 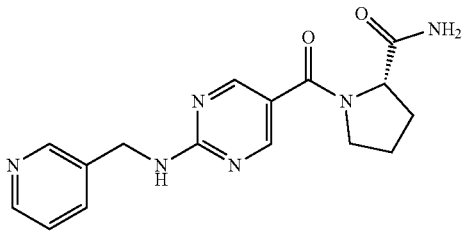<br>1-({2-[(pyridin-3-ylmethyl)amino]pyrimidin-5-yl}carbonyl)-L-prolinamide | LCMS RT = 1.679 mins<br>LCMS m/z = 327<br>[M + H]+ CD05 |

All amine starting materials are commercially available, with the exception of:
[a](3aR,4R,7aS)-rel-octahydro-1H-isoindol hydrochloride (Preparation 56)
[b](3-ethylpyrrolidin-3-yl)methanol (Preparation 66)

Examples 33 to 109 were prepared in a library through an amide coupling of 2-{[1-(pyrimidin-5-yl)cyclopropyl]amino}pyrimidine-5-carboxylic acid (Preparation 5) and 77 different amines or common amine salts, using the reaction protocol described below.

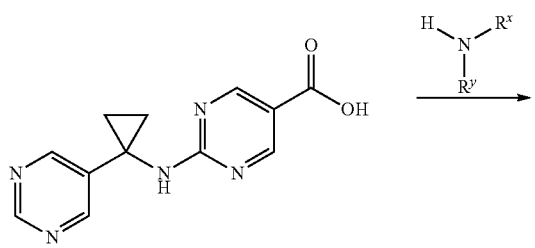

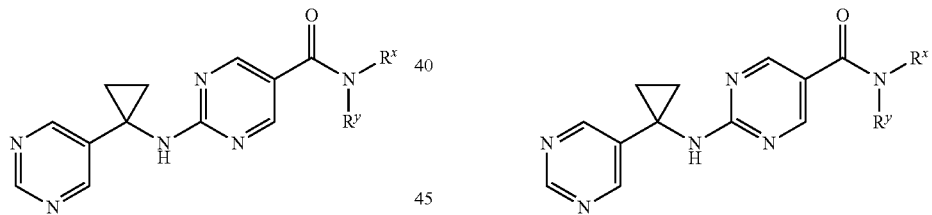

1. 2-{[1-(Pyrimidin-5-yl)cyclopropyl]amino}pyrimidine-5-carboxylic acid (0.2 M solution in DMF, 120 μmol, 1.2 eq.) was dispensed into 8 mL vials.
2. The selected amine ($R^1NHR^2$) (100 μmol, 1.0 eq.) was dispensed into each vial.
3. HATU (120 μmol, 1.2 eq., 0.24 M solution in DMF) was added to each vial.
4. DIPEA (70 μl, 400 μmol, 4.0 eq.) was added to each vial.
5. The vials were capped and shaken at 50° C. for 16 hrs.
6. The solvent was evaporated on Speedvac.
7. The residues were purified by preparative HPLC using the purification methods (PM) described in the table below and an appropriate solvent gradient, to provide the title compounds

| Example | Structure and name | PM, Analytical HPLC conditions Data |
|---|---|---|
| 33 | 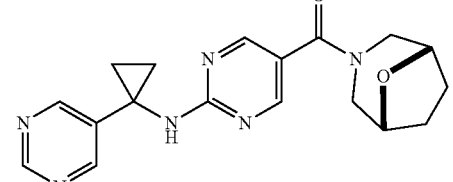<br>8-oxa-3-azabicyclo[3.2.1]oct-3-yl(2-{[1-(pyrimidin-5-yl)cyclopropyl]amino}pyrimidin-5-yl)methanone | AD01, CD05<br>RT = 1.802 mins<br>LCMS m/z = 353<br>[M + H]+ |

-continued

| Example | Structure and name | PM, Analytical HPLC conditions Data |
|---|---|---|
| 34 | 1-oxa-7-azaspiro[3.5]non-7-yl(2-{[1-(pyrimidin-5-yl)cyclopropyl]amino}pyrimidin-5-yl)methanone | PG02, CD05<br>RT = 1.833 mins<br>LCMS m/z = 367<br>[M + H]⁺ |
| 35 | [(7S,8aS)-7-fluorohexahydropyrrolo[1,2-a]pyrazin-2(1H)-yl](2-{[1-(pyrimidin-5-yl)cyclopropyl]amino}pyrimidin-5-yl)methanone | AD02, CD05<br>RT = 1.808 mins<br>LCMS m/z = 384<br>[M + H]⁺ |
| 36 | 4-ethyl-3-{1-[(2-{[1-(pyrimidin-5-yl)cyclopropyl]amino}pyrimidin-5-yl)carbonyl]piperidin-4-yl}-1,3-oxazolidin-2-one | AD01, CD05<br>RT = 1.999 mins<br>LCMS m/z = 438<br>[M + H]⁺ |
| 37 | (3,3-diethylpyrrolidin-1-yl)(2-{[1-(pyrimidin-5-yl)cyclopropyl]amino}pyrimidin-5-yl)methanone | PG02, AB01<br>RT = 2.632 mins<br>LCMS m/z = 367<br>[M + H]⁺ |
| 38 | (6-methyl-1,4-oxazepan-4-yl)(2-{[1-(pyrimidin-5-yl)cyclopropyl]amino}pyrimidin-5-yl)methanone | PG02, CD05<br>RT = 1.881 mins<br>LCMS m/z = 355<br>[M + H]⁺ |

-continued

| Example | Structure and name | PM, Analytical HPLC conditions Data |
|---|---|---|
| 39 | (3-methylpiperidin-1-yl)(2-{[1-(pyrimidin-5-yl)cyclopropyl]amino}pyrimidin-5-yl)methanone | PG02, CD05 RT = 2.173 mins LCMS m/z = 339 [M + H]$^+$ |
| 40[a] | [(3R,5R)-rel-3-hydroxy-5-(propan-2-yl)piperidin-1-yl](2-{[1-(pyrimidin-5-yl)cyclopropyl]amino}pyrimidin-5-yl)methanone | PG01, AB01 RT = 2.273 mins LCMS m/z = 383 [M + H]$^+$ |
| 41 | octahydropyrazino[1,2-a]azepin-2(1H)-yl(2-{[1-(pyrimidin-5-yl)cyclopropyl]amino}pyrimidin-5-yl)methanone | AD01, CD05 RT = 2.133 mins LCMS m/z = 394 [M + H]$^+$ |
| 42 | 1,4-oxazepan-4-yl(2-{[1-(pyrimidin-5-yl)cyclopropyl]amino}pyrimidin-5-yl)methanone | AD01, CD05 RT = 1.723 mins LCMS m/z = 341 [M + H]$^+$ |
| 43[b] | [3-(1H-pyrazol-3-yl)pyrrolidin-1-yl](2-{[1-(pyrimidin-5-yl)cyclopropyl]amino}pyrimidin-5-yl)methanone | PG02, CD05 RT = 1.852 mins LCMS m/z = 377 [M + H]$^+$ |

-continued

| Example | Structure and name | PM, Analytical HPLC conditions Data |
|---|---|---|
| 44 | [(3R,5S)-rel-4-hydroxy-3,5-dimethylpiperidin-1-yl](2-{[1-(pyrimidin-5-yl)cyclopropyl]amino}pyrimidin-5-yl)methanone | PG02, AB01<br>RT = 2.038 mins<br>LCMS m/z = 369<br>[M + H]+ |
| 45 | [(2S)-2-(hydroxymethyl)piperidin-1-yl](2-{[1-(pyrimidin-5-yl)cyclopropyl]amino}pyrimidin-5-yl)methanone | PG02, CD05<br>RT = 1.865 mins<br>LCMS m/z = 355<br>[M + H]+ |
| 46 | (4-ethyl-4-methylpiperidin-1-yl)(2-{[1-(pyrimidin-5-yl)cyclopropyl]amino}pyrimidin-5-yl)methanone | AD02, AB01<br>RT = 2.689 mins<br>LCMS m/z = 367<br>[M + H]+ |
| 47 | [(2S)-2-methylpyrrolidin-1-yl](2-{[1-(pyrimidin-5-yl)cyclopropyl]amino}pyrimidin-5-yl)methanone | AD02, AB01<br>RT = 2.215 mins<br>LCMS m/z = 325<br>[M + H]+ |
| 48 | [(2R,4S)-4-fluoro-2-(hydroxymethyl)pyrrolidin-1-yl](2-{[1-(pyrimidin-5-yl)cyclopropyl]amino}pyrimidin-5-yl)methanone | PG02, CD05<br>RT = 1.733 mins<br>LCMS m/z = 359<br>[M + H]+ |

-continued

| Example | Structure and name | PM, Analytical HPLC conditions Data |
|---|---|---|
| 49 | 8-azaspiro[4.5]dec-8-yl(2-{[1-(pyrimidin-5-yl)cyclopropyl]amino}pyrimidin-5-yl)methanone | PG02, AB01<br>RT = 2.745 mins<br>LCMS m/z = 379<br>[M + H]⁺ |
| 50 | 1-oxa-9-azaspiro[5.5]undec-9-yl(2-{[1-(pyrimidin-5-yl)cyclopropyl]amino}pyrimidin-5-yl)methanone | AD01, CD05<br>RT = 2.159 mins<br>LCMS m/z = 395<br>[M + H]⁺ |
| 51 | [(3S)-3-methoxypyrrolidin-1-yl](2-{[1-(pyrimidin-5-yl)cyclopropyl]amino}pyrimidin-5-yl)methanone | AD01, CD05<br>RT = 1.789 mins<br>LCMS m/z = 341<br>[M + H]⁺ |
| 52 | 6-oxa-9-azaspiro[4.5]dec-9-yl(2-{[1-(pyrimidin-5-yl)cyclopropyl]amino}pyrimidin-5-yl)methanone | AD01, CD05<br>RT = 2.106 mins<br>LCMS m/z = 381<br>[M + H]⁺ |
| 53ᶜ | [(3S,4S)-3-(hydroxymethyl)-4-(trifluoromethyl)pyrrolidin-1-yl](2-{[1-(pyrimidin-5-yl)cyclopropyl]amino}pyrimidin-5-yl)methanone | PG02, CD05<br>RT = 1.971 mins<br>LCMS m/z = 409<br>[M + H]⁺ |

-continued

| Example | Structure and name | PM, Analytical HPLC conditions Data |
|---|---|---|
| 54 | 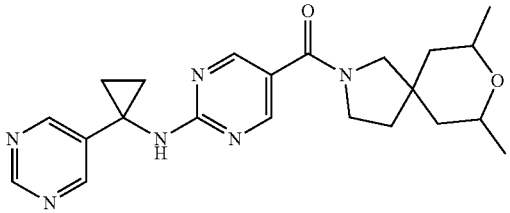<br>7,9-dimethyl-8-oxa-2-azaspiro[4.5]dec-2-yl)(2-{[1-(pyrimidin-5-yl)cyclopropyl]amino}pyrimidin-5-yl)methanone | PG02, AB01<br>RT = 2.306 mins<br>LCMS m/z = 409<br>[M + H]+ |
| 55 | 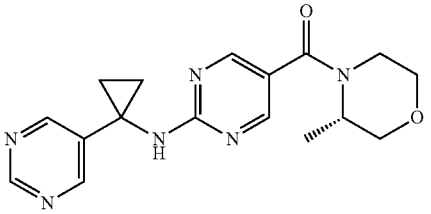<br>[(3S)-3-methylmorpholin-4-yl](2-{[1-(pyrimidin-5-yl)cyclopropyl]amino}pyrimidin-5-yl)methanone | AD01, CD05<br>RT = 1.812 mins<br>LCMS m/z = 341<br>[M + H]+ |
| 56 | 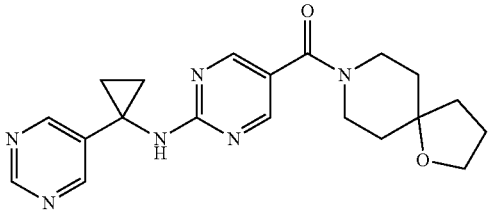<br>1-oxa-8-azaspiro[4.5]dec-8-yl(2-{[1-(pyrimidin-5-yl)cyclopropyl]amino}pyrimidin-5-yl)methanone | AD01, CD05<br>RT = 2.029 mins<br>LCMS m/z = 381<br>[M + H]+ |
| 57 | 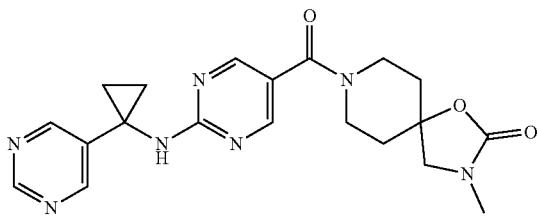<br>3-methyl-8-[(2-{[1-(pyrimidin-5-yl)cyclopropyl]amino}pyrimidin-5-yl)carbonyl]-1-oxa-3,8-diazaspiro[4.5]decan-2-one | PG02, CD05<br>RT = 1.766 mins<br>LCMS m/z = 410<br>[M + H]+ |
| 58 | 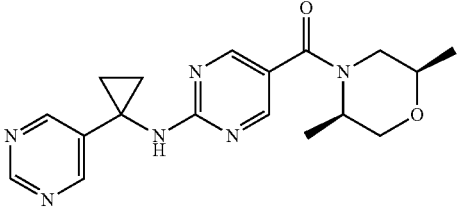<br>[(2R,5R)-2,5-dimethylmorpholin-4-yl](2-{[1-(pyrimidin-5-yl)cyclopropyl]amino}pyrimidin-5-yl)methanone | PG02, CD05<br>RT = 1.938 mins<br>LCMS m/z = 355<br>[M + H]+ |

-continued

| Example | Structure and name | PM, Analytical HPLC conditions Data |
|---|---|---|
| 59 | 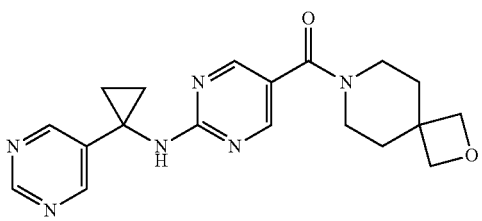<br>2-oxa-7-azaspiro[3.5]non-7-yl(2-{[1-(pyrimidin-5-yl)cyclopropyl]amino}pyrimidin-5-yl)methanone | AD01, CD05<br>RT = 1.787 mins<br>LCMS m/z = 367<br>[M + H]$^+$ |
| 60 | 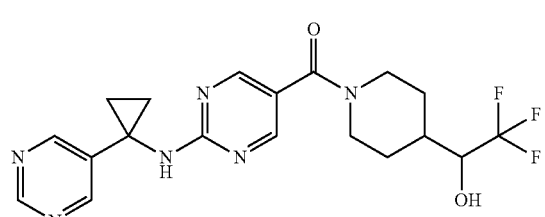<br>(2-{[1-(pyrimidin-5-yl)cyclopropyl]amino}pyrimidin-5-yl)[4-(2,2,2-trifluoro-1-hydroxyethyl)piperidin-1-yl]methanone | PG01, CD05<br>RT = 2.074 mins<br>LCMS m/z = 423<br>[M + H]$^+$ |
| 61$^d$ | 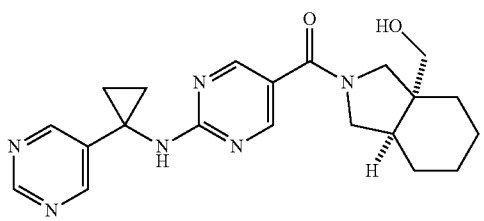<br>[(3aR,7aR)-rel-3a-(hydroxymethyl)octahydro-2H-isoindol-2-yl](2-{[1-(pyrimidin-5-yl)cyclopropyl]amino}pyrimidin-5-yl)methanone | AD01, CD05<br>RT = 2.043 mins<br>LCMS m/z = 395<br>[M + H]$^+$ |
| 62$^e$ | 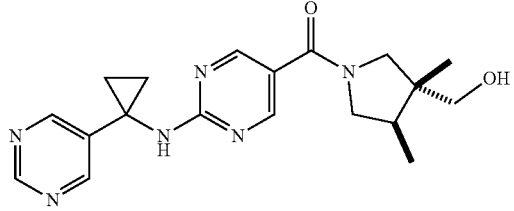<br>[(3R,7R)-rel-3-(hydroxymethyl)-3,4-dimethylpyrrolidin-1-yl](2-{[1-(pyrimidin-5-yl)cyclopropyl]amino}pyrimidin-5-yl)methanone | AD01, CD05<br>RT = 1.9 mins<br>LCMS m/z = 369<br>[M + H]$^+$ |
| 63 | 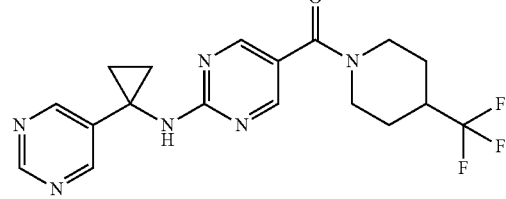<br>(2-{[1-(pyrimidin-5-yl)cyclopropyl]amino}pyrimidin-5-yl)[4-(trifluoromethyl)piperidin-1-yl]methanone | AD01, CD05<br>RT = 2.26 mins<br>LCMS m/z 393<br>[M + H]$^+$ |

-continued

| Example | Structure and name | PM, Analytical HPLC conditions Data |
|---|---|---|
| 64 | 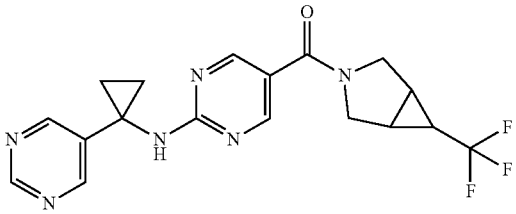<br>(2-{[1-(pyrimidin-5-yl)cyclopropyl]amino}pyrimidin-5-yl)[6-(trifluoromethyl)-3-azabicyclo[3.1.0]hex-3-yl]methanone | PG02, CD05<br>RT = 2.228 mins<br>LCMS m/z = 391<br>[M + H]⁺ |
| 65ᶠ | 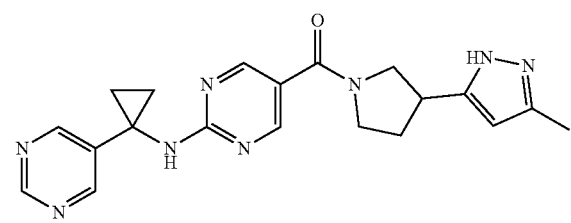<br>[3-(3-methyl-1H-pyrazol-5-yl)pyrrolidin-1-yl](2-{[1-(pyrimidin-5-yl)cyclopropyl]amino}pyrimidin-5-yl)methanone | PG02, CD05<br>RT = 1.945 mins<br>LCMS m/z = 391<br>[M + H]⁺ |
| 66 | 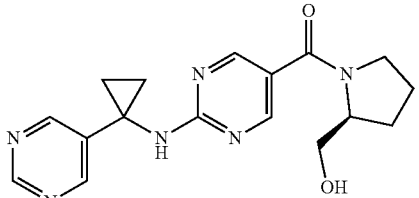<br>[(2S)-2-(hydroxymethyl)pyrrolidin-1-yl](2-{[1-(pyrimidin-5-yl)cyclopropyl]amino}pyrimidin-5-yl)methanone | PG02, CD05<br>RT = 1.756 mins<br>LCMS m/z = 341<br>[M + H]⁺ |
| 67 | 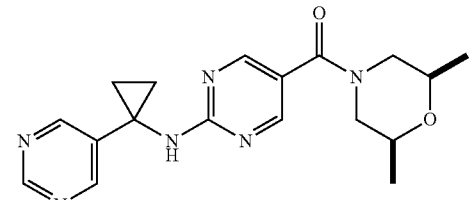<br>[(2R,6S)-rel-2,6-dimethylmorpholin-4-yl](2-{[1-(pyrimidin-5-yl)cyclopropyl]amino}pyrimidin-5-yl)methanone | AD01, CD05<br>RT = 1.954 mins<br>LCMS m/z = 355<br>[M + H]⁺ |
| 68 | 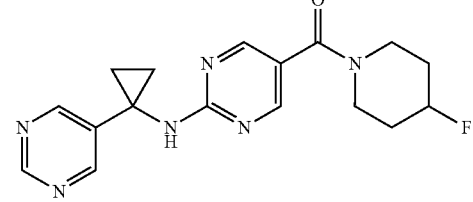<br>(4-fluoropiperidin-1-yl)(2-{[1-(pyrimidin-5-yl)cyclopropyl]amino}pyrimidin-5-yl)methanone | AD01, CD05<br>RT = 1.928 mins<br>LCMS m/z = 343<br>[M + H]⁺ |

| Example | Structure and name | PM, Analytical HPLC conditions Data |
|---|---|---|
| 69 | hexahydrocyclopenta[c]pyrrol-2(1H)-yl(2-{[1-(pyrimidin-5-yl)cyclopropyl]amino}pyrimidin-5-yl)methanone | AD02, CD05<br>RT = 2.197 mins<br>LCMS m/z = 351<br>$[M + H]^+$ |
| 70 | (3,3-difluoropiperidin-1-yl)(2-{[1-(pyrimidin-5-yl)cyclopropyl]amino}pyrimidin-5-yl)methanone | PG02, CD05<br>RT = 2.045 mins<br>LCMS m/z = 361<br>$[M + H]^+$ |
| 71 | [3-(methoxymethyl)piperidin-1-yl](2-{[1-(pyrimidin-5-yl)cyclopropyl]amino}pyrimidin-5-yl)methanone | AD01, CD05<br>RT = 2.048 mins<br>LCMS m/z = 369<br>$[M + H]^+$ |
| 72 | [(3S,5R)-rel-3-hydroxy-5-(propan-2-yl)piperidin-1-yl](2-{[1-(pyrimidin-5-yl)cyclopropyl]amino}pyrimidin-5-yl)methanone | PG01, CD05<br>RT = 2.101 mins<br>LCMS m/z = 383<br>$[M + H]^+$ |
| 73 | (2-{[1-(pyrimidin-5-yl)cyclopropyl]amino}pyrimidin-5-yl)[2-(trifluoromethyl)pyrrolidin-1-yl]methanone | AD01, CD05<br>RT = 2.22 mins<br>LCMS m/z = 379<br>$[M + H]^+$ |

-continued

| Example | Structure and name | PM, Analytical HPLC conditions Data |
|---|---|---|
| 74 | 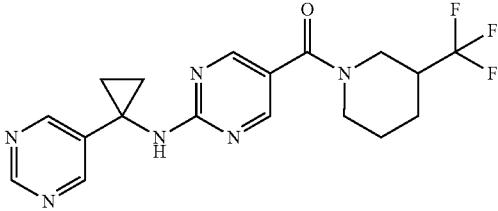<br>(2-{[1-(pyrimidin-5-yl)cyclopropyl]amino}pyrimidin-5-yl)[3-(trifluoromethyl)piperidin-1-yl]methanone | AD01, CD05<br>RT = 2.279 mins<br>LCMS m/z = 393<br>[M + H]+ |
| 75 | 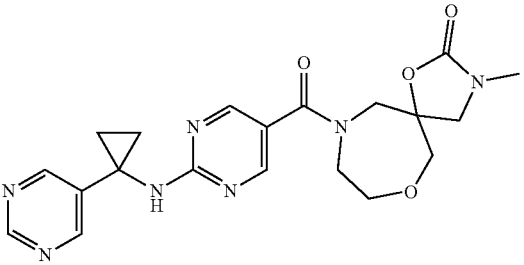<br>3-methyl-10-[(2-{[1-(pyrimidin-5-yl)cyclopropyl]amino}pyrimidin-5-yl)carbonyl]-1,7-dioxa-3,10-diazaspiro[4.6]undecan-2-one | PG02, CD05<br>RT = 1.688 mins<br>LCMS m/z = 426<br>[M + H]+ |
| 76 | 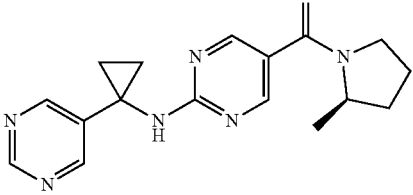<br>[(2R)-2-methylpyrrolidin-1-yl](2-{[1-(pyrimidin-5-yl)cyclopropyl]amino}pyrimidin-5-yl)methanone | PG01, CD05<br>RT = 1.987 mins<br>LCMS m/z = 325<br>[M + H]+ |
| 77 | 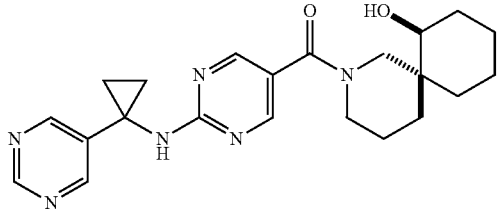<br>[(6S,7S)-rel-7-hydroxy-2-azaspiro[5.5]undec-2-yl](2-{[1-(pyrimidin-5-yl)cyclopropyl]amino}pyrimidin-5-yl)methanone | AD01, AB01<br>RT = 2.261 mins<br>LCMS m/z = 409<br>[M + H]+ |
| 78 | 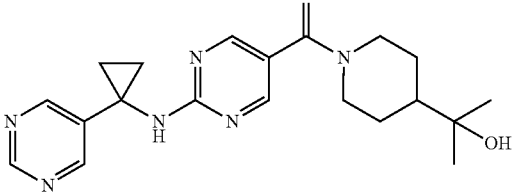<br>[4-(2-hydroxypropan-2-yl)piperidin-1-yl](2-{[1-(pyrimidin-5-yl)cyclopropyl]amino}pyrimidin-5-yl)methanone | AD01, CD05<br>RT = 1.905 mins<br>LCMS m/z = 383<br>[M + H]+ |

-continued

| Example | Structure and name | PM, Analytical HPLC conditions Data |
|---|---|---|
| 79 | [(3R)-3-methoxypyrrolidin-1-yl](2-{[1-(pyrimidin-5-yl)cyclopropyl]amino}pyrimidin-5-yl)methanone | AD01, CD05<br>RT = 1.791 mins<br>LCMS m/z = 341<br>$[M + H]^+$ |
| 80 | [(2S)-2-(2-hydroxyethyl)piperidin-1-yl](2-{[1-(pyrimidin-5-yl)cyclopropyl]amino}pyrimidin-5-yl)methanone | PG02, CD05<br>RT = 1.933 mins<br>LCMS m/z = 369<br>$[M + H]^+$ |
| 81 | [4-(difluoromethyl)piperidin-1-yl](2-{[1-(pyrimidin-5-yl)cyclopropyl]amino}pyrimidin-5-yl)methanone | PG02, CD05<br>RT = 2.104 mins<br>LCMS m/z = 375<br>$[M + H]^+$ |
| 82 | [(2R)-2-(hydroxymethyl)piperidin-1-yl](2-{[1-(pyrimidin-5-yl)cyclopropyl]amino}pyrimidin-5-yl)methanone | PG02, CD05<br>RT = 1.865 mins<br>LCMS m/z = 355<br>$[M + H]^+$ |
| 83 | [4-(hydroxymethyl)-4-methylpiperidin-1-yl](2-{[1-(pyrimidin-5-yl)cyclopropyl]amino}pyrimidin-5-yl)methanone | AD01, CD05<br>RT = 1.847 mins<br>LCMS m/z = 369<br>$[M + H]^+$ |

-continued

| Example | Structure and name | PM, Analytical HPLC conditions Data |
|---|---|---|
| 84 | 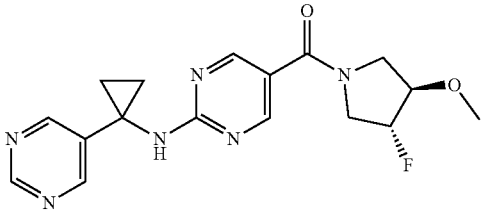<br>[(3R,4R)-3-fluoro-4-methoxypyrrolidin-1-yl](2-{[1-(pyrimidin-5-yl)cyclopropyl]amino}pyrimidin-5-yl)methanone | PG02, CD05<br>RT = 1.869 mins<br>LCMS m/z = 359<br>[M + H]⁺ |
| 85 | 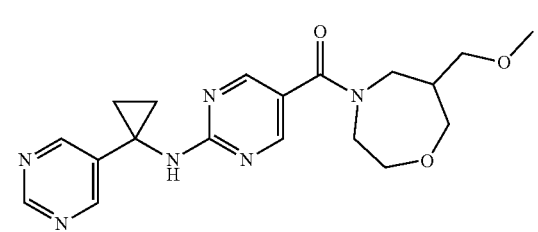<br>[6-(methoxymethyl)-1,4-oxazepan-4-yl](2-{[1-(pyrimidin-5-yl)cyclopropyl]amino}pyrimidin-5-yl)methanone | AD01, CD05<br>RT = 1.847 mins<br>LCMS m/z = 385<br>[M + H]⁺ |
| 86$^g$ | 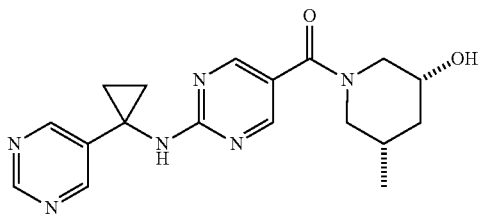<br>[(3R,5S)-rel-3-hydroxy-5-methylpiperidin-1-yl](2-{[1-(pyrimidin-5-yl)cyclopropyl]amino}pyrimidin-5-yl)methanone | PG01, CD05<br>RT = 1.837 mins<br>LCMS m/z = 355<br>[M + H]⁺ |
| 87 | 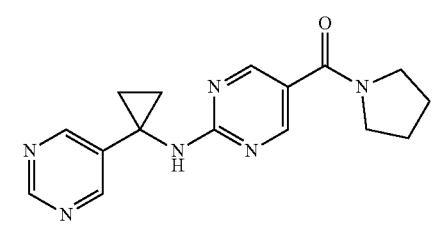<br>(2-{[1-(pyrimidin-5-yl)cyclopropyl]amino}pyrimidin-5-yl)(pyrrolidin-1-yl)methanone | AD01, CD05<br>RT = 1.85 mins<br>LCMS m/z = 311<br>[M + H]⁺ |
| 88$^h$ | 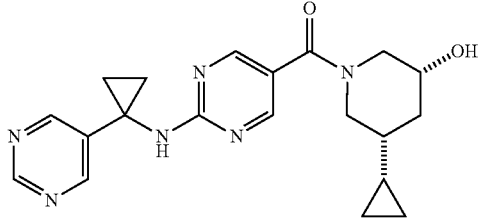<br>[(3R,5R)-rel-3-cyclopropyl-5-hydroxypiperidin-1-yl](2-{[1-(pyrimidin-5-yl)cyclopropyl]amino}pyrimidin-5-yl)methanone | PG02, CD05<br>RT = 2.015 mins<br>LCMS m/z = 381<br>[M + H]⁺ |

| Example | Structure and name | PM, Analytical HPLC conditions Data |
|---|---|---|
| 89 | 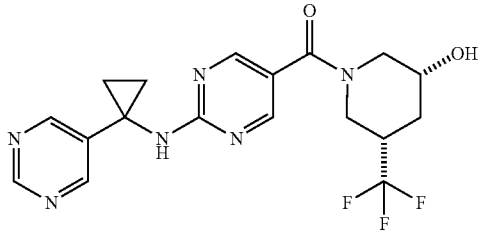<br>[(3R,5S)-rel-3-hydroxy-5-(trifluoromethyl)piperidin-1-yl](2-{[1-(pyrimidin-5-yl)cyclopropyl]amino}pyrimidin-5-yl)methanone | PG02, CD05<br>RT = 2.02 mins<br>LCMS m/z = 409<br>$[M + H]^+$ |
| 90 | 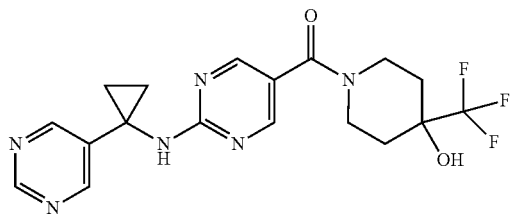<br>[4-hydroxy-4-(trifluoromethyl)piperidin-1-yl](2-{[1-(pyrimidin-5-yl)cyclopropyl]amino}pyrimidin-5-yl)methanone | AD01, CD05<br>RT = 2.004 mins<br>LCMS m/z = 409<br>$[M + H]^+$ |
| 91 | 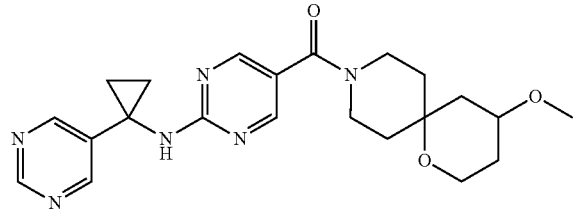<br>(4-methoxy-1-oxa-9-azaspiro[5.5]undec-9-yl)(2-{[1-(pyrimidin-5-yl)cyclopropyl]amino}pyrimidin-5-yl)methanone | PG02, CD05<br>RT = 2.002 mins<br>LCMS m/z = 425<br>$[M + H]^+$ |
| 92 | 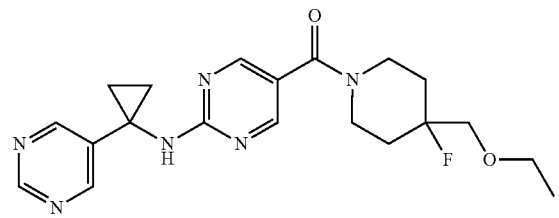<br>[4-(ethoxymethyl)-4-fluoropiperidin-1-yl](2-{[1-(pyrimidin-5-yl)cyclopropyl]amino}pyrimidin-5-yl)methanone | AD01, CD05<br>RT = 2.154 mins<br>LCMS m/z = 401<br>$[M + H]^+$ |
| 93 | 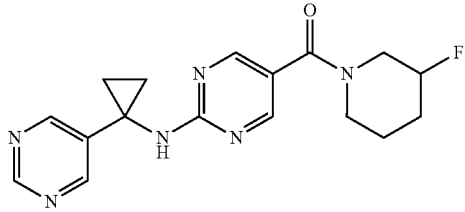<br>(3-fluoropiperidin-1-yl)(2-{[1-(pyrimidin-5-yl)cyclopropyl]amino}pyrimidin-5-yl)methanone | PG02, CD05<br>RT = 1.915 mins<br>LCMS m/z = 343<br>$[M + H]^+$ |

-continued

| Example | Structure and name | PM, Analytical HPLC conditions Data |
|---|---|---|
| 94 | [4-hydroxy-3-(trifluoromethyl)piperidin-1-yl](2-{[1-(pyrimidin-5-yl)cyclopropyl]amino}pyrimidin-5-yl)methanone | PG02, CD05<br>RT = 1.89 mins<br>LCMS m/z = 409<br>[M + H]+ |
| 95 | [4-ethyl-4-(hydroxymethyl)piperidin-1-yl](2-{[1-(pyrimidin-5-yl)cyclopropyl]amino}pyrimidin-5-yl)methanone | AD01, CD05<br>RT = 1.966 mins<br>LCMS m/z = 383<br>[M + H]+ |
| 96 | (3-methoxypiperidin-1-yl)(2-{[1-(pyrimidin-5-yl)cyclopropyl]amino}pyrimidin-5-yl)methanone | AD01, CD05<br>RT = 1.905 mins<br>LCMS m/z = 355<br>[M + H]+ |
| 97 | 3-oxa-8-azabicyclo[3.2.1]oct-8-yl(2-{[1-(pyrimidin-5-yl)cyclopropyl]amino}pyrimidin-5-yl)methanone | AD01, CD05<br>RT = 1.829 mins<br>LCMS m/z = 353<br>[M + H]+ |
| 98 | (4,4-difluoropiperidin-1-yl)(2-{[1-(pyrimidin-5-yl)cyclopropyl]amino}pyrimidin-5-yl)methanone | PG01, AB01<br>RT = 2.246 mins<br>LCMS m/z = 361<br>[M + H]+ |

-continued

| Example | Structure and name | PM, Analytical HPLC conditions Data |
|---|---|---|
| 99 | 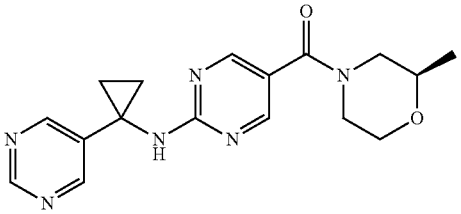<br>[(2R)-2-methylmorpholin-4-yl](2-{[1-(pyrimidin-5-yl)cyclopropyl]amino}pyrimidin-5-yl)methanone | AD01, CD05<br>RT = 1.827 mins<br>LCMS m/z = 341<br>$[M + H]^+$ |
| 100 | 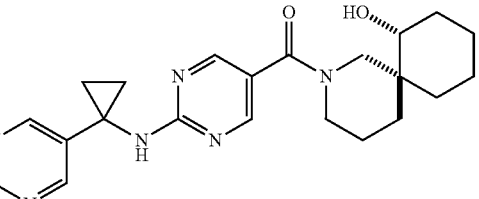<br>[(6S,7R)-rel-7-hydroxy-2-azaspiro[5.5]undec-2-yl](2-{[1-(pyrimidin-5-yl)cyclopropyl]amino}pyrimidin-5-yl)methanone | AD01, CD05<br>RT = 2.151 mins<br>LCMS m/z = 409<br>$[M + H]^+$ |
| 101 | 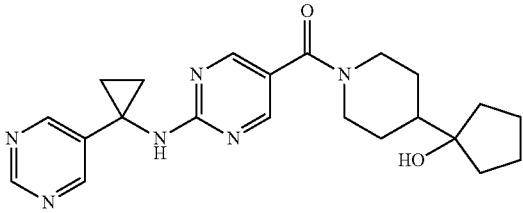<br>[4-(1-hydroxycyclopentyl)piperidin-1-yl](2-{[1-(pyrimidin-5-yl)cyclopropyl]amino}pyrimidin-5-yl)methanone | PG02, CD05<br>RT = 2.141 mins<br>LCMS m/z = 409<br>$[M + H]^+$ |
| 102 | 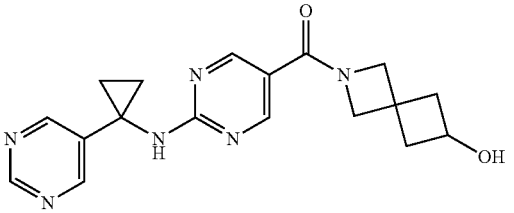<br>(6-hydroxy-2-azaspiro[3.3]hept-2-yl)(2-{[1-(pyrimidin-5-yl)cyclopropyl]amino}pyrimidin-5-yl)methanone | PG02, CD05<br>RT = 1.668 mins<br>LCMS m/z = 353<br>$[M + H]^+$ |
| 103 | 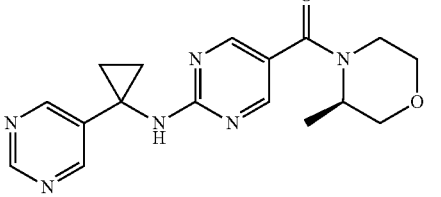<br>[(3R)-3-methylmorpholin-4-yl](2-{[1-(pyrimidin-5-yl)cyclopropyl]amino}pyrimidin-5-yl)methanone | AD01, CD05<br>RT = 1.792 mins<br>LCMS m/z = 341<br>$[M + H]^+$ |

-continued

| Example | Structure and name | PM, Analytical HPLC conditions Data |
|---|---|---|
| 104 | 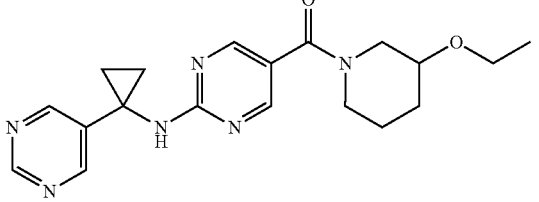<br>(3-ethoxypiperidin-1-yl)(2-{[1-(pyrimidin-5-yl)cyclopropyl]amino}pyrimidin-5-yl)methanone | AD01, CD05<br>RT = 2.042 mins<br>LCMS m/z = 369<br>[M + H]$^+$ |
| 105 | 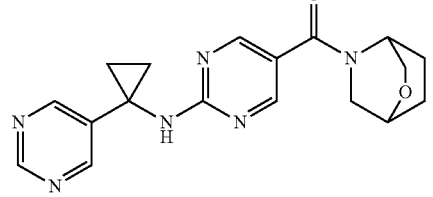<br>2-oxa-5-azabicyclo[2.2.2]oct-5-yl(2-{[1-(pyrimidin-5-yl)cyclopropyl]amino}pyrimidin-5-yl)methanone | PG02, CD05<br>RT = 1.742 mins<br>LCMS m/z = 353<br>[M + H]$^+$ |
| 106 | 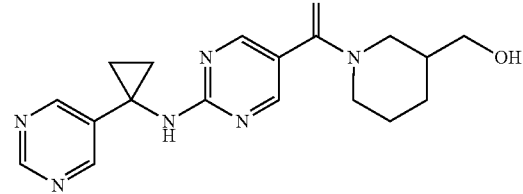<br>[3-(hydroxymethyl)piperidin-1-yl](2-{[1-(pyrimidin-5-yl)cyclopropyl]amino}pyrimidin-5-yl)methanone | AD01, CD05<br>RT = 1.792 mins<br>LCMS m/z = 355<br>[M + H]$^+$ |
| 107 | 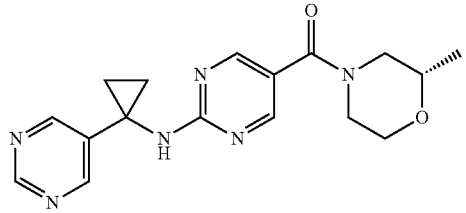<br>[(2S)-2-methylmorpholin-4-yl](2-{[1-(pyrimidin-5-yl)cyclopropyl]amino}pyrimidin-5-yl)methanone | AD01, CD05<br>RT = 1.818 mins<br>LCMS m/z = 341<br>[M + H]$^+$ |
| 108 | 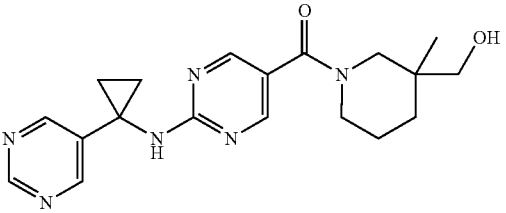<br>[3-(hydroxymethyl)-3-methylpiperidin-1-yl](2-{[1-(pyrimidin-5-yl)cyclopropyl]amino}pyrimidin-5-yl)methanone | AD01, CD05<br>RT = 1.893 mins<br>LCMS m/z = 369<br>[M + H]$^+$ |

| Example | Structure and name | PM, Analytical HPLC conditions Data |
|---|---|---|
| 109 | 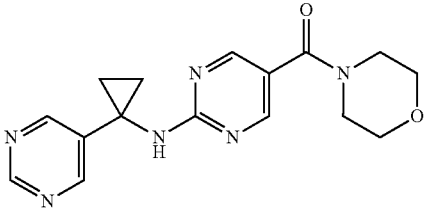morpholin-4-yl(2-{[1-(pyrimidin-5-yl)cyclopropyl]amino}pyrimidin-5-yl)methanone | AD02, CD05 RT = 1.66 mins LCMS m/z = 327 [M + H]+ |

All amine starting materials are commercially available, with the exception of:
[a] (3R,5R)-rel-5-isopropylpiperidin-3-ol (Preparation 75)
b 3-(pyrrolidin-3-yl)-1H-pyrazole hydrochloride (Preparation 59)
[c] [(3S,4S)-4-(trifluoromethyl)pyrrolidin-3-yl]methanol (Preparation 69)
[d] (3aR,7aR)-rel-octahydro-3aH-isoindol-3a-ylmethanol (Prepartation 80)
[e] [(3R,4R)-rel-3,4-dimethylpyrrolidin-3-yl]methanol (Preparation 83)
[f] 3-Methyl-5-(pyrrolidin-3-yl)-1H-pyrazole hydrochloride (Preparation 60)
[g] (3R,5S)-rel-5-methylpiperidin-3-ol hydrochloride (Preparation 71)
[h] (3R,5R)-rel-5-cyclopropylpiperidin-3-ol hydrochloride (Preparation 73)

Examples 110 to 129 were prepared in a library through an amide coupling of 2-[(pyrazin-2-ylmethyl)amino]pyrimidine-5-carboxylic acid (Preparation 3) or 2-{[(1S)-(1-(pyrazin-2-yl)ethyl]amino}pyrimidine-5-carboxylic acid (Preparation 4) with 10 different amines using the reaction protocol described below.

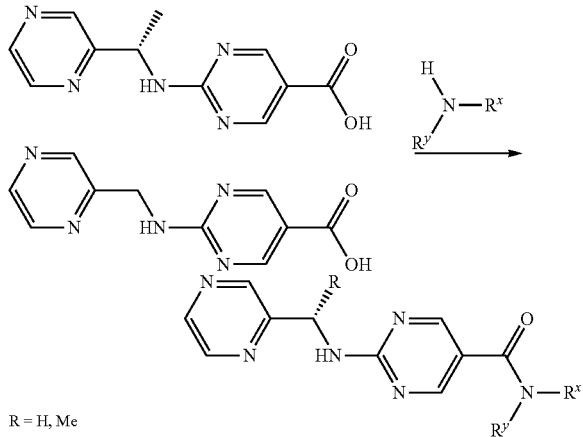

R = H, Me 1. 2-[(Pyrazin-2-ylmethyl)amino]pyrimidine-5-carboxylic acid (140 μmol, 1.0 eq.) was added to 10 separate 8 mL reaction vials.

2. 2-{[(1S)-(1-(pyrazin-2-yl)ethyl]amino}pyrimidine-5-carboxylic acid (140 μmol, 1.0 eq.) was added to 10 separate 8 mL reaction vials.

3. The selected amine ($R^1NHR^2$) (168 μmol, 1.2 eq.) was dispensed into each vial.

4. HATU (53.2 mg, 140 μmol, 1.0 eq.) was added to each vial.

5. DMA (1400 μL) was added to each vial.

6. DIPEA (~73 μL, 420 μmol, 3.0 eq.) was added to each vial.

7. The vials were capped and shaken at 50° C. for 16 hrs.

8. The solvent was evaporated by Speedvac.

9. The residues were purified by preparative HPLC using the columns described in the table below and an appropriate solvent gradient and flow rate, to provide the title compounds

| Example | Structure and Name | Data and HPLC |
|---|---|---|
| 110 | 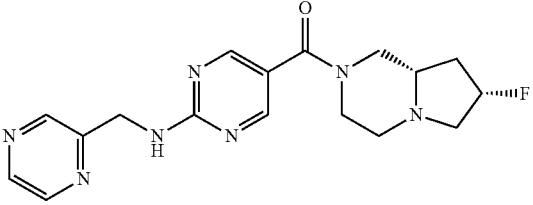[(7S,8aS)-7-fluorohexahydropyrrolo[1,2-a]pyrazin-2(1H)-yl]{2-[(pyrazin-2-ylmethyl)amino]pyrimidin-5-yl}methanone | WX01, CD05 RT = 1.806 mins LCMS m/z = 358 [M + H]+ |

-continued

| Example | Structure and Name | Data and HPLC |
|---|---|---|
| 111 | [(7R,8aS)-7-hydroxyhexahydropyrrolo[1,2-a]pyrazin-2(1H)-yl]{2-[(pyrazin-2-ylmethyl)amino]pyrimidin-5-yl}methanone | AD04, CD05<br>RT = 1.212 mins<br>LCMS m/z = 356 [M + H]+ |
| 112 | [(1S,4S)-5-methyl-2,5-diazabicyclo[2.2.1]hept-2-yl]{2-[(pyrazin-2-ylmethyl)amino]pyrimidin-5-yl}methanone | WX01, PF-CD05<br>RT = 1.64 mins<br>LCMS m/z = 326 [M + H]+ |
| 113 | [(3S,4S)-3-hydroxy-4-(morpholin-4-yl)pyrrolidin-1-yl](2-{[(1S)-1-(pyrazin-2-yl)ethyl]amino}pyrimidin-5-yl)methanone | AD03, CD05<br>RT = 1.742 mins<br>LCMS m/z = 400 [M + H]+ |
| 114 | (8aR)-hexahydropyrrolo[1,2-a]pyrazin-2(1H)-yl(2-{[(1S)-1-(pyrazin-2-yl)ethyl]amino}pyrimidin-5-yl)methanone | AD04, CD05<br>RT = 2.009 mins<br>LCMS m/z = 354 [M + H]+ |
| 115 | [(3S,4S)-3-hydroxy-4-(morpholin-4-yl)pyrrolidin-1-yl]{2-[(pyrazin-2-ylmethyl)amino]pyrimidin-5-yl}methanone | AD04, AB00<br>RT = 2.506 mins<br>LCMS m/z = 386 [M + H]+ |

| Example | Structure and Name | Data and HPLC |
|---|---|---|
| 116 | 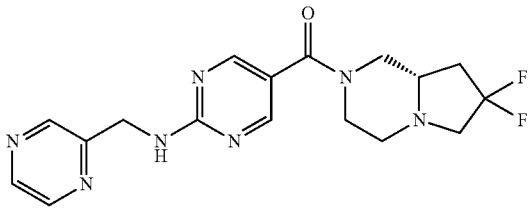<br>[(8aS)-7,7-difluorohexahydropyrrolo[1,2-a]pyrazin-2(1H)-yl]{2-[(pyrazin-2-ylmethyl)amino]pyrimidin-5-yl}methanone | AD04, CD05<br>RT = 2.007 mins<br>LCMS m/z = 376 [M + H]$^+$ |
| 117 | 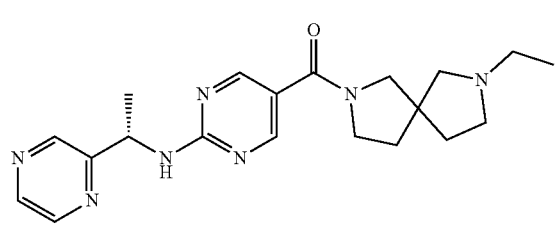<br>(7-ethyl-2,7-diazaspiro[4.4]non-2-yl)(2-{[(1S)-1-(pyrazin-2-yl)ethyl]amino}pyrimidin-5-yl)methanone | AD03, CD05<br>RT = 2.17 mins<br>LCMS m/z = 382 [M + H]$^+$ |
| 118 | 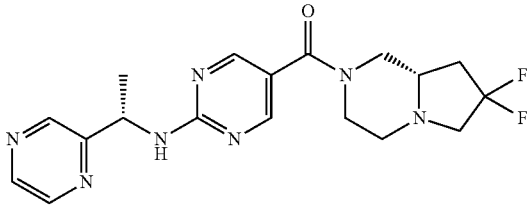<br>[(8aS)-7,7-difluorohexahydropyrrolo[1,2-a]pyrazin-2(1H)-yl](2-{[(1S)-1-(pyrazin-2-yl)ethyl]amino}pyrimidin-5-yl)methanone | AD04, CD05<br>RT = 2.146 mins<br>LCMS m/z = 390 [M + H]$^+$ |
| 119 | 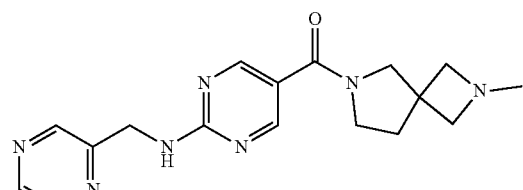<br>(2-methyl-2,6-diazaspiro[3.4]oct-6-yl){2-[(pyrazin-2-ylmethyl)amino]pyrimidin-5-yl}methanone | WX01, CD05<br>RT = 1.835 mins<br>LCMS m/z = 340 [M + H]$^+$ |
| 120 | 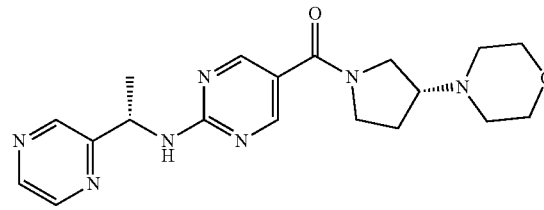<br>[(3R)-3-(morpholin-4-yl)pyrrolidin-1-yl](2-{[(1S)-1-(pyrazin-2-yl)ethyl]amino}pyrimidin-5-yl)methanone | AD04, CD05<br>RT = 1.887 mins<br>LCMS m/z = 384 [M + H]$^+$ |

-continued

| Example | Structure and Name | Data and HPLC |
|---|---|---|
| 121 | 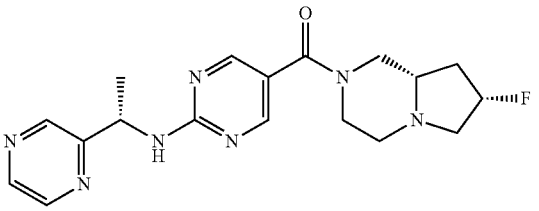<br>[(7S,8aS)-7-fluorohexahydropyrrolo[1,2-a]pyrazin-2(1H)-yl](2-{[(1S)-1-(pyrazin-2-yl)ethyl]amino}pyrimidin-5-yl)methanone | AD03, CD05<br>RT = 1.934 mins<br>LCMS m/z = 372 [M + H]$^+$ |
| 122 | 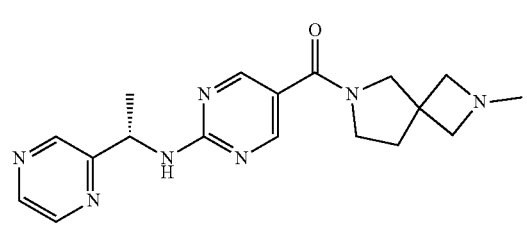<br>(2-methyl-2,6-diazaspiro[3.4]oct-6-yl)(2-{[(1S)-1-(pyrazin-2-yl)ethyl]amino}pyrimidin-5-yl)methanone | WX01, CD05<br>RT = 1.937 mins<br>LCMS m/z = 354 [M + H]$^+$ |
| 123 | 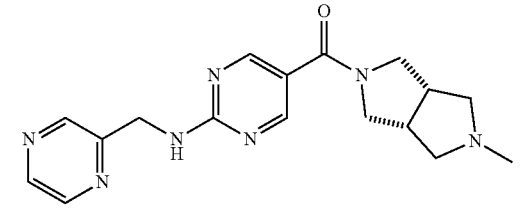<br>[(3aR,6aS)-5-methylhexahydropyrrolo[3,4-c]pyrrol-2(1H)-yl]{2-[(pyrazin-2-ylmethyl)amino]pyrimidin-5-yl}methanone | AD04, CD05<br>RT = 1.85 mins<br>LCMS m/z = 340 [M + H]$^+$ |
| 124 | 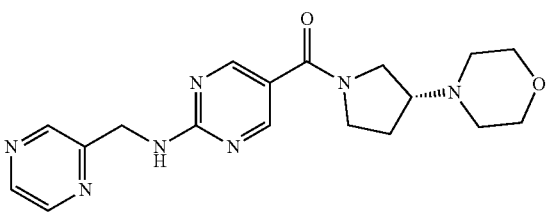<br>[(3R)-3-(morpholin-4-yl)pyrrolidin-1-yl]{2-[(pyrazin-2-ylmethyl)amino]pyrimidin-5-yl}methanone | AD04, AB01<br>RT = 1.348 mins<br>LCMS m/z = 370 [M + H]$^+$ |
| 125 | 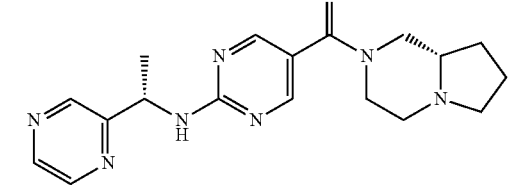<br>(8aS)-hexahydropyrrolo[1,2-a]pyrazin-2(1H)-yl(2-{[(1S)-1-(pyrazin-2-yl)ethyl]amino}pyrimidin-5-yl)methanone | AD04, CD05<br>RT = 2.005 mins<br>LCMS m/z = 354 [M + H]$^+$ |

-continued

| Example | Structure and Name | Data and HPLC |
|---|---|---|
| 126 | 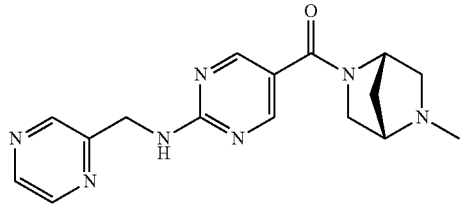<br>[(1S,4S)-5-methyl-2,5-diazabicyclo[2.2.1]hept-2-yl](2-{[(1S)-1-(pyrazin-2-yl)ethyl]amino}pyrimidin-5-yl)methanone | WX01, CD05<br>RT = 1.807 mins<br>LCMS m/z = 340 [M + H]+ |
| 127 | 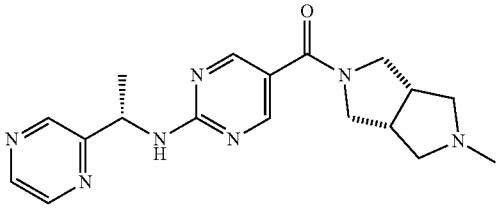<br>[(3aR,6aS)-5-methylhexahydropyrrolo[3,4-c]pyrrol-2(1H)-yl](2-{[(1S)-1-(pyrazin-2-yl)ethyl]amino}pyrimidin-5-yl)methanone | AD04, CD05<br>RT = 1.953 mins<br>LCMS m/z = 354 [M + H]+ |
| 128 | 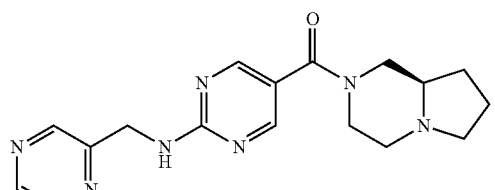<br>(8aR)-hexahydropyrrolo[1,2-a]pyrazin-2(1H)-yl{2-[(pyrazin-2-ylmethyl)amino]pyrimidin-5-yl}methanone | AD04, AB01<br>RT = 1.498 mins<br>LCMS m/z = 340 [M + H]+ |
| 129 | 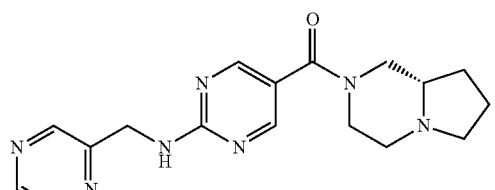<br>(8aS)-hexahydropyrrolo[1,2-a]pyrazin-2(1H)-yl{2-[(pyrazin-2-ylmethyl)amino]pyrimidin-5-yl}methanone | AD04, AB01<br>RT = 1.554 mins<br>LCMS m/z = 340 [M + H]+ |

Example 130

8-oxa-2-azaspiro[4.5]dec-2-yl(2-{[1-(pyrazin-2-yl)cyclobutyl]amino}pyrimidin-5-yl)methanone

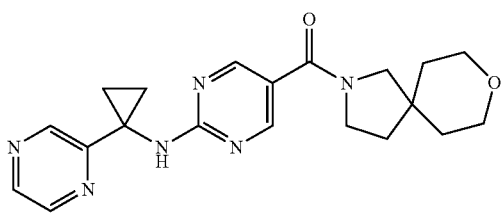 [SMILES: O=C(c1cnc(NC2(c3cnccn3)CC2)nc1)N1CCC2(CCOCC2)C1]

Ethyl 2-{[(1-(pyrazin-2-yl)cyclobutyl]amino} pyrimidine-5-carboxylate (Preparation 14, 2.1 g, 7.016 mmol), 8-oxa-2-azaspiro[4.5]decane (1.49 g, 10.5 mmol) and TBD (1.95 g, 14.0 mmol) were dissolved in DMF (40 mL) and the resulting mixture was stirred at 50° C. for 18 hrs. The reaction mixture was concentrated under reduced pressure to give a residue which was partially purified by column chromatography on silica gel eluting with petroleum ether:EtOAc (100:0 to 0:100) to give a yellow oil. The product was isolated using preparative HPLC using a Phenomenex Gemini C18 250*50 10p column, eluting with water (0.05% ammonium hydroxide):MeCN (10 to 34%) over 21 mins at a flow rate of 120 mL/min, to afford the title compound as a white solid (1.48 g, 53%).

$^1$H NMR (400 MHz, CDCl$_3$): δ 1.54-1.62 (m, 4H), 1.80-1.92 (m, 2H), 2.07-2.16 (m, 1H), 2.18-2.28 (m, 1H), 2.43-2.54 (m, 2H), 2.85-2.95 (m, 2H), 3.39 (br s, 1H), 3.53 (br s, 1H), 3.58-3.80 (m, 6H), 6.28 (br s, 1H), 8.42 (d, 1H), 8.47 (br s, 2H), 8.57 (s, 1H), 8.73 (br s, 1H). LCMS m/z=395 [M+H]$^+$

Example 131

7-oxa-2-azaspiro[3.5]non-2-yl(2-{[2-(pyrazin-2-yl)propan-2-yl]amino}pyrimidin-5-yl)methanone

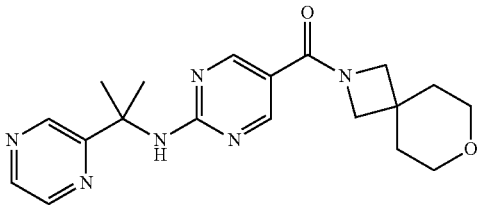 [SMILES: CC(C)(Nc1ncc(C(=O)N2CC3(CCOCC3)C2)cn1)c1cnccn1]

Ethyl 2-{[2-(pyrazin-2-yl)propan-2-yl]amino} pyrimidine-5-carboxylate (Preparation 15, 2.15 g, 7.48 mmol), 7-oxa-2-azaspiro[3.5]nonane (1.43 g, 11.2 mmol) and TBD (2.08 g, 15.0 mmol) were dissolved in DMF (40 mL) and the resulting mixture was stirred at 50° C. for 16 hrs. The reaction mixture was concentrated under reduced pressure to give a residue which was partially purified by column chromatography on silica gel eluting with petroleum ether:EtOAc (100:0 to 0:100) then EtOAC:MeOH (100:0 to 85:15) to give a yellow oil. The product was isolated using preparative HPLC using a Phenomenex Gemini C18 250*50 10p column, eluting with water (0.05% ammonium hydroxide):MeCN (10 to 31%) over 20 mins at a flow rate of 120 mL/min, to afford the title compound as a white solid (1.74 g, 63%). $^1$H NMR (400 MHz, CDCl$_3$): δ 1.79 (dd, 4H), 1.84 (s, 6H), 3.62 (dd, 4H), 3.85-4.09 (m, 4H), 6.42 (br s, 1H), 8.43 (d, 1H), 8.45-8.59 (m, 3H), 8.73 (s, 1H). LCMS m/z=369 [M+H]$^+$ The following Examples 132-142 were prepared according to the general synthetic schemes and methods outlined above for Example 130, using the appropriate ester and amine, in a transamidation reaction.

| Example | Structure and name | Starting ester; Yield; Data |
|---|---|---|
| 132 | 8-oxa-2-azaspiro[4.5]dec-2-yl(2-{[3-(pyrazin-2-yl)oxetan-3-yl]amino}pyrimidin-5-yl)methanone | ethyl 2-{[3-(pyrazin-2-yl)oxetan-3-yl]amino}pyrimidine-5-carboxylate; (Preparation 86); 62 mg, 32% <br> $^1$H NMR (400 MHz, MeOD-d$_4$): δ 1.50-1.72 (m, 4H), 1.86-1.97 (m, 2H), 3.49 (s, 2H), 3.55-3.80 (m, 6H), 4.97-5.04 (m, 2H), 5.17 (d, 2H), 8.40-8.80 (m, 5H). LCMS m/z = 397 [M + H$^+$] |
| 133 | 8-oxa-2-azaspiro[4.5]dec-2-yl(2-{[3-(pyrimidin-5-yl)oxetan-3-yl]amino}pyrimidin-5-yl)methanone | ethyl 2-{[3-(pyrimidin-5-yl)oxetan-3-yl]amino}pyrimidine-5-carboxylate; (Preparation 87); 13 mg, 24% <br> $^1$H NMR (400 MHz, MeOD-d$_4$): δ 1.50-1.68 (m, 4H), 1.83-1.96 (m, 2H), 3.48 (s, 2H), 3.55-3.80 (m, 6H), 4.90-5.00 (m, 4H), 5.04-5.11 (m, 2H), 8.51 (br s, 2H), 9.00 (d, 2H), 9.09 (s, 1H). LCMS m/z = 397 [M + H$^+$] |

| Example | Structure and name | Starting ester; Yield; Data |
|---|---|---|
| 134 | 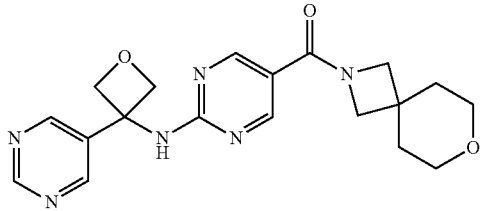<br>7-oxa-2-azaspiro[3.5]non-2-yl(2-{[3-(pyrimidin-5-yl)oxetan-3-yl]amino}pyrimidin-5-yl)methanone | ethyl 2-{[3-(pyrimidin-5-yl)oxetan-3-yl]amino}pyrimidine-5-carboxylate; (Preparation 87); 8 mg, 14%<br>$^1$H NMR (400 MHz, MeOD-d$_4$): δ 1.77-1.82 (m, 4H), 3.56-3.68 (m, 4H), 3.87 (s, 2H), 4.16 (s, 2H), 4.96 (d, 2H), 5.06 (d, 2H), 8.43-8.79 (br m, 2H), 8.99 (s, 2H), 9.09 (s, 1H). LCMS m/z = 383 [M + H]$^+$ |
| 135 | 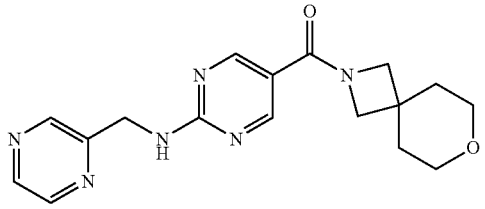<br>7-oxa-2-azaspiro[3.5]non-2-yl{2-[(pyrazin-2-ylmethyl)amino]pyrimidin-5-yl}methanone | ethyl 2-[(pyrazin-5-ylmethyl)amino]pyrimidine-5-carboxylate (Preparation 9); 27 mg, 26%<br>$^1$H NMR (400 MHz, DMSO-d$_6$): δ 1.66-1.70 (m, 4H), 3.40-3.60 (m, 4H), 3.73 (s, 2H), 4,12 (s, 2H), 4.69 (d, 2H), 8.40 (dd, 1H), 8.52 (s, 1H), 8.57-8.60 (m, 4H). LCMS m/z = 341 [M + H]$^+$ |
| 136 | 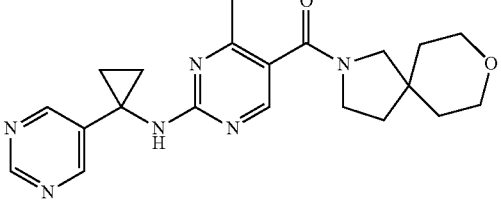<br>(4-methyl-2-{[1-(pyrimidin-5-yl)cyclopropyl]amino}pyrimidin-5-yl)(8-oxa-2-azaspiro[4.5]dec-2-yl)methanone | ethyl 4-methyl-2-{[1-(pyrimidin-5-yl)cyclopropyl]amino}pyrimidine-5-carboxylate; (Preparation 19); 15 mg, 11%<br>$^1$H NMR (400 MHz, CDCl$_3$): δ 1.32-1.46 (m, 2H), 1.48-1.65 (m, 4H), 1.80-1.85 (m, 1H), 1.88-2.00 (m, 3H), 2.35 (s, 3H), 3.10-3.17 (m, 1H), 3.29-3.38 (m, 1H), 3.55-3.74 (m, 6H), 6.07 (br s, 1H), 8.13 (d, 1H), 8.62-8.74 (m, 2H), 9.03 (d, 1H). LCMS m/z = 395 [M + H]$^+$ |
| 137 | 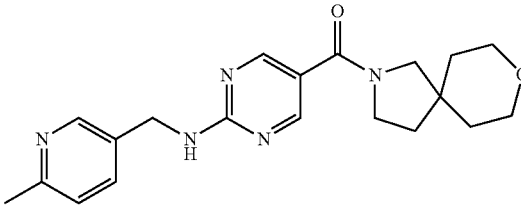<br>(2-{[(6-methylpyridin-3-yl)methyl]amino}pyrimidin-5-yl)(8-oxa-2-azaspiro[4.5]dec-2-yl)methanone | ethyl 2-{[(6-methylpyridin-3-yl)methyl]amino}pyrimidine-5-carboxylate; (Preparation 13); 1.00 g, 50%<br>$^1$H NMR (400 MHz, DMSO-d$_6$): δ 1.40-1.60 (m, 4H), 1.76-1.82 (m, 2H), 2.43 (s, 3H), 3.40-3.65 (m, 8H), 4.51 (d, 2H), 7.19 (d, 1H), 7.61 (d, 1H), 8.23 (br s, 1H), 8.48 (s, 1H), 8.53 (s, 2H). LCMS m/z = 390 [M + Na]$^+$ |

| Example | Structure and name | Starting ester; Yield; Data |
|---|---|---|
| 138 | 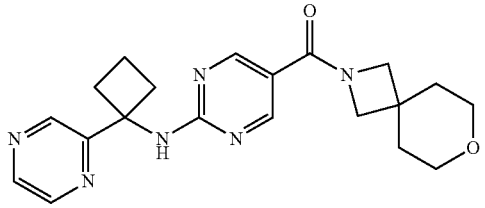<br>7-oxa-2-azaspiro[3.5]non-2-yl(2-{[1-(pyrazin-2-yl)cyclobutyl]amino}pyrimidin-5-yl)methanone | Ethyl 2-{[1-(pyrazin-2-yl)cyclobutyl]amino}pyrimidine-5-carboxylate; (Preparation 14); 298 mg, 65%.<br>$^1$H NMR (400 MHz, DMSO-$d_6$): δ 1.60-1.72 (m, 4H), 1.90-2.10 (m, 2H), 2.40-2.55 (m, 2H), 2.66-2.77 (m, 2H), 3.30-3.55 (m, 4H), 3.71 (s, 2H), 4.10 (s, 2H), 8.37 (br s, 1H), 8.47 (d, 1H), 8.56 (d, 1H), 8.63 (br s, 2H), 8.80 (s, 1H). LCMS m/z = 381 [M + H]$^+$ |
| 139 | 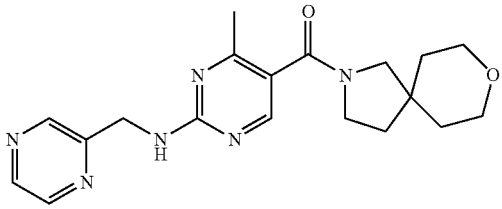 [SMILES: O=C(c1cnc(NCc2cnccn2)nc1)N1CCC2(CCOCC2)C1]<br>{4-methyl-2-[(pyrazin-2-ylmethyl)amino]pyrimidin-5-yl}(8-oxa-2-azaspiro[4.5]dec-2-yl)methanone | Ethyl 4-methyl-2-[(pyrazine-2-ylmethyl)amino]pyrimidine-5-carboxylate; (Preparation 20); 17 mg, 14%<br>$^1$H NMR (400 MHz, CDCl$_3$): δ 1.49-1.58 (m, 2H), 1.60-1.69 (m, 2H), 1.81-1.95 (m, 2H), 2.37 (s, 3H), 3.16 (s, 1H), 3.34-3.40 (m, 1H), 3.55-3.80 (m, 6H), 4.79-4.86 (m, 2H), 6.11-6.19 (m, 1H), 8.17 (d, 1H), 8.48 (s, 1H), 8.53 (s, 1H), 8.66 (d, 1H). LCMS m/z = 369 [M + H]$^+$ |
| 140 | 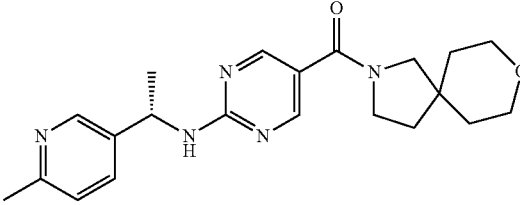<br>(2-{[(1S)-1-(6-methylpyridin-3-yl)ethyl]amino}pyrimidin-5-yl)(8-oxa-2-azaspiro[4.5]dec-2-yl)methanone | Ethyl 2-{[(1S)-1-(6-methylpyridin-3-yl)ethyl]amino}pyrimidine-5-carboxylate; (Preparation 17); 4.35 g, 63%<br>$^1$H NMR (400 MHz, CDCl$_3$): δ 1.45-1.65 (m, 7H), 1.81-1.92 (m, 2H), 2.52 (s, 3H), 3.35-3.80 (m, 8H), 5.18-5.26 (m, 1H), 5.62-5.69 (m, 1H), 7.11 (d, 1H), 7.56 (dd, 1H), 8.43-8.60 (m, 3H). LCMS m/z = 382 [M + H]$^+$ |
| 141 | 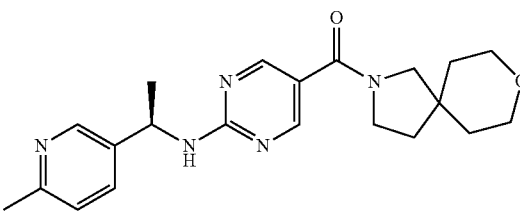<br>(2-{[(1R)-1-(6-methylpyridin-3-yl)ethyl]amino}pyrimidin-5-yl)(8-oxa-2-azaspiro[4.5]dec-2-yl)methanone | Ethyl 2-{[(1R)-1-(6-methylpyridin-3-yl)ethyl]amino}pyrimidine-5-carboxylate; (Preparation 18); 1.65 g, 56%<br>$^1$H NMR (400 MHz, CDCl$_3$): δ 1.52-1.68 (m, 7H), 1.81-1.93 (m, 2H), 2.54 (s, 3H), 3.39-3.83 (m, 8H), 5.17-5.27 (m, 1H), 5.61-5.67 (m, 1H), 7.13 (d, 1H), 7.54-7.60 (m, 1H), 8.52-8.56 (m, 3H). LCMS m/z = 382 [M + H]$^+$ |

Example 142

8-oxa-2-azaspiro[4.5]dec 1{2-[(pyrazin-2-ylmethyl)amino]pyrimidin-5-yl}methanone

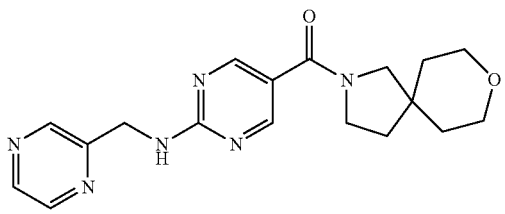

A 200-mL flask was charged with (2-chloropyrimidin-5-yl)(8-oxa-2-azaspiro[4.5]dec-2-yl)methanone (Preparation 22, 4.0 g 13.92 mmol), potassium carbonate (2.33 g, 16.7 mmol, 325 mesh), 1-(pyrazin-2-yl)methanamine (CAS#20010-99-5, 1.65 g, 14.7 mmol) at 25° C. An isopropanol/water solution (40 mL, 99:1 v/v) was added to the mixture which was heated at 80° C. for 2 h. The mixture was cooled down to 45° C., then acetone (80 mL) was added and the stirring was continued for 1 h at 45° C. the mixture was cooled down to 40° C. and filtered with a Buchner funnel and filter paper. The cake was washed with acetone (12 mL) and the combined filtrate was transferred in a 500-mL round bottom flask. The solvent was evaporated at 65° C. under reduced pressure while feeding the solution with isopropanol (80 mL), until a final volume of ~40 mL was obtained. Water (0.2 mL) was added to the solution which was slowly cooled from 65° C. to 2° C. over at least 10.5 h (~–0.1 C/min rate) and maintained at 2° C. for an extra 2 h period. The resulting slurry was filtered on a Buchner funnel with filter paper and isopropanol (12 mL) was used to rinse the flask and wash the cake. The off-white solid was dried under vacuum for 1 h then in a vacuum oven (house vacuum, 40° C.) for 2 h, affording the title compound, 4.25 g, 86%. $^1$H NMR (400 MHz, DMSO-d$_6$): δ 1.38-1.58 (m, 4H), 1.74-1.82 (m, 2H), 3.34 (br s, 1H), 3.44 (br s, 1H), 3.47-3.65 (m, 6H), 4.68 (d, 2H), 8.28 (br s, 1H), 8.48-8.55 (m, 3H), 8.56-8.62 (m, 2H). LCMS: m/z=355 [M+H]$^+$ Powder X-Ray Diffraction of Example 142:

The divergence slit was set at 0.6 mm while the secondary optics used variable slits. Diffracted radiation was detected by a PSD-Lynx Eye detector. The X-ray tube voltage and amperage were set to 40 kV and 40 mA respectively. Data was collected in the Theta-2Theta goniometer at the Cu wavelength (k-alpha average) from 3.0 to 40.0 degrees 2-Theta using a step size of 0.019 degrees and a step time of 5 second. Samples were prepared by placing them in a silicon low background sample holder (Bruker part number: C79298A3244B261) and rotated during collection. Data were collected using Bruker DIFFRAC Plus software and analysis was performed by EVA diffract plus software.

The PXRD data file was not processed prior to peak searching. Using the peak search algorithm in the EVA software, peaks selected with a threshold value of 5 and a width value of 0.3 were used to make preliminary peak assignments. The output of automated assignments was visually checked to ensure validity and adjustments were manually made if necessary. Peaks with relative intensity of >10% were generally chosen. The peaks which were not resolved or were consistent with noise were not selected. A typical error associated with the peak position from PXRD stated in USP is within +/−0.2° 2-Theta (USP-941). Table 1 details the PXRD peak list associated with Example 142. Asterisked peak positions represent characteristic peaks.

TABLE 1

PXRD peak list for EXAMPLE 142.

| Angle 2-Theta ° | Relative Intensity % |
|---|---|
| 14.0 | 17 |
| 14.6 | 2 |
| 15.9 | 14 |
| 17.2 | 24 |
| 17.3 | 28 |
| 18.4* | 42 |
| 20.3 | 27 |
| 20.6 | 21 |
| 20.9* | 48 |
| 21.2* | 48 |
| 22.4* | 100 |
| 23.9 | 12 |
| 26.4 | 25 |
| 28.4 | 15 |
| 28.4 | 15 |

Table 2 sets forth the comparison peak data for characteristic peaks from replicate preparations. All values listed are in Angles (2-Theta®). Asterisked peak positions represent characteristic peaks. See FIG. 1.

TABLE 2

Comparison of peak positions of the characteristics peaks

| Data presented in this document (rounded values) | Data presented in this document (unrounded) | Preparation 1 (unrounded) | Preparation 2 (unrounded) |
|---|---|---|---|
| 18.4* | 18.43* | 18.39 | 18.39 |
| 20.9* | 20.88* | 20.80 | 20.80 |
| 21.2* | 21.16* | 21.13 | 21.11 |
| 22.4* | 22.43* | 22.36 | 22.42 |

*Rounded values for important peaks are within 0.1 of each other.

Example 143

8-oxa-2-azaspiro[4.5]dec-2-yl(2-{[2-(pyrimidin-5-yl)propan-2-yl]amino}pyrimidin-5-yl)methanone

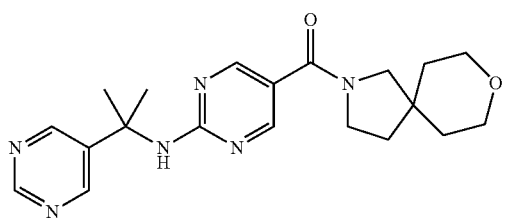 [SMILES: CC(C)(Nc1ncc(C(=O)N2CCC3(CCOCC3)C2)cn1)c1cncnc1]

To a solution of 2-(pyrimidin-5-yl)propan-2-amine hydrochloride (Preparation 24, 123 mg, 0.495 mmol) and DIPEA (183 mg, 1.42 mmol) in NMP (0.3 mL) was added (2-chloropyrimidin-5-yl)(8-oxa-2-azaspiro[4.5]dec-2-yl)methanone (Preparation 22, 100 mg, 0.355 mmol). The resulting mixture was stirred at 140° C. for 0.5 hr. The cooled reaction was purified directly by prep. HPLC using a Luna C18 150*25 5 u column, eluting with 18-38% (0.225% TFA in water):MeCN over 11 minutes at a flow rate of 35 mL/min to afford the title compound as a white solid, 21 mg, 15%. ¹H NMR (400 MHz, DMSO-$d_6$): δ 1.42-1.55 (m, 4H), 1.70-1.80 (m, 8H), 3.36 (s, 2H), 3.45-3.65 (s, 2H), 3.45-3.60 (m, 6H), 7.80 (br s, 1H), 8.40 (s, 2H), 8.76 (s, 2H), 8.98 (s, 1H). LCMS: m/z=383 [M+H]⁺

Example 145

8-oxa-2-azaspiro[4.5]dec-2-yl(2-{[(1S)-1-(pyrazin-2-yl)ethyl]amino}pyrimidin-5-yl)methanone

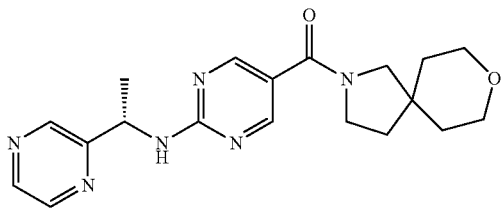 [SMILES: C[C@H](Nc1ncc(C(=O)N2CCC3(CCOCC3)C2)cn1)c1cnccn1]

A mixture of (1S)-1-(pyrazin-2-yl)ethanamine hydrochloride (Preparation 27, 529 mg, 4.29 mmol), (2-chloropyrimidin-5-yl)(8-oxa-2-azaspiro[4.5]dec-2-yl)methanone (Preparation 22, 1.1 g, 3.90 mmol), cesium carbonate (2.54 g, 7.81 mmol) and cesium fluoride (1.78 g, 11.70 mmol) in acetonitrile (50 mL) was stirred at 80° C. for 16 hours. The resulting suspension was filtered, and the filtrate was evaporated to dryness under reduced pressure. The residue was then purified by column chromatography on silica gel ($CH_2Cl_2$/MeOH, 100:0 to 80:20), to provide the title compound, 545 mg, 38%. ¹H NMR (400 MHz, CDCl₃): δ 1.53-1.68 (m, 7H), 1.82-1.92 (m, 2H), 3.43 (br s, 1H), 3.53-3.81 (m, 7H), 5.33-5.43 (m, 1H), 6.32 (br s, 1H), 8.49 (d, 1H), 8.54-8.57 (m, 3H), 8.66 (br s, 1H). LCMS: m/z=369 [M+H]⁺

Determination of Absolute Stereochemistry for Example 145a:

A single crystal structure of the methanesulfonate salt of Example 145 was obtained (FIG. 2). The absolute stereochemistry of Example 145a was determined as the S enantiomer from this crystal structure.

Example 145a 8-oxa-2-azaspiro[4.5]dec-2-yl(2-{[(1S)-1-(pyrazin-2-yl)ethyl]amino}pyrimidin-5-yl)methanone methanesulfonate

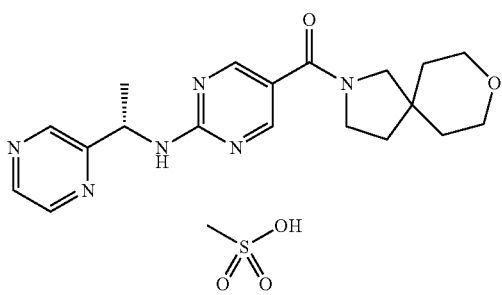

A solution of Example 145 (1.47 g. 3.89 mmol) in ethyl acetate (77.8 mL) stirred at room temperature was treated with a solution of methane sulfonic acid (CAS#75-75-2, 376 mg, 3.89 mmol) in ethyl acetate (266 μL). The resulting mixture was heated at 50° C. for 2 hrs, then slowly cooled down to room temperature, and further stirred at this temperature for 3 days. The slurry was then filtered off, rinsed with ethyl acetate and the solids were dried under vacuum, providing the title material as a white crystalline solid (1.66 g, 92%). ¹H NMR (400 MHz, CDCl₃): δ 1.55-1.66 (m, 4H), 1.75 (d, 3H), 1.92 (t, 2H), 2.94 (s, 3H), 3.40 (br. s., 1H), 3.55 (br. s., 1H), 3.61-3.81 (m, 6H), 5.42-5.51 (m, 1H), 8.29-8.41 (m, 1H), 8.53 (d, 1H), 8.57 (s, 1H), 8.71 (s, 1H), 8.95 (br. s., 1H), 9.98-10.20 (m, 1H). LCMS m/z 369 [M+H]⁺

Data collection was performed on a Bruker APEX diffractometer at room temperature. Data collection consisted of omega and phi scans. The structure was solved by direct methods using SHELX software suite in the space group P212121. The structure was subsequently refined by the full-matrix least squares method. All non-hydrogen atoms were found and refined using anisotropic displacement parameters.

The hydrogen atoms located on nitrogen were placed in reasonable constrained positions based on bond lengths. The bond lengths and the pkas of the acid/base support this assignment of the proton (salt).

The remaining hydrogen atoms were placed in calculated positions and were allowed to ride on their carrier atoms. The final refinement included isotropic displacement parameters for all hydrogen atoms.

The final R-index was 6%. A final difference Fourier revealed no missing or misplaced electron density. See FIG. 2 for an X-ray crystal structure (ORTEP drawing of Example 145a). Table 3 contains relevant structure data on Example 145a.

TABLE 3

Crystal data and structure refinement for Example 145a.

| | |
|---|---|
| Empirical formula | C20 H28 N6 O5 S |
| Formula weight | 464.54 |
| Temperature | 296(2) K |
| Wavelength | 1.54178 Å |
| Crystal system | Orthorhombic |
| Space group | P2₁2₁2₁ |
| Unit cell dimensions | a = 8.2609(17) Å    a = 90°. |
| | b = 14.686(3) Å    b = 90°. |
| | c = 18.670(4) Å    g = 90°. |
| Volume | 2265.1(8) ų |
| Z | 4 |
| Density (calculated) | 1.362 Mg/m³ |
| Goodness-of-fit on F² | 0.971 |
| Final R indices [I > 2sigma(I)] | R1 = 0.0597, wR2 = 0.1129 |
| R indices (all data) | R1 = 0.1178, wR2 = 0.1364 |

Inferred Assignment of Absolute Stereochemistry for Other Enantiomeric Pairs

Analysis of the absolute structure using likelihood methods (Hooft 2008) was performed using PLATON (Spek 2010). Assuming the sample submitted is enantiopure, the results indicate that the absolute stereochemistry was correctly assigned. Therefore, the single X-Ray of Example 145a is consistent with Example 145 having a "S" absolute configuration. By deduction, Example 146 is the "R" enantiomer of this pair, and it displayed a -100-fold loss of potency against vanin in the assay. This analysis was used to extrapolate absolute configurations of other enantiomeric pairs of this series: in each case, the most potent enantiomer was assigned with the "S" absolute configuration, based upon the above assumptions. The examples in which absolute stereochemistry was inferred are indicated as such in the description thereof.

Examples 144 and 146-181, Table 4, were prepared using the method of Example 143, from (2-chloropyrimidin-5-yl)(8-oxa-2-azaspiro[4.5]dec-2-yl)methanone (Preparation 22) or (2-chloropyrimidin-5-yl)(7-oxa-2-azaspiro[4.5]non-2-yl)methanone (Preparation 23) and the appropriate amine upon heating either with or without microwave irradiation.

TABLE 4

Data for Examples 144 and 146-181

| Example | Structure | Yield; Data |
|---|---|---|
| 144[a] | 7-oxa-2-azaspiro[3.5]non-2-yl(2-{[2-(pyrimidin-5-yl)propan-2-yl]amino}pyrimidin-5-yl)methanone | 7.3 g, 73%; $^1$H NMR (400 MHz, DMSO-$d_6$): δ 1.66-1.68 (m, 4H), 1.73 (s, 6H), 3.46-3.51 (m, 4H), 3.71 (s, 2H), 4.09 (s, 2H), 8.28 (br s, 1H), 8.30-8.60 (m, 2H), 8.75 (s, 2H), 9.01 (s, 1H). LCMS: m/z = 369 [M + H]$^+$ |
| 146[b] | 8-oxa-2-azaspiro[4.5]dec-2-yl(2-{[(1R)-1-(pyrazin-2-yl)ethyl]amino}pyrimidin-5-yl)methanone | 34 mg, 16%; $^1$H NMR (400 MHz, DMSO-$d_6$): δ 1.35-1.62 (m, 7H), 1.72-1.84 (m, 2H), 3.30-3.67 (m, 8H), 5.17-5.29 (m, 1H), 8.24 (br d, 1H), 8.40-8.62 (m, 4H), 8.67 (s, 1H). LCMS: m/z = 369 [M + H]$^+$ |
| 147[c] | absolute stereochemistry inferred 7-oxa-2-azaspiro[3.5]non-2-yl(2-{[(1S)-1-(pyrazin-2-yl)ethyl]amino}pyrimidin-5-yl)methanone | 16 mg, 7%; $^1$H NMR (400 MHz, DMSO-$d_6$): δ 1.53 (d, 3H), 1.68 (m, 4H), 3.52 (m, 4H), 3.73 (s, 2H), 4.11 (s, 2H), 5.23 (m, 1H), 8.37 (br d, 1H), 8.45-8.60 (m, 4H), 8.66 (3, 1H). LCMS: m/z = 355 [M + H]$^+$ |
| 148[b] | absolute stereochemistry inferred 7-oxa-2-azaspiro[3.5]non-2-yl(2-{[(1R)-1-(pyrazin-2-yl)ethyl]amino}pyrimidin-5-yl)methanone | 33 mg, 14%; $^1$H NMR (400 MHz, DMSO-$d_6$): δ 1.53 (d, 3H), 1.61-1.77 (m, 4H), 3.40-3.55 (m, 4H), 3.73 (s, 2H), 4.11 (s, 2H), 5.18-5.28 (m, 1H), 8.38 (br d, 1H), 8.46-8.58 (m, 4H), 8.66 (s, 1H). LCMS: m/z = 355 [M + H]$^+$ |

TABLE 4-continued

Data for Examples 144 and 146-181

| Example | Structure | Yield; Data |
|---|---|---|
| 149[d] | absolute stereochemistry inferred<br>8-oxa-2-azaspiro[4.5]dec-2-yl(2-{[(1S)-1-(pyrimidin-5-yl)ethyl]amino}pyrimidin-5-yl)methanone | 45 mg, 17% (after SFC Method CP-A); RT = 12.437 mins (Method CA-A); $^1$H NMR (400 MHz, DMSO-d$_6$): δ 1.30-1.58 (m, 7H), 1.71-1.83 (m, 2H), 3.30-3.67 (m, 8H), 5.13-5.24 (m, 1H), 8.31 (br d, 1H), 8.51 (br s, 2H), 8.82 (s, 2H), 9.06 (s, 1H). LCMS: m/z = 369 [M + H]$^+$ |
| 150[d] | absolute stereochemistry inferred<br>8-oxa-2-azaspiro[4.5]dec-2-yl(2-{[(1R)-1-(pyrimidin-5-yl)ethyl]amino}pyrimidin-5-yl)methanone | 54 mg, 21% (after SFC Method CP-A); RT = 8.151 mins (Method CA-A); $^1$H NMR (400 MHz, DMSO-d$_6$): δ 1.30-1.60 (m, 7H), 1.71-1.83 (m, 2H), 3.28-3.65 (m, 8H), 5.12-5.23 (m, 1H), 8.31 (br d, 1H), 8.51 (br s, 2H), 8.82 (s, 2H), 9.06 (s, 1H). LCMS: m/z = 369 [M + H]$^+$ |
| 151[d] | absolute stereochemistry inferred<br>7-Oxa-2-azaspiro[3.5]non-2-yl(2-{[(1S)-1-(pyrimidin-5-yl)ethyl]amino}pyrimidin-5-yl)methanone | 30 mg, 11% (after SFC Method CP-A); RT = 9.582 mins (Method CA-A); $^1$H NMR (400 MHz, DMSO-d$_6$): δ 1.52 (d, 3H), 1.66-1.69 (m, 4H), 3.41-3.54 (m, 4H), 3.72 (s, 2H), 4.10 (s, 2H), 5.15-5.22 (m, 1H), 8.42 (br d, 1H), 8.56 (br s, 2H), 8.81 (s, 2H), 9.06 (s, 1H). LCMS m/z = 355 [M + H]$^+$ |
| 152[d] | absolute stereochemistry inferred<br>7-Oxa-2-azaspiro[3.5]non-2-yl(2-{[(1R)-1-(pyrimidin-5-yl)ethyl]amino}pyrimidin-5-yl)methanone | 32 mg, 12% (after SFC Method CP-A); RT = 7.179 mins (Method CA-A); $^1$H NMR (400 MHz, DMSO-d$_6$): δ 1.53 (d, 3H), 1.65-1.69 (m, 4H), 3.41-3.54 (m, 4H), 3.72 (s, 2H), 4.10 (s, 2H), 5.15-5.22 (m, 1H), 8.42 (br d, 1H), 8.56 (br s, 2H), 8.81 (s, 2H), 9.06 (s, 1H). LCMS m/z = 355 [M + H]$^+$ |

TABLE 4-continued

Data for Examples 144 and 146-181

| Example | Structure | Yield; Data |
|---|---|---|
| 153 | absolute stereochemistry inferred<br>8-Oxa-2-azaspiro[4.5]dec-2-yl(2-{[(1S)-1-(pyridazin-4-yl)ethyl]amino}pyrimidin-5-yl)methanone | 8 mg, 3% (after SFC Method CP-B); RT = 5.801 mins (Method CA-B); $^1$H NMR (400 MHz, MeOD-d$_4$): δ 1.55-1.64 (m, 7H), 1.86-1.94 (m, 2H), 3.48 (d, 2H), 3.60-3.75 (m, 6H), 5.21-5.23 (m, 1H), 7.72 (br s, 1H), 8.51 (br s, 2H), 9.09 (d, 1H), 9.25 (s, 1H). LCMS m/z = 391 [M + Na]$^+$ |
| 154 | absolute stereochemistry inferred<br>8-Oxa-2-azaspiro[4.5]dec-2-yl(2-{[(1R)-1-(pyridazin-4-yl)ethyl]amino}pyrimidin-5-yl)methanone | 10 mg, 4% (after SFC Method CP-B); RT = 7.104 mins (Method CA-B); $^1$H NMR (400 MHz, MeOD-d$_4$): δ 1.55-1.64 (m, 7H), 1.86-1.94 (m, 2H), 3.48 (d, 2H), 3.60-3.75 (m, 6H), 5.21-5.23 (m, 1H), 7.72 (br s, 1H), 8.51 (br s, 2H), 9.09 (d, 1H), 9.25 (s, 1H). LCMS m/z = 391 [M + Na]$^+$ |
| 155 | absolute stereochemistry inferred<br>8-Oxa-2-azaspiro[4.5]dec-2-yl(2-{[(1S)-1-(pyrimidin-4-yl)ethyl]amino}pyrimidin-5-yl)methanone | 13 mg, 18% (after SFC Method CP-C); RT = 2.236 mins (Method CA-C); $^1$H NMR (400 MHz, DMSO-d$_6$): δ 1.39-1.60 (m, 7H), 1.75-1.78 (m, 2H), 3.40-3.64 (m, 8H), 5.04-5.15 (m, 1H), 7.46 (br s, 1H), 8.28 (d, 1H), 8.40-8.60 (m, 2H), 8.70 (s, 1H), 9.10 (s, 1H). LCMS m/z = 369 [M + H]$^+$ |
| 156 | absolute stereochemistry inferred<br>8-Oxa-2-azaspiro[4.5]dec-2-yl(2-{[(1R)-1-(pyrimidin-4-yl)ethyl]amino}pyrimidin-5-yl)methanone | 11 mg, 15% (after SFC Method CP-C); RT = 1.336 mins (Method CA-C); $^1$H NMR (400 MHz, DMSO-d$_6$): δ 1.40-1.60 (m, 7H), 1.75-1.79 (m, 2H), 3.40-3.60 (m, 8H), 5.04-5.15 (m, 1H), 7.47 (br s, 1H), 8.29 (d, 1H), 8.40-8.60 (m, 2H), 8.72 (d, 1H), 9.12 (s, 1H). LCMS m/z = 369 [M + H]$^+$ |

TABLE 4-continued

Data for Examples 144 and 146-181

| Example | Structure | Yield; Data |
|---|---|---|
| 157 | 8-oxa-2-azaspiro[4.5]dec-2-yl(2-{[1-(pyrazin-2-yl)cyclopropyl]amino}pyrimidin-5-yl)methanone | 5 mg, 4%; $^1$H NMR (400 MHz, MeOD-d$_4$): δ 1.36-1.44 (m, 2H), 1.55-1.61 (m, 2H), 1.63-1.69 (m, 2H), 1.71-1.76 (m, 2H), 1.91 (dt, 2H), 3.51 (d, 2H), 3.57-3.78 (m, 6H), 8.33 (s, 1H), 8.46-8.67 (m, 4H). LCMS: m/z = 381 [M + H]$^+$ |
| 158 | 7-oxa-2-azaspiro[3.5]non-2-yl(2-{[1-(pyrazin-2-yl)cyclopropyl]amino}pyrimidin-5-yl)methanone | 9 mg, 7%; $^1$H NMR (400 MHz, MeOD-d$_4$): δ 1.35-1.40 (m, 2H), 1.71-1.75 (m, 2H), 1.81 (t, 4H), 3.56-3.69 (m, 4H), 3.89 (s, 2H), 4.19 (s, 2H), 8.32 (d, 1H), 8.48-8.52 (m, 2H), 8.53-8.75 (m, 2H). LCMS: m/z = 367 [M + H]$^+$ |
| 159 | (2-{[1-(2-methylpyrimidin-5-yl)ethyl]amino}pyrimidin-5-yl)(8-oxa-2-azaspiro[4.5]dec-2-yl)methanone | 19 mg, 11%; $^1$H NMR (400 MHz, DMSO-d$_6$): δ 1.38-1.58 (m, 7H), 1.72-1.84 (m, 2H), 2.57 (s, 3H), 3.30-3.67 (m, 8H), 5.10-5.20 (m, 1H), 8.28 (d, 1H), 8.51 (br s, 2H), 8.70 (s, 2H). LCMS: m/z = 383 [M + H]$^+$ |
| 160 | (2-{[1-(2-methylpyrimidin-5-yl)ethyl]amino}pyrimidin-5-yl)(7-oxa-2-azaspiro[3.5]non-2-yl)methanone | 19 mg, 9%; $^1$H NMR (400 MHz, DMSO-d$_6$): δ 1.51 (d, 3H), 1.65-1.70 (m, 4H), 2.57 (s, 3H), 3.40-3.60 (m, 4H), 3.73 (s, 2H), 4.11 (s, 2H), 5.10-5.15 (m, 1H), 8.39 (d, 1H), 8.56 (br s, 2H), 8.69 (s, 2H). LCMS: m/z = 369 [M + H]$^+$ |
| 161 | (2-{[1-(5-methylpyridin-2-yl)ethyl]amino}pyrimidin-5-yl)(8-oxa-2-azaspiro[4.5]dec-2-yl)methanone | 315 mg, 55%; $^1$H NMR (400 MHz, MeOD-d$_4$): δ 1.54 (d, 5H), 1.60-1.68 (m, 2H), 1.90 (td, 2H), 2.32 (s, 3H), 3.49 (d, 2H), 3.54-3.79 (m, 6H), 4.83 (s, 3H), 5.21 (q, 1H), 7.33 (d, 1H), 7.59 (d, 1H), 8.32 (s, 1H), 8.50 (s, 2H). LCMS m/z = 382 [M + H]$^+$ |

TABLE 4-continued

Data for Examples 144 and 146-181

| Example | Structure | Yield; Data |
|---|---|---|
| 162[e] | (2-{[1-(6-methylpyridin-3-yl)ethyl]amino}pyrimidin-5-yl)(8-oxa-2-azaspiro[4.5]dec-2-yl)methanone | 15 mg, 11%; $^1$H NMR (400 MHz, MeOD-d$_4$): δ 1.50-1.69 (m, 7H), 1.85-1.97 (m, 2H), 2.52 (s, 3H), 3.50 (d, 2H), 3.55-3.80 (m, 6H), 5.17-5.27 (m, 1H), 7.28 (d, 1H), 7.80 (d, 1H), 8.46 (s, 1H), 8.52 (s, 2H). LCMS: m/z = 382 [M + H]$^+$ |
| 163[e] | (2-{[1-(6-methylpyridin-3-yl)ethyl]amino}pyrimidin-5-yl)(7-oxa-2-azaspiro[3.5]non-2-yl)methanone | 30 mg, 22%; $^1$H NMR (400 MHz, MeOD-d$_4$): δ 1.58 (d, 3H), 1.82 (dd, 4H), 2.52 (s, 3H), 3.55-3.70 (m, 4H), 3.89 (s, 2H), 4.18 (s, 2H), 5.19-5.28 (m, 1H), 7.29 (d, 1H), 7.79 (dd, 1H), 8.45 (d, 1H), 8.59 (s, 2H). LCMS: m/z = 368 [M + H]$^+$ |
| 164 | (2-{[(5-methylpyrazin-2-yl)methyl]amino}pyrimidin-5-yl)(8-oxa-2-azaspiro[4.5]dec-2-yl)methanone | 48 mg, 39%; $^1$H NMR (400 MHz, DMSO-d$_6$): δ 1.35-1.58 (m, 4H), 1.72-1.84 (m, 2H), 2.46 (s, 3H), 3.40-3.65 (m, 8H), 4.58-4.67 (m, 2H), 8.26-8.30 (m, 1H), 8.40-8.60 (m, 4H). LCMS: m/z = 369 [M + H]$^+$ |
| 165 | (2-{[(5-methylpyrazin-2-yl)methyl]amino}pyrimidin-5-yl)(7-oxa-2-azaspiro[3.5]non-2-yl)methanone | 25 mg, 30%; $^1$H NMR (400 MHz, DMSO-d$_6$): δ 1.66-1.70 (m, 4H), 2.46 (s, 3H), 3.40-3.55 (m, 4H), 3.74 (s, 2H), 4.12 (s, 2H), 4.64 (d, 2H), 8.34-8.40 (m, 1H), 8.44 (d, 2H), 8.56 (br d, 2H). LCMS: m/z = 355 [M + H]$^+$ |
| 166 | 8-oxa-2-azaspiro[4.5]dec-2-yl[2-({[4-(trifluoromethyl)pyrimidin-5-yl]methyl}amino)pyrimidin-5-yl]methanone | 33 mg, 33%; $^1$H NMR (400 MHz, DMSO-d$_6$): δ 1.40-1.60 (m, 4H), 1.72-1.84 (m, 2H), 3.40-3.65 (m, 8H), 4.73-4.79 (m, 2H), 8.30 (br s, 1H), 8.56 (br s, 2H), 9.06 (d, 1H), 9.34 (s, 1H). LCMS: m/z = 423 [M + H]$^+$ |

TABLE 4-continued

Data for Examples 144 and 146-181

| Example | Structure | Yield; Data |
|---|---|---|
| 167 | 7-oxa-2-azaspiro[3.5]non-2-yl[2-({[4-(trifluoromethyl)pyrimidin-5-yl]methyl}amino)pyrimidin-5-yl]methanone | 25 mg, 24%; $^1$H NMR (400 MHz, DMSO-$d_6$): δ 1.65-1.78 (m, 4H), 3.40-3.60 (m, 4H), 3.75 (s, 2H), 4.13 (s, 2H), 4.71-4.82 (m, 2H), 8.36-8.46 (m, 1H), 8.66 (br s, 2H), 9.05 (s, 1H), 9.34 (s, 1H). LCMS: m/z = 409 [M + H]$^+$ |
| 168 | 8-oxa-2-azaspiro[4.5]dec-2-yl[2-({[2-(trifluoromethyl)pyrimidin-5-yl]methyl}amino)pyrimidin-5-yl]methanone | 17 mg, 17%; $^1$H NMR (400 MHz, DMSO-$d_6$): δ 1.35-1.58 (m, 4H), 1.67-1.89 (m, 2H), 3.25-3.65 (m, 8H), 4.68 (s, 2H), 8.32 (br s, 1H), 8.56 (br s, 2H), 9.03 (s, 2H). LCMS: m/z = 423 [M + H]$^+$ |
| 169 | 7-oxa-2-azaspiro[3.5]non-2-yl[2-({[2-(trifluoromethyl)pyrimidin-5-yl]methyl}amino)pyrimidin-5-yl]methanone | 21 mg, 19%; $^1$H NMR (400 MHz, DMSO-$d_6$): δ 1.69 (s, 4H), 3.25-3.60 (m, 4H), 3.75 (s, 2H), 4.12 (s, 2H), 4.69 (s, 2H), 8.42 (br s, 1H), 8.69 (s, 2H), 9.02 (s, 2H). LCMS: m/z = 409 [M + H]$^+$ |
| 170 | (2-{[(2-methylpyrimidin-5-yl)methyl]amino}pyrimidin-5-yl)(8-oxa-2-azaspiro[4.5]dec-2-yl)methanone | 6 mg, 8%; $^1$H NMR (400 MHz, MeOD-$d_4$): δ 1.54-1.73 (m, 4H), 1.87-1.98 (m, 2H), 2.68 (s, 3H), 3.52 (d, 2H), 3.65-3.75 (m, 6H), 4.64 (s, 2H), 8.58 (s, 2H), 8.70 (s, 2H). LCMS: m/z = 369 [M + H]$^+$ |

TABLE 4-continued

Data for Examples 144 and 146-181

| Example | Structure | Yield; Data |
|---|---|---|
| 171 | (2-{[(2-methylpyrimidin-5-yl)methyl]amino}pyrimidin-5-yl)(7-oxa-2-azaspiro[3.5]non-2-yl)methanone | 11 mg, 10%; $^1$H NMR (400 MHz, MeOD-d$_4$): δ 1.80-1.85 (m, 4H), 2.69 (s, 3H), 3.60-3.70 (m, 4H), 3.91 (s, 2H), 4.21 (s, 2H), 4.65 (s, 2H), 8.67 (br s, 2H), 8.71 (s, 2H). LCMS: m/z = 355 [M + H]$^+$ |
| 172 | (2-{[(6-methylpyridin-3-yl)methyl]amino}pyrimidin-5-yl)(7-oxa-2-azaspiro[3.5]non-2-yl)methanone | 48 mg, 40% (as a 0.5 formate salt); $^1$H NMR (400 MHz, MeOD-d$_4$): δ 1.83 (dd, 4H), 2.53 (s, 3H), 3.60-3.70 (m, 4H), 3.91 (s, 2H), 4.21 (s, 2H), 4.65 (s, 2H), 7.30 (d, 1H), 7.78 (dd, 1H), 8.14 (s, 0.5H), 8.43 (s, 1H), 8.64 (s, 2H). LCMS: m/z = 354 [M + H]$^+$ |
| 173$^f$ | 8-oxa-2-azaspiro[4.5]dec-2-yl(2-{[1-(pyrimidin-5-yl)cyclobutyl]amino}pyrimidin-5-yl)methanone | 20 mg, 13%; $^1$H NMR (400 MHz, DMSO-d$_6$): δ 1.35-1.58 (m, 4H), 1.68-1.79 (m, 2H), 1.85-1.96 (m, 1H), 2.00-2.12 (m, 1H), 2.40-2.65 (m, 4H), 3.30-3.60 (m, 8H), 8.43 (br s, 2H), 8.62 (s, 1H), 8.84 (s, 2H), 8.99 (s, 1H). LCMS: m/z = 395 [M + H]$^+$ |
| 174$^f$ | 7-oxa-2-azaspiro[3.5]non-2-yl(2-{[1-(pyrimidin-5-yl)cyclobutyl]amino}pyrimidin-5-yl)methanone | 14 mg, 9%; $^1$H NMR (400 MHz, DMSO-d$_6$): δ 1.60-1.70 (m, 4H), 1.86-1.95 (m, 1H), 2.00-2.11 (m, 1H), 2.45-2.65 (m, 4H), 3.40-3.55 (m, 4H), 3.71 (s, 2H), 4.09 (s, 2H), 8.35-8.60 (m, 2H), 8.62 (s, 1H), 8.76 (s, 2H), 8.86 (s, 1H). LCMS: m/z = 381 [M + H]$^+$ |

TABLE 4-continued

Data for Examples 144 and 146-181

| Example | Structure | Yield; Data |
|---|---|---|
| 175 | (2-{[1-(6-methylpyridin-3-yl)cyclopropyl]amino}pyrimidin-5-yl)(8-oxa-2-azaspiro[4.5]dec-2-yl)methanone | 221 mg, 33%; $^1$H NMR (400 MHz, DMSO-d$_6$): δ 1.20-1.32 (m, 4H), 1.36-1.60 (m, 4H), 1.73-1.80 (m, 2H), 2.39 (3, 3H), 3.40-3.63 (m, 8H), 7.12 (d, 1H), 7.44 (d, 1H), 8.28 (s, 1H), 8.52 (br s, 2H), 8.57 (s, 1H). LCMS: m/z = 394 [M + H]$^+$ |
| 176 | (2-{[1-(6-methylpyridin-3-yl)cyclopropyl]amino}pyrimidin-5-yl)(7-oxa-2-azaspiro[3.5]non-2-yl)methanone | 131 mg, 17%; $^1$H NMR (400 MHz, DMSO-d$_6$): δ 1.15-1.30 (m, 4H), 1.59-1.74 (m, 4H), 2.37 (s, 3H), 3.33-3.60 (m, 4H), 3.71 (s, 2H), 4.09 (s, 2H), 7.10 (d, 1H), 7.41 (dd, 1H), 8.25 (d, 1H), 8.55 (br d, 2H), 8.65 (s, 1H). LCMS: m/z = 380 [M + H]$^+$ |
| 177 | 8-oxa-2-azaspiro[4.5]dec-2-yl(2-{[1-(pyridin-2-yl)cyclopropyl]amino}pyrimidin-5-yl)methanone | 400 mg, 59%; $^1$H NMR (400 MHz, DMSO-d$_6$): δ 1.21 (s, 2H), 1.35-1.58 (m, 6H), 1.71-1.83 (m, 2H), 3.40-3.65 (m, 8H), 7.11 (dd, 1H), 7.25 (dd, 1H), 7.62 (dd, 1H), 8.42 (d, 1H), 8.45-8.60 (m, 3H). LCMS: m/z = 380 [M + H]$^+$ |
| 178 | 8-oxa-2-azaspiro[4.5]dec-2-yl(2-{[1-(pyrimidin-2-yl)cyclopropyl]amino}pyrimidin-5-yl)methanone | 334 mg, 60%; $^1$H NMR (400 MHz, DMSO-d$_6$): δ 1.33 (s, 2H), 1.40-1.55 (m, 4H), 1.61-1.66 (m, 2H), 1.73-1.83 (m, 2H), 3.40-3.65 (m, 8H), 7.24 (dd, 1H), 8.45 (br s, 2H), 8.54 (br s, 1H), 8.63 (d, 2H). LCMS: m/z = 381 [M + H]$^+$ |
| 179 | 7-oxa-2-azaspiro[3.5]non-2-yl(2-{[1-(pyrimidin-2-yl)cyclobutyl]amino}pyrimidin-5-yl)methanone | 407 mg, 61%; $^1$H NMR (400 MHz, DMSO-d$_6$): δ 1.28-1.35 (m, 2H), 1.60-1.70 (m, 6H), 3.40-3.60 (m, 4H), 3.74 (s, 2H), 4.11 (s, 2H), 7.24 (dd, 1H), 8.50 (br s, 1H), 8.55-8.64 (m, 4H). LCMS: m/z 367 [M + H]$^+$ |

TABLE 4-continued

Data for Examples 144 and 146-181

| Example | Structure | Yield; Data |
|---|---|---|
| 180 | (2-{[2-(5-methylpyrazin-2-yl)propan-2-yl]amino}pyrimidin-5-yl)(7-oxa-2-azaspiro[3.5]non-2-yl)methanone | 223 mg, 27%; $^1$H NMR (400 MHz, DMSO-$d_6$): δ 1.63-1.70 (m, 10H), 2.43 (s, 3H), 3.40-3.57 (m, 4H), 3.70 (s, 2H), 4.08 (s, 2H), 8.23 (s, 1H), 8.26-8.70 (m, 4H). LCMS: m/z = 383 [M + H]$^+$ |
| 181 | 8-oxa-2-azaspiro[4.5]dec-2-yl(2-{[2-(pyrimidin-5-yl)ethyl]amino}pyrimidin-5-yl)methanone | 36 mg, 18%; $^1$H NMR (400 MHz, MeOD-$d_4$): δ 1.53-1.68 (m, 4H), 1.87-1.97 (m, 2H), 2.98 (t, 2H), 3.50 (d, 2H), 3.55-3.78 (m, 8H), 8.50 (s, 2H), 8.69 (s, 2H), 8.98 (s, 1H). LCMS: m/z = 369 [M + H]$^+$ |

All amines, or their common salts are commercially available with exception of:
$^a$2-(Pyrimidin-5-yl)propan-2-amine hydrochloride (Preparation 24)
$^b$(1R)-1-(Pyrazin-2-yl)ethanamine hydrochloride (Preparation 28)
$^c$(1S)-1-(Pyrazin-2-yl)ethanamine hydrochloride (Preparation 27)
$^d$1-(Pyrimidin-5-yl)ethanamine hydrochloride (Preparation 29)
$^e$1-(6-Methylpyridin-3-yl)ethanamine hydrochloride (Preparation 30)
$^f$1-(Pyrimidin-5-yl)cyclobutanamine hydrochloride (Preparation 25)

Example 182

8-oxa-2-azaspiro[4.5]dec-2-yl(2-{[2-(pyrazin-2-yl)propan-2-yl]amino}pyrimidin-5-yl)methanone

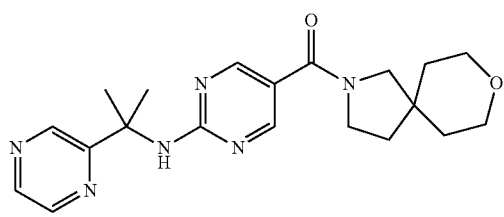 [SMILES: CC(C)(Nc1ncc(C(=O)N2CCC3(CCOCC3)C2)cn1)c1cnccn1]

To a mixture of 2-{[2-(pyrazin-2-yl)propan-2-yl]amino}pyrimidine-5-carboxylic acid, (Preparation 88, 571 mg, 2.20 mmol) and 8-oxa-2-azaspiro[4.5]decane (311 mg, 2.20 mmol) in THF (10 mL) was added DIPEA (1.73 g, 13.2 mmol) and T$_3$P (50% w in EtOAc, 2.8 g, 4.40 mmol) and the resulting mixture heated at 60° C. for 18 hrs. The mixture was cooled, partitioned between brine and EtOAc and the layers separated. The aqueous phase extracted with EtOAc and the combined extracts washed with brine, dried (Na$_2$SO$_4$) and concentrated under reduced pressure. The residue was purified by column chromatography on silica gel eluting with DCM:MeOH (90:10) to afford a tan foam which was further purified by column chromatography eluting with (EtOAc:MeCN). The residue was treated with Et$_2$O which was removed under reduced pressure to give the title compound as a white foam (319 mg, 38%). 1.42-1.62 (m, 4H), 1.77 (s, 6H), 1.78-1.84 (m, 2H), 3.38 (s, 2H), 3.46-3.68 (m, 6H), 6.66 (br s, 1H), 8.33 (br s, 2H), 8.38 (d, 1H), 8.46 (dd, 1H), 8.70 (s, 1H). LCMS: m/z=383 [M+H]$^+$

Example 188

8-oxa-2-azaspiro[4.5]dec-2-yl(2-{[1-(pyrimidin-5-yl)cyclopropyl]amino}pyrimidin-5-yl)methanone

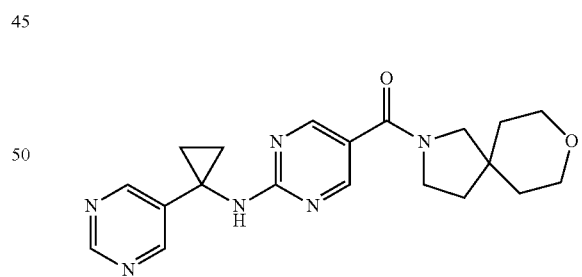

A suspension of 2-{[1-(Pyrimidin-5-yl)cyclopropyl]amino}pyrimidine-5-carboxylic acid (Preparation 5, 79.6 mg, 0.31 mmol), 8-oxa-2-azaspiro[4.5]decane hydrochloride (50.0 mg, 0.28 mmol), 2-chloro-1-methylpyridinium iodide (Mukaiyama reagent, CAS#14338-32-0, 108.0 mg, 0.42 mmol) and DIPEA (0.15 mL, 0.84 mmol) in THF (15 mL) was stirred at 65° C. for 18 hours. The reaction mixture was diluted with EtOAc/water (5:3, v/v, 80 mL), and the aqueous layer was extracted with EtOAc (50 mL*2). Combined organic layers were washed with brine (30 mL), dried over MgSO4, filtered and concentrated under reduced pressure to give a yellow oil. The crude product was purified by flash column (MeOH:CH₂Cl₂ from 0% to 10%, 12 g silica gel) to provide the title compound, 40 mg, 38%. ¹H NMR (400 MHz, MeOD-d₄): δ 1.40-1.70 (m, 8H), 1.87-1.98 (m, 2H), 3.52 (d, 2H), 3.57-3.80 (m, 6H), 8.58 (br s, 2H), 8.71 (d, 2H), 8.97 (s, 1H). LCMS m/z=381 [M+H]⁺

The following Examples 183-187 and 189-202 (Table 5) were prepared according to the general procedure outlined above for Example 182, using the appropriate carboxylic acid (Preparations 2, 5 and 6) and the appropriate amine. One skilled-in-the-art could also use any known peptidic coupling reagents and conditions.

TABLE 5

Data for Examples 183-187 and 189-202

| Example | Structure and Name | Yield; Data |
|---|---|---|
| 183 | 8-oxa-2-azaspiro[4.5]dec-2-yl(2-{[1-(pyrimidin-5-yl)ethyl]amino}pyrimidin-5-yl)methanone | 11 mg, 9%; ¹H NMR (400 MHz, CDCl₃): δ 1.45-1.70 (m, 7H), 1.81-1.93 (m, 2H), 3.35-3.80 (m, 8H), 5.15-5.26 (m, 1H), 5.70 (br s, 1H), 8.52 (s, 2H), 8.78 (s, 2H), 9.13 (s, 1H). LCMS m/z = 369 [M + H]⁺ |
| 184 | 7-oxa-2-azaspiro[3.5]non-2-yl(2-{[1-(pyrimidin-5-yl)ethyl]amino}pyrimidin-5-yl)methanone | 5 mg, 5%; ¹H NMR (400 MHz, CDCl₃): δ 1.66 (d, 3H), 1.72-1.87 (m, 4H), 3.55-3.68 (m, 4H), 3.85-4.10 (m, 4H), 5.16-5.26 (m, 1H), 5.92 (d, 1H), 8.59 (br s, 2H), 8.78 (s, 2H), 9.12 (s, 1H). LCMS m/z = 355 [M + H]⁺ |
| 185 | 8-oxa-2-azaspiro[4.5]dec-2-yl{2-[(pyrimidin-5-ylmethyl)amino]pyrimidin-5-yl}methanone | 14 mg, 9%; ¹H NMR (400 MHz, CDCl₃): δ 1.55-1.65 (m, 4H), 1.83-1.96 (m, 2H), 3.40-3.80 (m, 8H), 4.70 (d, 2H), 5.88 (br s, 1H), 8.57 (s, 2H), 8.78 (br s, 2H), 9.15 (s, 1H). LCMS m/z = 355 [M + H]⁺ |
| 186 | 7-oxa-2-azaspiro[3.5]non-2-yl{2-[(pyrimidin-5-ylmethyl)amino]pyrimidin-5-yl}methanone | 12 mg, 10%; ¹H NMR (400 MHz, CDCl₃): δ 1.82 (s, 4H), 3.64 (s, 4H), 3.85-4.10 (m, 4H), 4.70 (d, 2H), 5.90 (br s, 1H), 8.65 (s, 2H), 8.77 (br s, 2H), 9.15 (s, 1H). LCMS m/z = 341 [M + H]⁺ |

TABLE 5-continued

Data for Examples 183-187 and 189-202

| Example | Structure and Name | Yield; Data |
|---|---|---|
| 187 | 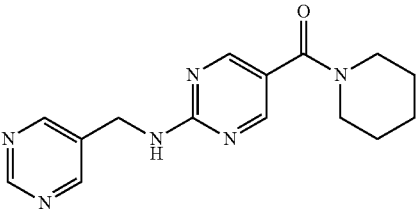<br>piperidin-1-yl{2-[(pyrimidin-5-ylmethyl)amino]pyrimidin-5-yl}methanone | 25 mg, 22%; $^1$H NMR (400 MHz, MeOD-d$_4$): δ 1.55-1.80 (m, 6H), 3.60 (br s, 4H), 4.68 (s, 2H), 8.42 (s, 2H), 8.83 (s, 2H), 9.06 (s, 1H). LCMS m/z = 299 [M + H]$^+$ |
| 189 | 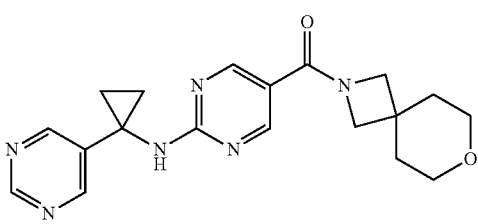<br>7-oxa-2-azaspiro[3.5]non-2-yl(2-{[1-(pyrimidin-5-yl)cyclopropyl]amino}pyrimidin-5-yl)methanone | 16 mg, 12%; $^1$H NMR (400 MHz, MeOD-d$_4$): δ 1.40-1.54 (m, 4H), 1.77-1.86 (m, 4H), 3.56-3.72 (m, 4H), 3.90 (s, 2H), 4.20 (s, 2H), 8.65 (brs, 2H), 8.76 (s, 2H), 8.91 (s, 1H). LCMS m/z = 367 [M + H]$^+$ |
| 190 | 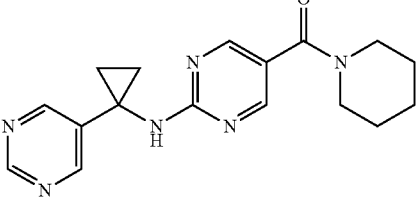<br>piperidin-1-yl(2-{[1-(pyrimidin-5-yl)cyclopropyl]amino}pyrimidin-5-yl)methanone | 233 mg, 53%; $^1$H NMR (400 MHz, MeOD-d$_4$): δ 1.35-1.53 (m, 4H), 1.57-1.78 (m, 6H), 3.59 (br s, 4H), 8.41 (br s, 2H), 8.71 (s, 2H), 8.97 (s, 1H). LCMS m/z = 347 [M + Na]$^+$ |
| 191 | 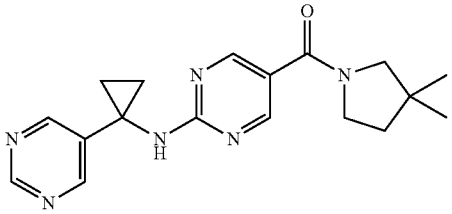<br>(3,3-dimethylpyrrolidin-1-yl)(2-{[1-(pyrimidin-5-yl)cyclopropyl]amino}pyrimidin-5-yl)methanone | 26 mg, 21%; $^1$H NMR (400 MHz, DMSO-d$_6$): δ 0.99 (s, 3H), 1.08 (s, 3H), 1.27-1.33 (m, 2H), 1.43-1.49 (m, 2H), 1.61-1.68 (m, 2H), 3.19 (s, 1H), 3.30 (s, 1H), 3.51 (dd, 1H), 3.62 (dd, 1H), 8.47-8.62 (m, 5H), 8.98 (s, 1H). LCMS m/z = 339 [M + H]$^+$ |
| 192 | 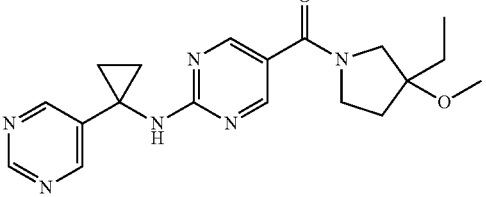<br>(3-ethyl-3-methoxypyrrolidin-1-yl)(2-{[1-(pyrimidin-5-yl)cyclopropyl]amino}pyrimidin-5-yl)methanone | 15 mg, 11%; $^1$H NMR (400 MHz, MeOD-d$_4$): δ 0.85-1.07 (m, 3H), 1.37-1.50 (m, 4H), 1.62-1.87 (m, 3H), 2.13-2.23 (m, 1H), 3.13 (s, 3H), 3.32-3.40 (m, 1H), 3.52-3.78 (m, 3H), 8.55 (br s, 2H), 8.69 (s, 2H), 8.95 (s, 1H). LCMS m/z = 369 [M + H]$^+$ |

TABLE 5-continued

Data for Examples 183-187 and 189-202

| Example | Structure and Name | Yield; Data |
|---|---|---|
| 193 | 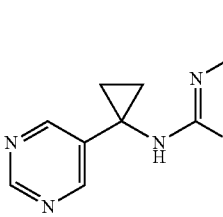<br>(2-{[1-(pyrimidin-5-yl)cyclopropyl]amino}pyrimidin-5-yl)[3-(trifluoromethyl)pyrrolidin-1-yl]methanone | First eluting enantiomer: 29 mg, 39% (after SFC Method CP-D); RT = 1.531 mins (Method CA-D); $^1$H NMR (400 MHz, DMSO-d$_6$): δ 1.31-1.34 (m, 2H), 1.46-1.49 (m, 2H), 1.95-2.05 (m, 1H), 2.12-2.22 (m, 1H), 3.25-3.35 (m, 1H), 3.52-3.95 (m, 4H), 8.55 (br s, 2H), 8.59 (s, 2H), 8.65 (s, 1H), 8.99 (s, 1H). LCMS m/z = 379 [M + H]$^+$ |
| 194 | 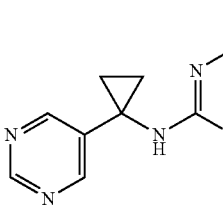<br>(2-{[1-(pyrimidin-5-yl)cyclopropyl]amino}pyrimidin-5-yl)[3-(trifluoromethyl)pyrrolidin-1-yl]methanone | Second eluting enantiomer: 31 mg, 42% (after SFC Method CP-D); RT = 2.217 mins (Method CA-D); $^1$H NMR (400 MHz, DMSO-d$_6$): δ 1.31-1.34 (m, 2H), 1.46-1.49 (m, 2H), 1.94-2.04 (m, 1H), 2.12-2.22 (m, 1H), 3.22-3.35 (m, 1H), 3.55-3.91 (m, 4H), 8.55 (br s, 2H), 8.60 (s, 2H), 8.65 (s, 1H), 8.99 (s, 1H). LCMS m/z = 379 [M + H]$^+$ |
| 195 | 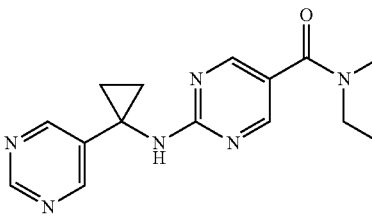<br>1-[(2-{[1-(pyrimidin-5-yl)cyclopropyl]amino}pyrimidin-5-yl)carbonyl]piperidine-3-carbonitrile | 81 mg, 50%; $^1$H NMR (400 MHz, MeOD-d$_4$): δ 1.40-1.53 (m, 4H), 1.65-1.75 (m, 1H), 1.78-1.93 (m, 1H), 1.96-2.11 (m, 2H), 3.02-3.10 (m, 1H), 3.36-3.48 (m, 1H), 3.65-3.99 (m, 3H), 8.45 (br s, 2H), 8.72 (s, 2H), 8.97 (s, 1H). LCMS: m/z = 350 [M + H]$^+$ |
| 196 | 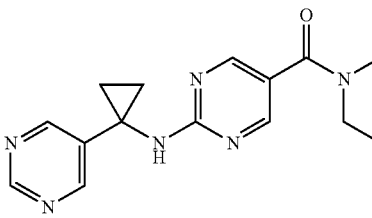<br>1-[((2-{[1-(Pyrimidin-5-yl)cyclopropyl]amino}pyrimidin-5-yl)carbonyl]piperidine-3-carbonitrile | First eluting enantiomer: 15 mg, 20% (after SFC on Example 195, Method CP-E); RT = 3.053 mins (Method CA-E); $^1$H NMR (400 MHz, MeOD-d$_4$): δ 1.42-1.52 (m, 4H), 1.65-1.75 (m, 1H), 1.78-1.91 (m, 1H), 1.98-2.09 (m, 2H), 3.05 (m, 1H), 3.36-3.47 (m, 1H), 3.68-3.97 (m, 3H), 8.45 (br s, 2H), 8.71 (s, 2H), 8.97 (s, 1H). LCMS m/z = 372 [M + Na]$^+$ |

TABLE 5-continued

Data for Examples 183-187 and 189-202

| Example | Structure and Name | Yield; Data |
|---|---|---|
| 197 | 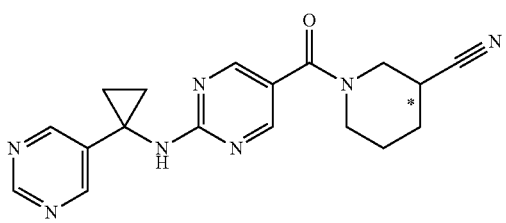<br>1-[(2-{[1-(Pyrimidin-5-yl)cyclopropyl]amino}pyrimidin-5-yl)carbonyl]piperidine-3-carbonitrile | Second eluting enantiomer: 13 mg, 17% (after SFC on Example 195, Method CP-E); RT = 3.262 mins (Method CA-E); $^1$H NMR (400 MHz, MeOD-d$_4$) : δ 1.41-1.53 (m, 4H), 1.65-1.75 (m, 1H), 1.78-1.92 (m, 1H), 1.99-2.09 (m, 2H), 3.05 (m, 1H), 3.36-3.47 (m, 1H), 3.68-3.99 (m, 3H), 8.45 (br s, 2H), 8.70 (s, 2H), 8.97 (s, 1H). LCMS m/z = 350 [M + H]$^+$ |
| 198 | 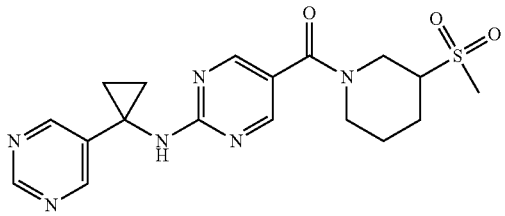<br>[3-(methylsulfonyl)piperidin-1-yl](2-{[1-(pyrimidin-5-yl)cyclopropyl]amino}pyrimidin-5-yl)methanone | 112 mg, 56%; $^1$H NMR (400 MHz, MeOH-d$_4$): δ 1.40-1.54 (m, 4H), 1.56-1.70 (m, 1H), 1.90-2.05 (m, 2H), 2.25-2.35 (m, 1H), 2.99 (s, 3H), 3.20-3.53 (m, 3H), 3.91 (br s, 1H), 4.54 (br s, 1H), 8.45 (br s, 2H), 8.71 (s, 2H), 8.97 (s, 1H). LCMS m/z = 403 [M + H]$^+$ |
| 199 | 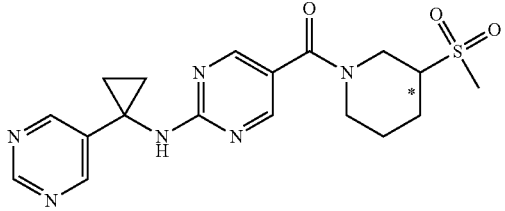<br>[3-(Methylsulfonyl)piperidin-1-yl](2-{[1-(pyrimidin-5-yl)cyclopropyl]amino}pyrimidin-5-yl)methanone | First eluting enantiomer: 35 mg, 25% (after SFC on 140 mg of Example 198, Method CP-F); RT = 3.731 mins (Method CA-D); $^1$H NMR (400 MHz, MeOH-d$_4$): δ 1.40-1.54 (m, 4H), 1.56-1.68 (m, 1H), 1.92-2.04 (m, 2H), 2.25-2.33 (m, 1H), 2.99 (s, 3H), 3.20-3.53 (m, 3H), 3.90 (br s, 1H), 4.54 (br s, 1H), 8.45 (br s, 2H), 8.71 (s, 2H), 8.97 (s, 1H). LCMS m/z = 425 [M + Na]$^+$ |
| 200 | 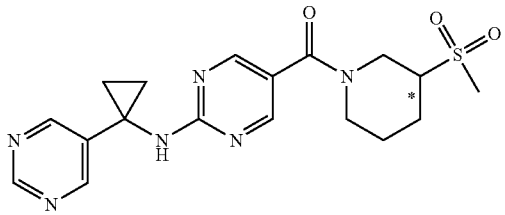<br>[3-(Methylsulfonyl)piperidin-1-yl](2-{[1-(pyrimidin-5-yl)cyclopropyl]amino}pyrimidin-5-yl)methanone | Second eluting enantiomer: 55 mg, 39% (after SFC on 140 mg of Example 198, Method CP-F); RT = 4.711 mins (Method CA-D); $^1$H NMR (400 MHz, MeOH-d$_4$): δ 1.40-1.54 (m, 4H), 1.56-1.70 (m, 1H), 1.91-2.05 (m, 2H), 2.25-2.35 (m, 1H), 2.99 (s, 3H), 3.20-3.54 (m, 3H), 3.90 (br s, 1H), 4.54 (br s, 1H), 8.45 (br s, 2H), 8.71 (s, 2H), 8.98 (s, 1H). LCMS m/z = 425 [M + Na]$^+$ |

TABLE 5-continued

Data for Examples 183-187 and 189-202

| Example | Structure and Name | Yield; Data |
|---|---|---|
| 201[a] | 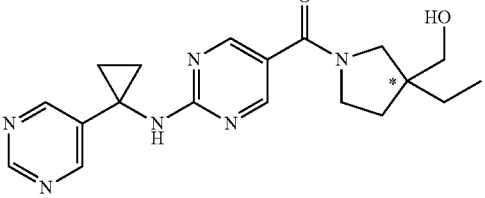<br>[3-Ethyl-3-(hydroxymethyl)pyrrolidin-1-yl](2-{[1-(pyrimidin-5-yl)cyclopropyl]amino}pyrimidin-5-yl)methanone | First eluting enantiomer: 21 mg, 7% (after SFC Method CP-G); RT = 4.818 mins (Method CA-F); $^1$H NMR (400 MHz, MeOH-d$_4$): δ 0.85-0.98 (m, 3H), 1.17 (d, 2H), 1.35-1.65 (m, 5H), 1.73-1.99 (m, 2H), 3.41-3.73 (m, 5H), 8.56 (br s, 2H), 8.71 (s, 2H), 8.97 (s, 1H). LCMS m/z = 369 [M + H]$^+$ |
| 202[a] | 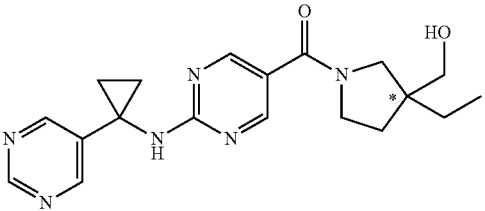<br>[3-Ethyl-3-(hydroxymethyl)pyrrolidin-1-yl](2-{[1-(pyrimidin-5-yl)cyclopropyl]amino}pyrimidin-5-yl)methanone | Second eluting enantiomer: 21 mg, 7% (after SFC Method CP-G); RT = 5.098 mins (Method CA-F); $^1$H NMR (400 MHz, MeOH-d$_4$): δ 0.86-0.98 (m, 3H), 1.17 (d, 2H), 1.37-1.66 (m, 5H), 1.72-1.97 (m, 2H), 3.41-3.74 (m, 5H), 8.56 (br s, 2H), 8.71 (s, 2H), 8.97 (s, 1H). LCMS m/z = 369 [M + H]$^+$ |

All amines, or their common salts are commercially available with the exception of:
[a]3-ethylpyrrolidin-3-yl)methanol (Preparation 66)

Example 203

8-oxa-2-azaspiro[4.5]dec-2-yl[2-(pyrimidin-5-ylmethoxy)pyrimidin-5-yl]methanone

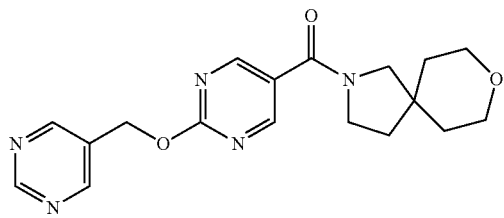 [SMILES: O=C(c1cnc(OCc2cncnc2)nc1)N1CCC2(CCOCC2)C1]

To a solution of pyrimidin-5-ylmethanol (70.4 mg, 0.639 mmol) and LiHMDS (1.33 mL, 1.33 mmol) in DMF (5 mL) at 0° C. was added (2-chloropyrimidin-5-yl)(8-oxa-2-azaspiro[4.5]dec-2-yl)methanone (Preparation 22, 150 mg, 0.532 mmol) and the resulting mixture stirred at 0° C. for 2 hr. The mixture was purified directly by HPLC using a DuraShell 150*25 mm*5 um column, eluting with 5-35% water (0.05% ammonium hydroxide):MeCN over 10 mins and a flow rate of 30 mL/min to afford the title compound as a white solid, 10 mg, 5%. $^1$H NMR (400 MHz, DMSO-d$_6$): δ 1.42-1.48 (m, 2H), 1.54-1.59 (m, 2H), 1.78-1.85 (m, 2H), 3.40-3.48 (m, 2H), 3.50-3.65 (m, 6H), 5.52 (s, 2H), 8.85 (d, 1H), 8.97 (d, 1H), 9.19 (s, 1H). LCMS m/z=356 [M+H]$^+$ Example 204

N-[5-(8-oxa-2-azaspiro[4.5]dec-2-ylcarbonyl)pyrimidin-2-yl]pyrazine-2-carboxamide

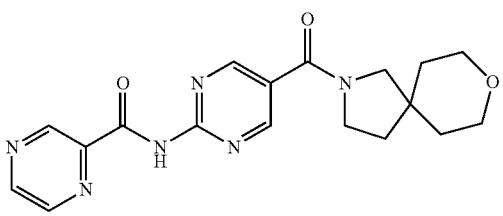 [SMILES: O=C(Nc1ncc(C(=O)N2CCC3(CCOCC3)C2)cn1)c1cnccn1]

To a −15° C. solution of pyrazine-2-carboxylic acid (CAS#98-97-5, 47.3 mg, 0.381 mmol) and (2-aminopyrimidin-5-yl)(8-oxa-2-azaspiro[4.5]dec-2-yl)methanone (Preparation 89, 100 mg, 0.381 mmol) in pyridine (0.5 mL), was added phosphoryl trichloride (70.1 mg, 0.457 mmol) dropwise. The cold bath was removed and the resulting yellow mixture was stirred at room temperature for 1 hour. The reaction was quenched with water (5 mL) and then extracted with EtOAc (5 mL) twice. The combined organic extracts were washed with 0.5N HCl (5 mL), sat.NaHCO$_3$(5 mL) and brine (5 mL) in turns, dried over Na$_2$SO$_4$ and concentrated to give crude product. Purification by preparative HPLC (Agela Durashell C18 150*25 5 μm, using water (0.225% FA)-MeCN, from 10% to 30% over 11 min, at a flow rate of 35 mL/min) followed by lyophilisation gave the title compound, 48 mg, 34%. $^1$H NMR (400 MHz, DMSO-d6): δ 1.41-1.64 (m, 4H), 1.82 (dt, 2H), 3.41 (s, 1H), 3.45-3.67 (m, 7H), 8.81-8.85 (m, 1H), 8.93 (s, 1H), 8.95 (s, 1H), 8.97 (t, 1H), 9.31 (dd, 1H), 10.83 (br s, 1H). LCMS m/z=369 [M+H]+

Example 205

N-[5-(8-oxa-2-azaspiro[4.5]dec-2-ylcarbonyl)pyrimidin-2-yl]pyrimidine-5-carboxamide

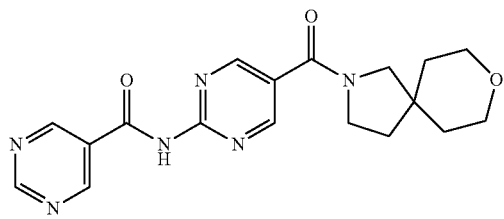 [SMILES: O=C(Nc1ncc(C(=O)N2CCC3(CCOCC3)C2)cn1)c1cncnc1]

To a solution of pyrimidine-5-carboxylic acid (CAS#4595-61-3, 400 mg, 3.22 mmol) in dichloromethane (30 mL) was added dropwise a solution of Ghosez reagent (861 mg, 6.45 mmol) in dichloromethane (10 mL). The solution was stirred at 20° C. for 30 minutes, then cooled to −5° C. in an ice-salt bath. A solution of (2-aminopyrimidin-5-yl)(8-oxa-2-azaspiro[4.5]dec-2-yl)methanone (Preparation 89, 676 mg, 2.58 mmol) and Et$_3$N (978 mg, 9.67 mmol) in dichloromethane (10 mL) was added slowly to the reaction mixture. The reaction was stirred at 20° C. for 2.5 hrs then quenched by NaHCO$_3$ aqueous solution. The layers were separated and the organic layer was evaporated to dryness. Purification by preparative HPLC (Daiso 150*25 5 μm, water (10 mM NH$_4$HCO$_3$)-MeCN, from 0% to 30% over 10 min, at a flow rate of 30 mL/min) gave the title product 7 mg, 1%. $^1$H NMR (400 MHz, CDCl$_3$): δ 1.22-1.71 (m, 4H), 1.84-2.00 (m, 2H), 3.39-3.82 (m, 8H), 5.25-5.37 (m, 1H), 8.57 (s, 1H), 8.89 (br. s., 2H), 9.27 (s, 2H), 9.43 (s, 1H). LCMS m/z=369 [M+H]+

Summary of Biological Assays and Data

Human Vanin-1 Enzyme Assay 1.

The in vitro assay measures enzymatic cleavage of the fluorescently-labeled vanin substrate, pantetheine 7-amino-4-trifluoromethylcoumarin, by human vanin-1.

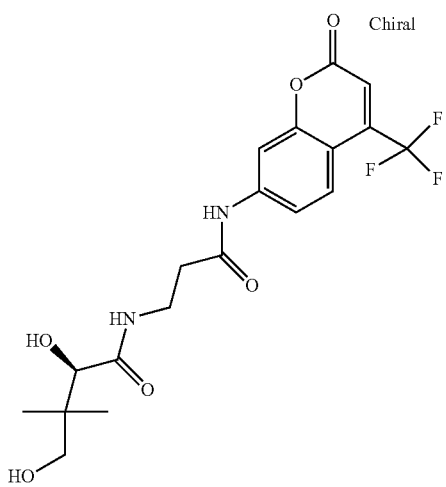 [SMILES: CC(C)(CO)[C@@H](O)C(=O)NCCC(=O)Nc1ccc2c(C(F)(F)F)cc(=O)oc2c1]

The vanin-1 protein was prepared in-house from a construct expressing the extracellular domain of human vanin-1 (GenBank ID NM_004666) preceded N-terminally by the honey bee melittin signal peptide, a GSG linker sequence, a His6× tag and a FLAG tag. The secreted, soluble enzyme was purified from the conditioned medium from a CHO cell line stably expressing the resulting protein. Enzyme purification was performed through sequential Ni NTA and size-exclusion chromatography steps.

The test inhibitors were solubilized in DMSO to a stock concentration of 30 mM. On the day of the assay, dose response plates were prepared by diluting the inhibitors in DMSO at compound concentration 200-fold the final in-assay concentration. Intermediate concentrations were prepared by diluting in DMSO in a four-fold series for a total of 11 data points.

To prepare a working solution of human vanin-1, the enzyme was diluted to 33.3 pM in the assay buffer consisting of 50 mM Tris-HCl pH=8.0, 50 mM KCl, 0.005% Brij-35 and 1.6 mM cysteamine. To begin the assay 100 nL was transferred from the compound plate to the assay plate. Next, 15 μL of the vanin-1 working solution were transferred to the assay plate. The inhibitor and enzyme were incubated at room temperature for 30 minutes. The enzyme reaction was then initiated by the addition of 5 μL of 200 μM pantetheine 7-amino-4-trifluoromethylcoumarin prepared in assay buffer. The final concentrations in the assay were 25 pM human vanin-1 and 50 uM substrate. The final concentration of DMSO was 0.5%. The assay plates were incubated for 60 minutes and before they were read on a Perkin Elmer EnVision Model 2103 using a 405 nm excitation wavelength and a 510 nm emission wavelength for detection.

Vanin-1 in Human Plasma Assay.

The in vitro assay measures enzymatic cleavage of the fluorescently-labeled vanin substrate, pantetheine 7-amino-4-trifluoromethylcoumarin, by human vanin-1 present in human plasma.

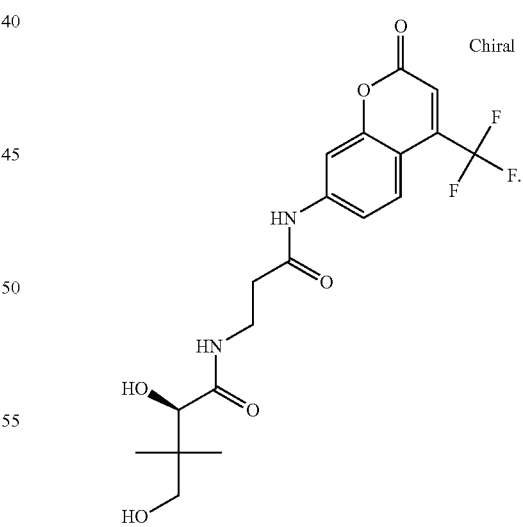

Human plasma was prepared from whole blood drawn from healthy donors, collected in tubes containing sodium heparin. The plasma fractions were separated from the whole blood by centrifugation for 10 minutes at 2000×g and pooled. The concentration of vanin-1 in the pooled plasma was determined by measuring the rate of enzymatic hydrolysis of the fluorescently-labeled substrate by the vanin-1 in the plasma sample and comparing the observed hydrolysis rate to a recombinant human vanin-1 standard.

The test inhibitors were solubilized in DMSO to a stock concentration of 30 mM. On the day of the assay, dose response plates were prepared by diluting the inhibitors in DMSO to a compound concentration 200-fold the final in-assay concentration. Concentration series were prepared by serially diluting in 100% DMSO in a three-fold series. Intermediate compound plates containing compound in 2% DMSO were then created by diluting the compounds 50-fold in assay buffer consisting of 50 mM Tris-HCl pH=8.0, 50 mM KCl, 0.005% Brij-35. From this intermediate compound plate, 10 μL were transferred to the assay plate and mixed with 20 uL of the pooled human plasma. The inhibitor and enzyme were co-incubated at room temperature for 30 minutes. The enzyme reaction was initiated by the addition of 10 μL of 200 uM pantetheine 7-amino-4-trifluoromethylcoumarin prepared in assay buffer. The final concentrations in the assay were 50% plasma, and 50 uM substrate. The final concentration of DMSO was 0.5%. Datapoints were measured over time using a Tecan Safire 2 platereader at 405 nm excitation wavelength and a 510 nm emission wavelength for detection.

The biological activity of certain compounds of the invention was tested in one or more of the assays described above. The results are shown in Table 6.

TABLE 6

| Example Number | Human Vanin-1 $IC_{50}$ (nM) | Vanin-1 Human Plasma $IC_{50}$ (nM) |
|---|---|---|
| 1 | 1.312 | |
| 2 | 1.332 | |
| 3 | 1.694 | |
| 4 | 8.578 | |
| 5 | 16.049 | |
| 6 | 17.942 | |
| 7 | 17.946 | |
| 8 | 37.101 | |
| 9 | 48.089 | |
| 10 | 75.872 | |
| 11 | 81.672 | |
| 12 | 94.108 | |
| 13 | 101.188 | |
| 14 | 155.857 | |
| 15 | 219.545 | |
| 16 | 323.011 | |
| 17 | 327.776 | |
| 18 | 384.808 | |
| 19 | 406.956 | |
| 20 | 452.621 | |
| 21 | 528.418 | |
| 22 | 559.349 | |
| 23 | 612.584 | |
| 24 | 749.160 | |
| 25 | 1039.731 | |
| 26 | 1226.543 | |
| 27 | 1372.853 | |
| 28 | 1547.699 | |
| 29 | 1916.482 | |
| 30 | 2170.505 | |
| 31 | 3086.957 | |
| 32 | 20000.000 | |
| 33 | 108.335 | |
| 34 | 47.165 | |
| 35 | 5.424 | |
| 36 | 1000.997 | |
| 37 | 0.504 | |
| 38 | 62.610 | |
| 39 | 9.438 | |
| 40 | 26.921 | |
| 41 | 45.005 | |
| 42 | 35.137 | |
| 43 | 1.353 | |
| 44 | 2269.128 | |
| 45 | 1848.644 | |
| 46 | 6.285 | |
| 47 | 29.564 | |
| 48 | 20000.000 | |
| 49 | 7.502 | |
| 50 | 19.855 | |
| 51 | 97.512 | |
| 52 | 60.278 | |
| 53 | 12.158 | |
| 54 | 0.283 | |
| 55 | 2519.219 | |
| 56 | 24.949 | |
| 57 | 610.814 | |
| 58 | 116.254 | |
| 59 | 47.374 | 49.159 |
| 60 | 2846.082 | |
| 61 | 2.507 | |
| 62 | 3.921 | |
| 63 | 420.940 | |
| 64 | 100.438 | |
| 65 | 1.822 | |
| 66 | 230.557 | |
| 67 | 4242.905 | |
| 68 | 8.135 | |
| 69 | 1.852 | |
| 70 | 175.384 | 205.142 |
| 71 | 5.411 | |
| 72 | 147.586 | |
| 73 | 829.361 | |
| 74 | 3.616 | |
| 75 | 1075.367 | |
| 76 | 122.487 | |
| 77 | 31.293 | |
| 78 | 1598.104 | |
| 79 | 21.320 | |
| 80 | 545.210 | |
| 81 | 101.565 | |
| 82 | 146.851 | |
| 83 | 55.133 | |
| 84 | 75.401 | |
| 85 | 167.434 | |
| 86 | 24.159 | |
| 87 | 79.792 | 68.047 |
| 88 | 28.653 | |
| 89 | 34.957 | |
| 90 | 347.876 | |
| 91 | 315.544 | |
| 92 | 50.914 | |
| 93 | 40.492 | |
| 94 | 20.448 | |
| 95 | 30.075 | |
| 96 | 10.931 | 9.855 |
| 97 | 344.799 | |
| 98 | 5.657 | |
| 99 | 590.914 | |
| 100 | 135.449 | |
| 101 | 1355.166 | |
| 102 | 40.820 | |
| 103 | 590.277 | |
| 104 | 2.446 | |
| 105 | 35.950 | |
| 106 | 30.756 | |
| 107 | 38.597 | |
| 108 | 387.300 | 451.801 |
| 109 | 249.066 | |
| 110 | 171.121 | |
| 111 | 3585.665 | |
| 112 | >18897.44 | |
| 113 | 508.231 | |
| 114 | 20.878 | |
| 115 | 16011.757 | |
| 116 | 112.894 | |

TABLE 6-continued

| Example Number | Human Vanin-1 IC$_{50}$ (nM) | Vanin-1 Human Plasma IC$_{50}$ (nM) |
|---|---|---|
| 117 | 5.109 | |
| 118 | 4.642 | |
| 119 | 1369.249 | |
| 120 | 84.111 | |
| 121 | 3.948 | |
| 122 | 43.903 | |
| 123 | 11387.672 | |
| 124 | 4616.109 | |
| 125 | 3.038 | |
| 126 | 604.220 | |
| 127 | 586.544 | |
| 128 | 383.800 | |
| 129 | 65.881 | |
| 130 | <0.041 | 0.743 |
| 131 | <0.094 | 0.838 |
| 132 | 0.349 | |
| 133 | 0.430 | 0.524 |
| 134 | 0.504 | |
| 135 | 3.384 | 3.705 |
| 136 | 2330.344 | |
| 137 | 5.236 | 5.017 |
| 138 | 0.043 | |
| 139 | >17588.525 | |
| 140 | 0.283 | 0.950 |
| 141 | 87.341 | |
| 142 | 7.656 | 10.147 |
| 143 | 0.082 | 1.219 |
| 144 | 0.743 | |
| 145 | 0.242 | 1.222 |
| 146 | 31.264 | 72.617 |
| 147 | 0.650 | 1.887 |
| 148 | 54.546 | |
| 149 | 0.677 | 1.297 |
| 150 | 27.832 | 35.632 |
| 151 | 0.955 | |
| 152 | 91.346 | |
| 153 | 4.291 | |
| 154 | 336.856 | |
| 155 | 4.394 | 27.468 |
| 156 | 838.451 | |
| 157 | 0.875 | 12.945 |
| 158 | 1.112 | 2.031 |
| 159 | 1.291 | |
| 160 | 2.837 | |
| 161 | 8.057 | |
| 162 | 0.629 | 2.967 |
| 163 | 1.770 | |
| 164 | 27.300 | |
| 165 | 26.305 | |
| 166 | 32.596 | 39.069 |
| 167 | 57.694 | |
| 168 | 191.839 | |
| 169 | 157.567 | |
| 170 | 6.330 | 16.459 |
| 171 | 7.333 | |
| 172 | 4.528 | 17.434 |
| 173 | 0.116 | 1.608 |
| 174 | 0.293 | 0.905 |
| 175 | 0.240 | |
| 176 | 0.911 | |
| 177 | 0.551 | |
| 178 | 2.184 | |
| 179 | 7.330 | 14.408 |
| 180 | 0.196 | |
| 181 | 200.058 | |
| 182 | 0.062 | 1.085 |
| 183 | 0.745 | |
| 184 | 1.446 | 2.210 |
| 185 | 7.707 | |
| 186 | 5.482 | 4.627 |
| 187 | 83.711 | |
| 188 | 0.277 | 1.167 |
| 189 | 0.867 | |
| 190 | 12.516 | 12.418 |
| 191 | 1.571 | |

TABLE 6-continued

| Example Number | Human Vanin-1 IC$_{50}$ (nM) | Vanin-1 Human Plasma IC$_{50}$ (nM) |
|---|---|---|
| 192 | 2.209 | |
| 193 | 7.117 | 5.392 |
| 194 | 20.155 | |
| 195 | 10.650 | |
| 196 | 1176.654 | >792.957 |
| 197 | 5.221 | |
| 198 | 20.487 | |
| 199 | 1175.069 | |
| 200 | 10.580 | 32.612 |
| 201 | 0.582 | |
| 202 | 14.259 | |
| 203 | 1087.464 | |
| 204 | 5156.678 | |
| 205 | 8801.420 | |

Variations, modifications, and other implementations of what is described herein will occur to those skilled in the art without departing from the spirit and the essential characteristics of the present teachings. Accordingly, the scope of the present teachings is to be defined not by the preceding illustrative description but instead by the following claims, and all changes that come within the meaning and range of equivalency of the claims are intended to be embraced therein.

Each of the printed publications, including but not limited to patents, patent applications, books, technical papers, trade publications and journal articles described or referenced in this specification are herein incorporated by reference in their entirety and for all purposes.

We claim:
1. A compound of Formula I,

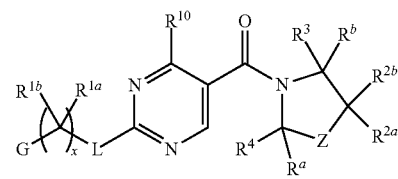

wherein
G is a 6-membered heteroaryl, with one, two or three N, wherein the heteroaryl is optionally substituted with one, two or three substituents selected from the group consisting of $C_1$-$C_4$alkyl, —NR$^{8a}$C(O)R$^{8b}$, —NR$^{8a}$SO$_2$R$^{8b}$, (CR$^{6a}$R$^{6b}$)$_t$C(O)N(R$^{8a}$)$_2$, —C(O)OH, halogen, cyano, —N(R$^{8a}$)$_2$, —(CR$^{6a}$R$^{6b}$)$_t$SO$_2$R$^{8b}$, —(CR$^{6a}$R$^{6b}$)$_t$SO$_2$N(R$^{8a}$)$_2$, $C_1$-$C_4$alkoxy, OH, S($C_1$-$C_3$alkyl) and $C_3$-$C_5$cycloalkyl, wherein the alkyl, cycloalkyl and alkoxy are optionally substituted with one, two or three halogen, OH, OCH$_3$, or $C_3$-$C_5$cycloalkyl;
L is NH or O;
Z is a bond; —(CR$^{5a}$R$^{5b}$)$_q$; —CH$_2$(CR$^{5a}$R$^{5b}$)$_m$—; or —(CR$^{5a}$R$^{5b}$)$_m$—W—(CR$^{5a}$R$^{5b}$)$_n$—, wherein W is S, O or NR$^7$;
R$^a$, R$^b$, and R$^{1a}$ are each independently hydrogen or $C_1$-$C_4$alkyl, wherein the alkyl is optionally substituted with one, two or three halogen, OH, cyano, —S($C_1$-$C_3$alkyl) or $C_1$-$C_4$alkoxy, optionally substituted with one, two or three fluoro;

$R^{1b}$ is $C_1$-$C_4$alkyl, wherein the alkyl is optionally substituted with one, two or three halogen, OH, cyano, —S($C_1$-$C_3$alkyl) or $C_1$-$C_4$alkoxy, optionally substituted with one, two or three fluoro;

or $R^{1a}$ and $R^{1b}$, together with the carbon to which they are bonded, form an oxo, $C_3$-$C_5$cycloalkyl, -(4- to 5-membered heterocycloalkyl) wherein said cycloalkyl or heterocycloalkyl are optionally substituted with one, two, three or four halogen, OH, $C_1$-$C_4$alkyl, —S($C_1$-$C_3$alkyl) $C_1$-$C_4$alkoxy or cyano;

and the heteroatom is selected from the group consisting of one or two N, S and O;

$R^{2a}$ and $R^{2b}$ are each independently hydrogen, —($CR^{6a}R^{6b}$)$_t$SO$_2$R$^{8b}$, OH, halogen, —($CR^{6a}R^{6b}$)$_t$C(O)N($R^{8a}$)$_2$, —NR$^{8a}$C(O)R$^{8b}$, —NR$^{8a}$C(O)N($R^{8a}$)$_2$, —SO$_2$N($R^{8a}$)$_2$, $C_1$-$C_4$alkyl, $C_1$-$C_4$alkoxy, S($C_1$-$C_3$alkyl), —($CR^{6a}R^{6b}$)$_t$—($C_3$-$C_6$cycloalkyl), cyano, —($CR^{6a}R^{6b}$)$_n$-(5- to 6-membered heterocycloalkyl) or —($CR^{6a}R^{6b}$)$_n$-(5- to 6-membered heteroaryl), wherein said heteroatoms of said heteroalkyl and heteroaryl are selected from the group consisting of one, two or three N, O and S; wherein said alkyl, cycloalkyl, heterocycloakyl and heteroaryl are optionally substituted with one, two, three or four $R^9$; or $R^{2a}$ and $R^{2b}$ together with the carbon to which they are bonded form a $C_3$-$C_9$cycloalkyl or a -(4- to 11-membered heterocycloalkyl), having one to three heteroatoms selected from N, O or S; wherein the cycloalkyl and heterocycloalkyl are optionally substituted with one, two or three $C_1$-$C_4$alkyl, S($C_1$-$C_3$alkyl), OH, halogen, oxo, —C(O)NH$_2$, —C(O)NHCH$_3$, —C(O)N(CH$_3$)$_2$, $C_3$-$C_5$cycloalkyl or $C_1$-$C_4$alkoxy; or if substitution is at a N atom, then such N atom is substituted with $R^7$; or $R^{2a}$ or $R^{2b}$, and one of $R^{5a}$ or $R^{5b}$, together with the respective carbons to which they are bonded, form a $C_3$-$C_{12}$cycloalkyl, $C_6$-$C_{10}$aryl, -(5- to 6-membered heteroaryl) or a -(4- to 12-membered heterocycloalkyl), wherein said heteroaryl or heterocycloalkyl is optionally substituted with one, two, three or four $R^9$; or if substitution is at a N atom, then such N atom is substituted with $R^7$; or $R^{2a}$ or $R^{2b}$, and $R^7$, together with the respective atoms to which they are bonded form a -(4- to 12-membered heterocycloalkyl) or a -(5- to 6-membered heteroaryl), wherein said heterocycloalkyl or heteroaryl have one, two to three heteroatoms selected from N, O or S, wherein said heterocycloalkyl and heteroaryl are optionally substituted with one, two, three or four $R^9$; or if substitution is at a N atom, then such N atom is substituted with $R^7$;

$R^3$ is hydrogen, —($CR^{6a}R^{6b}$)$_t$C(O)NH$_2$, or $C_1$-$C_4$alkyl, wherein said alkyl is optionally substituted with one, two, three or four $R^9$; or $R^3$ and $R^b$, together with the carbon to which they are attached, form an oxo;

$R^4$ is hydrogen, —($CR^{6a}R^{6b}$)$_t$C(O)NH$_2$, or $C_1$-$C_4$alkyl, wherein said alkyl is optionally substituted with one, two, three or four $R^9$; or $R^3$ and $R^4$ taken together with the respective carbons to which they are bonded form a -(4- to 11-membered heterocycloalkyl), having one to two heteroatoms selected from N, O or S, wherein the heterocycloalkyl are optionally substituted with one, two, three or four $R^9$; or if substitution is at a N atom, then such N atom is substituted with $R^7$; or $R^4$ and $R^a$, together with the carbon to which they are attached, form an oxo;

$R^{5a}$ and $R^{5b}$ are each independently hydrogen, halogen, OH, —($CR^{6a}R^{6b}$)$_t$C(O)R$^{8b}$, ($CR^{6a}R^{6b}$)$_t$C(O)NH$_2$, $C_1$-$C_4$alkyl, S($C_1$-$C_3$alkyl), $C_1$-$C_4$alkoxy, cyano, —($CR^{6a}R^{6b}$)$_t$—($C_3$-$C_6$cycloalkyl) or —($CR^{6a}R^{6b}$)$_t$—($C_3$-$C_6$heterocycloalkyl), wherein said alkyl, cycloalkyl and heterocycloalkyl are optionally substituted with one, two, three or four $R^9$; and the heteroatom is selected from the group consisting of one or two N, O, and S; or $R^{5a}$ and $R^{5b}$ taken together with the carbon to which they are bonded form a $C_3$-$C_9$cycloalkyl or a 4- to 11-membered heterocycloalkyl, wherein the heteroatom is selected from the group consisting of one or two N, S and O, wherein said cycloalkyl or heterocycloalkyl is optionally substituted with one, two, three or four $R^9$; or if substitution is at a N atom, then such N atom is substituted with $R^7$; or $R^3$ and either $R^{5a}$ or $R^{5b}$ taken together with the respective carbons to which they are bonded form a $C_3$-$C_{10}$cycloalkyl or -(4- to 12-membered heterocycloalkyl), wherein the heteroatom is selected from the group consisting of one or two N and O, wherein said cycloalkyl and heterocycloalkyl are optionally substituted with one, two, three or four $R^9$ or oxo; or if substitution is at a N atom, then such N atom is substituted with $R^7$;

$R^{6a}$ and $R^{6b}$ are each independently hydrogen, $C_1$-$C_4$alkyl, S($C_1$-$C_3$alkyl), OH, $C_1$-$C_4$alkoxy, cyano or halogen;

$R^7$ is hydrogen; -(4- to 6-membered heterocycloalkyl), having 1 to 2 heteroatoms wherein said heteroatom is selected from O, N and S; $C_1$-$C_5$alkyl; S($C_1$-$C_3$alkyl); C(O)R$^{8b}$; SO$_2$R$^{8b}$; SO$_2$N($R^{8a}$)$_2$; C(O)N($R^{8a}$)$_2$ or —($C_3$-$C_7$cycloalkyl), wherein said alkyl, heterocycloalkyl and cycloalkyl are optionally substituted with $R^a$;

$R^{8a}$ is hydrogen, $C_1$-$C_4$alkyl or —($C_3$-$C_7$cycloalkyl);

$R^{8b}$ is $C_1$-$C_4$alkyl, —($C_3$-$C_7$cycloalkyl), ($CR^{6a}R^{6b}$)$_t$SO$_2$N($R^{8a}$)$_2$, —($CR^{6a}R^{6b}$)$_t$SO$_2$R$^{8a}$ or —($CR^{6a}R^{6b}$)$_t$NHC(O)N($R^{8a}$)$_2$;

$R^9$ is hydrogen, $C_1$-$C_4$alkyl, S($C_1$-$C_3$alkyl), OH, CH$_2$OH, halogen, $C_1$-$C_4$alkoxy, cyano or —C(O)NH$_2$, wherein said alkyl and alkoxy are optionally substituted with OH, halogen, —C(O)NH$_2$, —C(O)NHCH$_3$, —C(O)N(CH$_3$)$_2$, —S($C_1$-$C_4$alkyl) or $C_3$-$C_5$cycloalkyl; or $R^9$ is oxo, provided that it is attached to a non-aromatic group;

$R^{10}$ is hydrogen or $C_1$-$C_3$alkyl;

m, n and t are each independently 0, 1 or 2;

q is 1, 2 or 3; and x is 1 or 2;

or a pharmaceutically acceptable salt thereof.

2. A compound of formula Ia, Ib, Ic, Id, Ie, If or Ig,

Ia

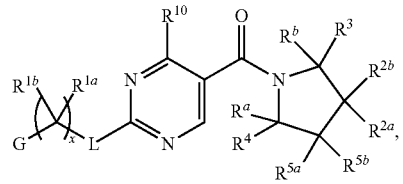

-continued

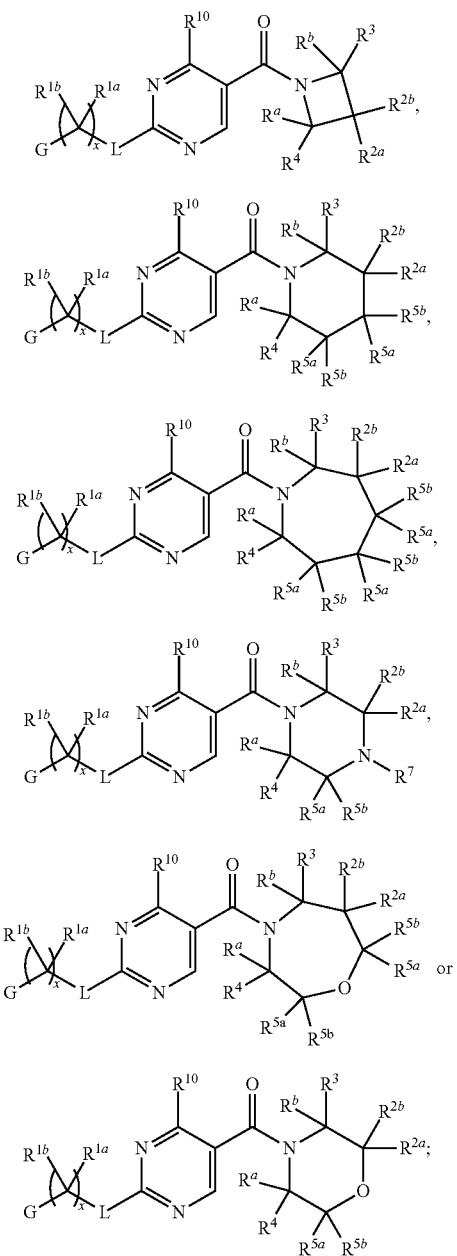

wherein
G is a triazinyl, pyridazinyl, pyridonyl, pyridinyl, pyrazinyl or pyrimidinyl, optionally substituted with one, two or three substituents selected from the group consisting of halogen, OH, cyano, $C_1$-$C_4$alkyl, $-NR^{8a}C(O)R^{8b}$, $-NR^{8a}SO_2R^{8b}$, $-(CR^{6a}R^{6b})_tC(O)N(R^{8a})_2$, C(O)OH, $-N(R^{8a})_2$, $-(CR^{6a}R^{6b})_tSO_2R^{8b}$, $-(CR^{6a}R^{6b})_tSO_2N(R^{8a})_2$, $C_1$-$C_4$alkoxy, $S(C_1$-$C_3$alkyl) and $C_3$-$C_5$cycloalkyl, wherein the alkyl, cycloalkyl and alkoxy are optionally substituted with one, two or three halogen, OH, $OCH_3$, or $C_3$-$C_5$cycloalkyl;

L is NH or O;

$R^a$, $R^b$, and $R^{1a}$ are each independently hydrogen, $C_1$-$C_4$alkyl, wherein the alkyl is optionally substituted with one, two or three halogen, OH, cyano or $C_1$-$C_4$alkoxy (optionally substituted with one, two or three fluoro);

$R^{1b}$ is $C_1$-$C_4$alkyl, wherein the alkyl is optionally substituted with one, two or three halogen, OH, cyano or $C_1$-$C_4$alkoxy (optionally substituted with one, two or three fluoro);

or $R^{1a}$ and $R^{1b}$, together with the carbon to which they are bonded, form an oxo, $C_3$-$C_5$cycloalkyl, or -(4- to 5-membered heterocycloalkyl) wherein said cycloalkyl or heterocycloalkyl are optionally substituted with one, two, three or four halogen, OH, $C_1$-$C_4$alkyl, $C_1$-$C_4$alkoxy or cyano;

$R^{2a}$ and $R^{2b}$ are each independently hydrogen, halogen, $C_1$-$C_4$alkyl, $-(CR^{6a}R^{6b})_tSO_2R^{8b}$, $-(CR^{6a}R^{6b})_tC(O)N(R^{8a})_2$, $-NR^8C(O)R^{8b}$, $-SO_2N(R^{8a})_2$, $-NR^8C(O)N(R^{8a})_2$, $S(C_1$-$C_3$alkyl), cyano, $-(CR^{6a}R^{6b})_t(C_3$-$C_6$cycloalkyl), OH, $C_1$-$C_4$alkoxy, $-(CR^{6a}R^{6b})_n(5$- to 6-membered heterocycloalkyl), having one to three heteroatoms selected from N, O or S, or $-(CR^{6a}R^{6b})_n$-(5- to 6-membered heteroaryl), having one to three heteroatoms selected from the group consisting of N, O and S, wherein said alkyl, cycloalkyl, heterocloakyl and heteroaryl are optionally substituted with one, two, three or four $R^9$; or $R^{2a}$ and $R^{2b}$ together with the carbon to which they are bonded form a $C_3$-$C_7$cycloalkyl or a -(4- to 12-membered heterocycloalkyl), having one to three heteroatoms selected from the group consisting of N, O and S; wherein the cycloalkyl and heterocycloalkyl are optionally substituted with one, two or three $C_1$-$C_4$alkyl, $S(C_1$-$C_3$alkyl), OH, halogen, oxo, C(O)NH$_2$, C(O)NHCH$_3$, C(O)N(CH$_3$)$_2$, $C_3$-$C_5$cycloalkyl or $C_1$-$C_4$alkoxy; or if substitution is at a N atom, then such N atom is substituted with $R^7$; or $R^{2a}$ or $R^{2b}$, and one of $R^{5a}$ or $R^{5b}$, together with the respective carbons to which they are bonded, form a $C_3$-$C_{12}$cycloalkyl, $C_6$-$C_{10}$aryl, -(5- to 6-membered heteroaryl) or a -(4- to 12-membered heterocycloalkyl), wherein said heteroaryl or heterocycloalkyl is optionally substituted with one, two, three or four $R^9$; or if substitution is at a N atom, then such N atom is substituted with $R^7$; or $R^{2a}$ or $R^{2b}$, and $R^7$, together with the respective atoms to which they are bonded form a -(4- to 12-membered heterocycloalkyl) or a -(5- to 6-membered heteroaryl), wherein said heterocycloalkyl or heteroaryl have one, two to three heteroatoms selected from the group consisting of N, O and S, wherein said heterocycloalkyl and heteroaryl are optionally substituted with one, two, three or four $R^9$;

$R^3$ is hydrogen, $-(CR^{6a}R^{6b})_tC(O)NH_2$ or $C_1$-$C_4$alkyl, wherein said alkyl is optionally substituted with one, two, three or four $R^9$; or $R^3$ and $R^b$, together with the carbon to which they are attached, form an oxo;

$R^4$ is hydrogen, $-(CR^{6a}R^{6b})_tC(O)NH_2$ or $C_1$-$C_4$alkyl, wherein said alkyl is optionally substituted with one, two, three or four $R^9$; or $R^4$ and $R^a$, together with the carbon to which they are attached, form an oxo; or $R^3$ and $R^4$ taken together with the respective carbons to which they are bonded form a -(4- to 12-membered heterocycloalkyl), having one to two heteroatoms selected from N, O or S, wherein the heterocycloalkyl are optionally substituted with one, two, three or four $R^9$;

$R^{5a}$ and $R^{5b}$ are each independently hydrogen, halogen, OH, $-(CR^{6a}R^{6b})_tC(O)R^{8b}$, $(CR^{6a}R^{6b})_tC(O)NH_2$, $C_1$-$C_4$alkyl, $S(C_1$-$C_3$alkyl), $C_1$-$C_4$alkoxy, cyano, —(CR$^{6a}$R$^{6b}$)$_t$—(C$_3$-C$_6$cycloalkyl) or —(CR$^{6a}$R$^{6b}$)$_t$—(C$_3$-C$_6$heterocycloalkyl) (having one, to two heteroatoms selected from the group consisting of N, O and S), wherein said alkyl, cycloalkyl and heterocycloalkyl are optionally substituted with one, two, three or four R$^9$; or R$^{5a}$ and R$^{5b}$ taken together with the carbon to which they are bonded form a C$_3$-C$_6$cycloalkyl or a 4- to 7-membered heterocycloalkyl, wherein the heteroatom is selected from the group consisting of one or two N, S and O, wherein said cycloalkyl or heterocycloalkyl is optionally substituted with one, two, three or four R$^9$; or R$^3$ and either R$^{5a}$ or R$^{5b}$ taken together with the respective carbons to which they are bonded form a C$_3$-C$_7$cycloalkyl or -(4- to 12-membered heterocycloalkyl), wherein the heteroatom is selected from the group consisting of one or two N and O, wherein said cycloalkyl and heterocycloalkyl are optionally substituted with one, two, three or four R$^9$ or oxo;

R$^{6a}$ and R$^{6b}$ are each independently hydrogen, C$_1$-C$_4$alkyl, S(C$_1$-C$_3$alkyl), OH, C$_1$-C$_4$alkoxy, —S(C$_1$-C$_4$alkyl), cyano or halogen;

R$^7$ is hydrogen; -(4- to 6-membered heterocycloalkyl), having 1 to 2 heteroatoms wherein said heteroatom is selected from O, N and S; C$_1$-C$_5$alkyl; S(C$_1$-C$_3$alkyl); C(O)R$^{8b}$; SO$_2$R$^{8b}$; SO$_2$N(R$^{8a}$)$_2$; C(O)N(R$^{8a}$)$_2$ or —(C$_3$-C$_7$cycloalkyl), wherein said alkyl, heterocycloalkyl and cycloalkyl are optionally substituted with R$^a$;

R$^{8a}$ is hydrogen, C$_1$-C$_4$alkyl or —(C$_3$-C$_7$cycloalkyl);

R$^{8b}$ is C$_1$-C$_4$alkyl, —(C$_3$-C$_7$cycloalkyl), —(CR$^{6a}$R$^{6b}$)$_t$ SO$_2$N(R$^{8a}$)$_2$, —(CR$^{6a}$R$^{6b}$)$_t$SO$_2$R$^{8a}$ or —(CR$^{6a}$R$^{6b}$)$_t$ NHC(O)N(R$^{8a}$)$_2$;

R$^9$ is hydrogen, C$_1$-C$_4$alkyl, S(C$_1$-C$_3$alkyl), oxo, OH, CH$_2$OH, halogen, C$_1$-C$_4$alkoxy, cyano or C(O)NH$_2$, wherein said alkyl and alkoxy are optionally substituted with OH, halogen, C(O)NH$_2$, C(O)NHCH$_3$, C(O)N (CH$_3$)$_2$, —S(C$_1$-C$_4$alkyl) or C$_3$-C$_5$cycloalkyl;

R$^{10}$ is hydrogen or C$_1$-C$_3$alkyl;

m, n and t are each independently 0, 1 or 2;

q is 1, 2 or 3; and x is 1 or 2;

or a pharmaceutically acceptable salt thereof.

3. The compound of claim 2 wherein R$^{1a}$ is hydrogen or C$_1$-C$_3$alkyl, wherein the alkyl is optionally substituted with one, two or three fluoro, OH, cyano or C$_1$-C$_4$alkoxy, optionally substituted with one, two or three fluoro;

R$^{1b}$ is C$_1$-C$_3$alkyl, wherein the alkyl is optionally substituted with one, two or three fluoro, OH, cyano or C$_1$-C$_4$alkoxy, optionally substituted with one, two or three fluoro;

or R$^{1a}$ and R$^{1b}$, together with the carbon to which they are bonded, form a C$_3$-C$_4$cycloalkyl or a 4-membered heterocycloalkyl, wherein said cycloalkyl or heterocycloalkyl are optionally substituted with one, two, three or four halogen, OH, C$_1$-C$_4$alkyl, S(C$_1$-C$_3$alkyl), C$_1$-C$_4$alkoxy or cyano;

or a pharmaceutically acceptable salt thereof.

4. The compound of claim 3 wherein R$^{1a}$ is hydrogen or methyl;

R$^{1b}$ is methyl;

or R$^{1a}$ and R$^{1b}$, together with the carbon to which they are bonded, form a cyclopropyl, cyclobutyl or an oxetane; or a pharmaceutically acceptable salt thereof.

5. The compound of claim 4 wherein L is NH; R$^a$ and R$^b$ are H; and x is 1; or a pharmaceutically acceptable salt thereof.

6. The compound of claim 5 wherein R$^3$ and R$^4$ are each independently hydrogen or C$_1$-C$_4$alkyl, wherein said alkyl is optionally substituted with one, two, three or four R$^9$; or R$^3$ and R$^4$ taken together with the respective carbons to which they are bonded form a -(4- to 12-membered heterocycloalkyl), having one to two heteroatoms selected from the group consisting of N, O and S, wherein the heterocycloalkyl is optionally substituted with one, two, three or four R$^9$; R$^9$ is OH, CH$_2$OH, halogen, C$_1$-C$_4$alkyl, C$_1$-C$_4$alkoxy or cyano; or a pharmaceutically acceptable salt thereof.

7. The compound of claim 6 wherein G is selected from the group consisting of pyrazinyl, pyrimidinyl, pyridinyl and pyridazinyl, optionally substituted with methyl, CH$_2$F, CHF$_2$ or CF$_3$; or a pharmaceutically acceptable salt thereof.

8. The compound of claim 7 wherein R$^{2a}$ and R$^{2b}$ together with the carbon to which they are bonded form a oxetane, tetrahydrofuran, tetrahydropyran, cyclobutyl, cyclopentyl, or cyclohexyl, each of which is optionally substituted with one or two C$_1$-C$_4$alkyl or OH; or a pharmaceutically acceptable salt thereof.

9. The compound of claim 7 wherein R$^{2a}$ and R$^{2b}$ are each independently hydrogen; fluoro; OH; C$_1$-C$_4$alkyl; C$_1$-C$_4$alkoxy; C$_3$-C$_6$cycloalkyl; 5-membered heteroaryl, having one or two N; cyano; —SO$_2$CH$_3$; —C(O)NHR$^{8a}$; or —NHC(O)NHR$^{8a}$; wherein said alkyl, alkoxy, cycloalkyl and heteroaryl are optionally substituted by one, two, three or four R$^9$; wherein R$^9$ is OH, fluoro, methyl, ethyl, methoxy or ethoxy; or a pharmaceutically acceptable salt thereof.

10. The compound of claim 7 wherein one of R$^{2a}$ or R$^{2b}$, taken together with the carbon to which they are bonded, and one of R$^{5a}$ or R$^{5b}$, form a cyclopropyl, cyclobutyl, cyclopentyl, cyclohexyl, tetrahydrofuran or phenyl, wherein each is optionally substituted with one, two, three or four R$^9$, wherein R$^9$ is OH, CH$_2$F, CHF$_2$, CF$_3$, or CH$_2$OH; or a pharmaceutically acceptable salt thereof.

11. The compound of claim 2 having Formula Ia

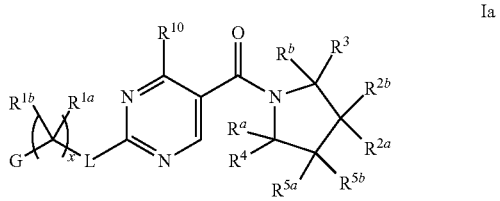

or a pharmaceutically acceptable salt thereof.

12. The compound of claim 11 wherein R$^{2a}$ and R$^{2b}$ are each independently hydrogen, methyl, ethyl, propyl, isopropyl, methoxy or ethoxy, optionally substituted with R$^9$ wherein R$^9$ is OH; or R$^{2a}$ and R$^{2b}$, together with the carbon to which they are bonded, form a tetrahydrofuran, cyclobutane, cyclopentane, cyclohexane, oxetane, tetrahydropyran, pyrrolidine, or azetidine, each of which is optionally substituted with one, two, three or four R$^9$; or R$^{2a}$ or R$^{2b}$, and one of R$^{5a}$ or R$^{5b}$, together with the respective carbons to which they are bonded, form a cyclopentane or cyclohexane, optionally substituted with one, two or three R$^9$; or a pharmaceutically acceptable salt of said compound or a tautomer of said compound or said salt.

13. The compound of claim 11 having formula IIa

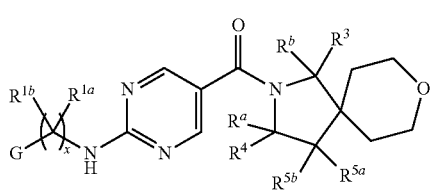

wherein G is pyrimidinyl or pyrazinyl; or a pharmaceutically acceptable salt thereof.

14. The compound of claim 13

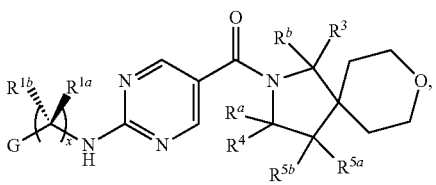

wherein $R^{1a}$ is hydrogen; and $R^{1b}$ is methyl, ethyl, or propyl, wherein each is optionally substituted with one, two or three fluoro; or a pharmaceutically acceptable salt thereof.

15. The compound of claim 14 wherein $R^a$, $R^b$, $R^3$, $R^4$, $R^{5a}$ and $R^{5b}$ are hydrogen; and x is 1; $R^{1b}$ is methyl or ethyl, optionally substituted with one, two or three fluoro, or a pharmaceutically acceptable salt thereof.

16. The compound of claim 2 having Formula Ib

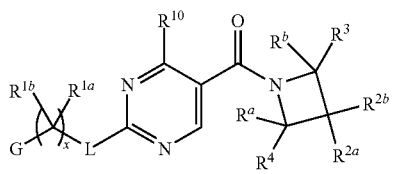

or a pharmaceutically acceptable salt thereof.

17. The compound of claim 16 wherein $R^{2a}$ and $R^{2b}$ are each independently hydrogen, methyl, ethyl, propyl, isopropyl, methoxy or ethoxy, optionally substituted with $R^9$ wherein $R^9$ is OH; or $R^{2a}$ and $R^{2b}$ together with the carbon to which they are bonded form a tetrahydrofuran, cyclobutane, cyclopentane, cyclohexane, oxetane, tetrahydropyran, pyrrolidine, or azetidine, each of which is optionally substituted with one, two, three or four $R^9$; or a pharmaceutically acceptable salt thereof.

18. The compound of claim 17 having formula IIb

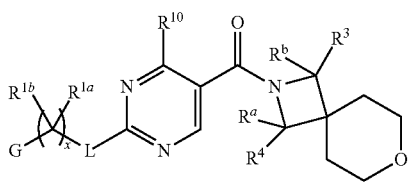

wherein $R^{10}$ is hydrogen; and L is NH; or a pharmaceutically acceptable salt thereof.

19. The compound of claim 18

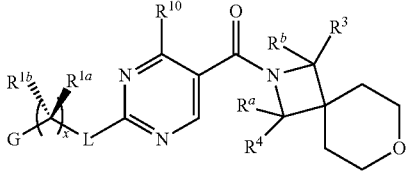

wherein $R^{1a}$ is hydrogen; and $R^{1b}$ is methyl, ethyl or propyl, each of which is optionally substituted by one, two or three fluoro; or a pharmaceutically acceptable salt thereof.

20. The Compound of claim 19 wherein $R^a$, $R^b$, $R^3$ and $R^4$ are hydrogen; x is 1; $R^{1b}$ is methyl or ethyl, optionally substituted with one, two or three fluoro; and G is pyrimidinyl or pyrazinyl; or a pharmaceutically acceptable salt thereof.

21. The compound of claim 2 having Formula Ie

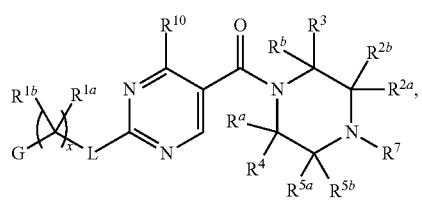

or a pharmaceutically acceptable salt thereof.

22. The compound of claim 21 wherein L is NH; and $R^{2a}$ or $R^{2b}$ and $R^7$, together with the respective atoms to which they are bonded form a -(4- to 12-membered heterocycloalkyl), having one or two heteroatoms selected the group consisting of from N and O, wherein said heterocycloalkyl is optionally substituted with one, two, three or four $R^9$; or a pharmaceutically acceptable salt thereof.

23. The compound of claim 22 having formula IIe,

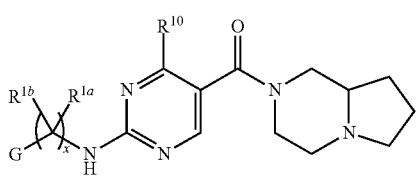

or a pharmaceutically acceptable salt thereof.

24. The compound of claim 23

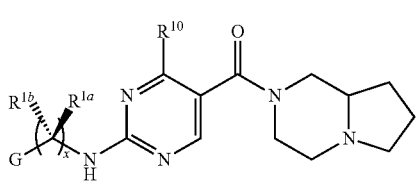

wherein R$^{1a}$ is hydrogen; and R$^{1b}$ is methyl, ethyl, or propyl, each of which is optionally substituted by one, two or three fluoro; or a pharmaceutically acceptable salt thereof.

25. The Compound of claim 24 wherein G is pyrimidinyl or pyrazinyl, or a pharmaceutically acceptable salt thereof.

26. The compound of claim 2 having Formula Ic

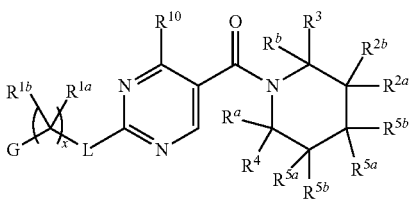

wherein
R$^{5a}$ and R$^{5b}$ are each independently hydrogen, OH, fluoro, cyano, C$_1$-C$_4$alkyl, C$_1$-C$_4$alkoxy, cyclopropyl, cyclobutyl, cyclopentyl, —(CR$^{6a}$R$^{6b}$)$_t$C(O)NH$_2$, or oxazolidinone, optionally substituted with one, two, three or four R$^9$; or
R$^{5a}$ and R$^{5b}$ taken together with the carbon to which they are bonded form a oxetane, tetrahydrofuran, tetrahydropyran, oxazolidinone, cyclopentane, cyclohexane, cyclobutane, or cyclopropane, wherein said cycloalkyl or heterocycloalkyl are optionally substituted with one, two, three or four R$^9$;
R$^9$ is fluoro, OH or C$_1$-C$_4$alkoxy, and
t is 0 or 1;
or a pharmaceutically acceptable salt thereof.

27. The compound of claim 26 having formula IIc,

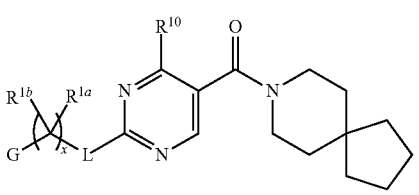

wherein G is pyrimidinyl or pyrazinyl; or a pharmaceutically acceptable salt thereof.

28. The compound of claim 26

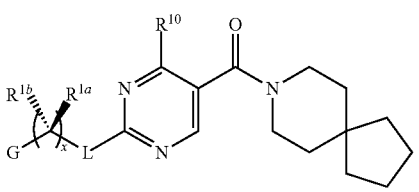

wherein R$^{1a}$ is hydrogen; and R$^{1b}$ is methyl, ethyl, or propyl, each of which is optionally substituted with one, two or three fluoro; or a pharmaceutically acceptable salt thereof.

29. A compound selected from the group consisting of
7-oxa-2-azaspiro[3.5]non-2-yl(2-{[1-(pyrazin-2-yl)cyclobutyl]amino}pyrimidin-5-yl)methanone;
8-oxa-2-azaspiro[4.5]dec-2-yl(2-{[1-(pyrazin-2-yl)cyclobutyl]amino}pyrimidin-5-yl)methanone;
8-oxa-2-azaspiro[4.5]dec-2-yl(2-{[2-(pyrazin-2-yl)propan-2-yl]amino}pyrimidin-5-yl)methanone;
8-oxa-2-azaspiro[4.5]dec-2-yl(2-{[2-(pyrimidin-5-yl)propan-2-yl]amino}pyrimidin-5-yl)methanone;
7-oxa-2-azaspiro[3.5]non-2-yl(2-{[2-(pyrazin-2-yl)propan-2-yl]amino}pyrimidin-5-yl)methanone;
8-oxa-2-azaspiro[4.5]dec-2-yl(2-{[1-(pyrimidin-5-yl)cyclobutyl]amino}pyrimidin-5-yl)methanone;
(2-{[2-(5-methylpyrazin-2-yl)propan-2-yl]amino}pyrimidin-5-yl)(7-oxa-2-azaspiro[3.5]non-2-yl)methanone;
8-oxa-2-azaspiro[4.5]dec-2-yl(2-{[(1S)-1-(pyrazin-2-yl)ethyl]amino}pyrimidin-5-yl)methanone;
(2-{[1-(6-methylpyridin-3-yl)cyclopropyl]amino}pyrimidin-5-yl)(8-oxa-2-azaspiro[4.5]dec-2-yl)methanone;
8-oxa-2-azaspiro[4.5]dec-2-yl(2-{[1-(pyrimidin-5-yl)cyclopropyl]amino}pyrimidin-5-yl)methanone;
(2-{[(1S)-1-(6-methylpyridin-3-yl)ethyl]amino}pyrimidin-5-yl)(8-oxa-2-azaspiro[4.5]dec-2-yl)methanone;
7-oxa-2-azaspiro[3.5]non-2-yl(2-{[1-(pyrimidin-5-yl)cyclobutyl]amino}pyrimidin-5-yl)methanone;
8-oxa-2-azaspiro[4.5]dec-2-yl(2-{[3-(pyrazin-2-yl)oxetan-3-yl]amino}pyrimidin-5-yl)methanone;
8-oxa-2-azaspiro[4.5]dec-2-yl(2-{[3-(pyrimidin-5-yl)oxetan-3-yl]amino}pyrimidin-5-yl)methanone;
7-oxa-2-azaspiro[3.5]non-2-yl(2-{[3-(pyrimidin-5-yl)oxetan-3-yl]amino}pyrimidin-5-yl)methanone;
(2-{[1-(5-methylpyridin-2-yl)ethyl]amino}pyrimidin-5-yl)(8-oxa-2-azaspiro[4.5]dec-2-yl)methanone;
8-oxa-2-azaspiro[4.5]dec-2-yl(2-{[1-(pyridin-2-yl)cyclopropyl]amino}pyrimidin-5-yl)methanone;
7-oxa-2-azaspiro[3.5]non-2-yl(2-{[2-(pyrimidin-5-yl)propan-2-yl]amino}pyrimidin-5-yl)methanone;
7-oxa-2-azaspiro[3.5]non-2-yl(2-{[(1S)-1-(pyrazin-2-yl)ethyl]amino}pyrimidin-5-yl)methanone;
8-oxa-2-azaspiro[4.5]dec-2-yl(2-{[(1S)-1-(pyrimidin-5-yl)ethyl]amino}pyrimidin-5-yl)methanone;
(2-{[1-(6-methylpyridin-3-yl)ethyl]amino}pyrimidin-5-yl)(8-oxa-2-azaspiro[4.5]dec-2-yl)methanone;
8-oxa-2-azaspiro[4.5]dec-2-yl(2-{[1-(pyrimidin-5-yl)ethyl]amino}pyrimidin-5-yl)methanone;
(2-{[1-(6-methylpyridin-3-yl)cyclopropyl]amino}pyrimidin-5-yl)(7-oxa-2-azaspiro[3.5]non-2-yl)methanone;
7-oxa-2-azaspiro[3.5]non-2-yl(2-{[1-(pyrimidin-5-yl)cyclopropyl]amino}pyrimidin-5-yl)methanone;
8-oxa-2-azaspiro[4.5]dec-2-yl(2-{[1-(pyrazin-2-yl)cyclopropyl]amino}pyrimidin-5-yl)methanone;
7-oxa-2-azaspiro[3.5]non-2-yl(2-{[(1S)-1-(pyrimidin-5-yl)ethyl]amino}pyrimidin-5-yl)methanone;
7-oxa-2-azaspiro[3.5]non-2-yl(2-{[1-(pyrazin-2-yl)cyclopropyl]amino}pyrimidin-5-yl)methanone;
(2-{[1-(2-methylpyrimidin-5-yl)ethyl]amino}pyrimidin-5-yl)(8-oxa-2-azaspiro[4.5]dec-2-yl)methanone;
8-oxa-2-azaspiro[4.5]dec-2-yl{2-[(pyridin-3-ylmethyl)amino]pyrimidin-5-yl}methanone;
7-oxa-2-azaspiro[3.5]non-2-yl{2-[(pyridin-3-ylmethyl)amino]pyrimidin-5-yl}methanone;
7-oxa-2-azaspiro[3.5]non-2-yl(2-{[1-(pyrimidin-5-yl)ethyl]amino}pyrimidin-5-yl)methanone;
(2-{[1-(6-methylpyridin-3-yl)ethyl]amino}pyrimidin-5-yl)(7-oxa-2-azaspiro[3.5]non-2-yl)methanone;

8-oxa-2-azaspiro[4.5]dec-2-yl(2-{[1-(pyrimidin-2-yl)cyclopropyl]amino}pyrimidin-5-yl)methanone;
(2-{[1-(2-methylpyrimidin-5-yl)ethyl]amino}pyrimidin-5-yl)(7-oxa-2-azaspiro[3.5]non-2-yl)methanone;
7-oxa-2-azaspiro[3.5]non-2-yl{2-[(pyrazin-2-ylmethyl)amino]pyrimidin-5-yl}methanone;
8-oxa-2-azaspiro[4.5]dec-2-yl(2-{[(1S)-1-(pyridazin-4-yl)ethyl]amino}pyrimidin-5-yl)methanone;
8-oxa-2-azaspiro[4.5]dec-2-yl(2-{[(1S)-1-(pyrimidin-4-yl)ethyl]amino}pyrimidin-5-yl)methanone;
(2-{[(6-methylpyridin-3-yl)methyl]amino}pyrimidin-5-yl)(7-oxa-2-azaspiro[3.5]non-2-yl)methanone;
(2-{[(6-methylpyridin-3-yl)methyl]amino}pyrimidin-5-yl)(8-oxa-2-azaspiro[4.5]dec-2-yl)methanone;
7-oxa-2-azaspiro[3.5]non-2-yl{2-[(pyrimidin-5-ylmethyl)amino]pyrimidin-5-yl}methanone;
(2-{[(2-methylpyrimidin-5-yl)methyl]amino}pyrimidin-5-yl)(8-oxa-2-azaspiro[4.5]dec-2-yl)methanone;
8-oxa-2-azaspiro[4.5]dec-2-yl{2-[(pyrimidin-5-ylmethyl)amino]pyrimidin-5-yl}methanone;
8-oxa-2-azaspiro[4.5]dec-2-yl{2-[(pyrazin-2-ylmethyl)amino]pyrimidin-5-yl}methanone;
(7,9-dimethyl-8-oxa-2-azaspiro[4.5]dec-2-yl)(2-{[1-(pyrimidin-5-yl)cyclopropyl]amino}pyrimidin-5-yl)methanone;
(3,3-diethylpyrrolidin-1-yl)(2-{[1-(pyrimidin-5-yl)cyclopropyl]amino}pyrimidin-5-yl)methanone;
[(3S)-3-ethyl-3-(hydroxymethyl)pyrrolidin-1-yl](2-{[1-(pyrimidin-5-yl)cyclopropyl]amino}pyrimidin-5-yl)methanone;
[3-(1H-pyrazol-3-yl)pyrrolidin-1-yl](2-{[1-(pyrimidin-5-yl)cyclopropyl]amino}pyrimidin-5-yl)methanone;
(3,3-dimethylpyrrolidin-1-yl)(2-{[1-(pyrimidin-5-yl)cyclopropyl]amino}pyrimidin-5-yl)methanone;
[(3aR,4R,7aS)-4-hydroxyoctahydro-2H-isoindol-2-yl]{2-[(pyridin-3-ylmethyl)amino]pyrimidin-5-yl}methanone;
[3-(3-methyl-1H-pyrazol-5-yl)pyrrolidin-1-yl](2-{[1-(pyrimidin-5-yl)cyclopropyl]amino}pyrimidin-5-yl)methanone;
hexahydrocyclopenta[c]pyrrol-2(1H)-yl(2-{[1-(pyrimidin-5-yl)cyclopropyl]amino}pyrimidin-5-yl)methanone;
(3-ethyl-3-methoxypyrrolidin-1-yl)(2-{[1-(pyrimidin-5-yl)cyclopropyl]amino}pyrimidin-5-yl)methanone;
(3-ethoxypiperidin-1-yl)(2-{[1-(pyrimidin-5-yl)cyclopropyl]amino}pyrimidin-5-yl)methanone;
[(3aR,7aR)-3a-(hydroxymethyl)octahydro-2H-isoindol-2-yl](2-{[1-(pyrimidin-5-yl)cyclopropyl]amino}pyrimidin-5-yl)methanone;
(2-{[1-(pyrimidin-5-yl)cyclopropyl]amino}pyrimidin-5-yl)[3-(trifluoromethyl)piperidin-1-yl]methanone;
[(3R,4R)-3-(hydroxymethyl)-3,4-dimethylpyrrolidin-1-yl](2-{[1-(pyrimidin-5-yl)cyclopropyl]amino}pyrimidin-5-yl)methanone;
(3R)-1-[(2-{[1-(pyrimidin-5-yl)cyclopropyl]amino}pyrimidin-5-yl)carbonyl]piperidine-3-carbonitrile;
[3-(methoxymethyl)piperidin-1-yl](2-{[1-(pyrimidin-5-yl)cyclopropyl]amino}pyrimidin-5-yl)methanone;
[(7S,8aS)-7-fluorohexahydropyrrolo[1,2-a]pyrazin-2(1H)-yl](2-{[1-(pyrimidin-5-yl)cyclopropyl]amino}pyrimidin-5-yl)methanone;
(4,4-difluoropiperidin-1-yl)(2-{[1-(pyrimidin-5-yl)cyclopropyl]amino}pyrimidin-5-yl)methanone;
(4-ethyl-4-methylpiperidin-1-yl)(2-{[1-(pyrimidin-5-yl)cyclopropyl]amino}pyrimidin-5-yl)methanone;
(2-{[1-(pyrimidin-5-yl)cyclopropyl]amino}pyrimidin-5-yl)[(3R)-3-(trifluoromethyl)pyrrolidin-1-yl]methanone;
8-azaspiro[4.5]dec-8-yl(2-{[1-(pyrimidin-5-yl)cyclopropyl]amino}pyrimidin-5-yl)methanone;
(4-fluoropiperidin-1-yl)(2-{[1-(pyrimidin-5-yl)cyclopropyl]amino}pyrimidin-5-yl)methanone;
[3-ethyl-3-(hydroxymethyl)pyrrolidin-1-yl]{2-[(pyridin-3-ylmethyl)amino]pyrimidin-5-yl}methanone;
(3-methylpiperidin-1-yl)(2-{[1-(pyrimidin-5-yl)cyclopropyl]amino}pyrimidin-5-yl)methanone;
[(3R)-3-(methylsulfonyl)piperidin-1-yl](2-{[1-(pyrimidin-5-yl)cyclopropyl]amino}pyrimidin-5-yl)methanone;
1-[(2-{[1-(pyrimidin-5-yl)cyclopropyl]amino}pyrimidin-5-yl)carbonyl]piperidine-3-carbonitrile;
(3-methoxypiperidin-1-yl)(2-{[1-(pyrimidin-5-yl)cyclopropyl]amino}pyrimidin-5-yl)methanone;
[(3S,4S)-3-(hydroxymethyl)-4-(trifluoromethyl)pyrrolidin-1-yl](2-{[1-(pyrimidin-5-yl)cyclopropyl]amino}pyrimidin-5-yl)methanone;
piperidin-1-yl(2-{[1-(pyrimidin-5-yl)cyclopropyl]amino}pyrimidin-5-yl)methanone;
[(3R)-3-ethyl-3-(hydroxymethyl)pyrrolidin-1-yl](2-{[1-(pyrimidin-5-yl)cyclopropyl]amino}pyrimidin-5-yl)methanone;
(3-cyclopropyl-3-hydroxyazetidin-1-yl){2-[(pyridin-3-ylmethyl)amino]pyrimidin-5-yl}methanone;
[(3R,4R)-3-(hydroxymethyl)-4-methylpyrrolidin-1-yl]{2-[(pyridin-3-ylmethyl)amino]pyrimidin-5-yl}methanone;
{2-[(pyridin-3-ylmethyl)amino]pyrimidin-5-yl}[3-(trifluoromethyl)pyrrolidin-1-yl]methanone;
1-oxa-9-azaspiro[5.5]undec-9-yl(2-{[1-(pyrimidin-5-yl)cyclopropyl]amino}pyrimidin-5-yl)methanone;
(2-{[1-(pyrimidin-5-yl)cyclopropyl]amino}pyrimidin-5-yl)[(3S)-3-(trifluoromethyl)pyrrolidin-1-yl]methanone;
[4-hydroxy-3-(trifluoromethyl)piperidin-1-yl](2-{[1-(pyrimidin-5-yl)cyclopropyl]amino}pyrimidin-5-yl)methanone;
[3-(methylsulfonyl)piperidin-1-yl](2-{[1-(pyrimidin-5-yl)cyclopropyl]amino}pyrimidin-5-yl)methanone;
[(3R)-3-methoxypyrrolidin-1-yl](2-{[1-(pyrimidin-5-yl)cyclopropyl]amino}pyrimidin-5-yl)methanone;
[(3R,5S)-3-hydroxy-5-methylpiperidin-1-yl](2-{[1-(pyrimidin-5-yl)cyclopropyl]amino}pyrimidin-5-yl)methanone;
1-oxa-8-azaspiro[4.5]dec-8-yl(2-{[1-(pyrimidin-5-yl)cyclopropyl]amino}pyrimidin-5-yl)methanone;
(2-{[(5-methylpyrazin-2-yl)methyl]amino}pyrimidin-5-yl)(7-oxa-2-azaspiro[3.5]non-2-yl)methanone;
[(3R,5R)-3-hydroxy-5-(propan-2-yl)piperidin-1-yl](2-{[1-(pyrimidin-5-yl)cyclopropyl]amino}pyrimidin-5-yl)methanone;
(2-{[(5-methylpyrazin-2-yl)methyl]amino}pyrimidin-5-yl)(8-oxa-2-azaspiro[4.5]dec-2-yl)methanone;
8-oxa-2-azaspiro[4.5]dec-2-yl(2-{[(1R)-1-(pyrimidin-5-yl)ethyl]amino}pyrimidin-5-yl)methanone;
[(3R,5R)-3-cyclopropyl-5-hydroxypiperidin-1-yl](2-{[1-(pyrimidin-5-yl)cyclopropyl]amino}pyrimidin-5-yl)methanone;
[(2S)-2-methylpyrrolidin-1-yl](2-{[1-(pyrimidin-5-yl)cyclopropyl]amino}pyrimidin-5-yl)methanone;
[4-ethyl-4-(hydroxymethyl)piperidin-1-yl](2-{[1-(pyrimidin-5-yl)cyclopropyl]amino}pyrimidin-5-yl)methanone;

[3-(hydroxymethyl)piperidin-1-yl](2-{[1-(pyrimidin-5-yl)cyclopropyl]amino}pyrimidin-5-yl)methanone;
8-oxa-2-azaspiro[4.5]dec-2-yl(2-{[(1R)-1-(pyrazin-2-yl)ethyl]amino}pyrimidin-5-yl)methanone;
8-oxa-2-azaspiro[4.5]dec-2-yl[2-({[4-(trifluoromethyl)pyrimidin-5-yl]methyl}amino)pyrimidin-5-yl]methanone;
[(3R,5S)-3-hydroxy-5-(trifluoromethyl)piperidin-1-yl](2-{[1-(pyrimidin-5-yl)cyclopropyl]amino}pyrimidin-5-yl)methanone;
1,4-oxazepan-4-yl(2-{[1-(pyrimidin-5-yl)cyclopropyl]amino}pyrimidin-5-yl)methanone;
2-oxa-5-azabicyclo[2.2.2]oct-5-yl(2-{[1-(pyrimidin-5-yl)cyclopropyl]amino}pyrimidin-5-yl)methanone;
5,6-dihydroimidazo[1,2-a]pyrazin-7(8H)-yl{2-[(pyridin-3-ylmethyl)amino]pyrimidin-5-yl}methanone;
[(2S)-2-methylmorpholin-4-yl](2-{[1-(pyrimidin-5-yl)cyclopropyl]amino}pyrimidin-5-yl)methanone;
(3-fluoropiperidin-1-yl)(2-{[1-(pyrimidin-5-yl)cyclopropyl]amino}pyrimidin-5-yl)methanone;
(6-hydroxy-2-azaspiro[3.3]hept-2-yl)(2-{[1-(pyrimidin-5-yl)cyclopropyl]amino}pyrimidin-5-yl)methanone;
octahydropyrazino[1,2-a]azepin-2(1H)-yl(2-{[1-(pyrimidin-5-yl)cyclopropyl]amino}pyrimidin-5-yl)methanone;
1-oxa-7-azaspiro[3.5]non-7-yl(2-{[1-(pyrimidin-5-yl)cyclopropyl]amino}pyrimidin-5-yl)methanone;
2-oxa-7-azaspiro[3.5]non-7-yl(2-{[1-(pyrimidin-5-yl)cyclopropyl]amino}pyrimidin-5-yl)methanone;
(4-hydroxy-4-methylpiperidin-1-yl){2-[(pyridin-3-ylmethyl)amino]pyrimidin-5-yl}methanone;
[4-(ethoxymethyl)-4-fluoropiperidin-1-yl](2-{[1-(pyrimidin-5-yl)cyclopropyl]amino}pyrimidin-5-yl)methanone;
7-oxa-2-azaspiro[3.5]non-2-yl(2-{[(1R)-1-(pyrazin-2-yl)ethyl]amino}pyrimidin-5-yl)methanone;
[4-(hydroxymethyl)-4-methylpiperidin-1-yl](2-{[1-(pyrimidin-5-yl)cyclopropyl]amino}pyrimidin-5-yl)methanone;
7-oxa-2-azaspiro[3.5]non-2-yl[2-({[4-(trifluoromethyl)pyrimidin-5-yl]methyl}amino)pyrimidin-5-yl]methanone;
6-oxa-9-azaspiro[4.5]dec-9-yl(2-{[1-(pyrimidin-5-yl)cyclopropyl]amino}pyrimidin-5-yl)methanone;
(6-methyl-1,4-oxazepan-4-yl)(2-{[1-(pyrimidin-5-yl)cyclopropyl]amino}pyrimidin-5-yl)methanone;
[(3R,4R)-3-fluoro-4-methoxypyrrolidin-1-yl](2-{[1-(pyrimidin-5-yl)cyclopropyl]amino}pyrimidin-5-yl)methanone;
(3-ethoxypyrrolidin-1-yl){2-[(pyridin-3-ylmethyl)amino]pyrimidin-5-yl}methanone;
(2-{[1-(pyrimidin-5-yl)cyclopropyl]amino}pyrimidin-5-yl)(pyrrolidin-1-yl)methanone;
[3-(hydroxymethyl)pyrrolidin-1-yl]{2-[(pyridin-3-ylmethyl)amino]pyrimidin-5-yl}methanone;
piperidin-1-yl{2-[(pyrimidin-5-ylmethyl)amino]pyrimidin-5-yl}methanone;
(2-{[(1R)-1-(6-methylpyridin-3-yl)ethyl]amino}pyrimidin-5-yl)(8-oxa-2-azaspiro[4.5]dec-2-yl)methanone;
7-oxa-2-azaspiro[3.5]non-2-yl(2-{[(1R)-1-(pyrimidin-5-yl)ethyl]amino}pyrimidin-5-yl)methanone;
[(8-anti)-8-methoxy-3-azabicyclo[3.2.1]oct-3-yl]{2-[(pyridin-3-ylmethyl)amino]pyrimidin-5-yl}methanone;
[(3S)-3-methoxypyrrolidin-1-yl](2-{[1-(pyrimidin-5-yl)cyclopropyl]amino}pyrimidin-5-yl)methanone;
[(7S,8aS)-7-fluorohexahydropyrrolo[1,2-a]pyrazin-2(1H)-yl]{2-[(pyrazin-2-ylmethyl)amino]pyrimidin-5-yl}methanone;
[(7R,8aS)-7-hydroxyhexahydropyrrolo[1,2-a]pyrazin-2(1H)-yl]{2-[(pyrazin-2-ylmethyl)amino]pyrimidin-5-yl}methanone;
[(1S,4S)-5-methyl-2,5-diazabicyclo[2.2.1]hept-2-yl]{2-[(pyrazin-2-ylmethyl)amino]pyrimidin-5-yl}methanone;
[(3S,4S)-3-hydroxy-4-(morpholin-4-yl)pyrrolidin-1-yl](2-{[(1S)-1-(pyrazin-2-yl)ethyl]amino}pyrimidin-5-yl)methanone;
(8aR)-hexahydropyrrolo[1,2-a]pyrazin-2(1H)-yl(2-{[(1S)-1-(pyrazin-2-yl)ethyl]amino}pyrimidin-5-yl)methanone;
[(3S,4S)-3-hydroxy-4-(morpholin-4-yl)pyrrolidin-1-yl]{2-[(pyrazin-2-ylmethyl)amino]pyrimidin-5-yl}methanone;
[(8aS)-7,7-difluorohexahydropyrrolo[1,2-a]pyrazin-2(1H)-yl]{2-[(pyrazin-2-ylmethyl)amino]pyrimidin-5-yl}methanone;
(7-ethyl-2,7-diazaspiro[4.4]non-2-yl)(2-{[(1S)-1-(pyrazin-2-yl)ethyl]amino}pyrimidin-5-yl)methanone;
[(8aS)-7,7-difluorohexahydropyrrolo[1,2-a]pyrazin-2(1H)-yl](2-{[(1S)-1-(pyrazin-2-yl)ethyl]amino}pyrimidin-5-yl)methanone;
(2-methyl-2,6-diazaspiro[3.4]oct-6-yl){2-[(pyrazin-2-ylmethyl)amino]pyrimidin-5-yl}methanone;
[(3R)-3-(morpholin-4-yl)pyrrolidin-1-yl](2-{[(1S)-1-(pyrazin-2-yl)ethyl]amino}pyrimidin-5-yl)methanone;
[(7S,8aS)-7-fluorohexahydropyrrolo[1,2-a]pyrazin-2(1H)-yl](2-{[(1S)-1-(pyrazin-2-yl)ethyl]amino}pyrimidin-5-yl)methanone;
(2-methyl-2,6-diazaspiro[3.4]oct-6-yl)(2-{[(1S)-1-(pyrazin-2-yl)ethyl]amino}pyrimidin-5-yl)methanone;
[(3aR,6aS)-5-methylhexahydropyrrolo[3,4-c]pyrrol-2(1H)-yl]{2-[(pyrazin-2-ylmethyl)amino]pyrimidin-5-yl}methanone;
[(3R)-3-(morpholin-4-yl)pyrrolidin-1-yl]{2-[(pyrazin-2-ylmethyl)amino]pyrimidin-5-yl}methanone;
(8aS)-hexahydropyrrolo[1,2-a]pyrazin-2(1H)-yl(2-{[(1S)-1-(pyrazin-2-yl)ethyl]amino}pyrimidin-5-yl)methanone;
[(1S,4S)-5-methyl-2,5-diazabicyclo[2.2.1]hept-2-yl](2-{[(1S)-1-(pyrazin-2-yl)ethyl]amino}pyrimidin-5-yl)methanone;
[(3aR,6aS)-5-methylhexahydropyrrolo[3,4-c]pyrrol-2(1H)-yl](2-{[(1S)-1-(pyrazin-2-yl)ethyl]amino}pyrimidin-5-yl)methanone;
(8aR)-hexahydropyrrolo[1,2-a]pyrazin-2(1H)-yl{2-[(pyrazin-2-ylmethyl)amino]pyrimidin-5-yl}methanone;
(8aS)-hexahydropyrrolo[1,2-a]pyrazin-2(1H)-yl{2-[(pyrazin-2-ylmethyl)amino]pyrimidin-5-yl}methanone; and
((6S,7S)-7-hydroxy-2-azaspiro[5.5]undecan-2-yl)(2-((1-(pyrimidin-5-yl)cyclopropyl)amino)pyrimidin-5-yl)methanone;
and a pharmaceutically acceptable salt thereof.

30. A compound selected from the group consisting of
7-oxa-2-azaspiro[3.5]non-2-yl(2-{[1-(pyrazin-2-yl)cyclobutyl]amino}pyrimidin-5-yl)methanone;
8-oxa-2-azaspiro[4.5]dec-2-yl(2-{[1-(pyrazin-2-yl)cyclobutyl]amino}pyrimidin-5-yl)methanone;
8-oxa-2-azaspiro[4.5]dec-2-yl(2-{[2-(pyrazin-2-yl)propan-2-yl]amino}pyrimidin-5-yl)methanone;

8-oxa-2-azaspiro[4.5]dec-2-yl(2-{[2-(pyrimidin-5-yl)
propan-2-yl]amino}pyrimidin-5-yl)methanone;
7-oxa-2-azaspiro[3.5]non-2-yl(2-{[2-(pyrazin-2-yl)pro-
pan-2-yl]amino}pyrimidin-5-yl)methanone;
8-oxa-2-azaspiro[4.5]dec-2-yl(2-{[1-(pyrimidin-5-yl)cy-
clobutyl]amino}pyrimidin-5-yl)methanone;
(2-{[2-(5-methylpyrazin-2-yl)propan-2-yl]
amino}pyrimidin-5-yl)(7-oxa-2-azaspiro[3.5]non-2-yl)
methanone;
8-oxa-2-azaspiro[4.5]dec-2-yl(2-{[(1S)-1-(pyrazin-2-yl)
ethyl]amino}pyrimidin-5-yl)methanone;
(2-{[1-(6-methylpyridin-3-yl)cyclopropyl]
amino}pyrimidin-5-yl)(8-oxa-2-azaspiro[4.5]dec-2-yl)
methanone;
8-oxa-2-azaspiro[4.5]dec-2-yl(2-{[1-(pyrimidin-5-yl)cy-
clopropyl]amino}pyrimidin-5-yl)methanone;
(2-{[(1S)-1-(6-methylpyridin-3-yl)ethyl]
amino}pyrimidin-5-yl)(8-oxa-2-azaspiro[4.5]dec-2-yl)
methanone;
7-oxa-2-azaspiro[3.5]non-2-yl(2-{[1-(pyrimidin-5-yl)cy-
clobutyl]amino}pyrimidin-5-yl)methanone;
8-oxa-2-azaspiro[4.5]dec-2-yl(2-{[3-(pyrazin-2-yl)
oxetan-3-yl]amino}pyrimidin-5-yl)methanone;
8-oxa-2-azaspiro[4.5]dec-2-yl(2-{[3-(pyrimidin-5-yl)
oxetan-3-yl]amino}pyrimidin-5-yl)methanone;
7-oxa-2-azaspiro[3.5]non-2-yl(2-{[3-(pyrimidin-5-yl)
oxetan-3-yl]amino}pyrimidin-5-yl)methanone;
(2-{[1-(5-methylpyridin-2-yl)ethyl]amino}pyrimidin-5-
yl)(8-oxa-2-azaspiro[4.5]dec-2-yl)methanone;
8-oxa-2-azaspiro[4.5]dec-2-yl(2-{[1-(pyridin-2-yl)cyclo-
propyl]amino}pyrimidin-5-yl)methanone;
7-oxa-2-azaspiro[3.5]non-2-yl(2-{[2-(pyrimidin-5-yl)
propan-2-yl]amino}pyrimidin-5-yl)methanone;
7-oxa-2-azaspiro[3.5]non-2-yl(2-{[(1S)-1-(pyrazin-2-yl)
ethyl]amino}pyrimidin-5-yl)methanone;
8-oxa-2-azaspiro[4.5]dec-2-yl(2-{[(1S)-1-(pyrimidin-5-
yl)ethyl]amino}pyrimidin-5-yl)methanone;
(2-{[1-(6-methylpyridin-3-yl)ethyl]amino}pyrimidin-5-
yl)(8-oxa-2-azaspiro[4.5]dec-2-yl)methanone;
8-oxa-2-azaspiro[4.5]dec-2-yl(2-{[1-(pyrimidin-5-yl)
ethyl]amino}pyrimidin-5-yl)methanone;
(2-{[1-(6-methylpyridin-3-yl)cyclopropyl]
amino}pyrimidin-5-yl)(7-oxa-2-azaspiro[3.5]non-2-yl)
methanone;
7-oxa-2-azaspiro[3.5]non-2-yl(2-{[1-(pyrimidin-5-yl)cy-
clopropyl]amino}pyrimidin-5-yl)methanone;
8-oxa-2-azaspiro[4.5]dec-2-yl(2-{[1-(pyrazin-2-yl)cyclo-
propyl]amino}pyrimidin-5-yl)methanone;
7-oxa-2-azaspiro[3.5]non-2-yl(2-{[(1S)-1-(pyrimidin-5-
yl)ethyl]amino}pyrimidin-5-yl)methanone;
7-oxa-2-azaspiro[3.5]non-2-yl(2-{[1-(pyrazin-2-yl)cy-
clopropyl]amino}pyrimidin-5-yl)methanone;
(2-{[1-(2-methylpyrimidin-5-yl)ethyl]amino}pyrimidin-
5-yl)(8-oxa-2-azaspiro[4.5]dec-2-yl)methanone;
8-oxa-2-azaspiro[4.5]dec-2-yl{2-[(pyridin-3-ylmethyl)
amino]pyrimidin-5-yl}methanone;
7-oxa-2-azaspiro[3.5]non-2-yl{2-[(pyridin-3-ylmethyl)
amino]pyrimidin-5-yl}methanone;
7-oxa-2-azaspiro[3.5]non-2-yl(2-{[1-(pyrimidin-5-yl)
ethyl]amino}pyrimidin-5-yl)methanone;
(2-{[1-(6-methylpyridin-3-yl)ethyl]amino}pyrimidin-5-
yl)(7-oxa-2-azaspiro[3.5]non-2-yl)methanone;
8-oxa-2-azaspiro[4.5]dec-2-yl(2-{[1-(pyridin-2-yl)cy-
clopropyl]amino}pyrimidin-5-yl)methanone;
(2-{[1-(2-methylpyrimidin-5-yl)ethyl]amino}pyrimidin-
5-yl)(7-oxa-2-azaspiro[3.5]non-2-yl)methanone;

7-oxa-2-azaspiro[3.5]non-2-yl{2-[(pyrazin-2-ylmethyl)
amino]pyrimidin-5-yl}methanone;
8-oxa-2-azaspiro[4.5]dec-2-yl(2-{[(1S)-1-(pyridazin-4-
yl)ethyl]amino}pyrimidin-5-yl)methanone;
8-oxa-2-azaspiro[4.5]dec-2-yl(2-{[(1S)-1-(pyrimidin-4-
yl)ethyl]amino}pyrimidin-5-yl)methanone;
(2-{[(6-methylpyridin-3-yl)methyl]amino}pyrimidin-5-
yl)(7-oxa-2-azaspiro[3.5]non-2-yl)methanone;
(2-{[(6-methylpyridin-3-yl)methyl]amino}pyrimidin-5-
yl)(8-oxa-2-azaspiro[4.5]dec-2-yl)methanone;
7-oxa-2-azaspiro[3.5]non-2-yl{2-[(pyrimidin-5-ylm-
ethyl)amino]pyrimidin-5-yl}methanone;
(2-{[(2-methylpyrimidin-5-yl)methyl]amino}pyrimidin-
5-yl)(8-oxa-2-azaspiro[4.5]dec-2-yl)methanone;
8-oxa-2-azaspiro[4.5]dec-2-yl{2-[(pyrimidin-5-ylmethyl)
amino]pyrimidin-5-yl}methanone; and
8-oxa-2-azaspiro[4.5]dec-2-yl{2-[(pyrazin-2-ylmethyl)
amino]pyrimidin-5-yl}methanone;
and a pharmaceutically acceptable salt thereof.

31. A pharmaceutical composition comprising a compound of claim 1, or a pharmaceutically acceptable salt thereof, and a pharmaceutically acceptable vehicle, diluent, carrier or other excipient.

32. A method of treating a disease or disorder selected from the group consisting of inflammatory bowel disease, ulcerative colitis, and Crohn's disease in a human comprising administering to the human in need of such treatment a therapeutically effective amount of a B compound of claim 1 or a pharmaceutically acceptable salt thereof.

33. A pharmaceutical combination comprising a therapeutically effective amount of a composition comprising:
   a first compound, wherein the first compound is a compound of claim 1, or a pharmaceutically acceptable salt thereof;
   a second compound, wherein the second compound is useful for the treatment of infectious or inflammatory diseases; and
   an optional pharmaceutically acceptable carrier, vehicle or diluent.

34. The pharmaceutical combination of claim 33 wherein the second compound is selected from the group consisting of an anti-TNFα agent, an anti-IL12 and/or IL23 agent, a modulator of S1P receptors, an integrin antagonist, an inhibitor of JAK kinases JAK1, JAK2, JAK3 and/or TYK2, a PDE4 inhibitor, and a SMAD7 antisense oligonucleotide.

35. The pharmaceutical composition of claim 34 wherein the second compound is selected from the group consisting of infliximab, adalimumab, golimumab, certolizumab pegol, ustekinumab, ozanimod, vedolizumab, etrolizumab, natalizumab, tofacitinib, filgotinib, PF-04965842, PF-06651600, PF-06263276, apremilast, and mongersen.

36. A compound selected from the group consisting of
[(8aS)-7,7-difluorohexahydropyrrolo[1,2-a]pyrazin-2
(1H)-yl](2-{[(1S)-1-(pyrazin-2-yl)ethyl]
amino}pyrimidin-5-yl)methanone;
[(7S,8aS)-7-fluorohexahydropyrrolo[1,2-a]pyrazin-2
(1H)-yl](2-{[(1S)-1-(pyrazin-2-yl)ethyl]
amino}pyrimidin-5-yl)methanone;
(8aS)-hexahydropyrrolo[1,2-a]pyrazin-2(1H)-yl(2-{
[(1S)-1-(pyrazin-2-yl)ethyl]amino}pyrimidin-5-yl)
methanone;
8-oxa-2-azaspiro[4.5]dec-2-yl(2-{[1-(pyrazin-2-yl)cy-
clobutyl]amino}pyrimidin-5-yl)methanone;
7-oxa-2-azaspiro[3.5]non-2-yl(2-{[2-(pyrazin-2-yl)pro-
pan-2-yl]amino}pyrimidin-5-yl)methanone;
8-oxa-2-azaspiro[4.5]dec-2-yl(2-{[3-(pyrimidin-5-yl)
oxetan-3-yl]amino}pyrimidin-5-yl)methanone;

7-oxa-2-azaspiro[3.5]non-2-yl{2-[(pyrazin-2-ylmethyl) amino]pyrimidin-5-yl}methanone;

(2-{[(6-methylpyridin-3-yl)methyl]amino}pyrimidin-5-yl)(8-oxa-2-azaspiro[4.5]dec-2-yl)methanone;

8-oxa-2-azaspiro[4.5]dec-2-yl{2-[(pyrazin-2-ylmethyl) amino]pyrimidin-5-yl}methanone;

7-oxa-2-azaspiro[3.5]non-2-yl(2-{[2-(pyrimidin-5-yl) propan-2-yl]amino}pyrimidin-5-yl)methanone;

8-oxa-2-azaspiro[4.5]dec-2-yl(2-{[(1S)-1-(pyrazin-2-yl) ethyl]amino}pyrimidin-5-yl)methanone;

7-oxa-2-azaspiro[3.5]non-2-yl(2-{[1-(pyrazin-2-yl)cyclopropyl]amino}pyrimidin-5-yl)methanone;

8-oxa-2-azaspiro[4.5]dec-2-yl(2-{[1-(pyridin-2-yl)cyclopropyl]amino}pyrimidin-5-yl)methanone;

(2-{[2-(5-methylpyrazin-2-yl)propan-2-yl] amino}pyrimidin-5-yl)(7-oxa-2-azaspiro[3.5]non-2-yl) methanone; and 8-oxa-2-azaspiro[4.5]dec-2-yl(2-{[1-(pyrimidin-5-yl)cyclopropyl]amino}pyrimidin-5-yl)methanone;

or a pharmaceutically acceptable salt of said compounds.

* * * * *